United States Patent
Min et al.

(10) Patent No.: US 10,446,764 B2
(45) Date of Patent: Oct. 15, 2019

(54) ORGANIC COMPOUND, COMPOSITION, ORGANIC OPTOELECTRIC DEVICE, AND DISPLAY DEVICE

(71) Applicant: SAMSUNG SDI CO., LTD., Yongin-si, Gyeonggi-do (KR)

(72) Inventors: Soohyun Min, Suwon-si (KR); Youngkwon Kim, Suwon-si (KR); Jun Seok Kim, Suwon-si (KR); Jinhyun Lui, Suwon-si (KR); Eun Sun Yu, Suwon-si (KR); Sangshin Lee, Suwon-si (KR); Seungjae Lee, Suwon-si (KR); Hanill Lee, Suwon-si (KR); Hyungyu Lee, Suwon-si (KR); Sooyoung Jeong, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 0 days.

(21) Appl. No.: 15/307,108

(22) PCT Filed: Apr. 17, 2015

(86) PCT No.: PCT/KR2015/003882
§ 371 (c)(1),
(2) Date: Oct. 27, 2016

(87) PCT Pub. No.: WO2015/178589
PCT Pub. Date: Nov. 26, 2015

(65) Prior Publication Data
US 2017/0047529 A1    Feb. 16, 2017

(30) Foreign Application Priority Data

May 22, 2014  (KR) .......................... 10-2014-0061892
Apr. 16, 2015  (KR) .......................... 10-2015-0053922

(51) Int. Cl.
*H01L 51/00*    (2006.01)
*C09K 11/02*    (2006.01)
(Continued)

(52) U.S. Cl.
CPC ........ *H01L 51/0072* (2013.01); *C07D 209/86* (2013.01); *C07D 239/74* (2013.01);
(Continued)

(58) Field of Classification Search
None
See application file for complete search history.

(56) References Cited

U.S. PATENT DOCUMENTS 8,278,651 B2    10/2012  Rostovtsev
2009/0045731 A1    2/2009  Nishimura et al.
(Continued)

FOREIGN PATENT DOCUMENTS

CN    102439004 A    5/2012
CN    103221406 A    7/2013
(Continued)

OTHER PUBLICATIONS

Machine English translation of Goromaru et al. (JP 2009-227663 A). Dec. 30, 2017.*
(Continued)

*Primary Examiner* — Jay Yang
(74) *Attorney, Agent, or Firm* — Lee & Morse, P.C.

(57) ABSTRACT

Related are: an organic compound represented by Chemical Formula 1; a composition for an organic optoelectric device, which includes the organic compound; an organic optoelectric device that employs the organic compound or the composition; and a display device including the organic optoelectric device.

16 Claims, 1 Drawing Sheet

(51) Int. Cl.

| | | |
|---|---|---|
| *C07D 487/04* | (2006.01) | |
| *C07D 401/14* | (2006.01) | |
| *C07D 209/86* | (2006.01) | |
| *C09K 11/06* | (2006.01) | |
| *C07D 239/74* | (2006.01) | |
| *H01L 51/50* | (2006.01) | |

(52) U.S. Cl.
CPC ......... *C07D 401/14* (2013.01); *C07D 487/04* (2013.01); *C09K 11/025* (2013.01); *C09K 11/06* (2013.01); *H01L 51/0054* (2013.01); *H01L 51/0067* (2013.01); *H01L 51/0085* (2013.01); *C09K 2211/1007* (2013.01); *C09K 2211/1029* (2013.01); *C09K 2211/185* (2013.01); *H01L 51/5016* (2013.01); *H01L 2251/5384* (2013.01)

(56) References Cited

U.S. PATENT DOCUMENTS

| | | |
|---|---|---|
| 2009/0091240 A1 | 4/2009 | Ikeda et al. |
| 2014/0131665 A1 | 5/2014 | Xia et al. |

FOREIGN PATENT DOCUMENTS

| | | | |
|---|---|---|---|
| CN | 103534251 A | | 1/2014 |
| JP | 08-3547 | * | 1/1996 |
| JP | 2003-040873 | | 2/2003 |
| JP | 2003-045662 | | 2/2003 |
| JP | 2007-015993 A | | 1/2007 |
| JP | 3945032 B2 | | 7/2007 |
| JP | 2008-127446 | | 6/2008 |
| JP | 4158426 B2 | | 10/2008 |
| JP | 2009227663 A | * | 10/2009 |
| JP | 2010-275255 A | | 12/2010 |
| JP | 2012-092047 | | 5/2012 |
| JP | 2012-121857 | | 6/2012 |
| JP | 5120398 B2 | | 1/2013 |
| JP | 2013-038432 | | 2/2013 |
| JP | 5135657 B2 | | 2/2013 |
| JP | 5266514 B2 | | 8/2013 |
| JP | 2013-180979 A | | 9/2013 |
| JP | 5321710 B2 | | 10/2013 |
| JP | 5340999 B2 | | 11/2013 |
| JP | 2014-096586 A | | 5/2014 |
| KR | 10-2009-0130008 | | 12/2009 |
| KR | 10-2011-0077930 | * | 7/2011 |
| KR | 10-1144358 | | 5/2012 |
| KR | 10-2012-0102374 | | 9/2012 |
| KR | 10-2012-0109744 A | | 10/2012 |
| KR | 10-1197218 | | 10/2012 |
| KR | 10-1251624 | | 4/2013 |
| KR | 10-2013-0102673 A | | 9/2013 |
| KR | 10-2013-0114785 | | 10/2013 |
| KR | 10-2013-0119740 | | 11/2013 |
| KR | 10-2013-0139535 A | | 12/2013 |
| KR | 10-2014-0128653 | * | 11/2014 |
| KR | 10-2015-0064410 A | | 6/2015 |
| WO | WO 2005/085387 A1 | | 9/2005 |
| WO | WO 2006/104118 A1 | | 10/2006 |
| WO | WO-2011/081431 | * | 7/2011 |
| WO | WO 2012/137958 A1 | | 10/2012 |
| WO | WO-2014/069637 A1 | * | 5/2014 |
| WO | WO 2014-069637 A1 | | 5/2014 |
| WO | WO-2014/178532 A1 | * | 11/2014 |

OTHER PUBLICATIONS

Machine English translation of Park et al. (KR 10-2014-0128653). Dec. 30, 2017.*
Machine English translation of Himeshima et al. (JP 08-3547). Dec. 30, 2017.*
Machine English translation of Okaniwa et al. (WO 2014/069637 A1). Dec. 30, 2017.*
Machine English translation of Lee et al. (KR-10-2011-0077930). (Year: 2018).*
Chinese Office Action dated Apr. 23, 2018, and the accompanying Search Report dated Apr. 12, 2018, of the corresponding Korean Patent Application No. 201580026671.8.

* cited by examiner

[Fig. 1]
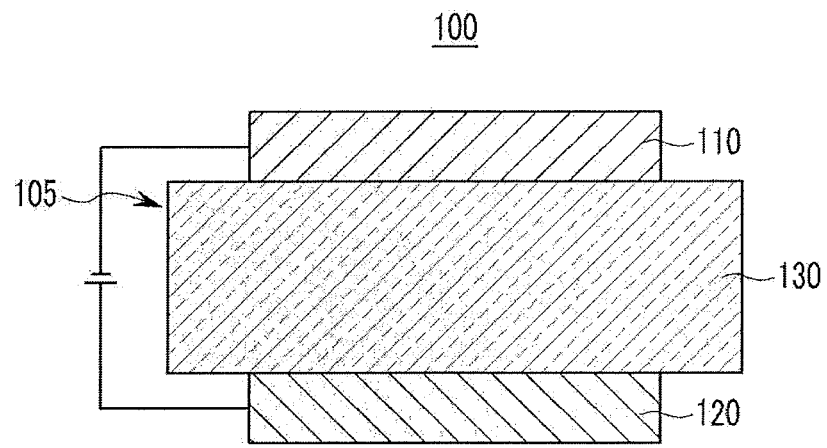
[Fig. 2]
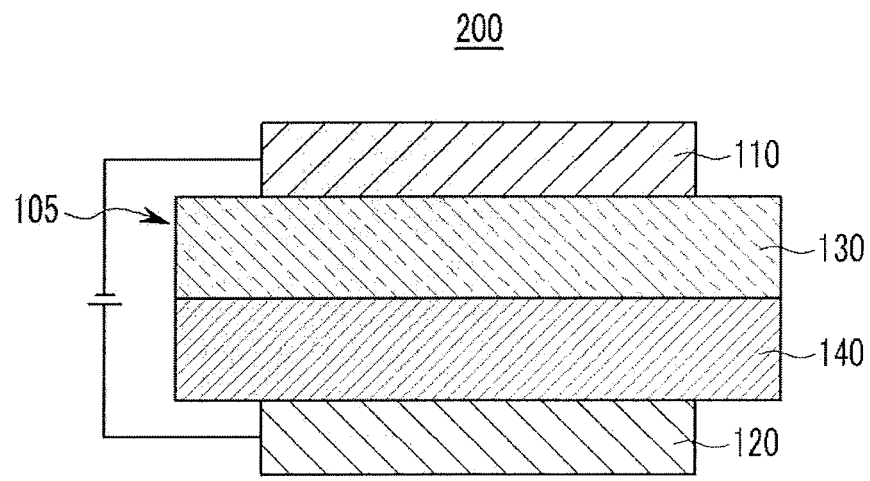

ORGANIC COMPOUND, COMPOSITION, ORGANIC OPTOELECTRIC DEVICE, AND DISPLAY DEVICE

CROSS REFERENCE TO RELATED APPLICATIONS

This is the U.S. national phase application based on PCT Application No. PCT/KR2015/003882, filed Apr. 17, 2015, which is based on Korean Patent Application Nos. 10-2014-0061892, filed May 22, 2014, and 10-2015-0053922, filed Apr. 16, 2015, the entire contents of all of which are hereby incorporated by reference.

BACKGROUND OF THE INVENTION (a) Field of the Invention

An organic compound, a composition, an organic optoelectric device, and a display device are disclosed.

(b) Description of the Related Art

An organic optoelectric device is a device that converts electrical energy into photoenergy, and vice versa.

An organic optoelectric device may be classified as follows in accordance with its driving principles. One is a photoelectric device where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of the organic optoelectric device may be an organic photoelectric device, an organic light emitting diode, an organic solar cell, an organic photo conductor drum, and the like.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode. Herein, the organic layer may include an emission layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides an organic compound capable of realizing an organic optoelectric device having high efficiency and a long life-span.

Another embodiment provides a composition for an organic optoelectric device, which includes the organic compound.

Yet another embodiment provides an organic optoelectric device including the organic compound or the composition.

Still another embodiment provides a display device including the organic optoelectric device.

According to one embodiment, an organic compound represented by Chemical Formula 1 is provided.

[Chemical Formula 1]

In Chemical Formula 1,

Z is independently C, N, or $CR^a$, at least one of Z's is N, $R^1$ to $R^3$ and $R^a$ are independently hydrogen, deuterium, a substituted or unsubstituted C1 to C20 alkyl group, a substituted or unsubstituted C6 to C20 aryl group, a substituted or unsubstituted C3 to C30 heterocyclic group, or a combination thereof, and $Ar^1$ is a substituted or unsubstituted biphenyl group, a substituted or unsubstituted terphenyl group, a substituted or unsubstituted quarterphenyl group, a substituted or unsubstituted fused ring, or a combination thereof.

According to another embodiment, provided is a composition for an organic optoelectric device including a first organic compound that is the organic compound and at least one second organic compound having a carbazole moiety.

According to yet another embodiment, provided is an organic optoelectric device including an anode and a cathode facing each other and at least one organic layer between the anode and the cathode, wherein the organic layer includes the organic compound or composition for an organic optoelectric device.

According to still another embodiment, provided is a display device including the organic optoelectric device.

An organic optoelectric device having high efficiency and long life-span may be realized.

BRIEF DESCRIPTION OF THE DRAWINGS

FIGS. 1 and 2 are cross-sectional views showing organic light emitting diodes according to an embodiment.

DETAILED DESCRIPTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to one substituted with a deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heterocyclic group, a C1 to C20 alkoxy group, a fluoro group, a C1 to C10 trifluoroalkyl group such as a trifluoromethyl group, or a cyano group, instead of at least one hydrogen of a substituent or a compound.

In addition, two adjacent substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heterocyclic group, C1 to C20 alkoxy group, fluoro group, C1 to C10 trifluoroalkyl group such as trifluoromethyl group and the like, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one hetero atom selected from the group consisting of N, O, S, P, and Si, and remaining carbons in one functional group.

In the present specification, "aryl group" refers to a group including at least one hydrocarbon aromatic moiety, and includes carbocyclic aromatic moieties linked by a single bond and carbocyclic aromatic moieties fused directly or indirectly to provide a non-aromatic fused ring. The aryl group may include a monocyclic, polycyclic or fused polycyclic (i.e., rings sharing adjacent pairs of carbon atoms) functional group.

In the present specification, "heterocyclic group" is a concept including a heteroaryl group, and may include at least one hetero atom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, a combination thereof, or a fused form of combinations thereof, but are not limited thereto.

In the present specification, the substituted or unsubstituted arylene group or the substituted or unsubstituted heteroarylene group or the substituted or unsubstituted divalent heterocyclic group has two linking groups in the substituted or unsubstituted aryl group or the substituted or unsubstituted heterocyclic group, and may be, for example, a substituted or unsubstituted phenylene group, a substituted or unsubstituted naphthalene group, a substituted or unsubstituted anthracenylene group, a substituted or unsubstituted phenanthrylene group, a substituted or unsubstituted naphthacenylene group, a substituted or unsubstituted pyrenylene group, a substituted or unsubstituted biphenylene group, a substituted or unsubstituted terphenylene group, a substituted or unsubstituted quarterphenylene group, a substituted or unsubstituted chrysenylene group, a substituted or unsubstituted triperylenylene group, a substituted or unsubstituted perylenylene group, a substituted or unsubstituted indenylene group, a substituted or unsubstituted furanylene group, a substituted or unsubstituted thiophenylene group, a substituted or unsubstituted pyffolylene group, a substituted or unsubstituted pyrazolene group, a substituted or unsubstituted imidazolylene group, a substituted or unsubstituted triazolylene group, a substituted or unsubstituted oxazolylene group, a substituted or unsubstituted thiazolylene group, a substituted or unsubstituted oxadiazolylene group, a substituted or unsubstituted thiadiazolylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted benzofuranylene group, a substituted or unsubstituted benzothiophenylene group, a substituted or unsubstituted benzimidazolylene group, a substituted or unsubstituted indolylene group, a substituted or unsubstituted quinolinylene group, a substituted or unsubstituted isoquinolinylene group, a substituted or unsubstituted quinazolinylene group, a substituted or unsubstituted quinoxalinylene group, a substituted or unsubstituted naphthyridinylene group, a substituted or unsubstituted benzoxazinylene group, a substituted or unsubstituted benzthiazinylene group, a substituted or unsubstituted acridinylene group, a substituted or unsubstituted phenazinylene group, a substituted or unsubstituted phenothiazinylene group, a substituted or unsubstituted phenoxazinylene group, a substituted or unsubstituted fluorenylene group, a substituted or unsubstituted dibenzofuranylene group, a substituted or unsubstituted dibenzothiophenylene group, a substituted or unsubstituted carbazolene group, a combination thereof, or a fused form of combinations thereof, but are not limited thereto.

In one example of the present invention, the substituted or unsubstituted arylene group or the substituted or unsubstituted heteroarylene group or the substituted or unsubstituted divalent heterocyclic group may be one of a substituted or unsubstituted phenylene group, a substituted or unsubstituted biphenylene group, a substituted or unsubstituted terphenylene group, a substituted or unsubstituted quarterphenylene group, a substituted or unsubstituted naphthalene group, and a substituted or unsubstituted pyrimidylene group, or a combination thereof.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

Hereinafter, an organic compound according to an embodiment is described.

An organic compound according to an embodiment is represented by Chemical Formula.

[Chemical Formula 1]

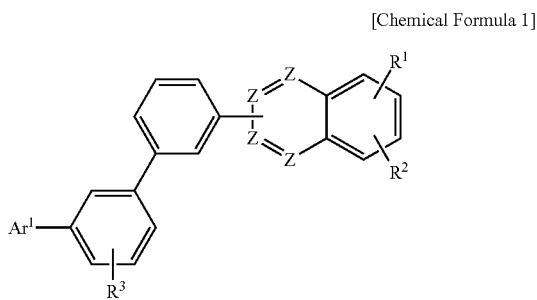

In Chemical Formula 1,
Z is independently C, N, or CR$^a$,
at least one of Z's is N,
R$^1$ to R$^3$ and R$^a$ are independently hydrogen, deuterium, a substituted or unsubstituted C1 to C20 alkyl group, a substituted or unsubstituted C6 to C20 aryl group, a substituted or unsubstituted C3 to C30 heterocyclic group, or a combination thereof, and
Ar$^1$ is a substituted or unsubstituted biphenyl group, a substituted or unsubstituted terphenyl group, a substituted or unsubstituted quarterphenyl group, a substituted or unsubstituted fused ring, or a combination thereof.

The organic compound represented by Chemical Formula 1 includes two phenylene groups in the center, and a substituted or unsubstituted biphenyl group, a substituted or unsubstituted terphenyl group, a substituted or unsubstituted quarterphenyl group, a substituted or unsubstituted fused ring, or a combination thereof, and a fused ring including at least one nitrogen which are linked at each meta position of the two phenylene groups.

For example, the Ar$^1$ may be a substituted or unsubstituted o-biphenyl group, a substituted or unsubstituted m-biphenyl group, a substituted or unsubstituted p-biphenyl group, a substituted or unsubstituted o-terphenyl group, a substituted or unsubstituted m-terphenyl group, a substituted or unsubstituted p-terphenyl group, a substituted or unsubstituted o-quarterphenyl group, a substituted or unsubstituted m-quarterphenyl group, a substituted or unsubstituted p-quarterphenyl group, or a substituted or unsubstituted fused ring having hole characteristics, and the a substituted or unsubstituted fused ring having hole characteristics may be, for example a substituted or unsubstituted triphenylene group.

For example, one or two of the Z's may be nitrogen and at least one of the Z's may be CR$^a$, wherein R$^a$ is for example a substituted or unsubstituted C6 to C20 aryl group, a substituted or unsubstituted C3 to C30 heterocyclic group, or a combination thereof. The R$^a$ may be, for example a phenyl group, a biphenyl group, a terphenyl group, a naphthyl group, a heterocyclic group having at least one nitrogen, or a combination thereof, and the heterocyclic group having at least one nitrogen may be, for example pyridinyl, pyridazinyl, pyrimidinyl, pyrazinyl, or triazinyl but is not limited thereto.

The organic compound includes a fused ring having at least one nitrogen and thus may have a structure of easily receiving electrons when an electric field is applied thereto and accordingly, lower a driving voltage of an organic optoelectric device.

In addition, the organic compound includes a plurality of substituted or unsubstituted phenyl group moiety or fused ring moiety easily receiving holes and a nitrogen-containing fused ring moiety easily receiving electrons and thus may form a bipolar structure and may balance flows of the holes and the electrons and resultantly, improve efficiency of an organic optoelectric device.

In addition, the organic compound includes two phenylene groups linked in each meta position and thus may appropriately localize a region for the plurality of substituted or unsubstituted aryl group easily receiving holes and for the nitrogen-containing ring moiety easily receiving electrons in the above bipolar structure and control a flow of a conjugation system and resultantly, exhibit excellent bipolar characteristics. Herein, one or two of the two phenylene groups may be an unsubstituted phenylene group. Accordingly, the organic compound may appropriately improve a life-span of an organic optoelectric device.

In addition, the organic compound has a substantial linear structure and may be self-arranged during the deposition and thus increase process stability thin film uniformity.

The organic compound may be, for example represented by Chemical Formula 2.

[Chemical Formula 2]

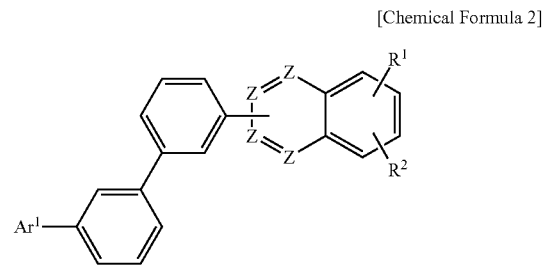

In Chemical Formula 2, Z, R$^1$, R$^2$, and Ar$^1$ are the same as described above.

In Chemical Formula 2, the two phenylene groups linked in each meta position may be unsubstituted phenylene groups.

The organic compound may be, for example represented by one of Chemical Formulae 3 to 7.

[Chemical Formula 3]

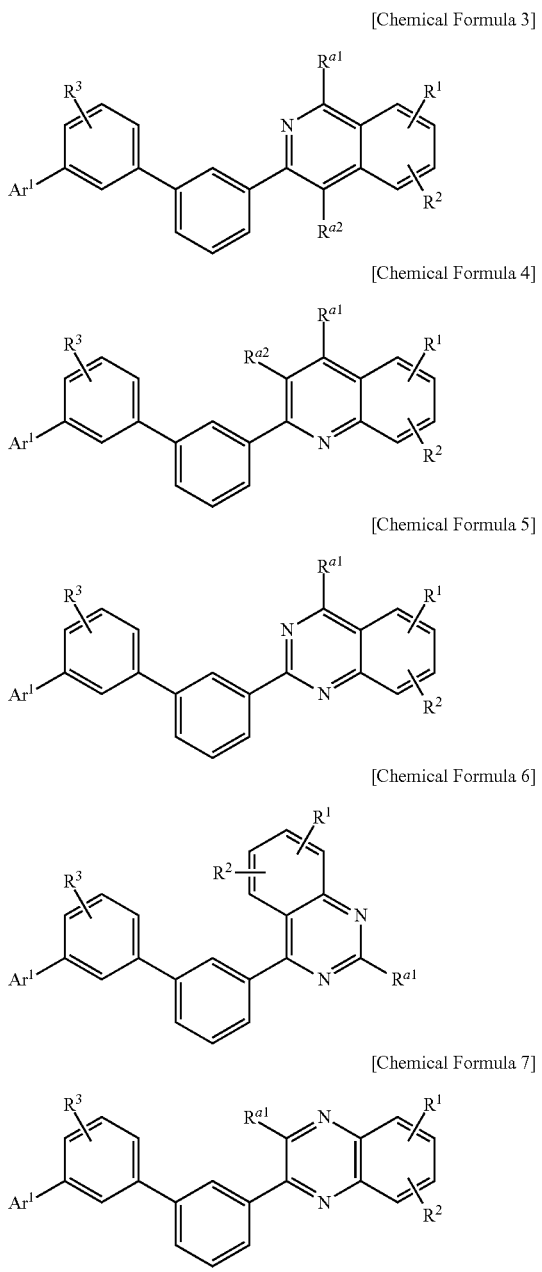

[Chemical Formula 4]

[Chemical Formula 5]

[Chemical Formula 6]

[Chemical Formula 7]

In Chemical Formulae 3 to 7, $R^1$ to $R^3$ and $Ar^1$ are the same as described above, and $R^{a1}$ and $R^{a2}$ are the same as $R^a$.

In Chemical Formulae 3 to 7, $R^{a1}$ may be, for example a substituted or unsubstituted C6 to C20 aryl group, a substituted or unsubstituted C3 to C30 heterocyclic group, or a combination thereof. $R^{a1}$ may be, for example a phenyl group, a biphenyl group, a terphenyl group, a naphthyl group, a heterocyclic group having at least one nitrogen, or a combination thereof, wherein the heterocyclic group having at least one nitrogen may be for example pyridinyl, pyridazinyl, pyrimidinyl, pyrazinyl, or triazinyl, but is not limited thereto.

In Chemical Formulae 3 to 7, for example, $Ar^1$ may be, for example a substituted or unsubstituted o-biphenyl group, a substituted or unsubstituted m-biphenyl group, a substituted or unsubstituted p-biphenyl group, a substituted or unsubstituted o-terphenyl group, a substituted or unsubstituted m-terphenyl group, a substituted or unsubstituted p-terphenyl group, a substituted or unsubstituted o-quarterphenyl group, a substituted or unsubstituted m-quarterphenyl group, a substituted or unsubstituted p-quarterphenyl group, or a substituted or unsubstituted fused ring having hole characteristics, and the fused ring having hole characteristics may be, for example a substituted or unsubstituted triphenylene group.

The organic compound may be, for example represented by one of Chemical Formulae 8 to 10.

[Chemical Formula 8]

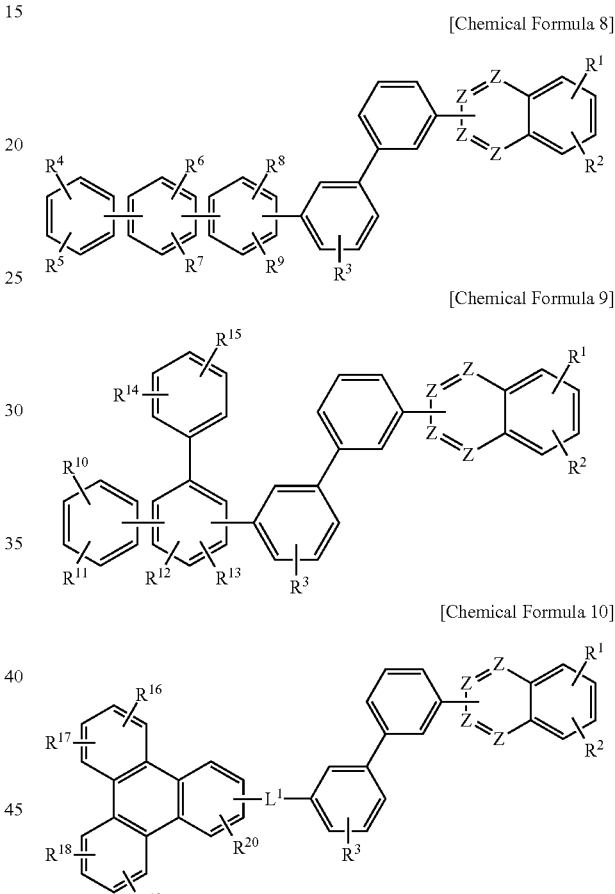

[Chemical Formula 9]

[Chemical Formula 10]

In Chemical Formulae 8 to 10,

Z is the same as described above, $L^1$ is a single bond or a substituted or unsubstituted C6 to C20 arylene group, $R^1$ to $R^{20}$ are independently hydrogen, deuterium, a substituted or unsubstituted C1 to C20 alkyl group, a substituted or unsubstituted C6 to C20 aryl group, a substituted or unsubstituted C3 to C30 heterocyclic group, or a combination thereof, and $R^4$ and $R^5$, $R^6$ and $R^7$, $R^8$ and $R^9$, $R^{10}$ and $R^{11}$, $R^{12}$ and $R^{13}$, $R^{14}$ and $R^{15}$, $R^{16}$ and $R^{17}$ and $R^{18}$ and $R^{19}$ are independently present or linked with each other to provide a ring.

In Chemical Formulae 8 to 10, for example one or two of the Z's may be nitrogen and at least one of the Z's may be $CR^a$, wherein $R^a$ is for example a substituted or unsubstituted C6 to C20 aryl group, a substituted or unsubstituted C3 to C30 heterocyclic group, or a combination thereof. $R^a$ may for example be a phenyl group, a biphenyl group, a terphenyl group, a naphthyl group, a heterocyclic group having at least one nitrogen, or a combination thereof, and the heterocyclic group having at least one nitrogen may be, for example pyridinyl, pyridazinyl, pyrimidinyl, pyrazinyl, or triazinyl, but is not limited thereto.

The organic compound represented by Chemical Formula 8 may be, for example one of Chemical Formulae 8a to 8c, but is not limited thereto.

[Chemical Formula 8a]

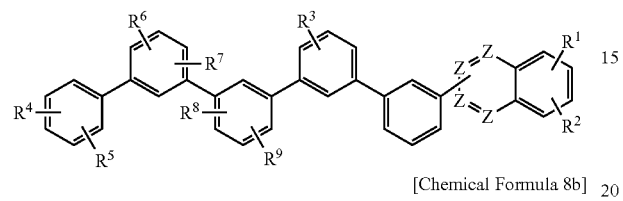

[Chemical Formula 8b]

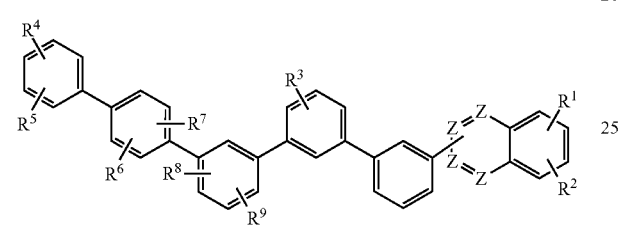

[Chemical Formula 8c]

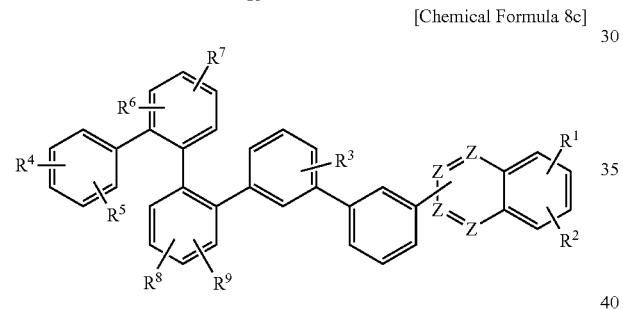

In Chemical Formulae 8a to 8c, Z and $R^1$ to $R^9$ are the same as described above.

The organic compound represented by Chemical Formula 9 may be, for example an organic compound represented by Chemical Formula 9a, but is not limited thereto.

[Chemical Formula 9a]

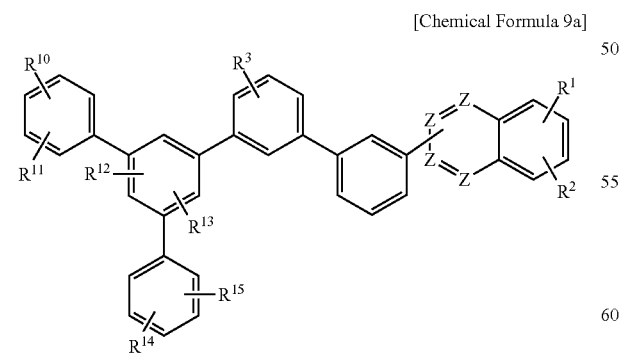

In Chemical Formula 9a, Z, $R^1$ to $R^3$ and $R^{10}$ to $R^{15}$ are the same as described above.

The organic compound may be, for example an organic compound of Group 1, but is not limited thereto.

[Group 1]

1

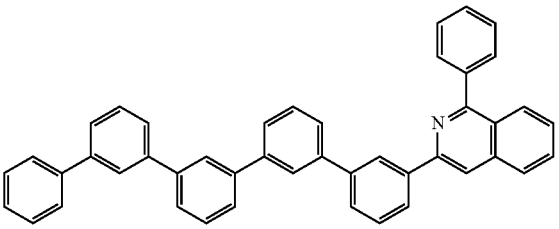

2

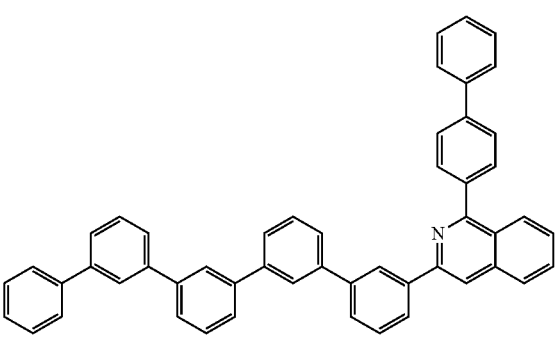

3

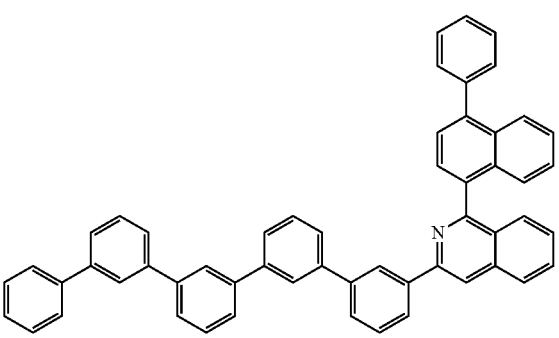

4

5

6
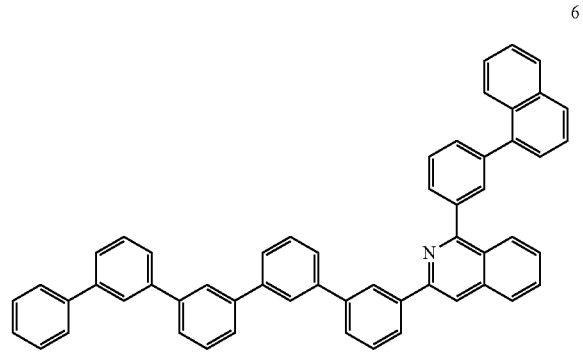
7
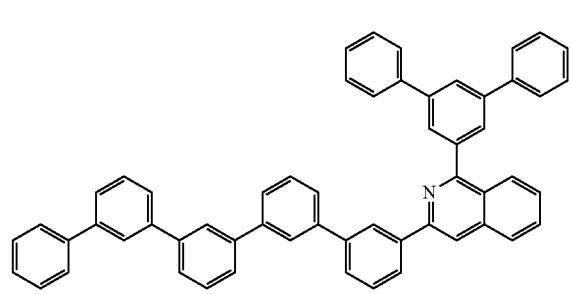
8
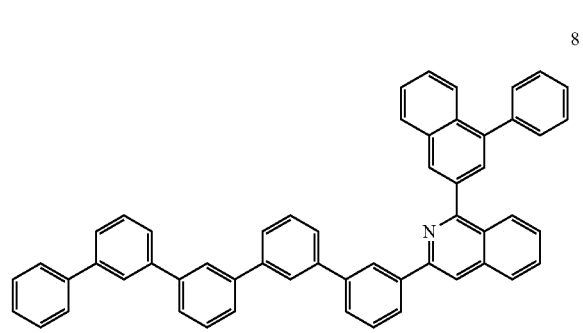
9
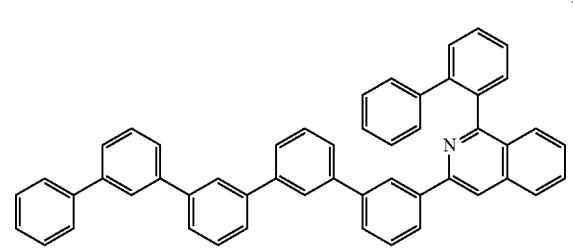
10
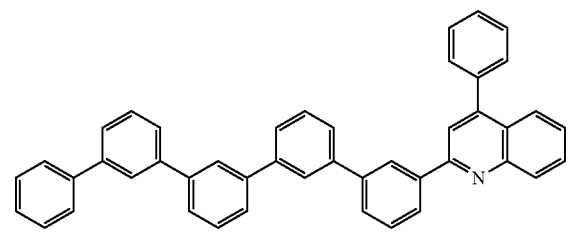
11
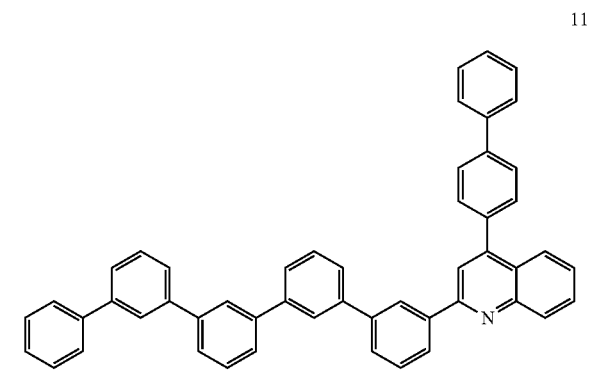
12
13
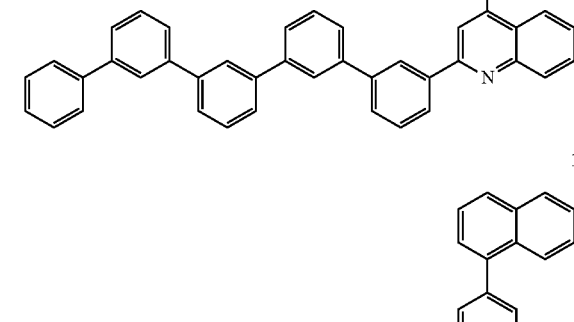
14
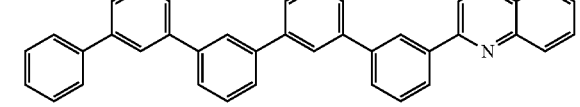

15
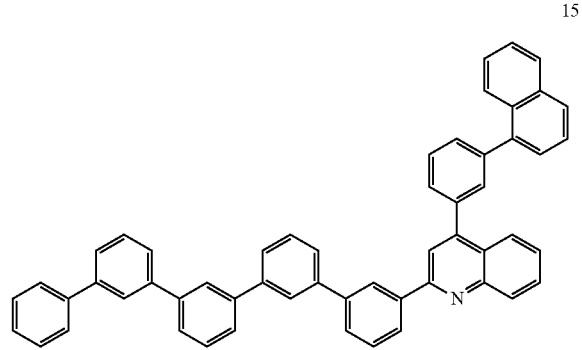
16
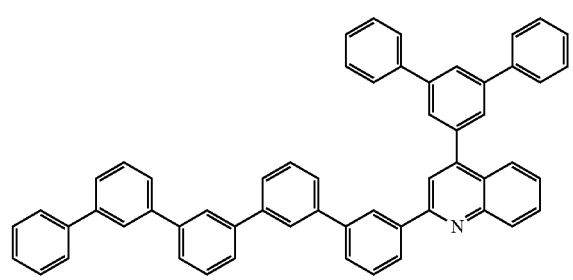
17
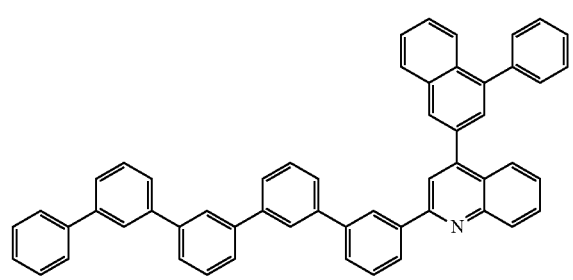
18
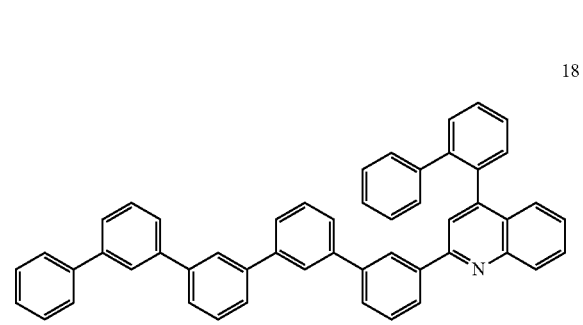
19
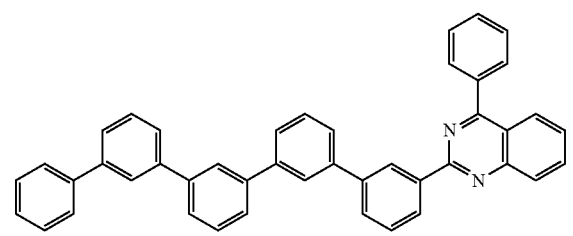
20
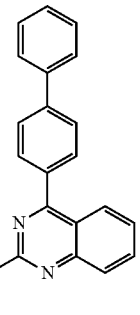
21
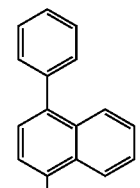
22
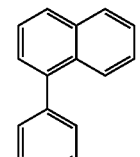
23
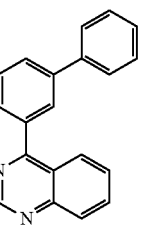

24
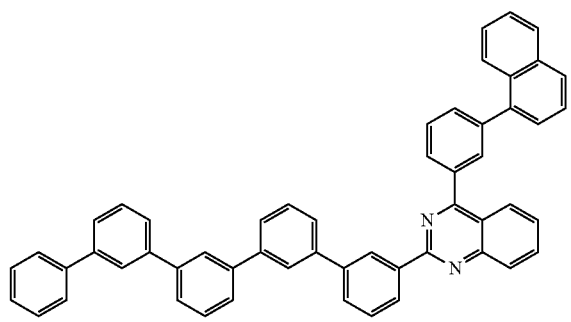
25
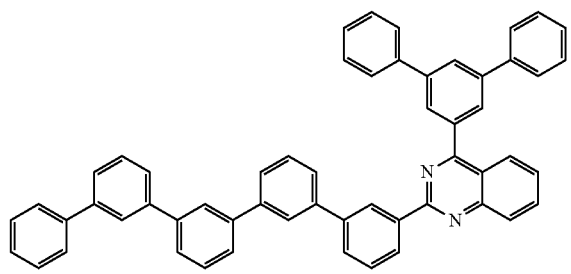
26
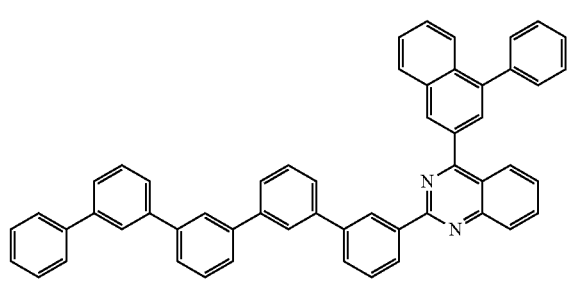
27
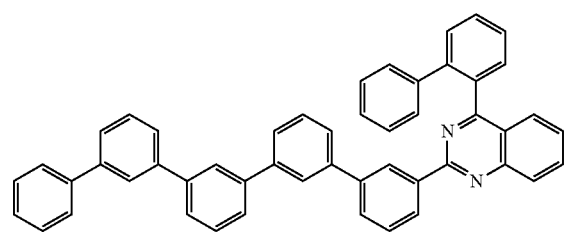
28
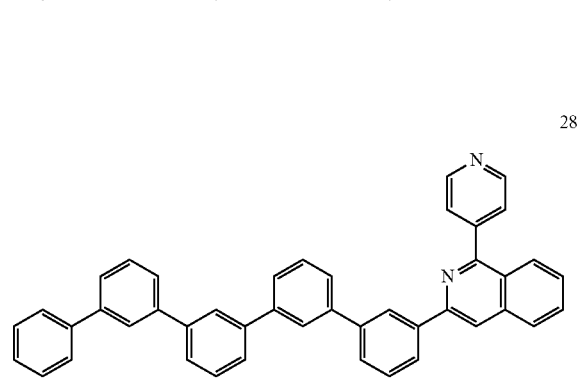
29
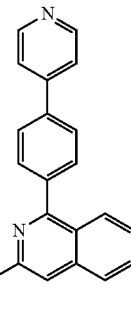
30
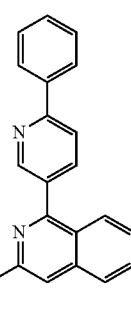
31
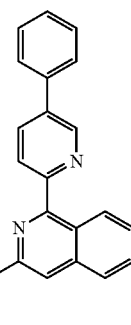
32
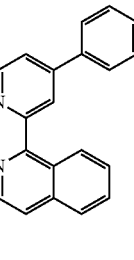
33
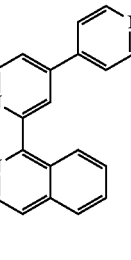

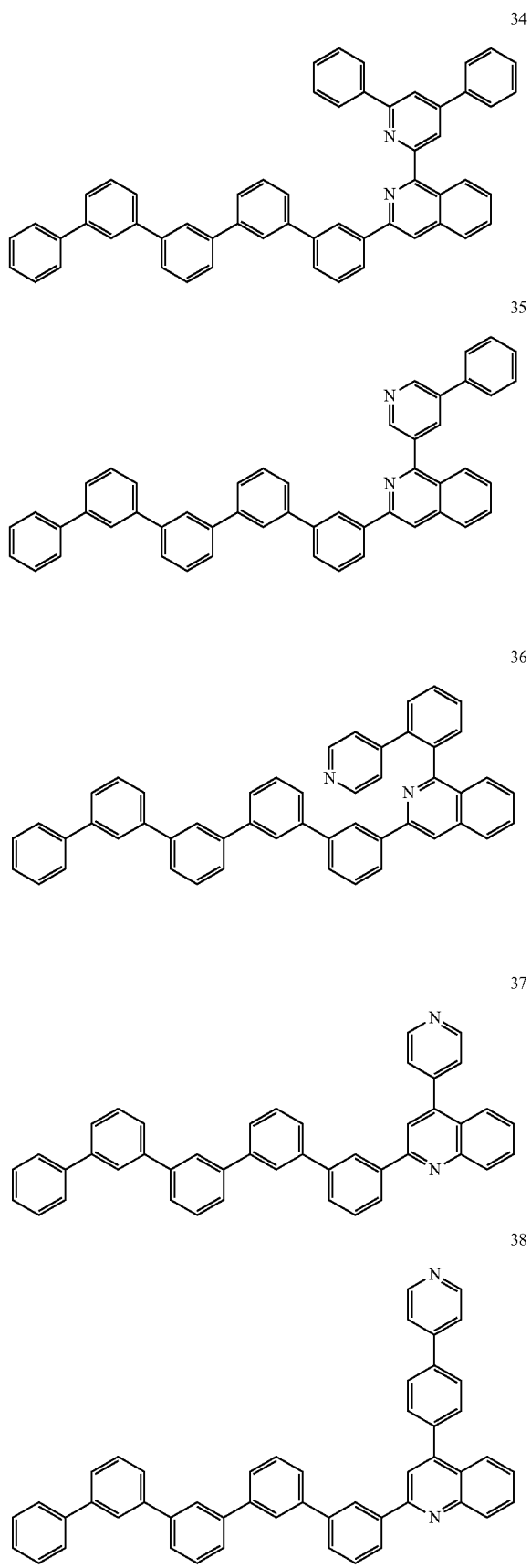
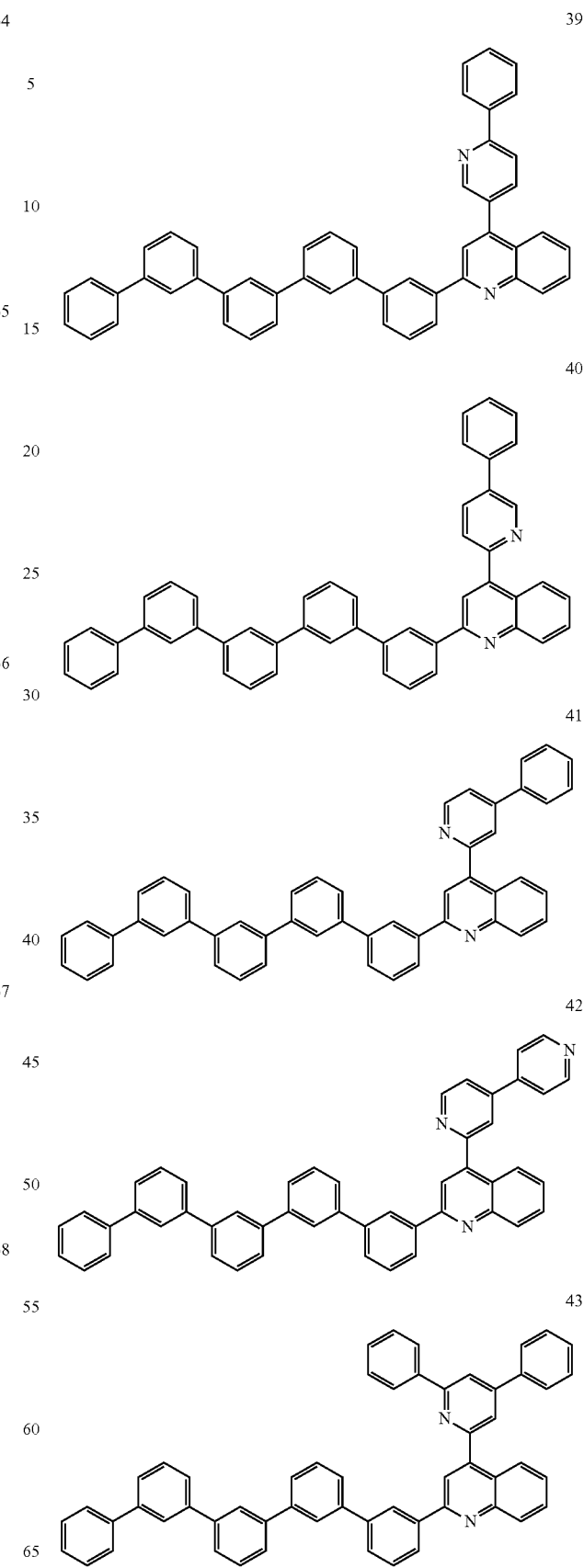

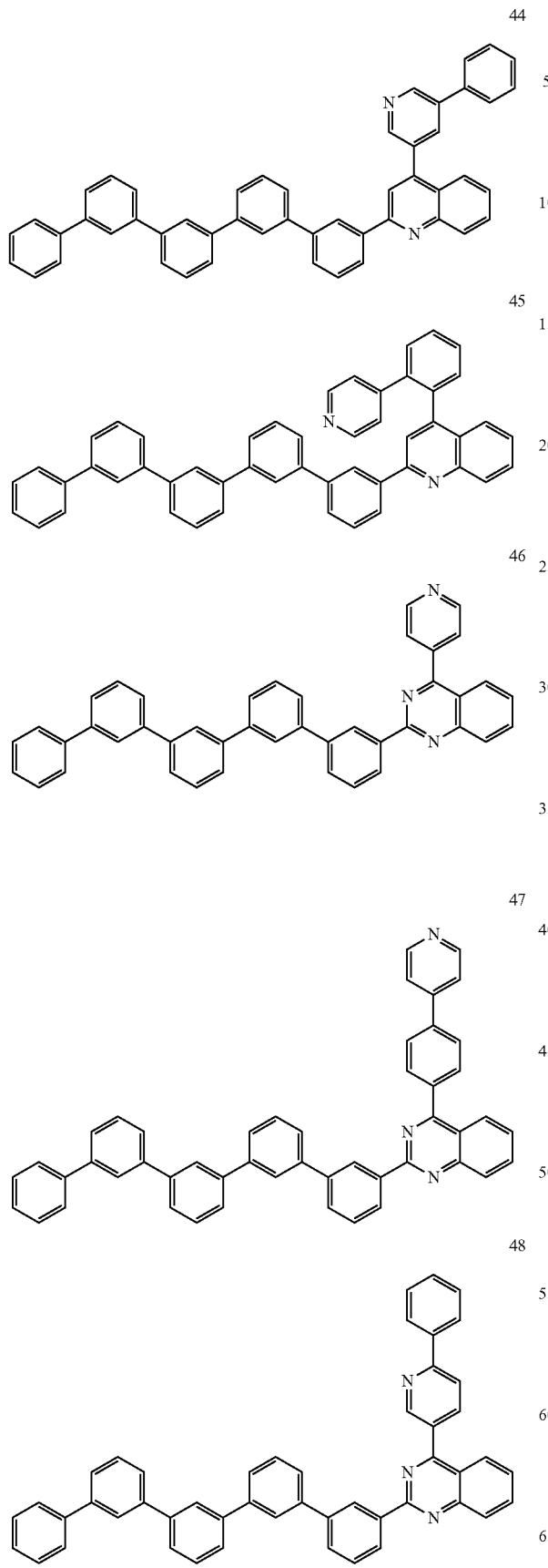
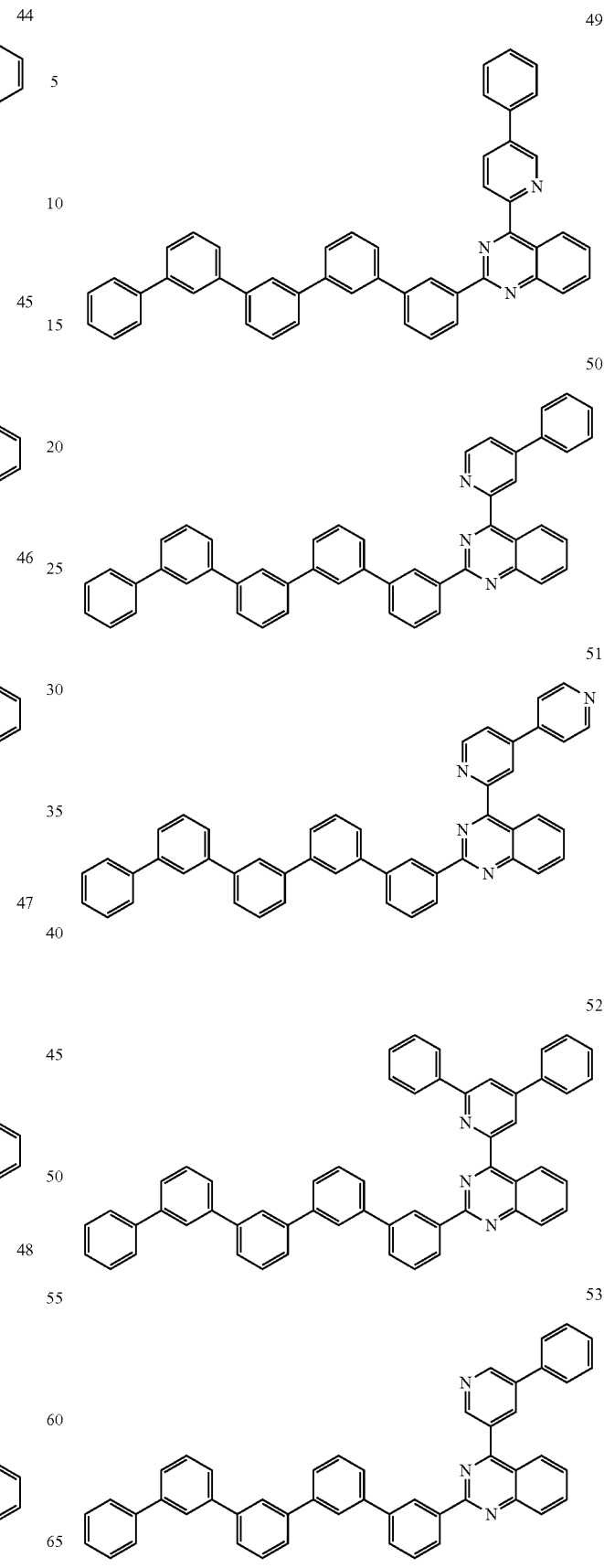

54
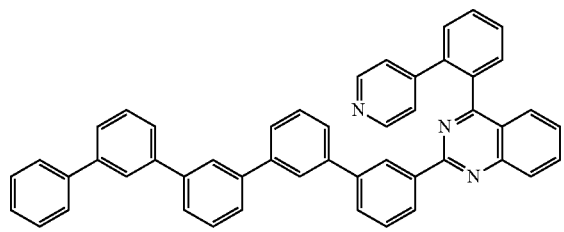
55
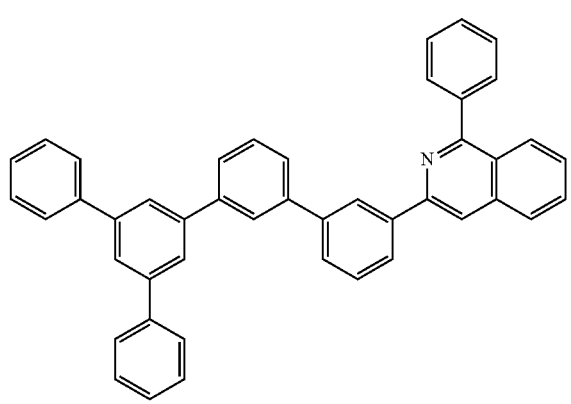
56
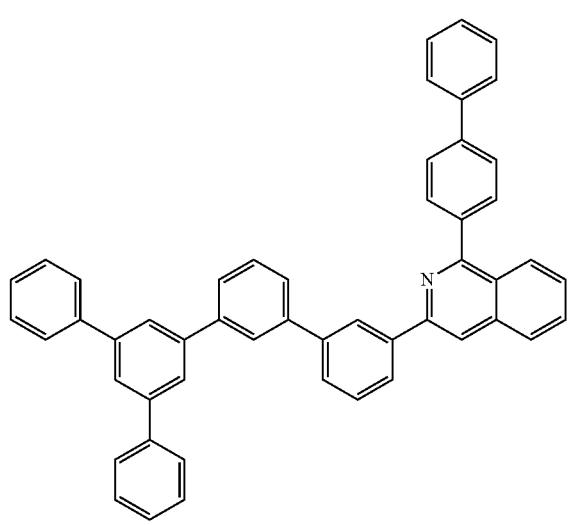
57
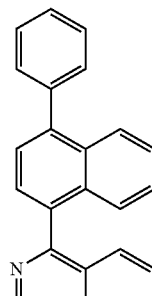
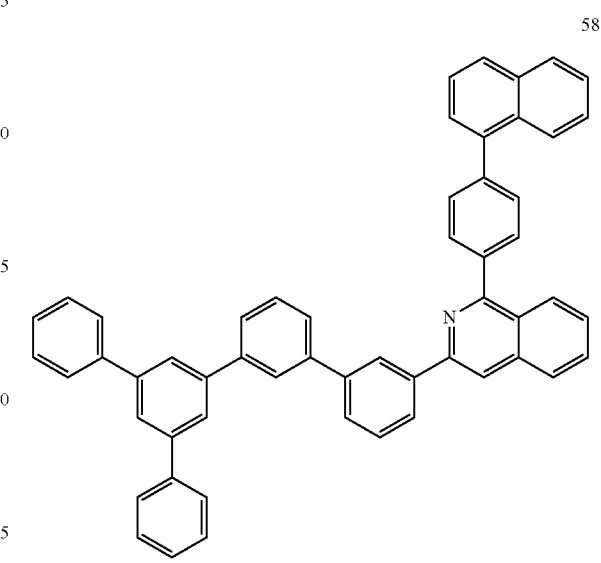
58
59
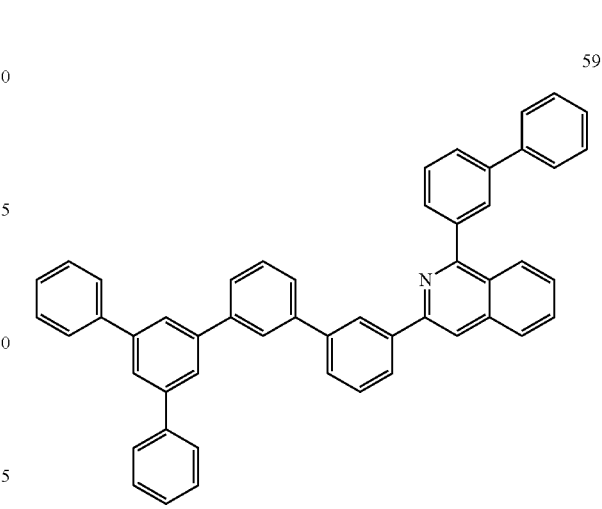

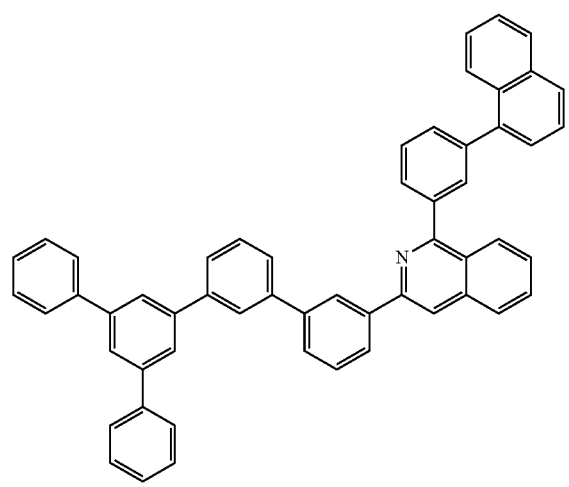
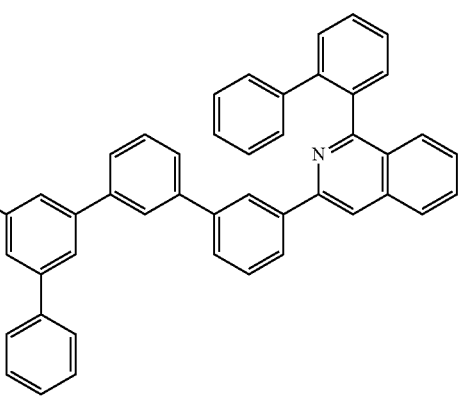
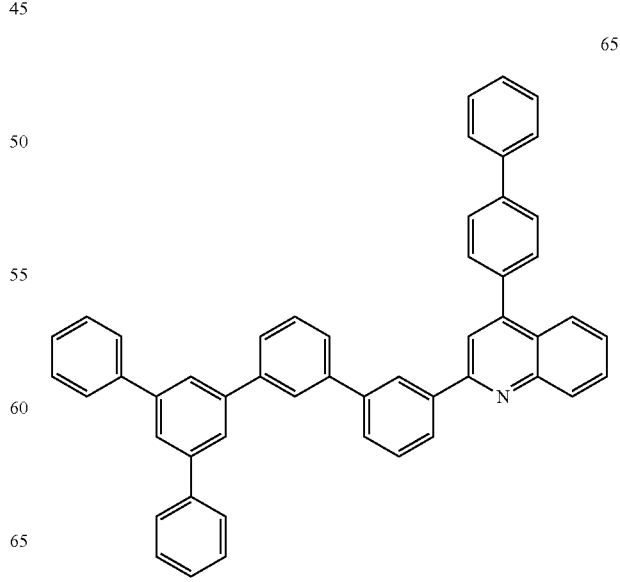

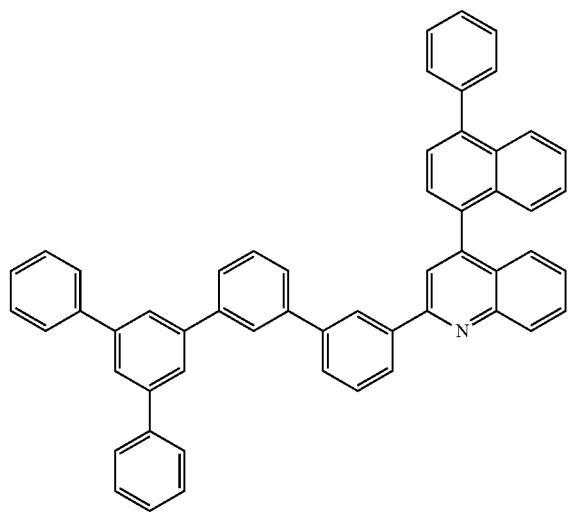
66
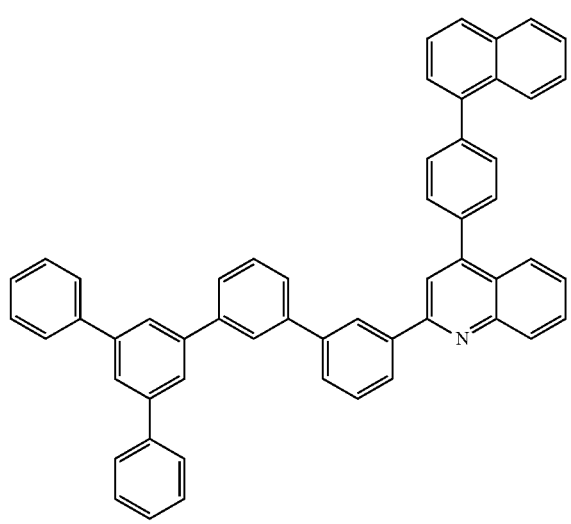
67
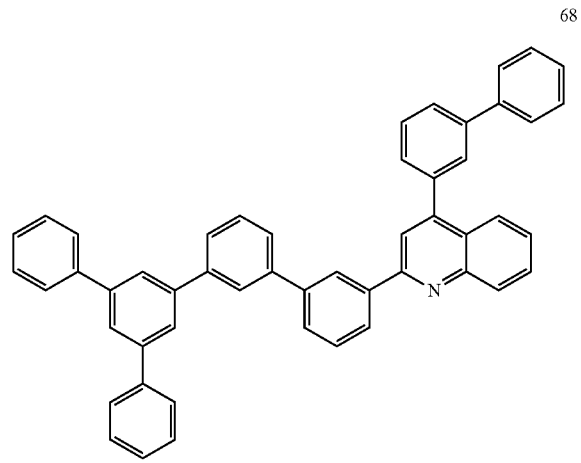
68
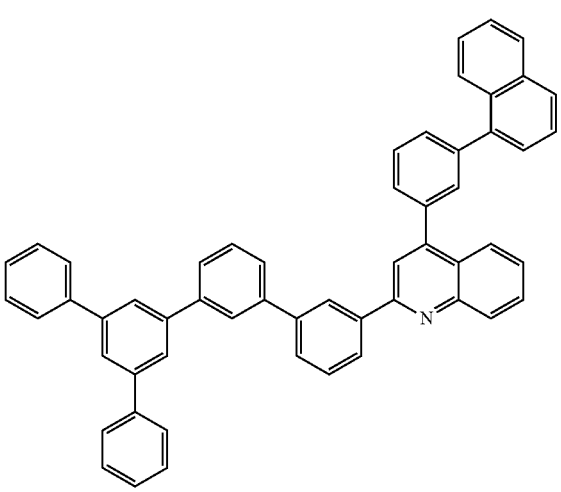
69
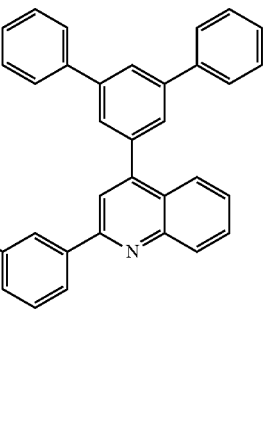
70
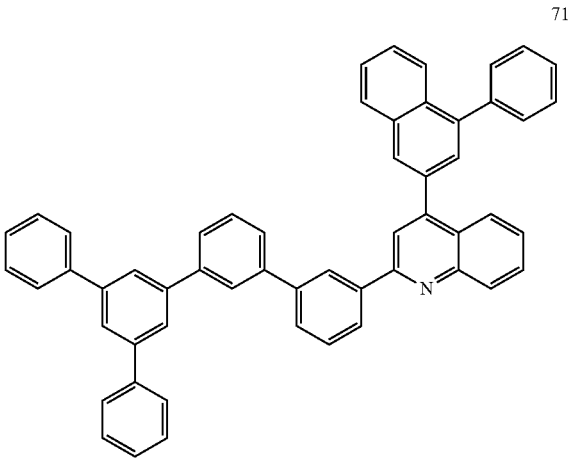
71

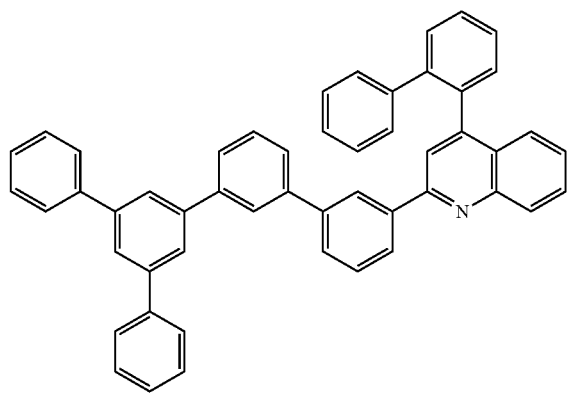
72
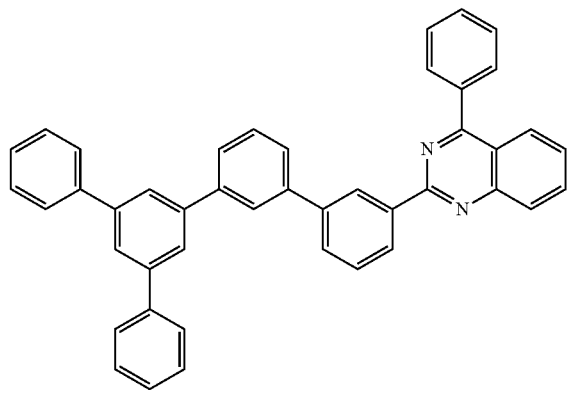
73
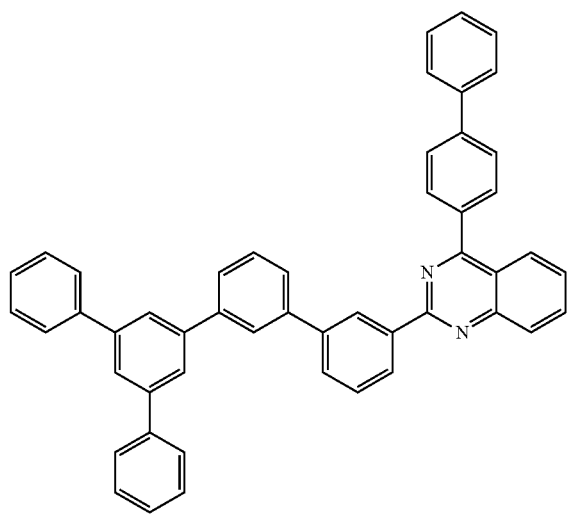
74
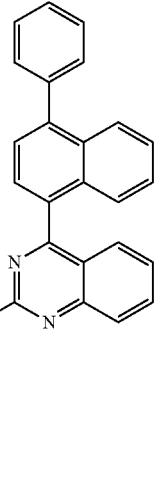
75
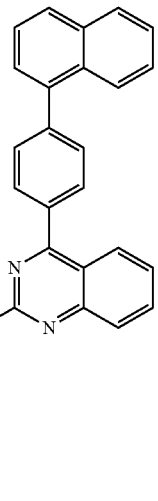
76
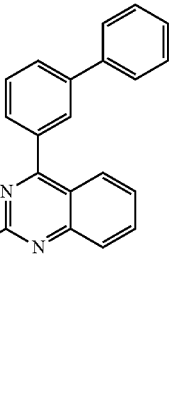
77

78
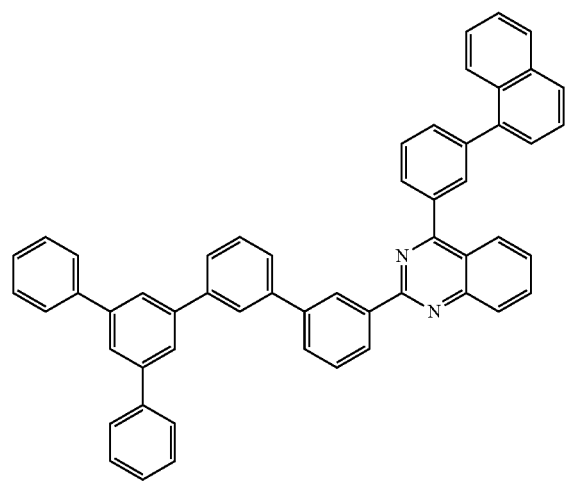
79
81
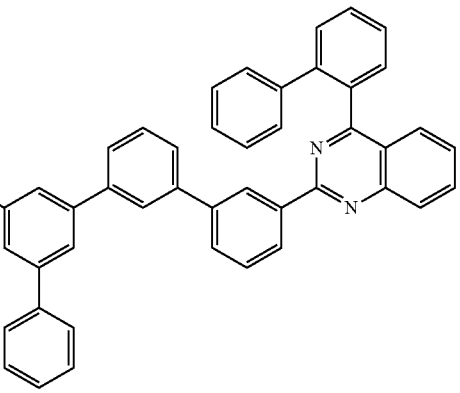
82
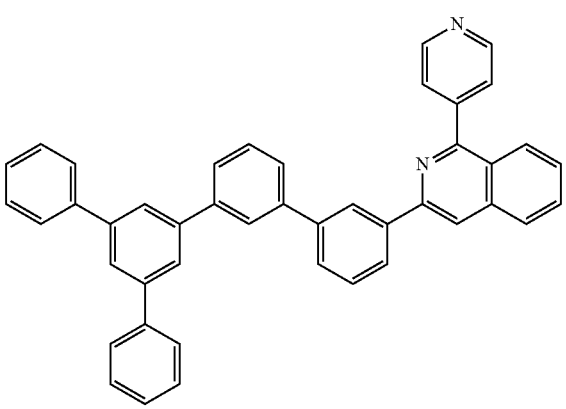
80
83
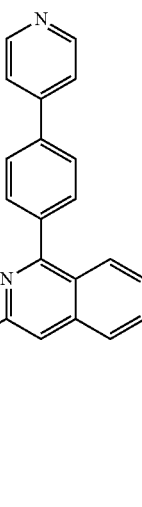

84
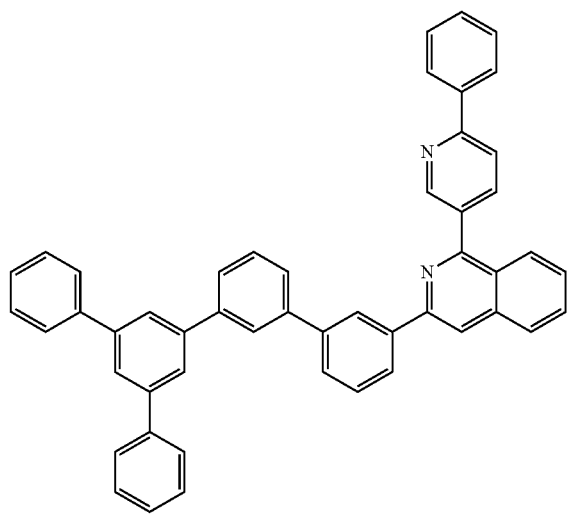
85
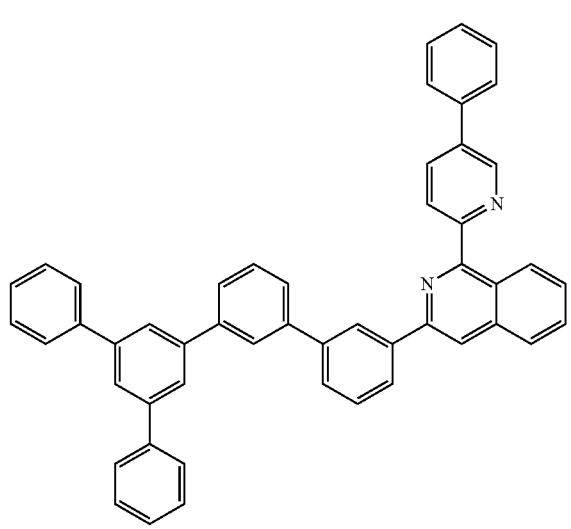
86
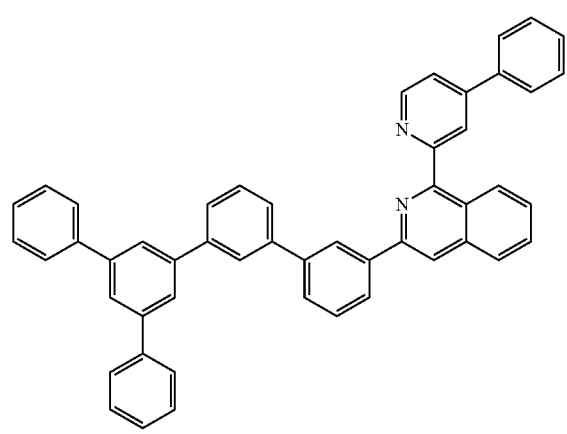
87
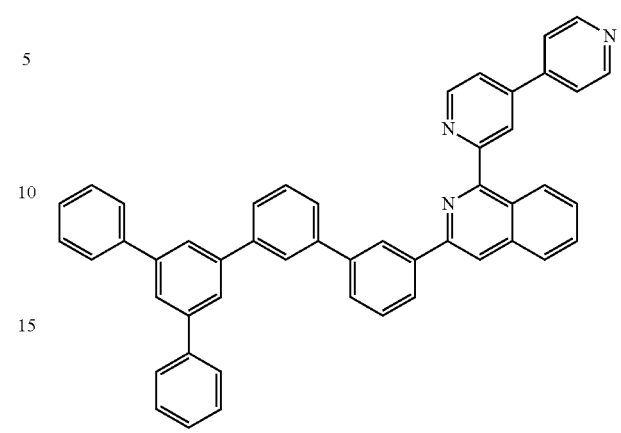
88
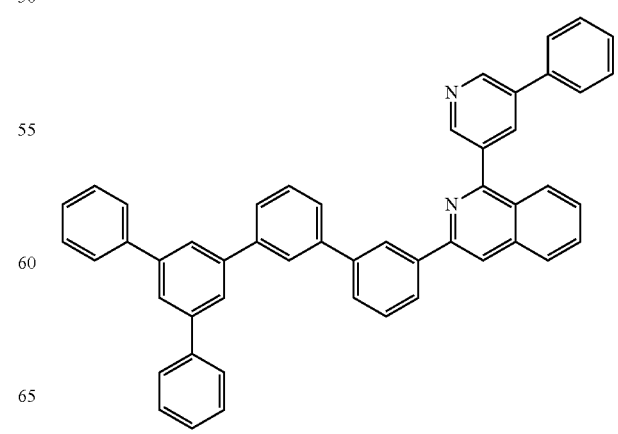
89

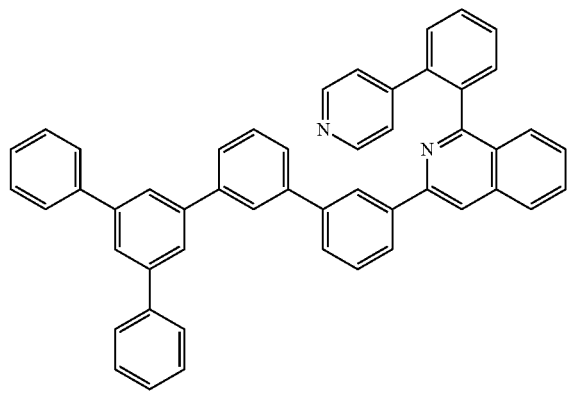
90
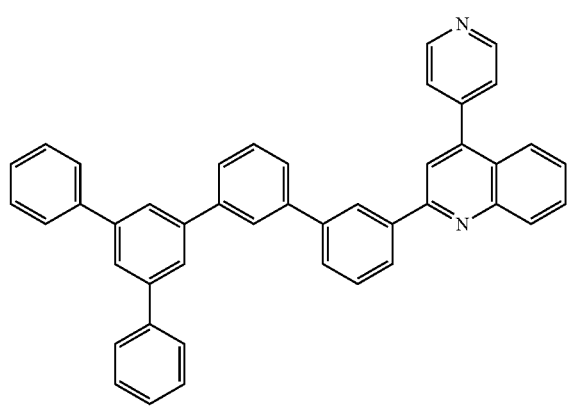
91
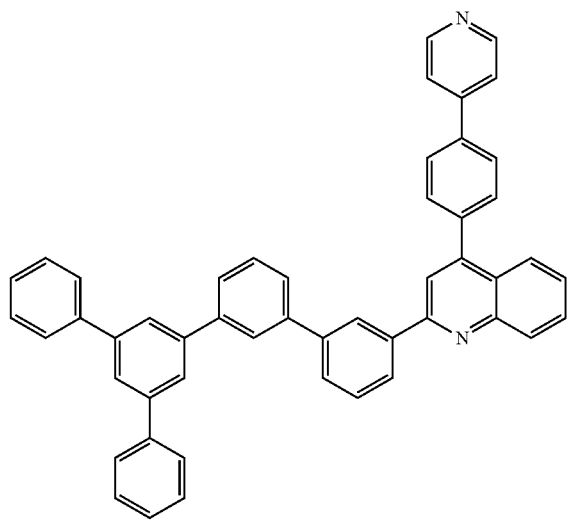
92
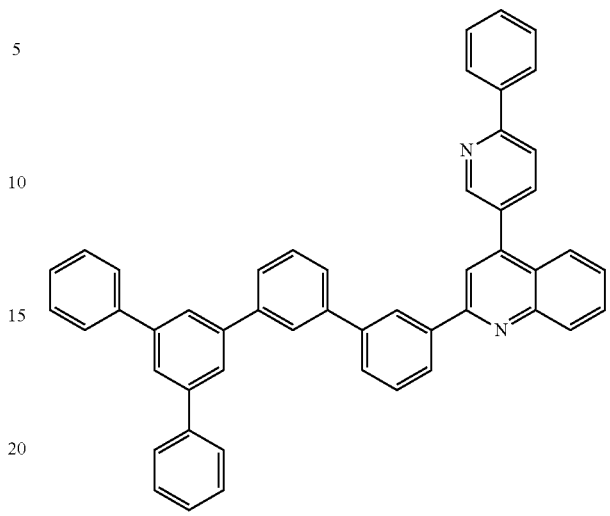
93
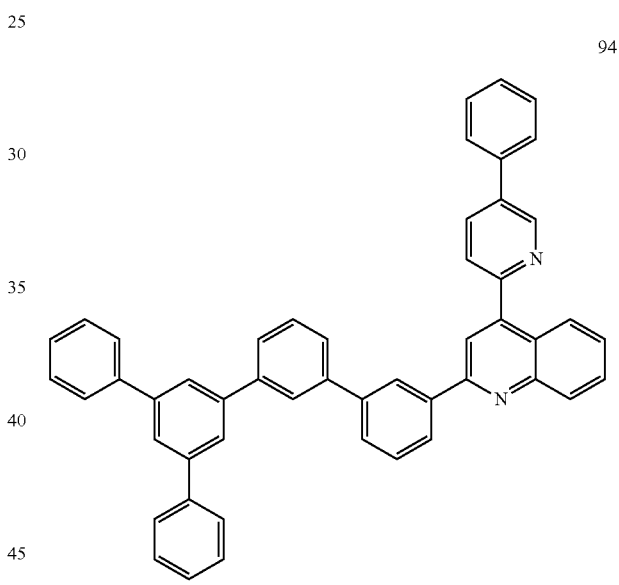
94
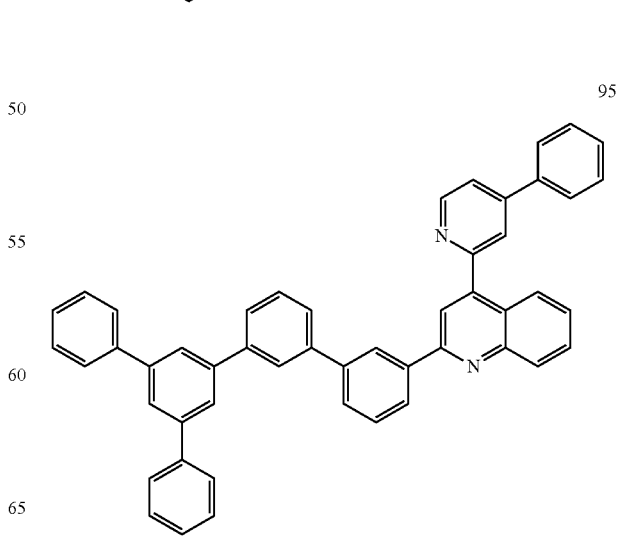
95

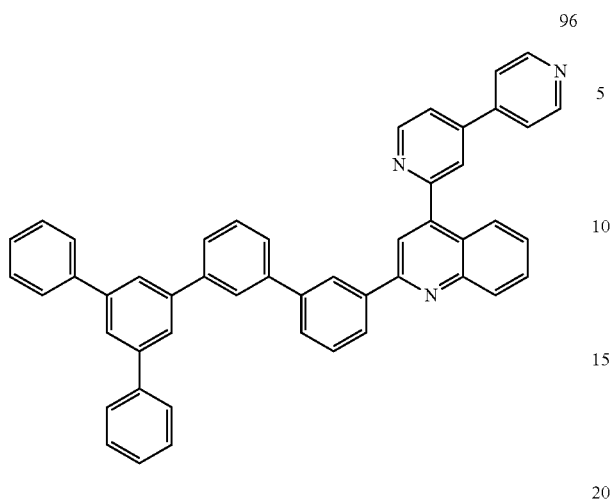
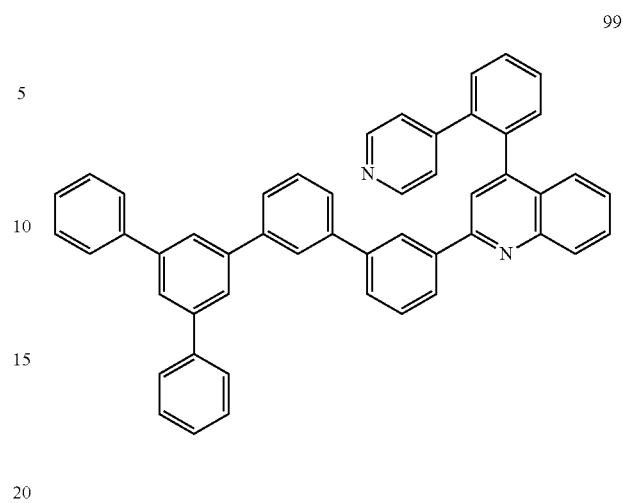
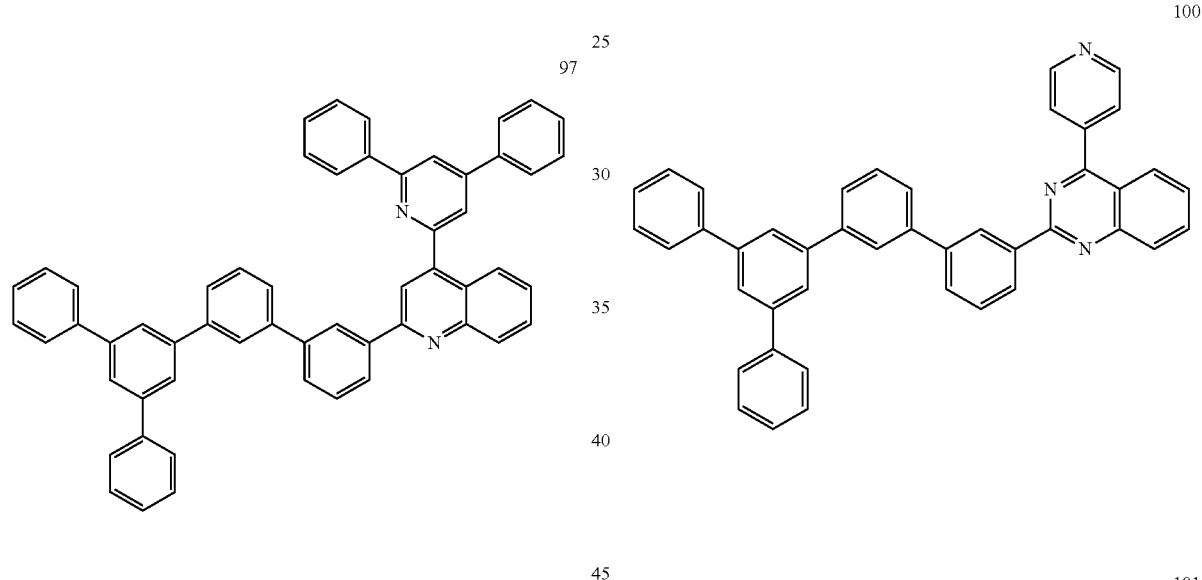
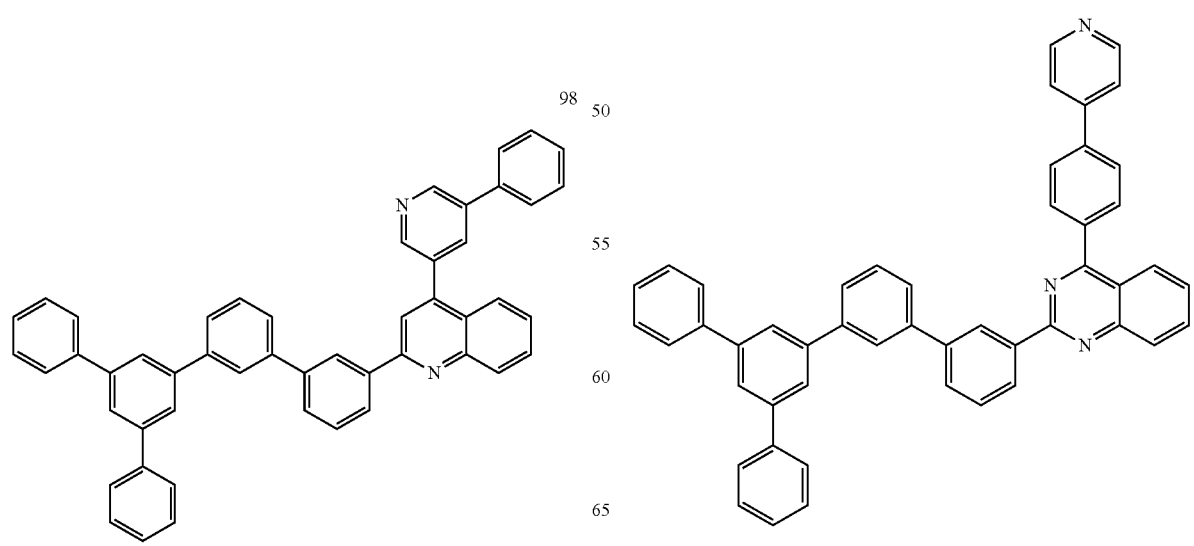

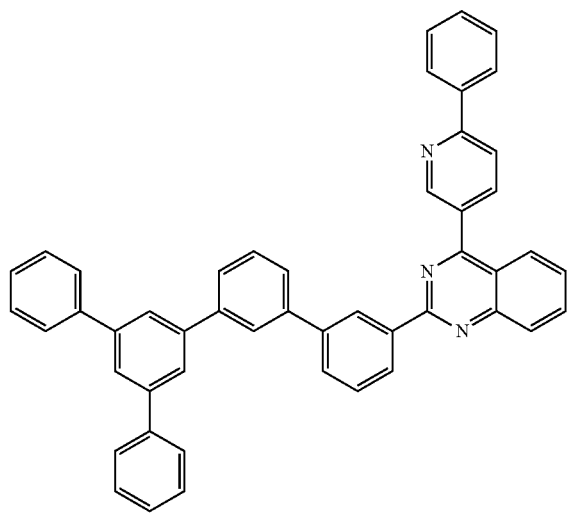
102
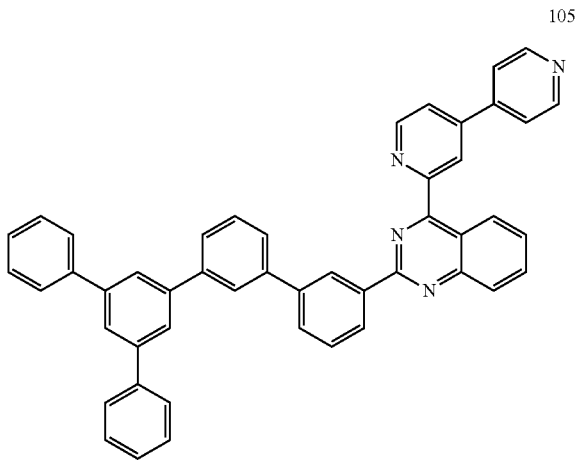
105
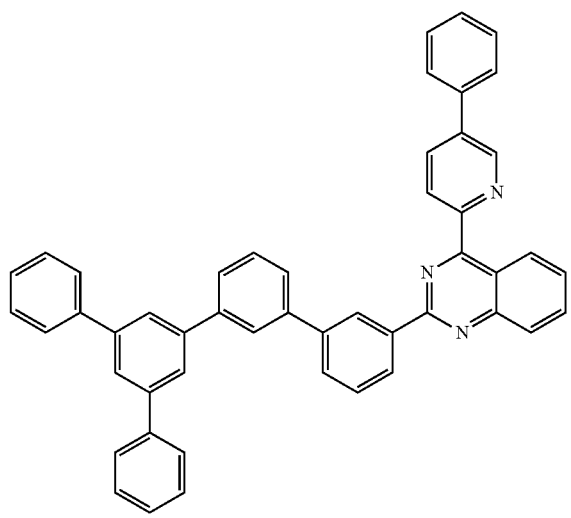
103
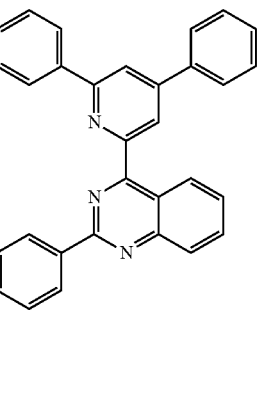
106
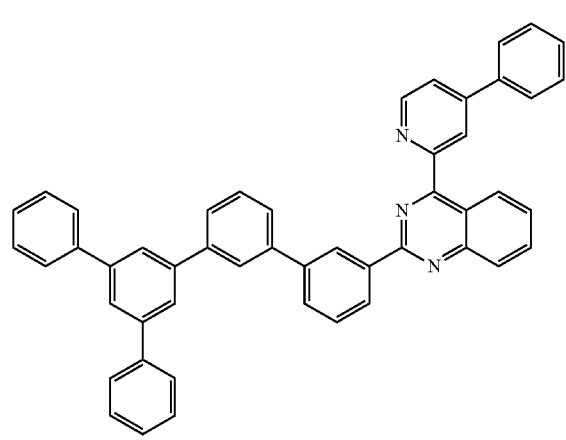
104
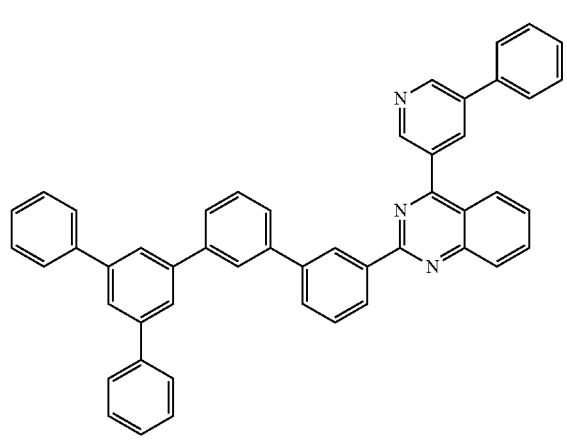
107

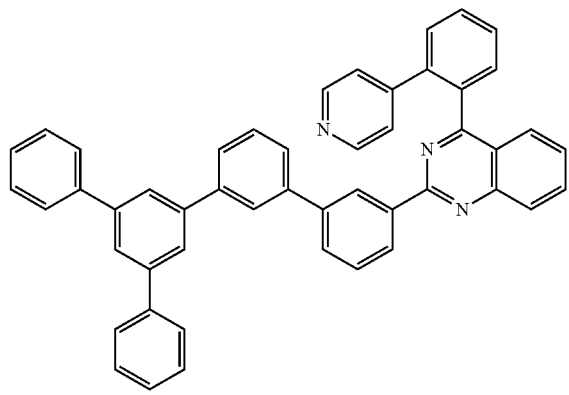
108
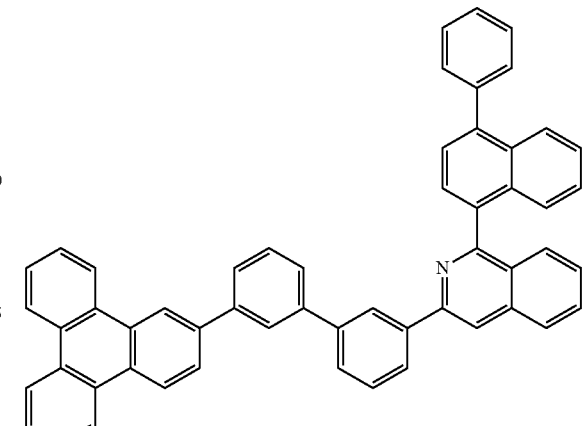
111
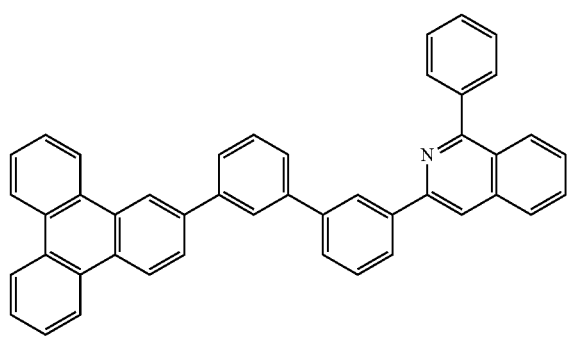
109
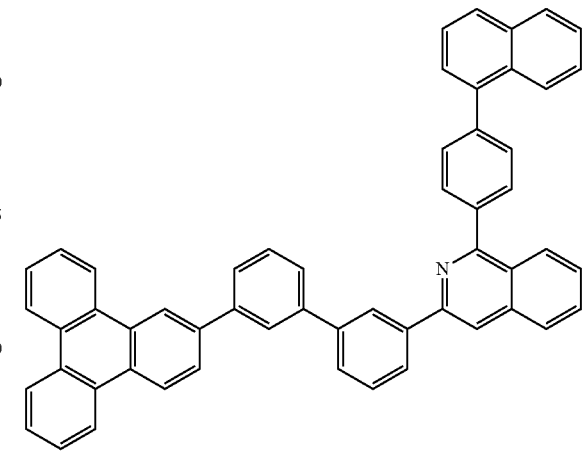
112
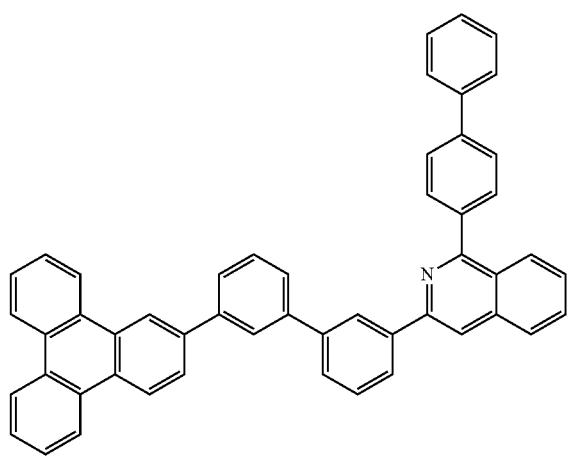
110

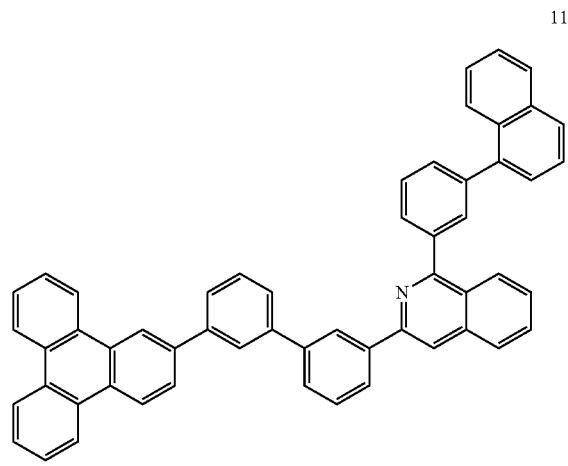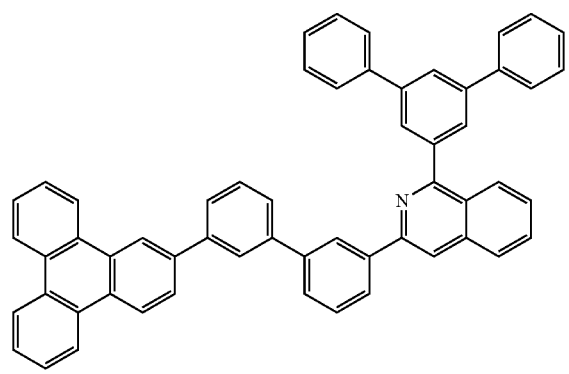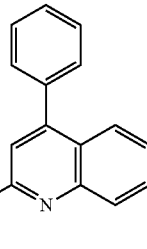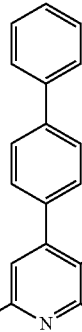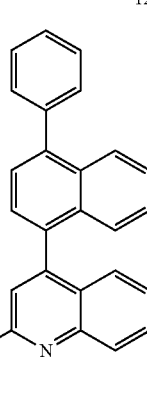

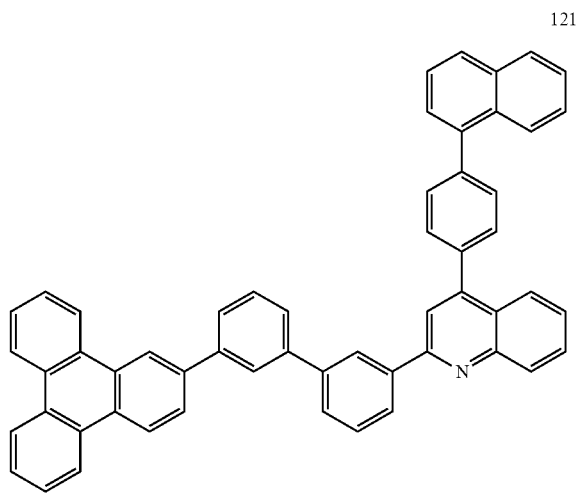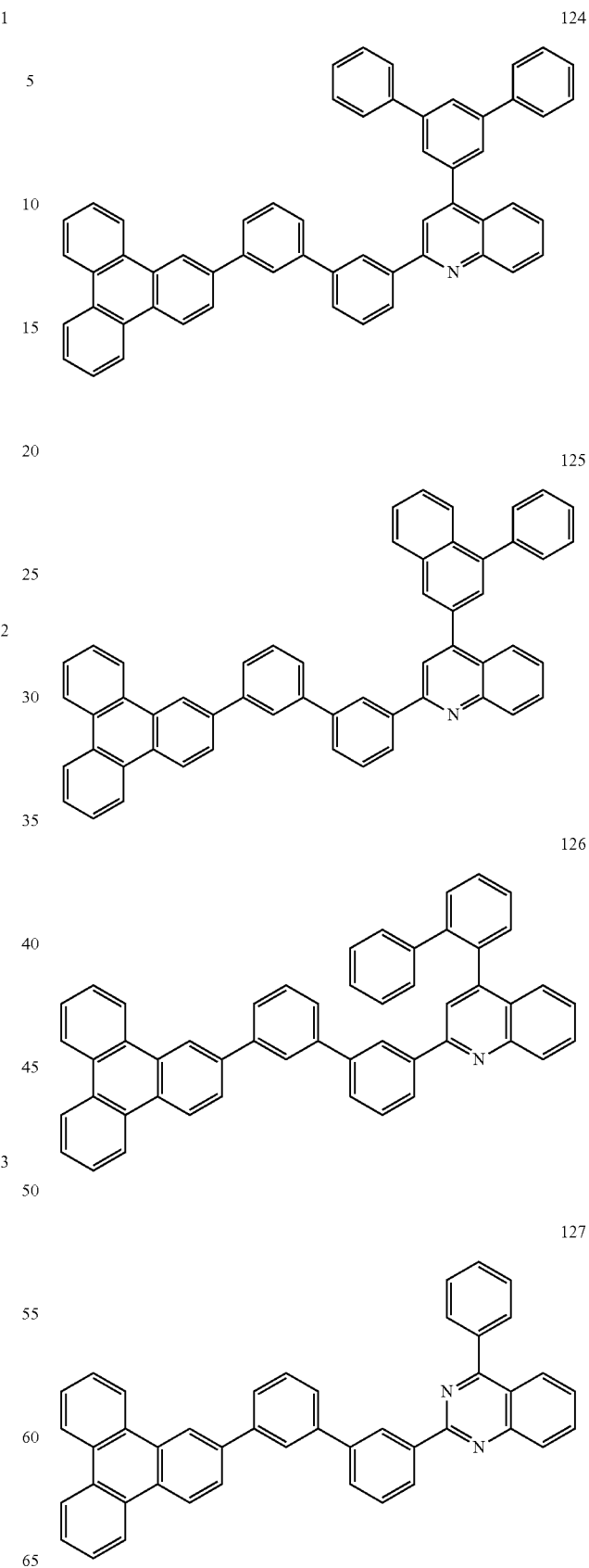

128
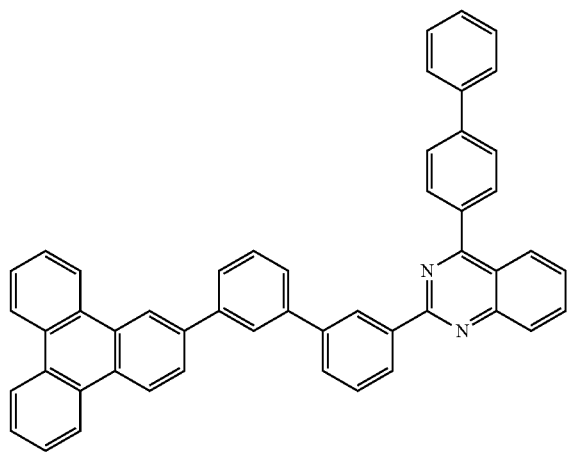
129
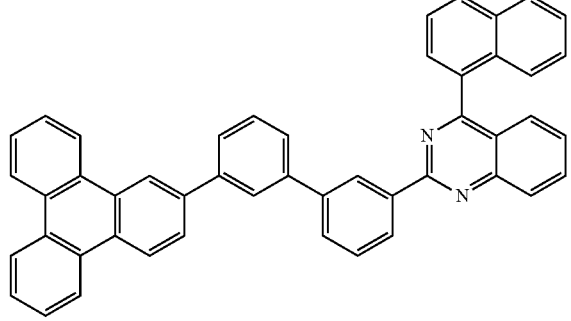
130
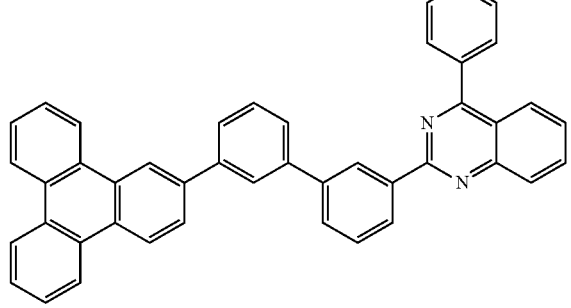
131
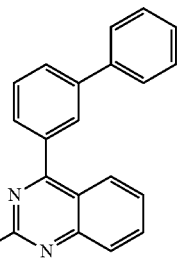
132
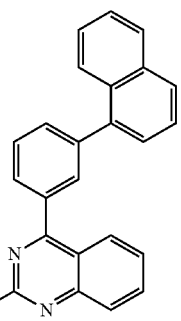
133
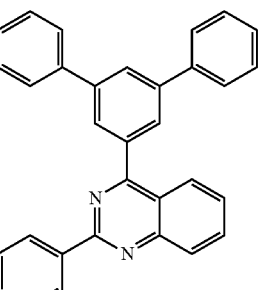
134
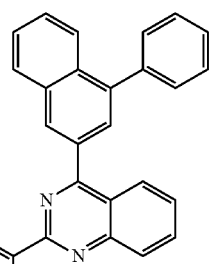

135
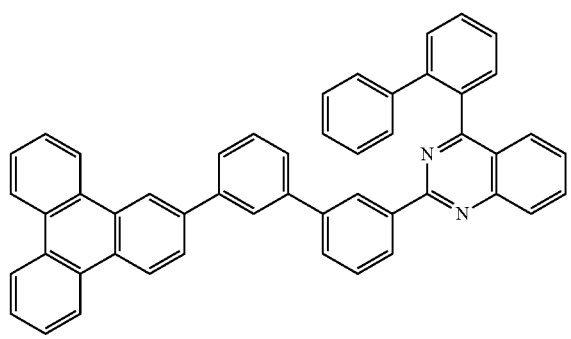
136
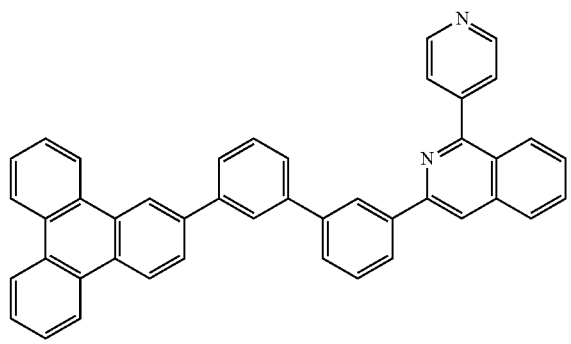
137
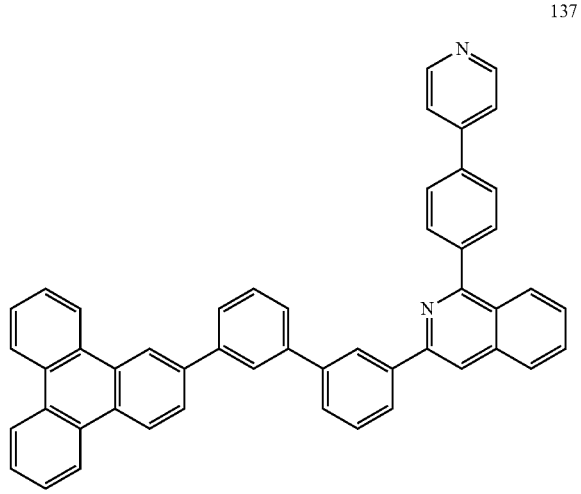
138
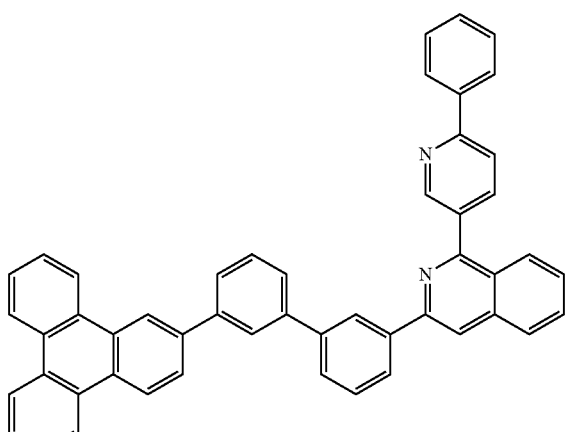
139
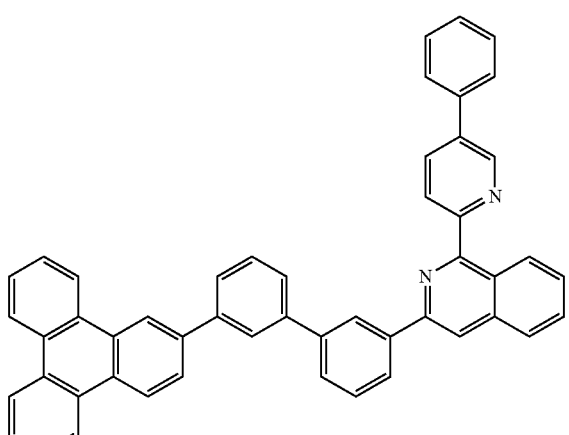
140
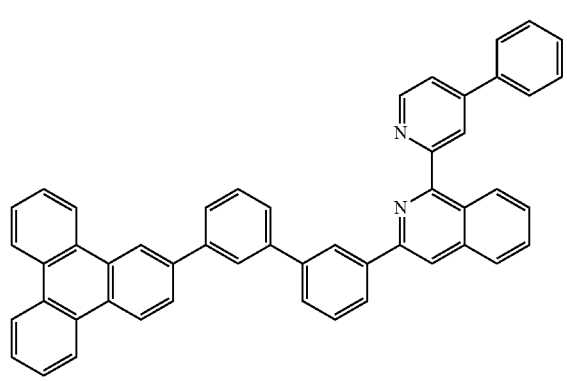

141
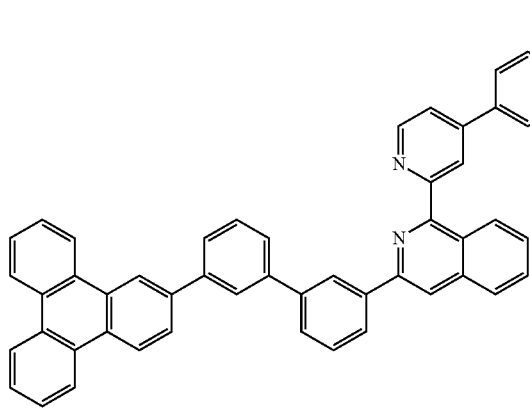
142
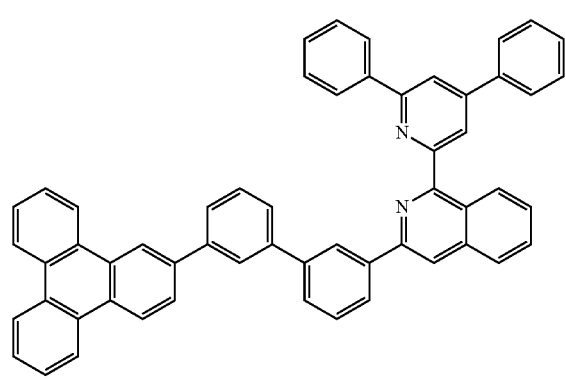
143
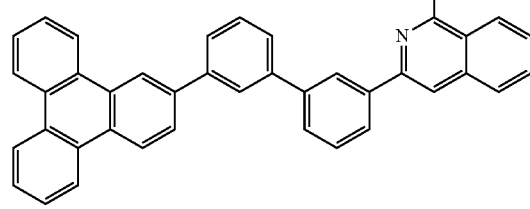
144
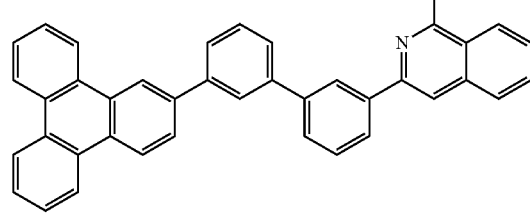
145
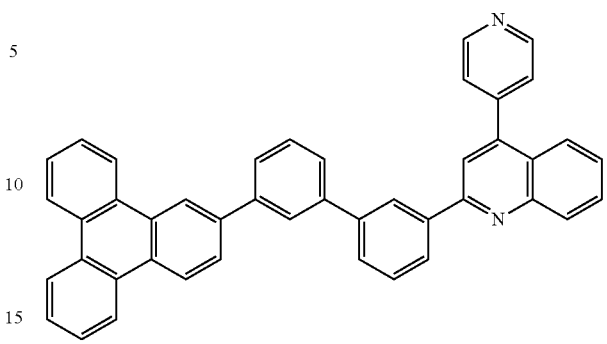
146
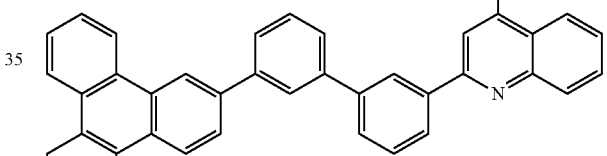
147
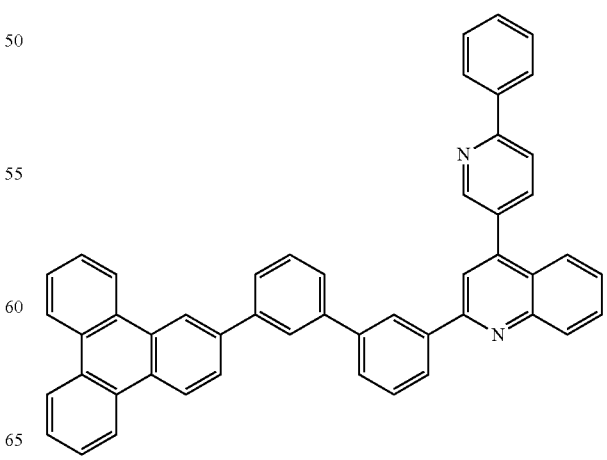

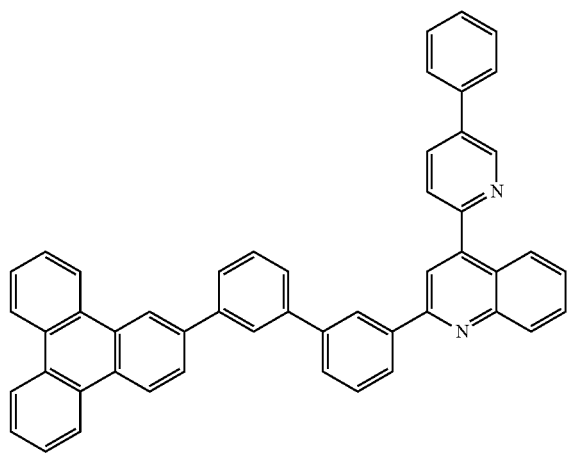
148
149
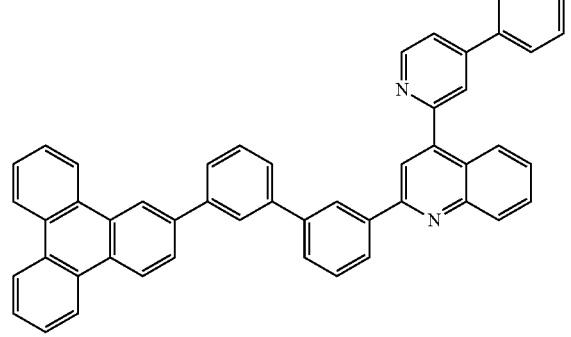
150
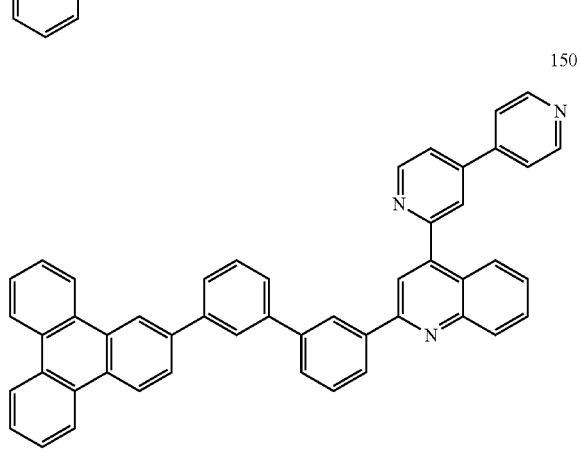
151
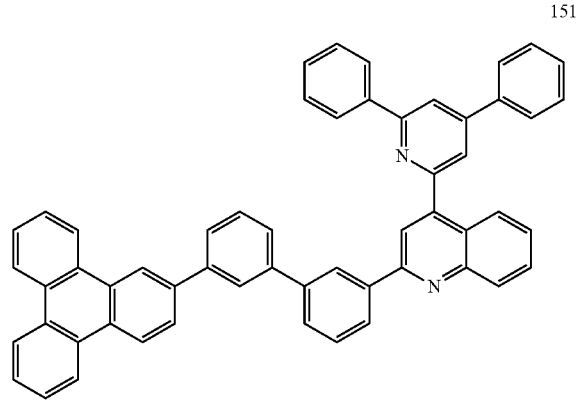
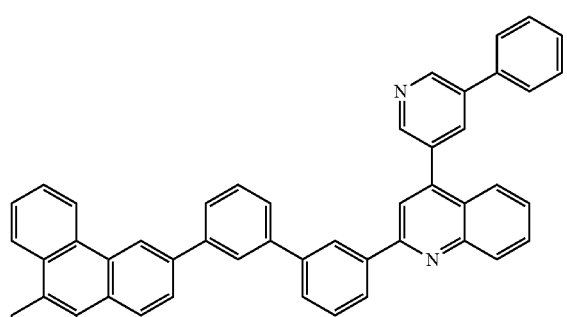
152
153
154
155

156
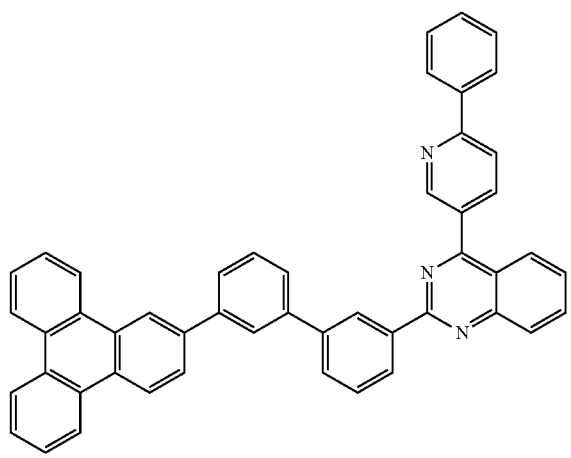
157
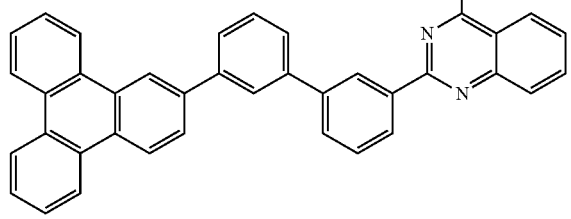
158
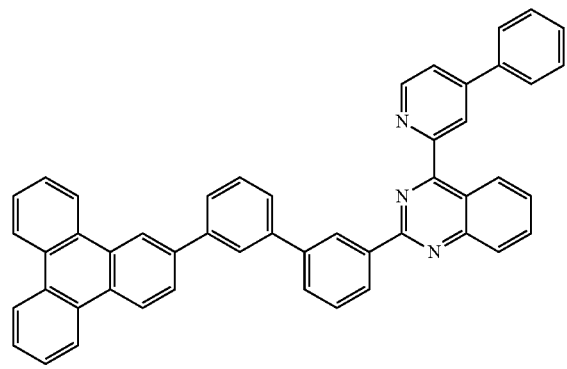
159
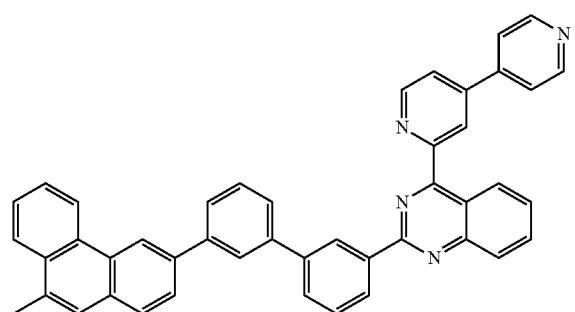
160
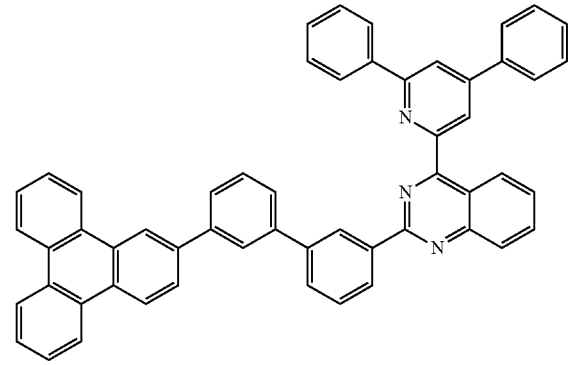
161
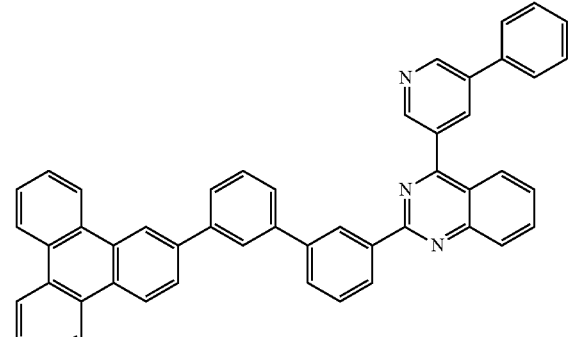
162
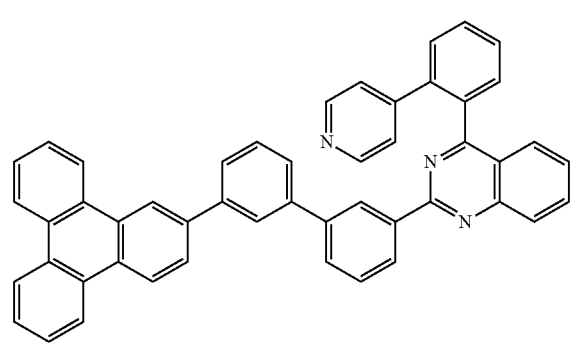

163
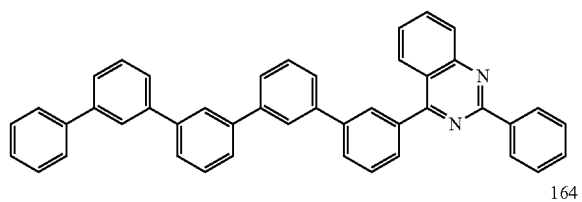
164
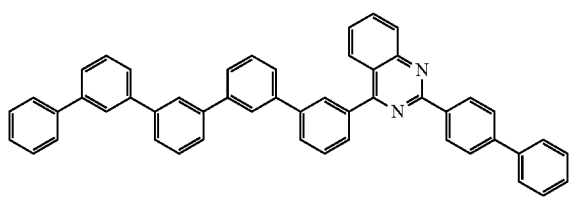
165
166

167
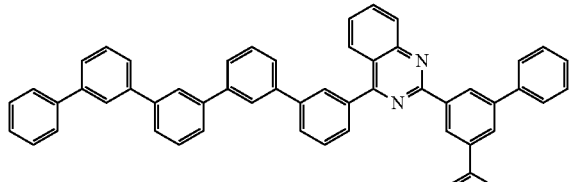
168
169
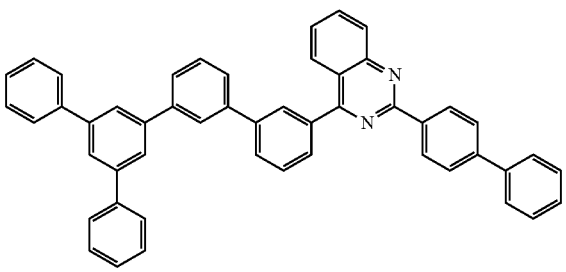
170
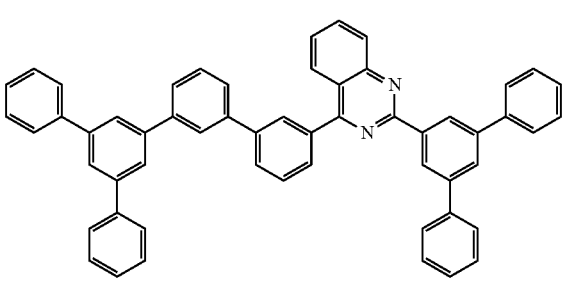
171
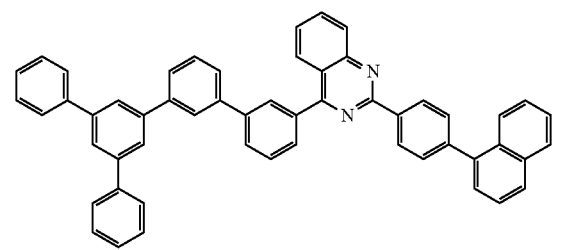
172
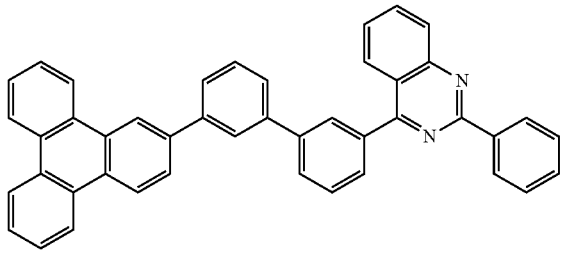
173
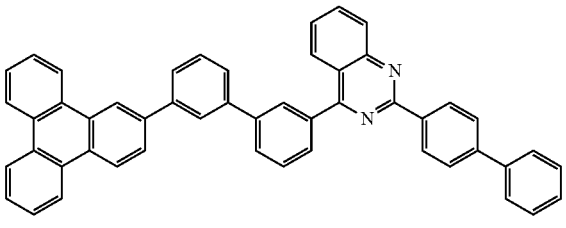
174
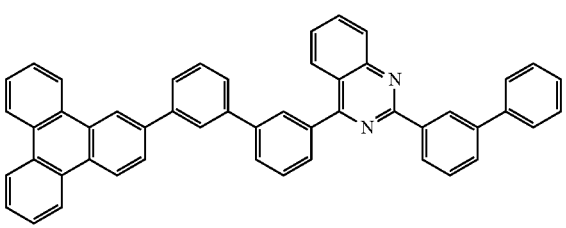

175
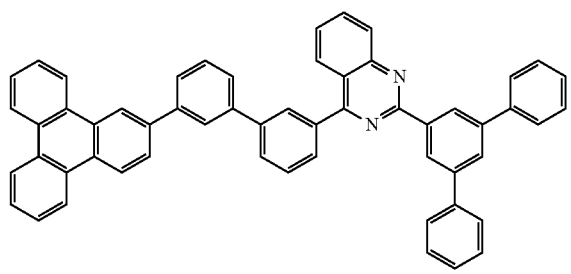
176
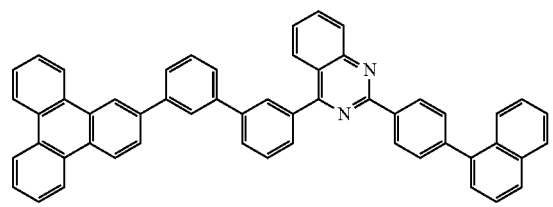
177
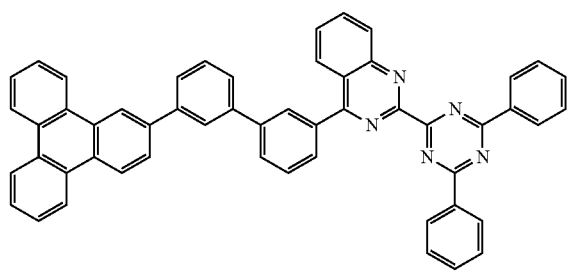
178
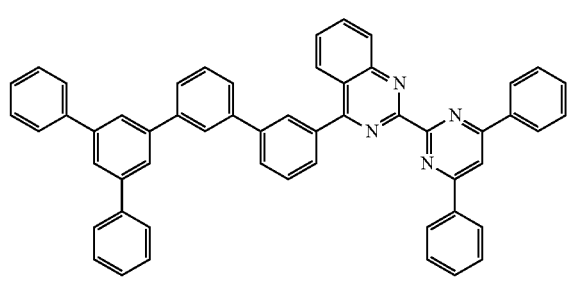
179
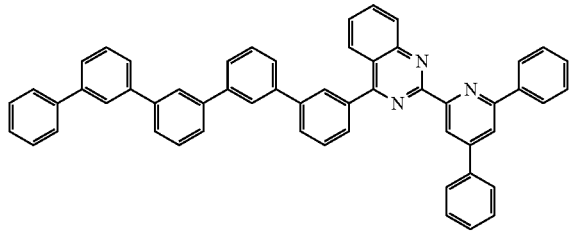
180
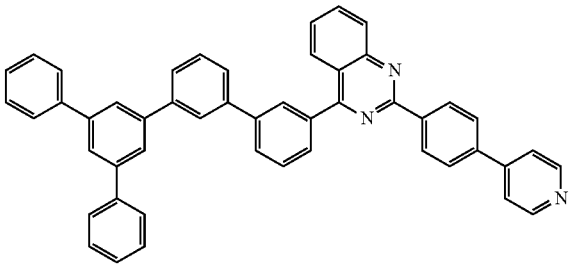
181
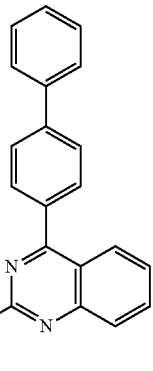
182
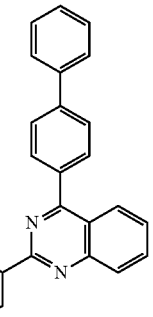
183
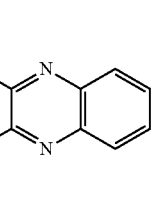
184

-continued

185
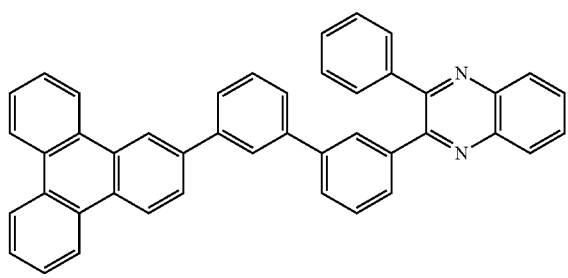

186
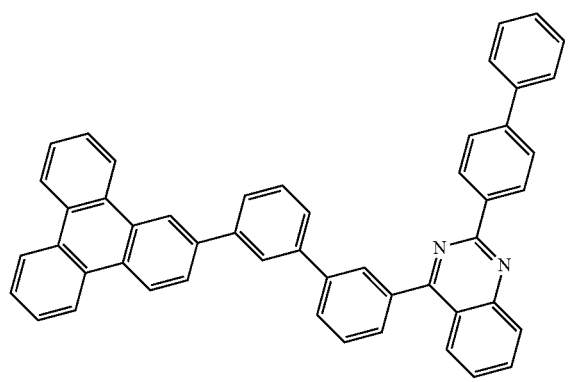

187
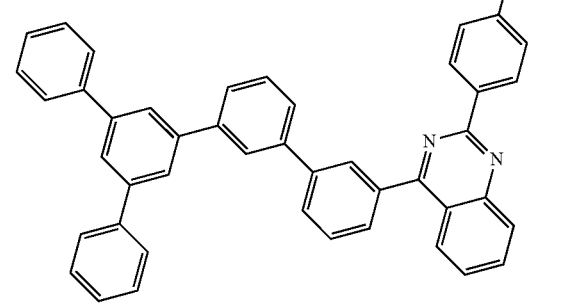

-continued

188
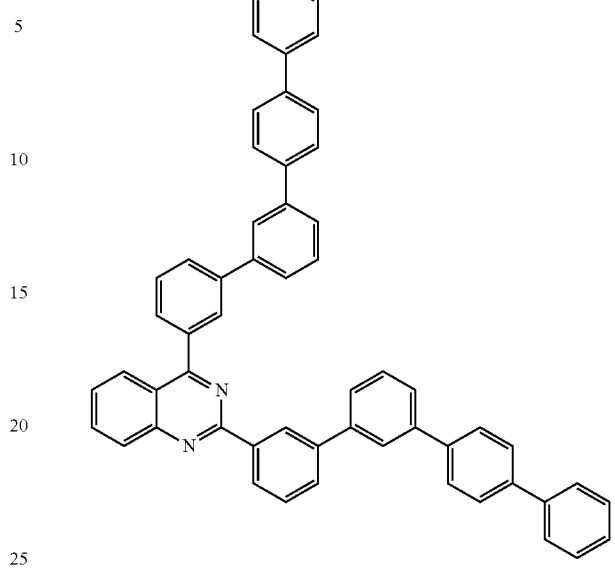

The organic compound may be applied to an organic optoelectric device.

The organic compound may be employed in an organic optoelectric device alone or with other organic compounds. When the organic compound is employed with other organic compound, it may be employed in a form of a composition.

Hereinafter, one example of a composition for an organic optoelectric device including the organic compound is described.

The composition for an organic optoelectric device may be, for example a composition of the organic compound and at at least one organic compound having a carbazole moiety. Hereinafter, the organic compound is referred to as 'a first organic compound' and the at least one organic compound having a carbazole moiety is referred to as 'a second organic compound'.

The second organic compound may be, for example a compound represented by Chemical Formula 11.

[Chemical Formula 11]

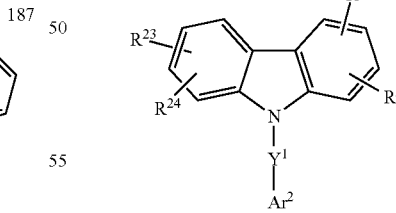

In Chemical Formula 11, $Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heterocyclic group, or a combination thereof, $Ar^2$ is a substituted or unsubstituted C6 to C30 aryl group, a substituted or unsubstituted C2 to C30 heterocyclic group, or a combination thereof, $R^{21}$ to $R^{24}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and at least one of $R^{21}$ to $R^{24}$ and $Ar^2$ includes a substituted or unsubstituted triphenylene group or a substituted or unsubstituted carbazole group.

The second organic compound represented by Chemical Formula 11 may be, for example represented by at least one of Chemical Formulae 11-I to 11-III:

[Chemical Formula 11-I]

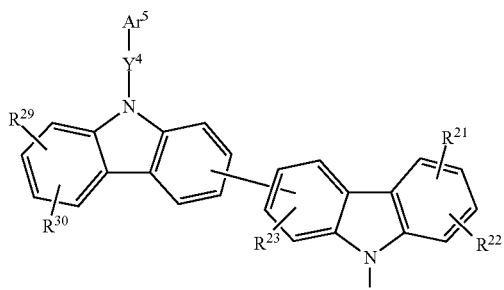

[Chemical Formula 11-II]

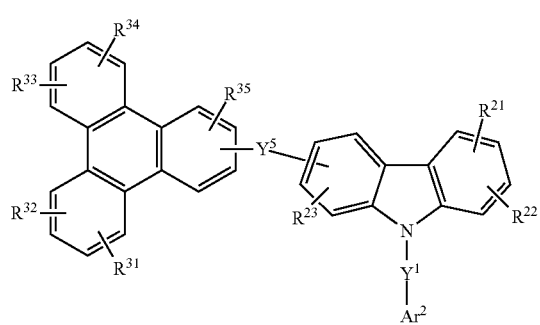

[Chemical Formula 11-III]

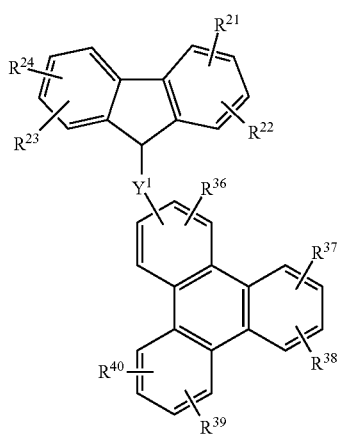

In Chemical Formulae 11-I to 11-III, $Y^1$, $Y^4$, and $Y^5$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heterocyclic group, or a combination thereof, $Ar^2$ and $Ar^5$ are independently a substituted or unsubstituted C6 to C30 aryl group, a substituted or unsubstituted C2 to C30 heterocyclic group, or a combination thereof, and $R^{21}$ to $R^{24}$ and $R^{29}$ to $R^{40}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof.

The second organic compound represented by Chemical Formula 11 may be, for example selected from compounds of Group 2, but is not limited thereto.

[Group 2]

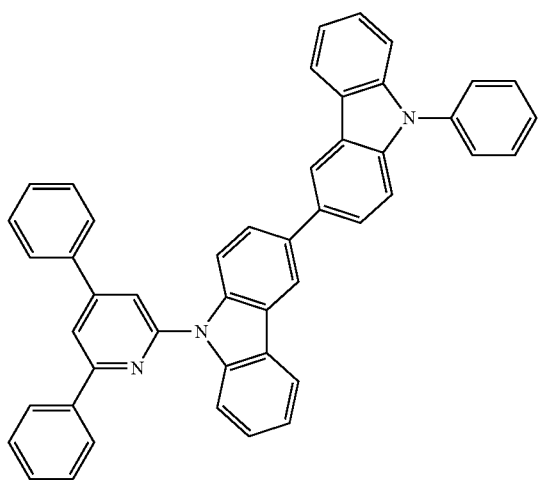

B-10

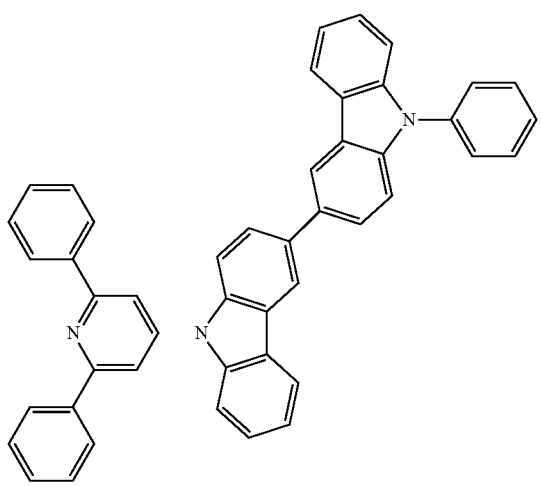

B-11

-continued
B-12
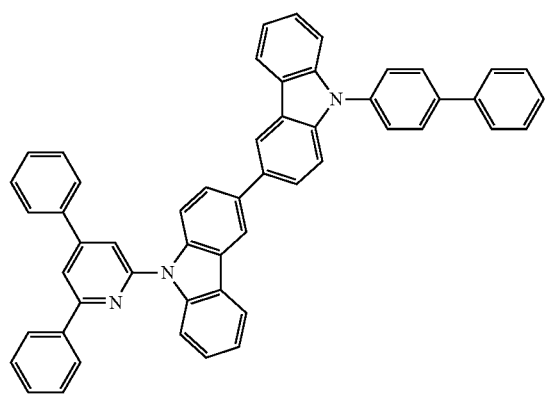
B-13
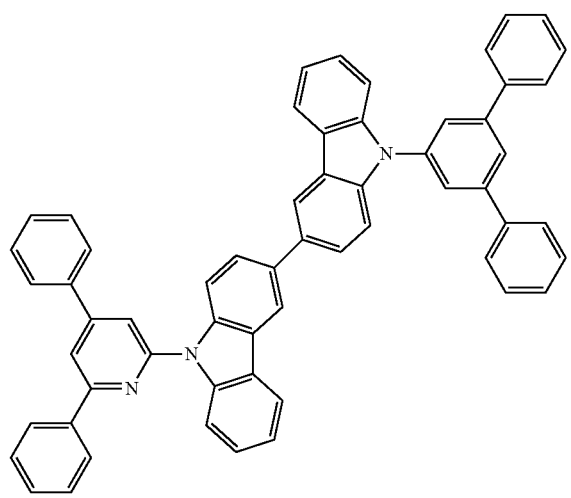
B-14
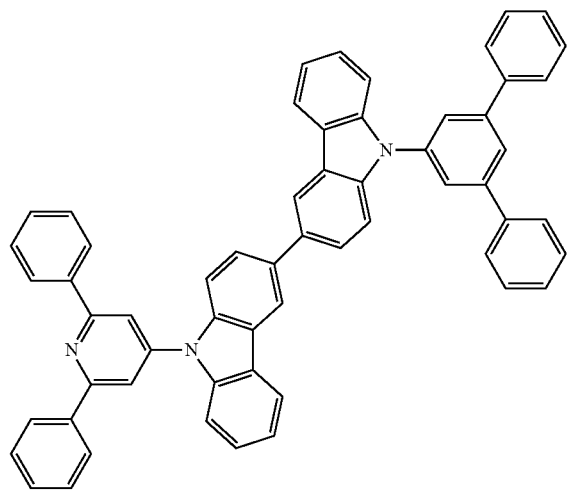
-continued
B-15
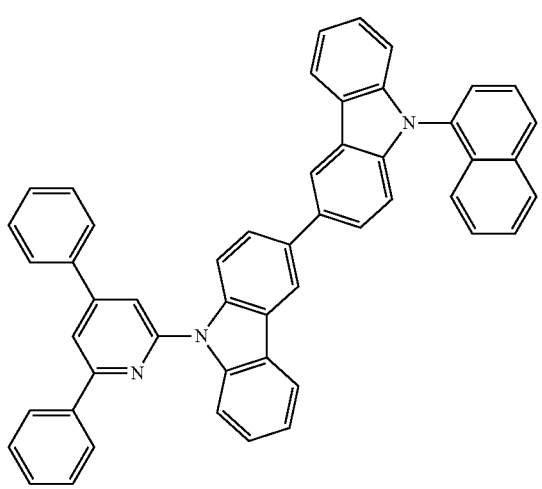
B-16
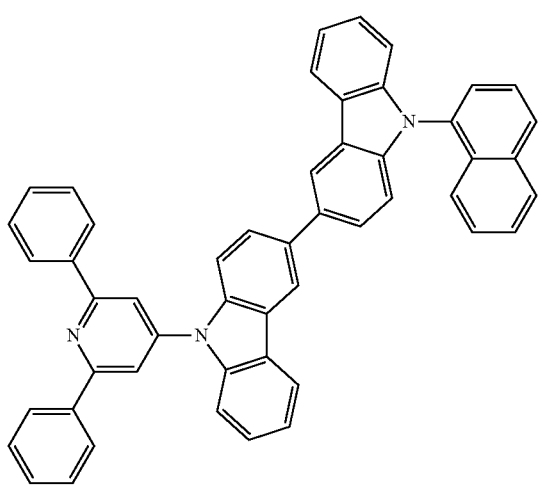
B-17
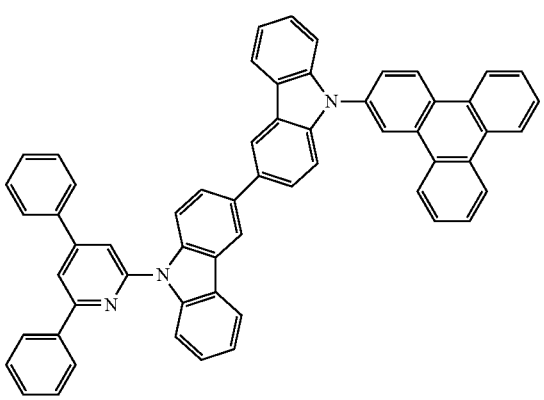

B-18
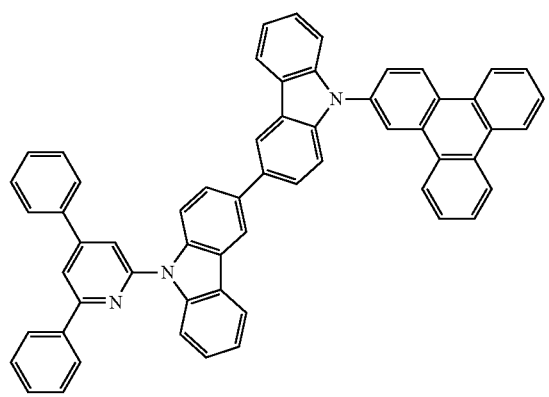
B-19
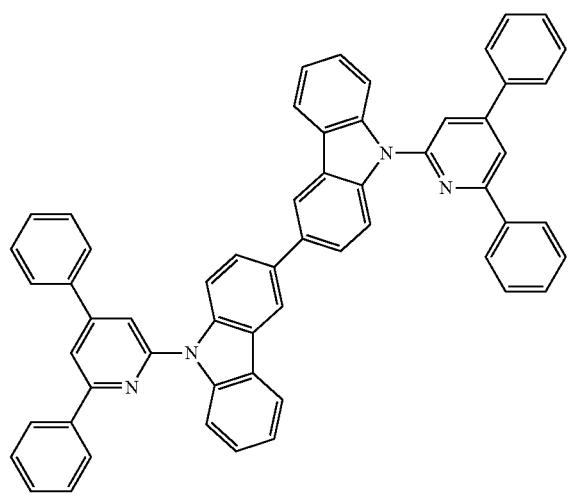
B-20
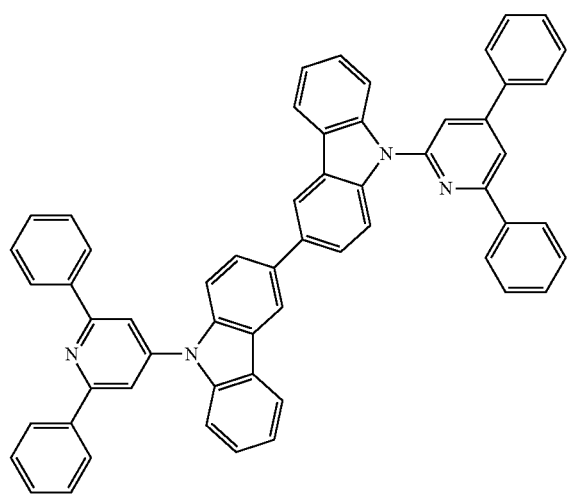
B-21
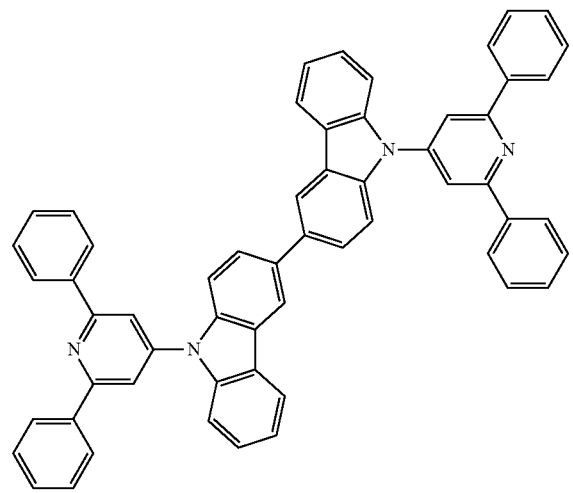
B-22
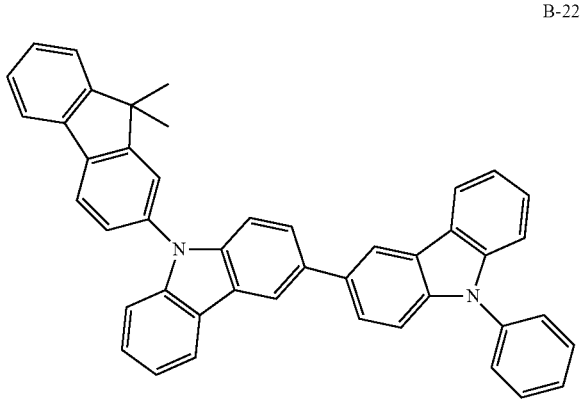
B-23
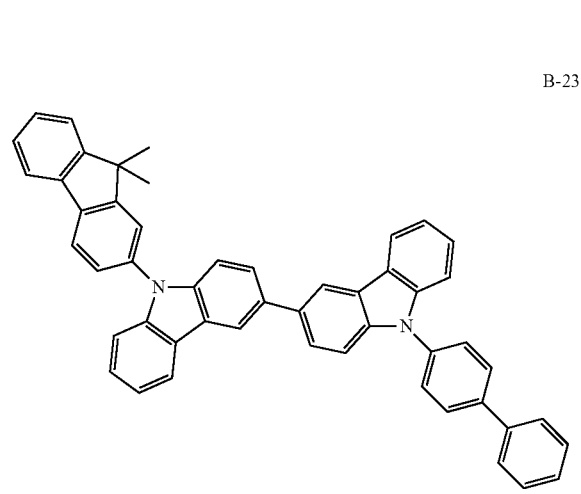

B-24
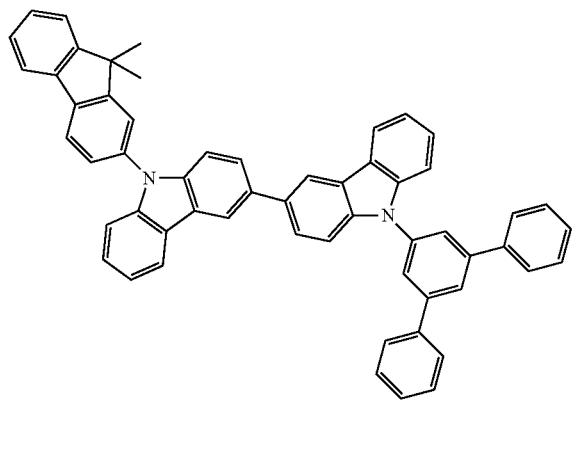
B-27
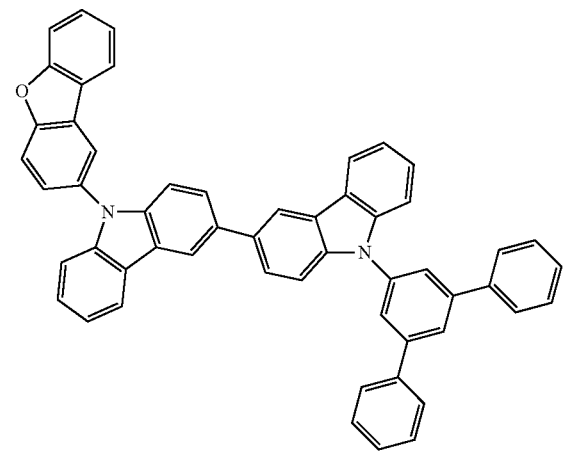
B-25
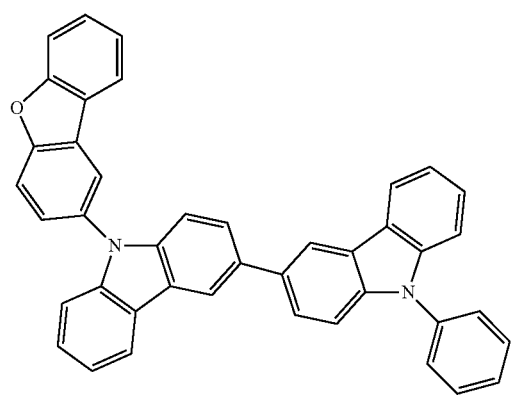
B-28
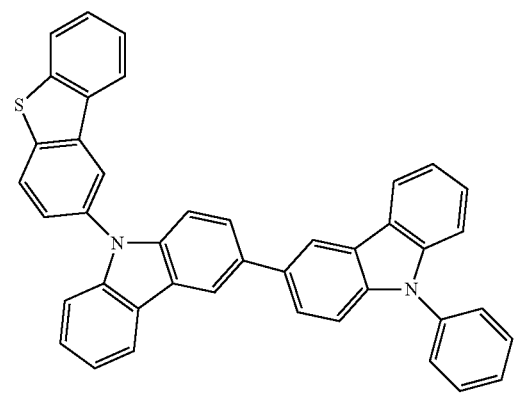
B-26
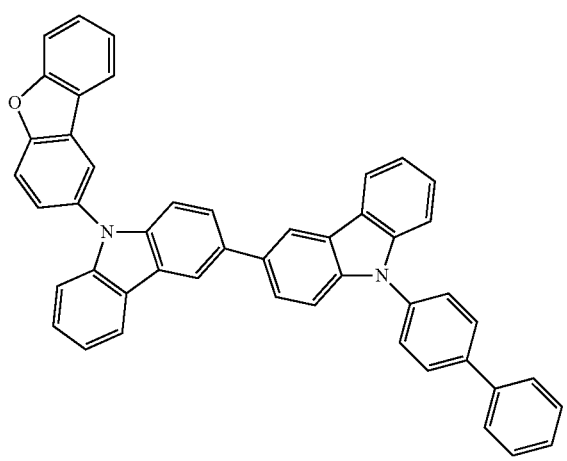
B-29
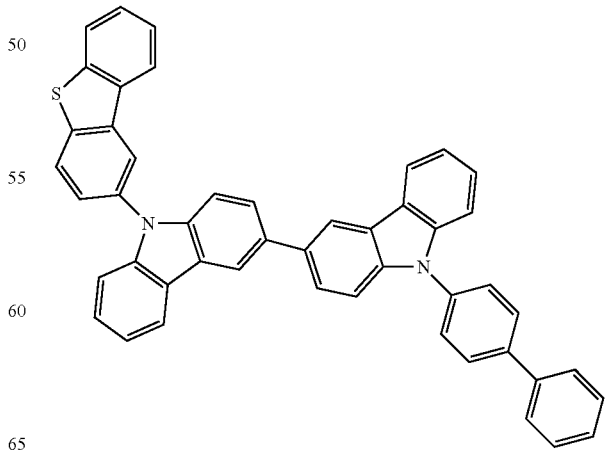

B-30
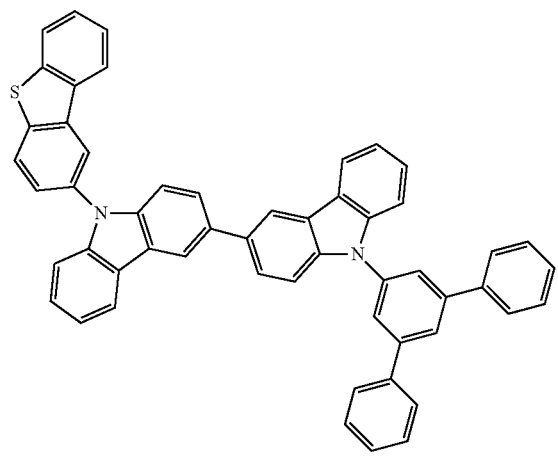
B-31
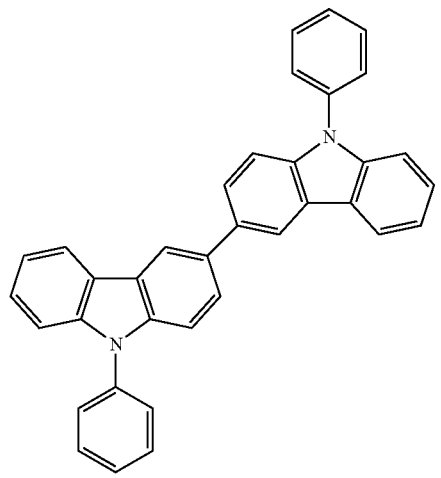
B-32
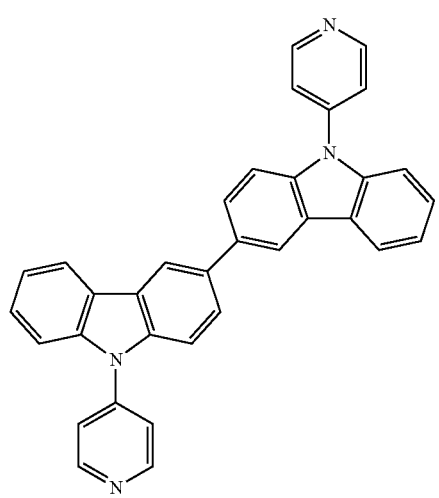
B-33
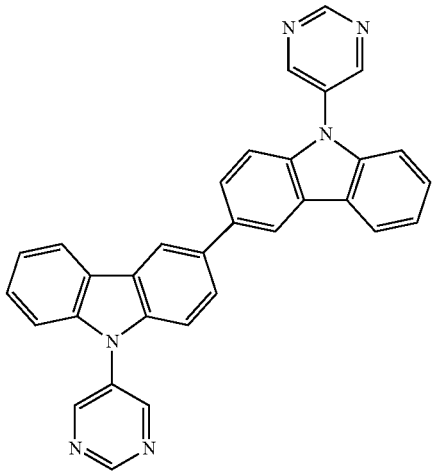
B-34
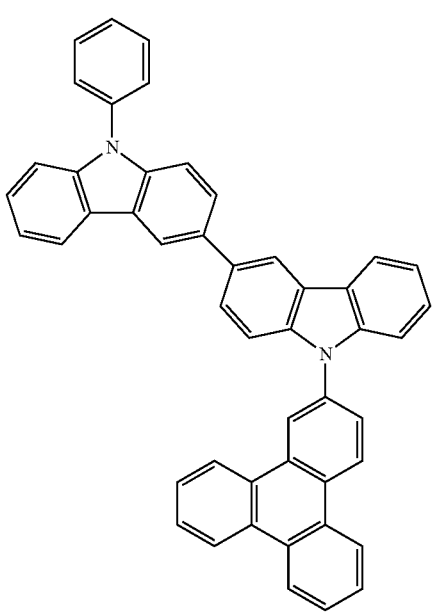

B-35
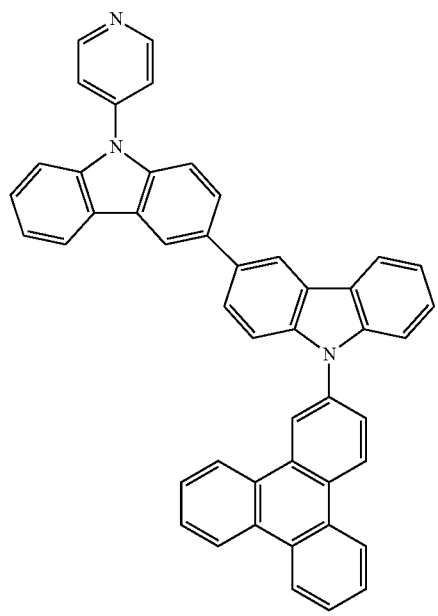
B-37
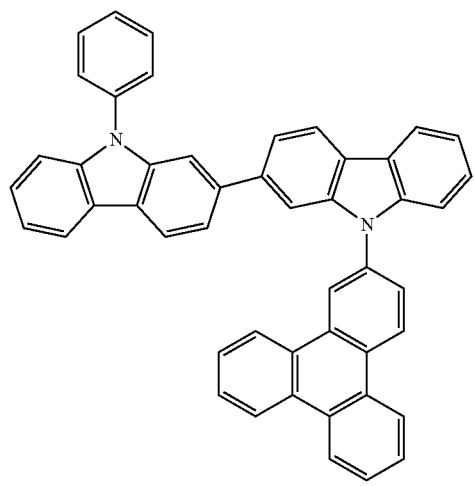
B-38
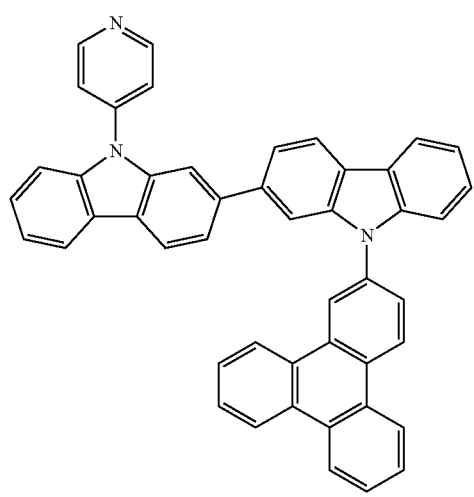
B-40
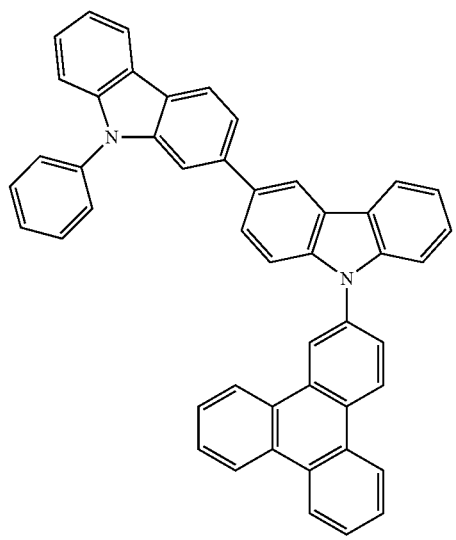
B-41
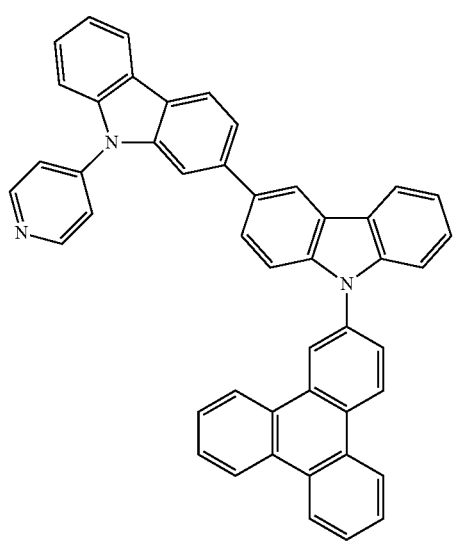
B-43
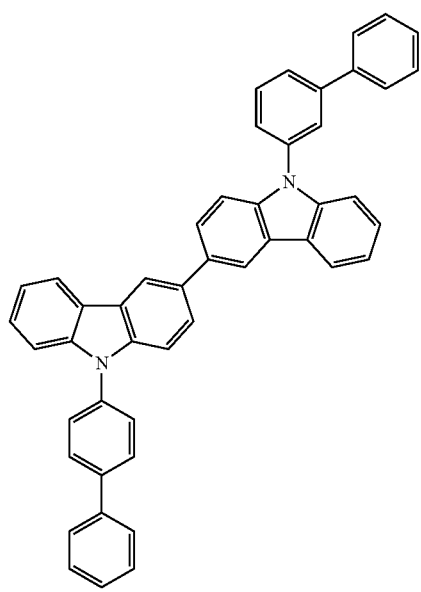

B-44
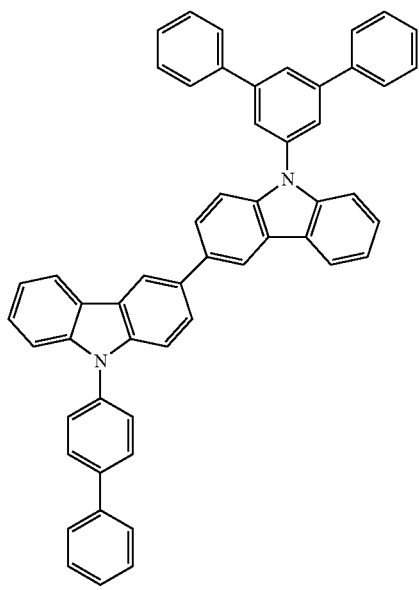
B-45
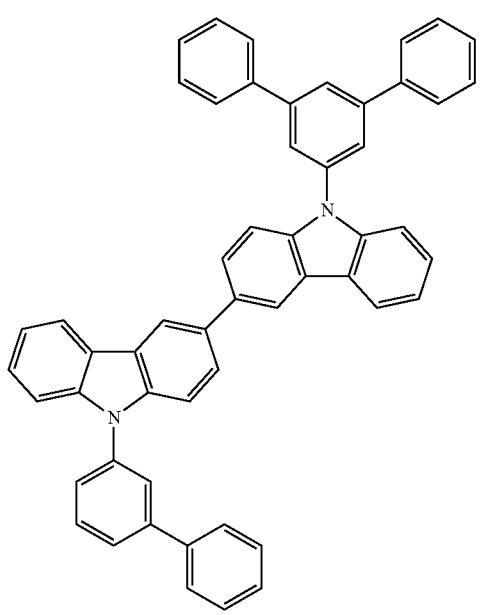
B-46
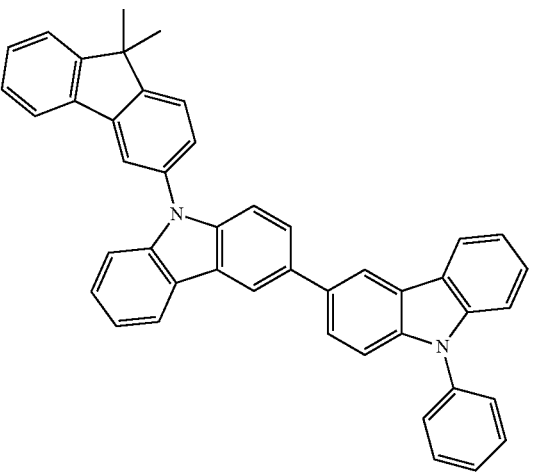
B-47
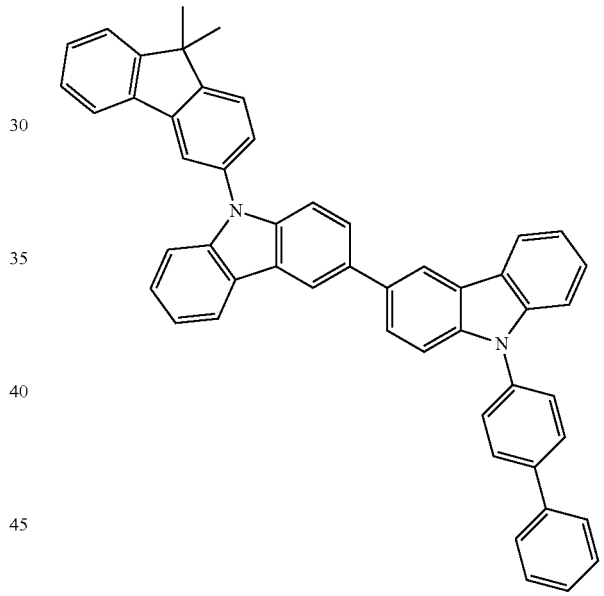
B-48
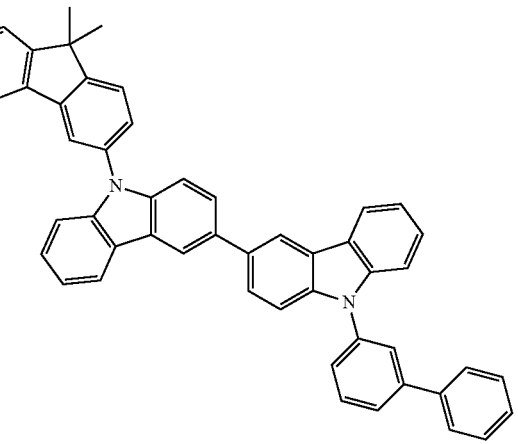

B-49
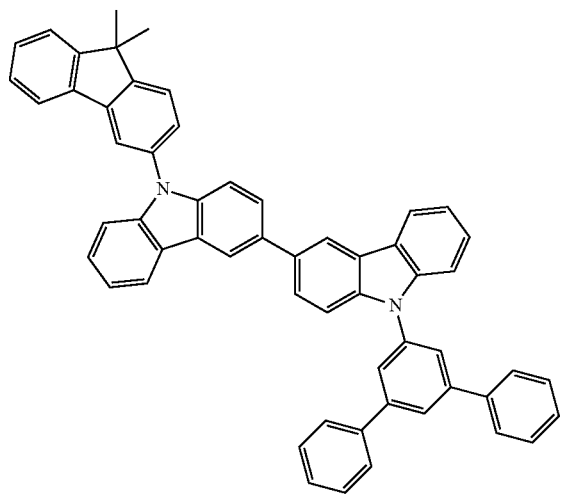
B-52
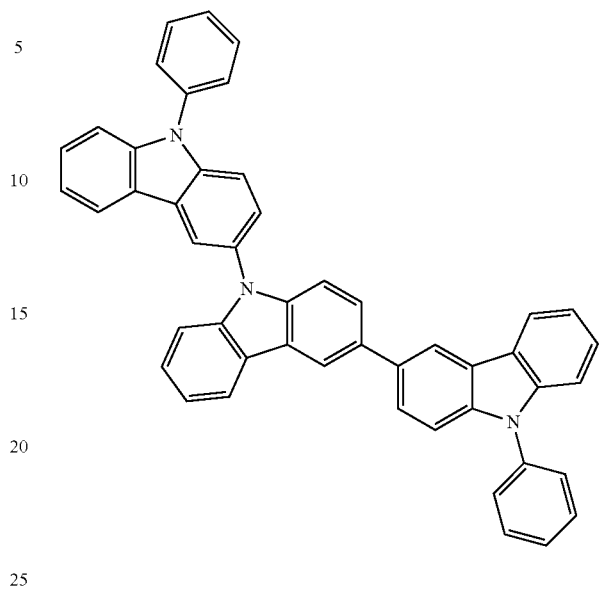
B-50
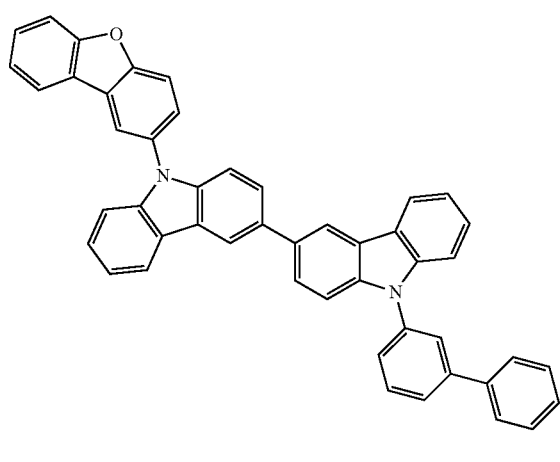
B-53
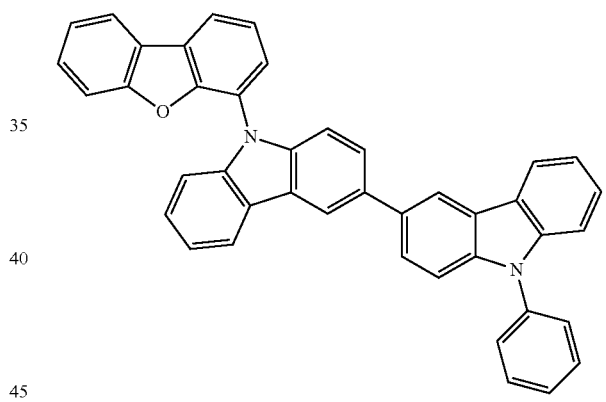
B-51
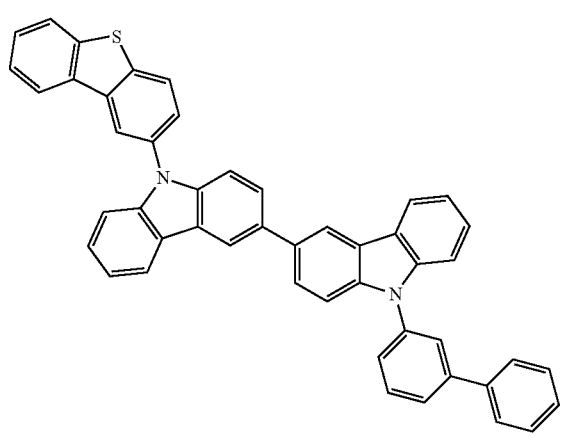
B-54
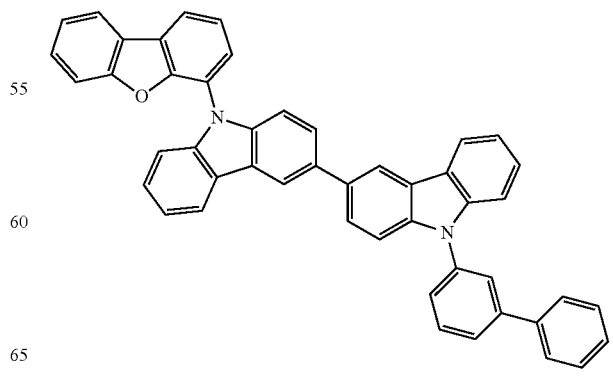

B-55
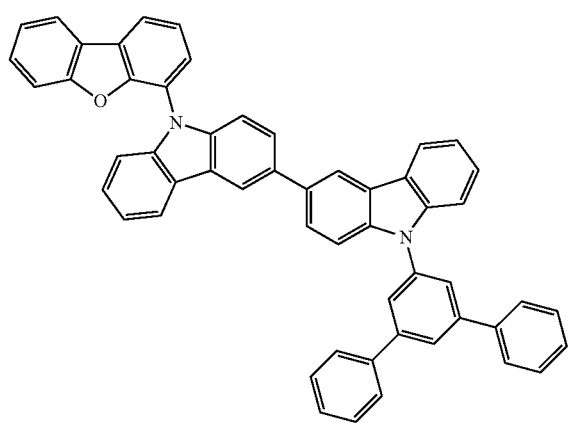
B-56
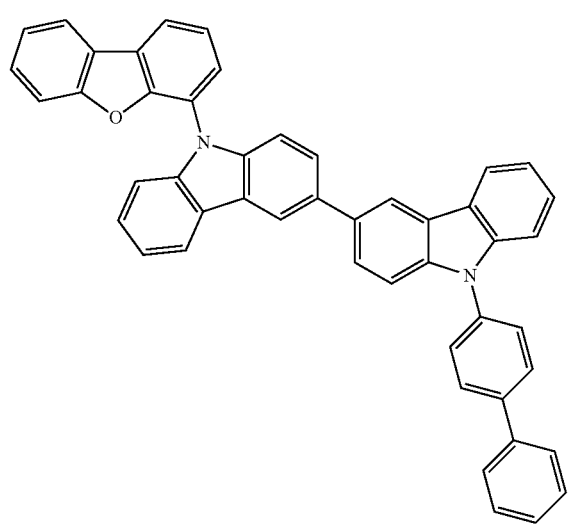
B-57
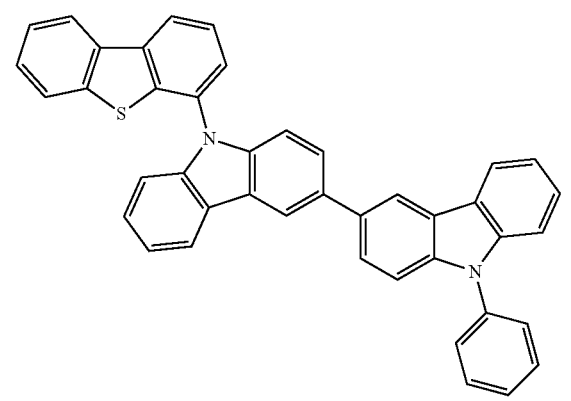
B-58
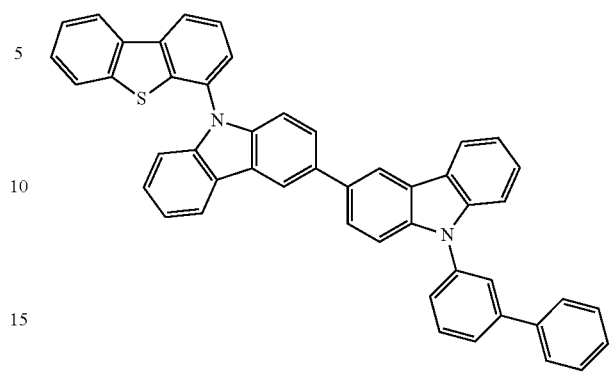
B-59
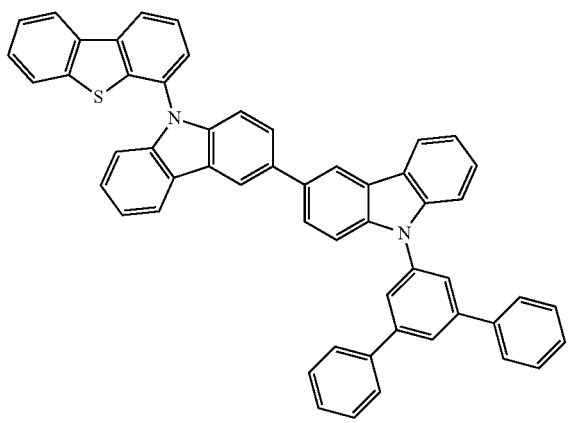
B-60
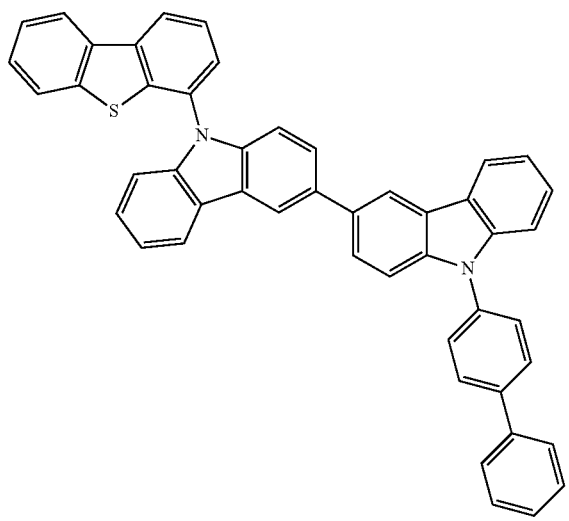

-continued
B-61
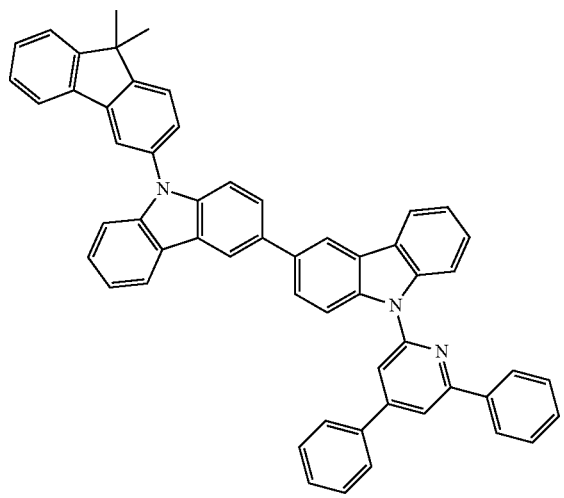
B-62
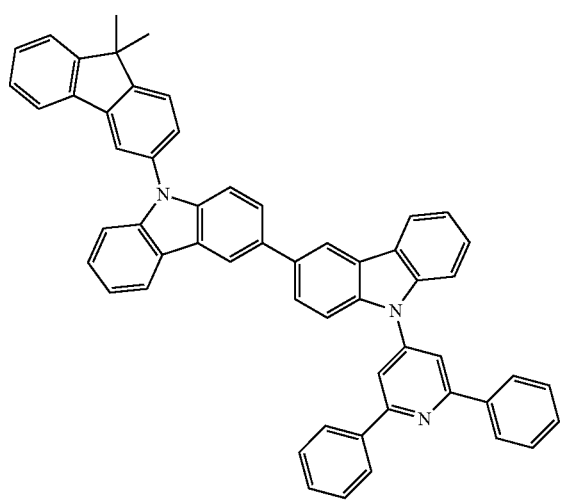
B-63
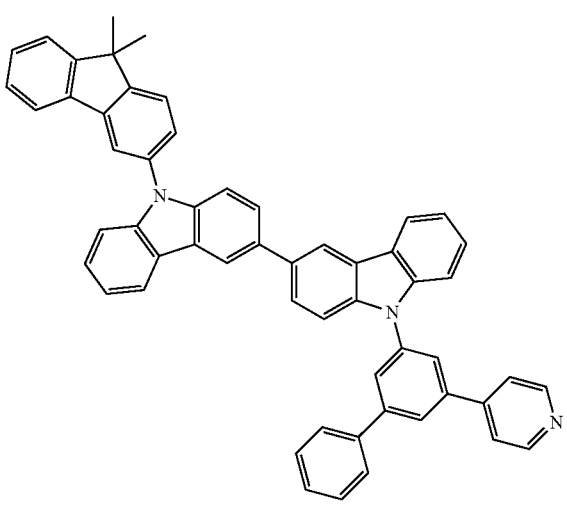
-continued
B-64
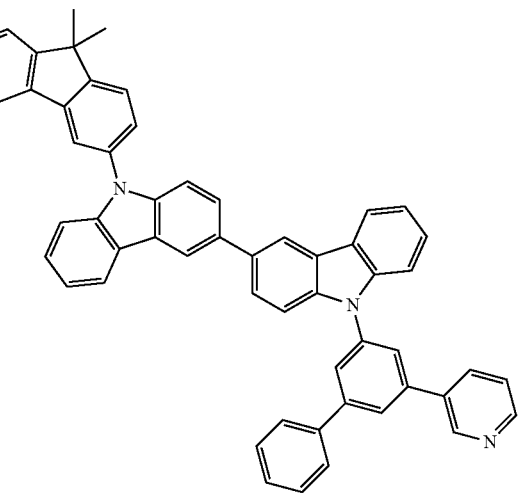
B-65
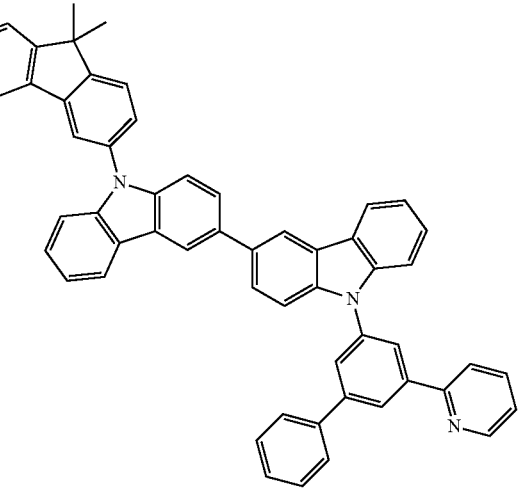
B-66
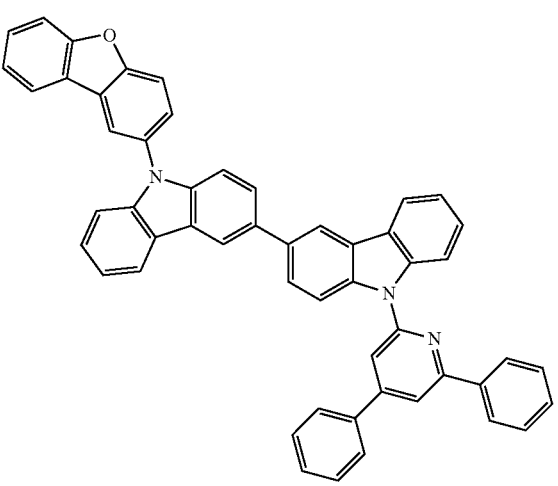

B-67
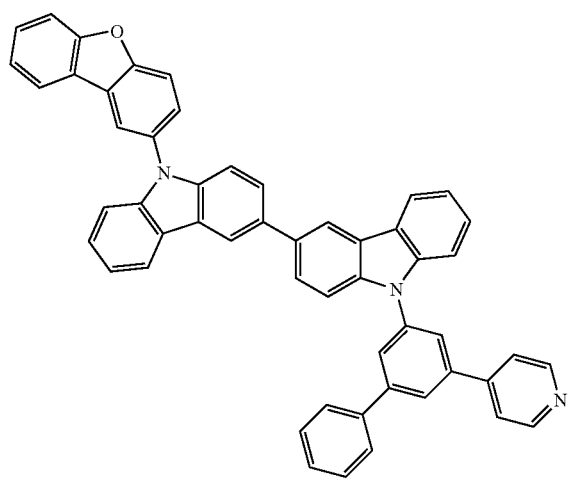
B-70
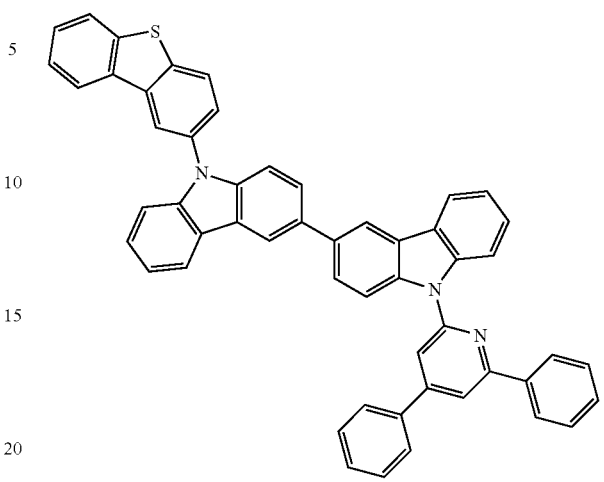
B-68
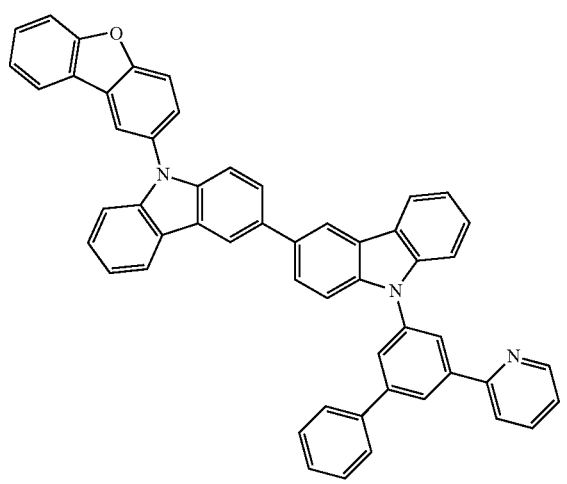
B-71
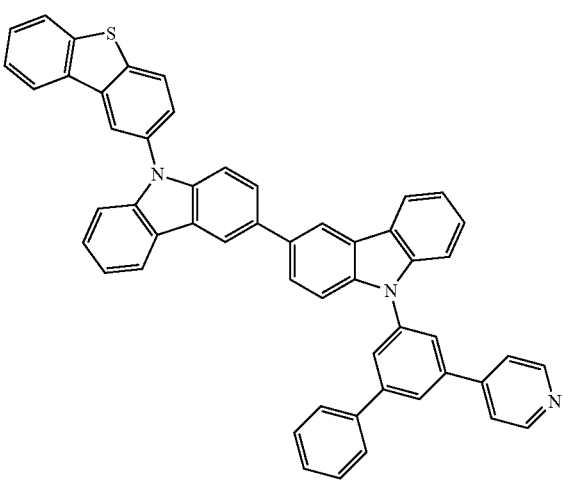
B-69
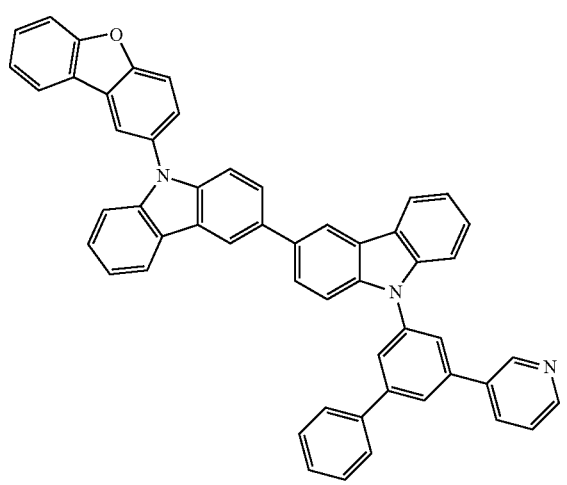
B-72
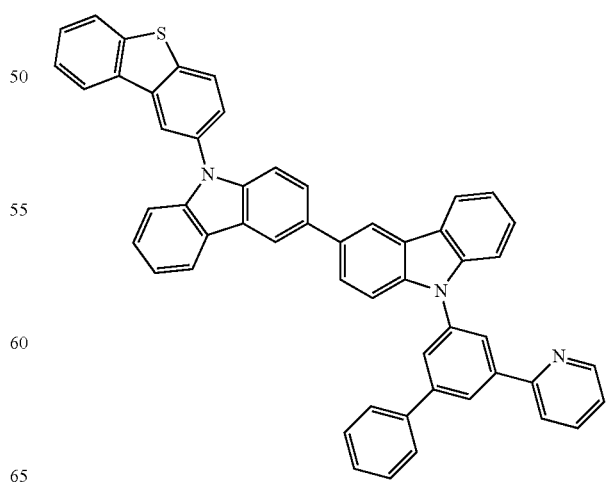

B-73

B-74

B-75

B-76

B-77

B-78

B-79

B-80

B-81
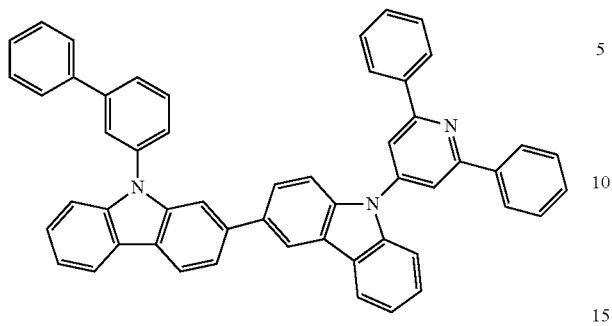
B-85
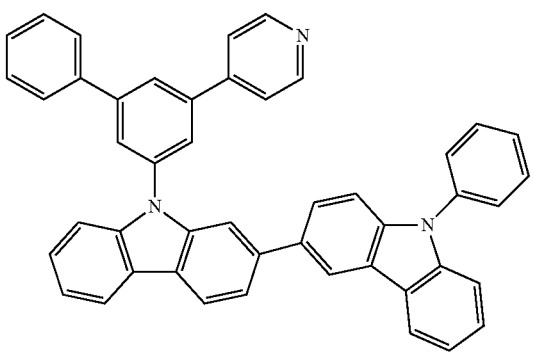
B-82
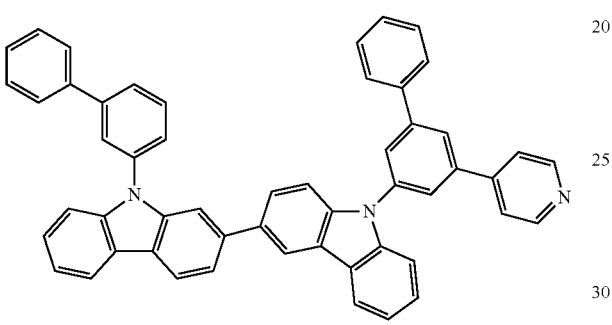
B-86
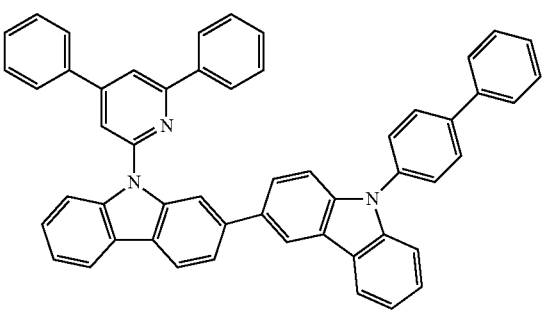
B-83
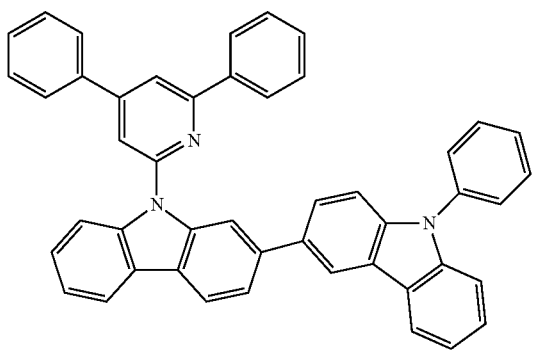
B-87
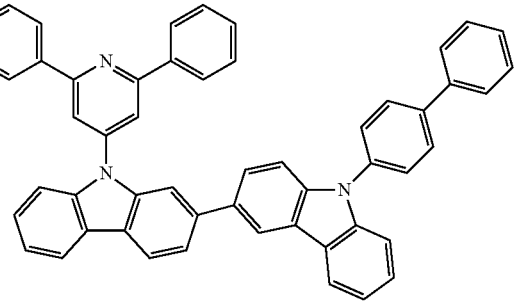
B-84
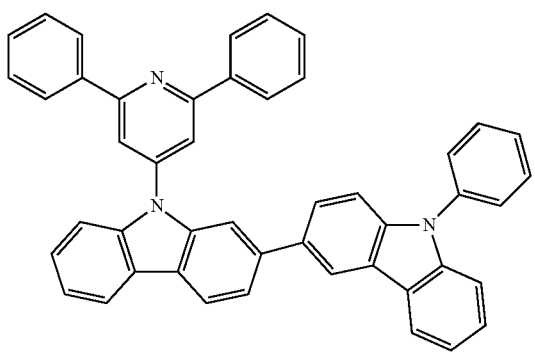
B-88
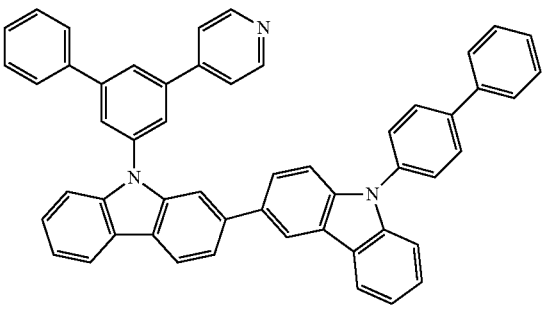

-continued
B-89
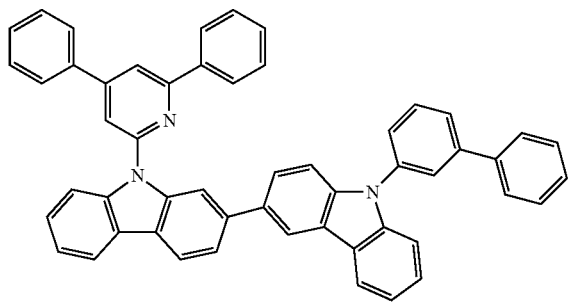
B-90
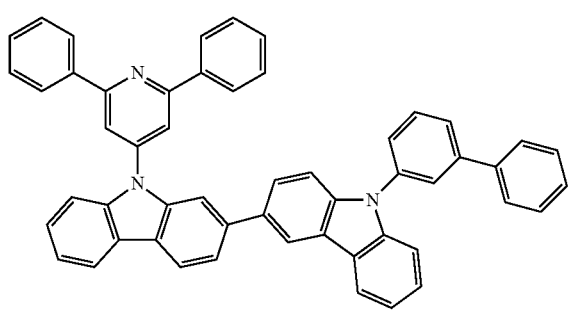
B-91
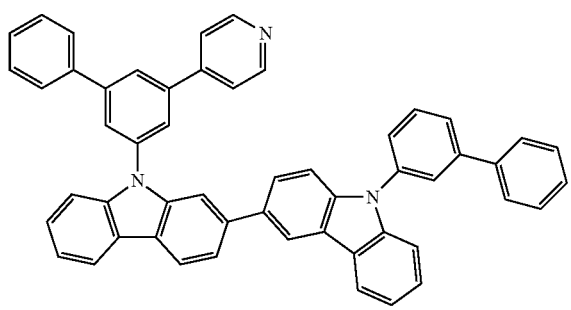
B-92
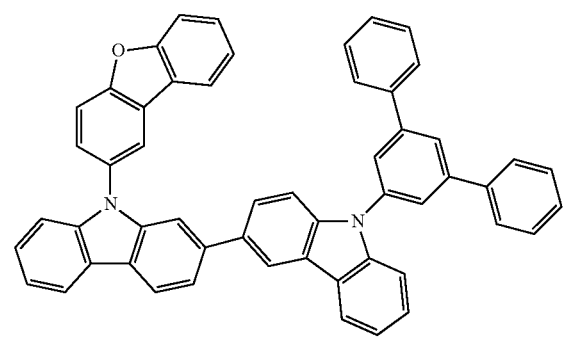
-continued
B-93
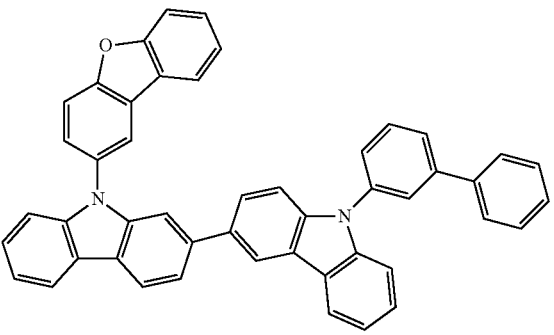
B-94
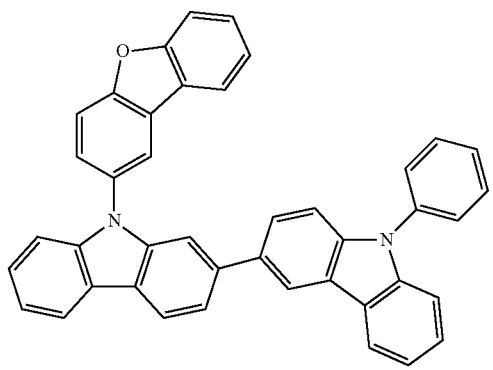
B-95
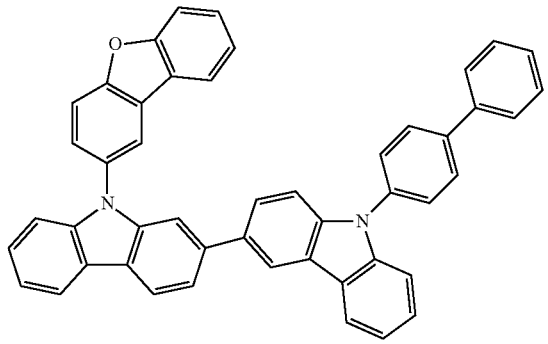
B-96
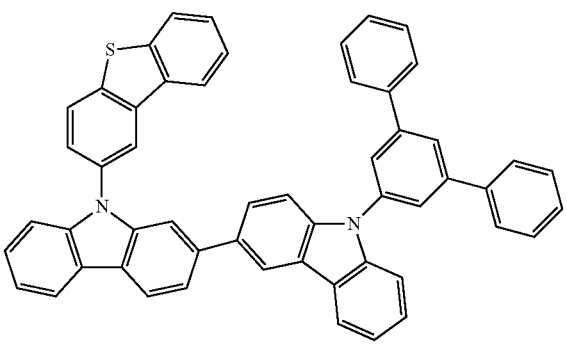

B-97
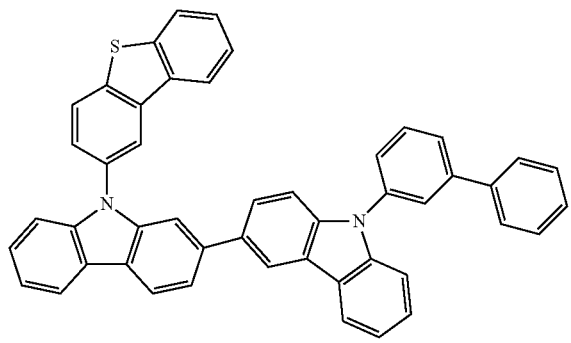
B-98
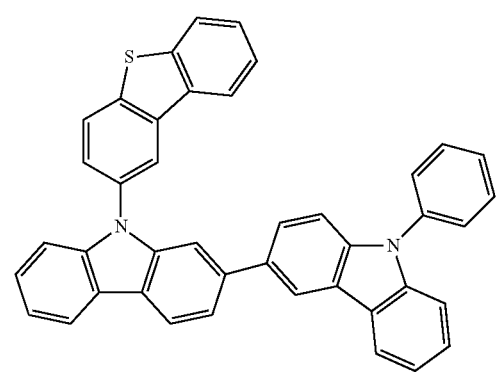
B-99
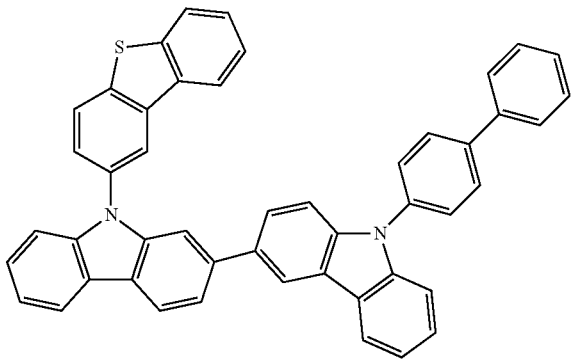
B-100
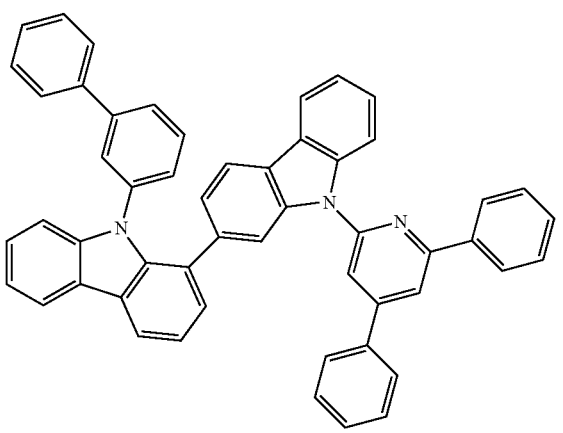
B-101
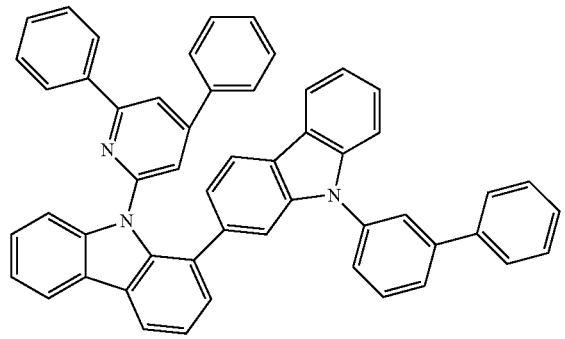
B-102
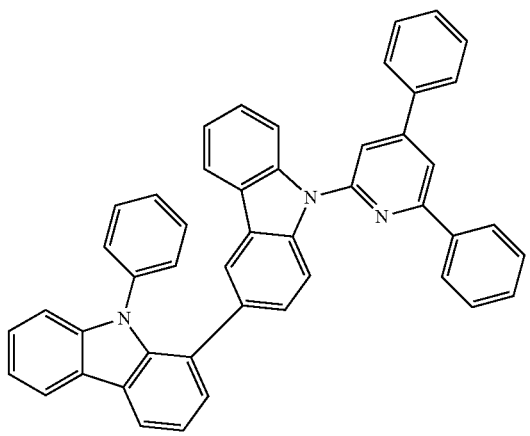
B-103
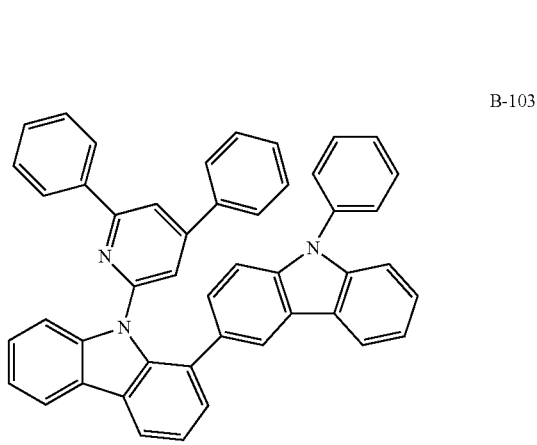
B-104
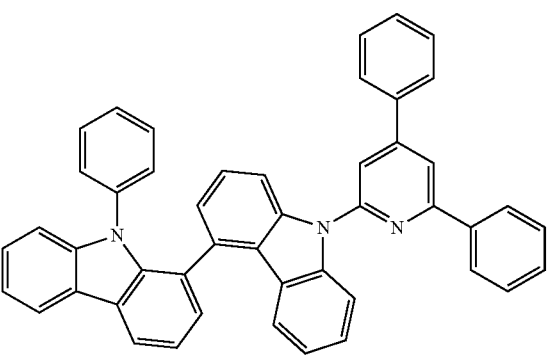

B-105
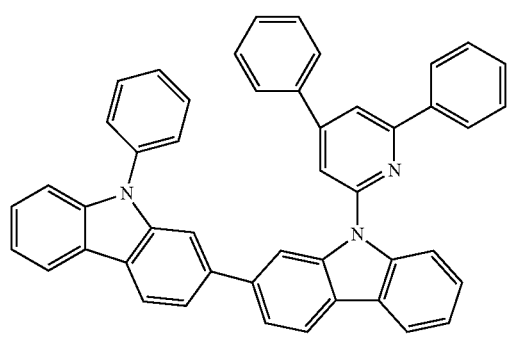
B-109
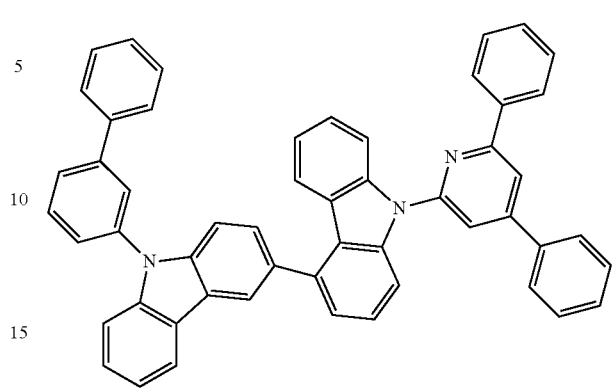
B-106
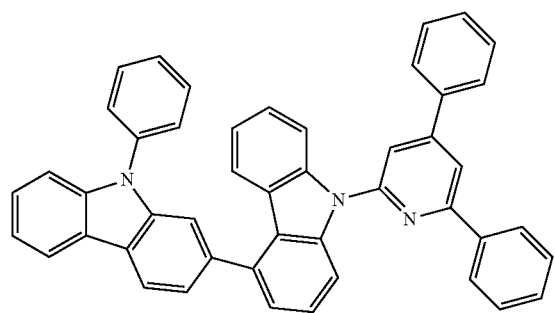
B-110
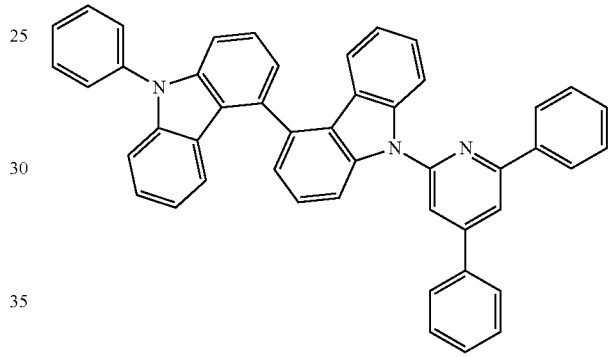
B-107
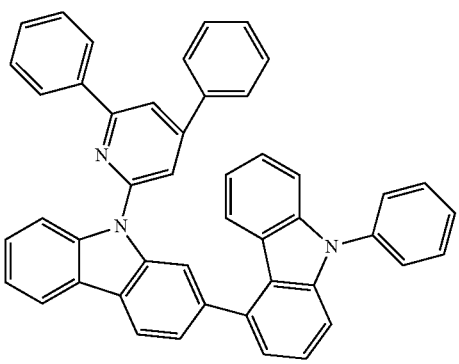
B-111
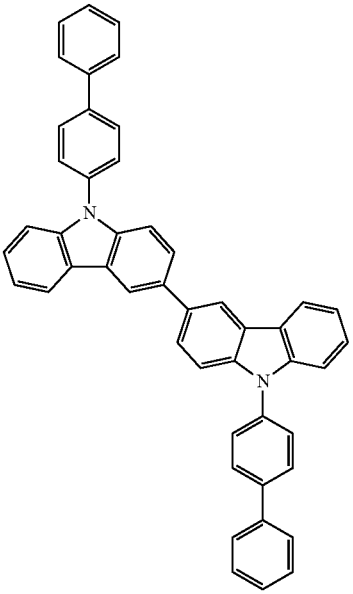
B-108
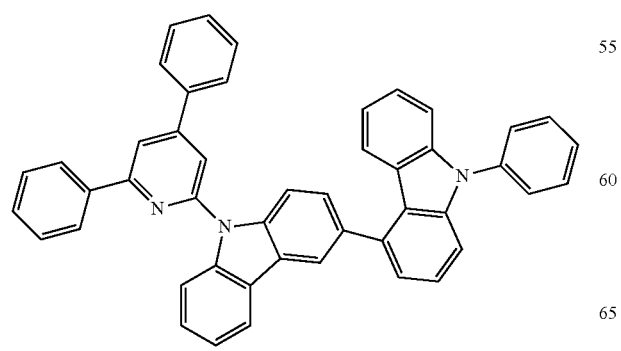

B-112
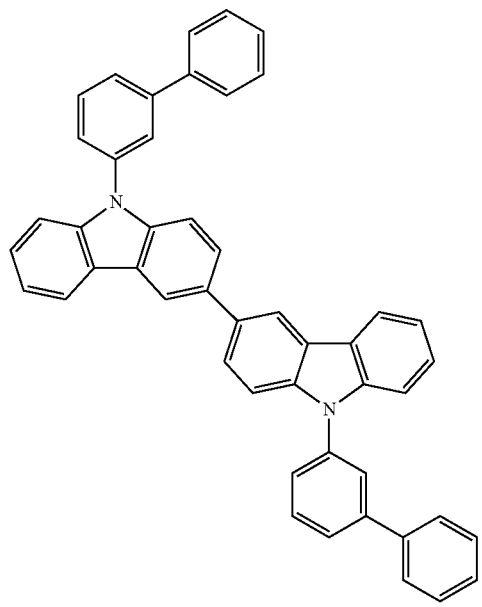
B-113
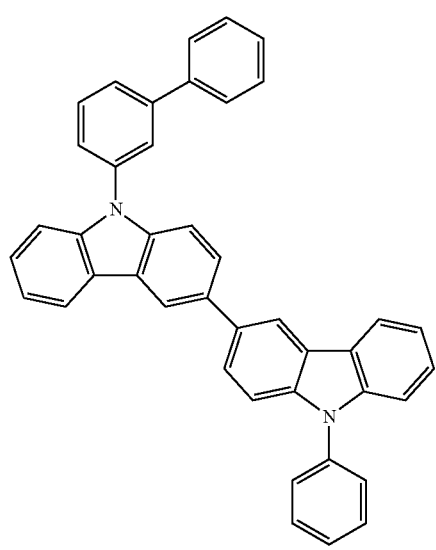
C-10
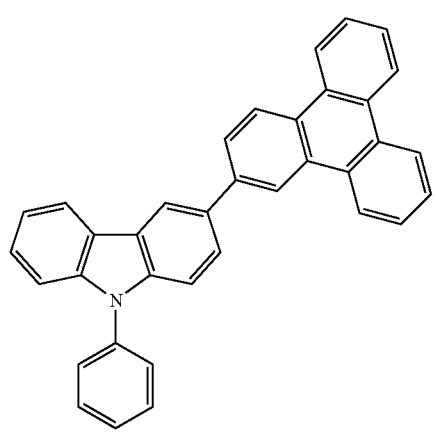
C-11
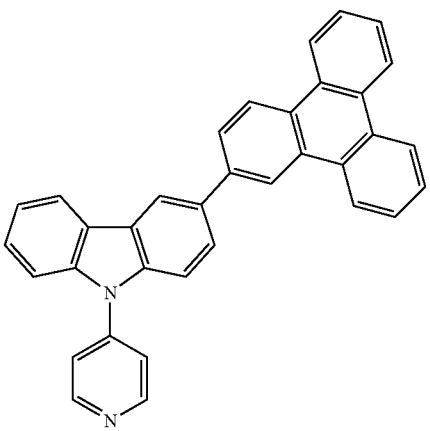
C-12
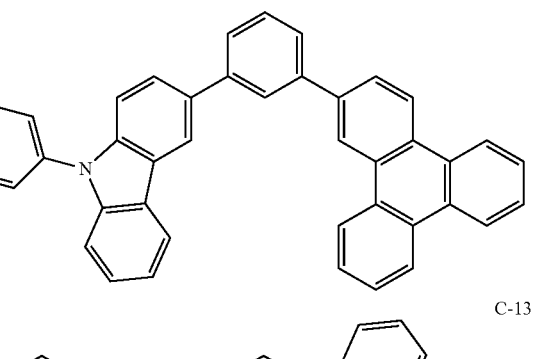
C-13
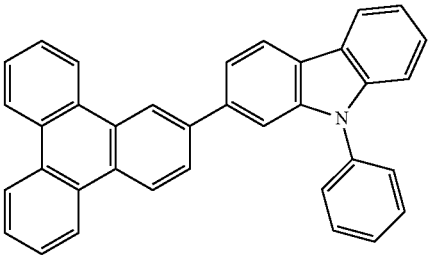
C-14
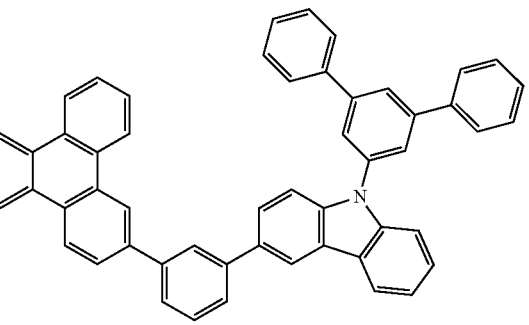
C-15
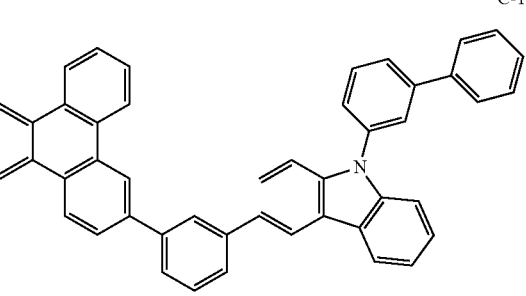

C-16

C-17

C-18

C-19

C-20

C-21

C-22

C-23

C-24

C-25
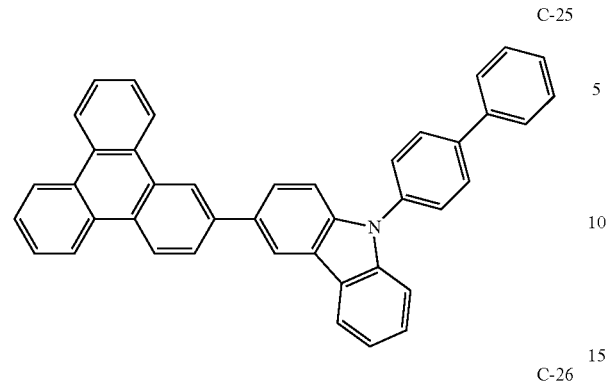
C-26
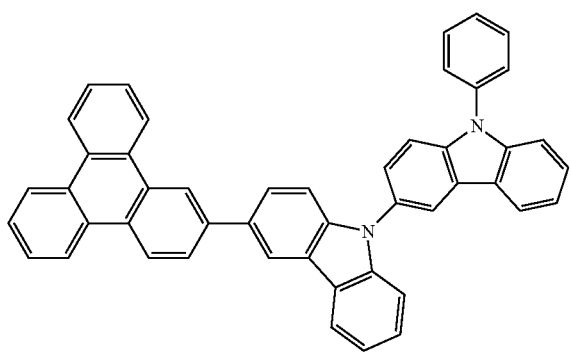
C-27
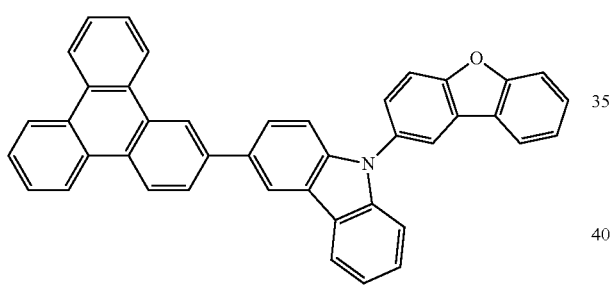
C-28
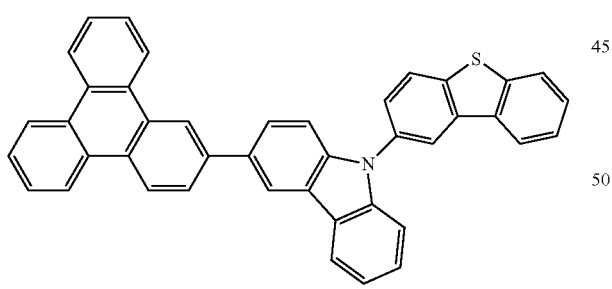
C-29
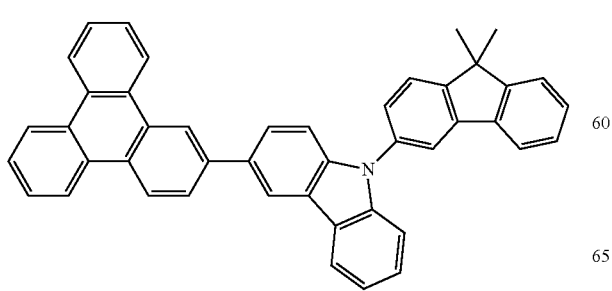
C-30
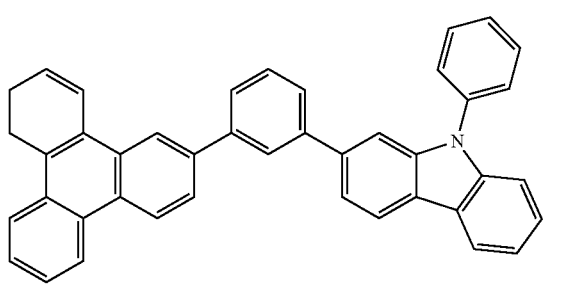
C-31
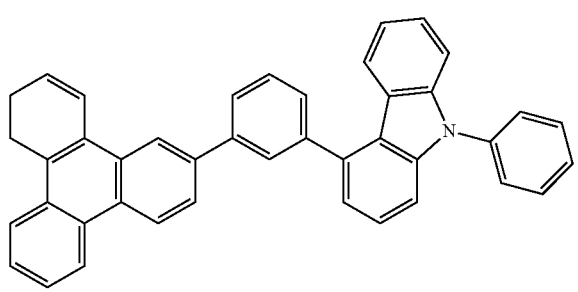
C-32
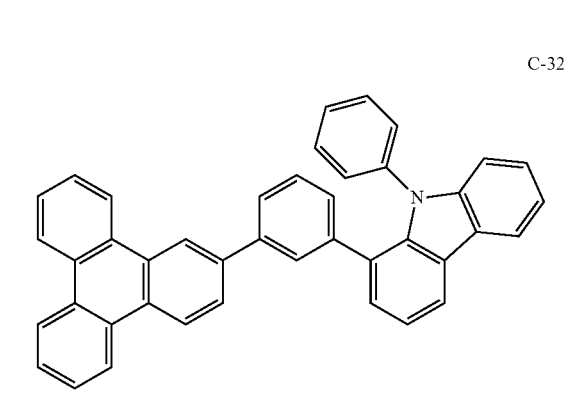
C-33
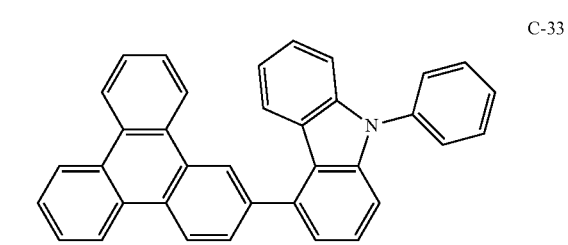
D-10
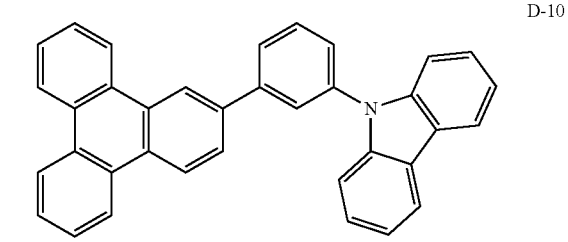

D-11
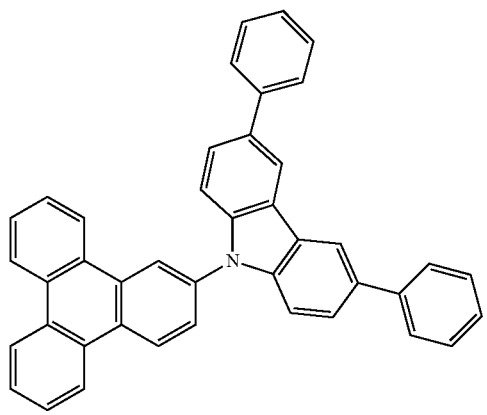
D-12
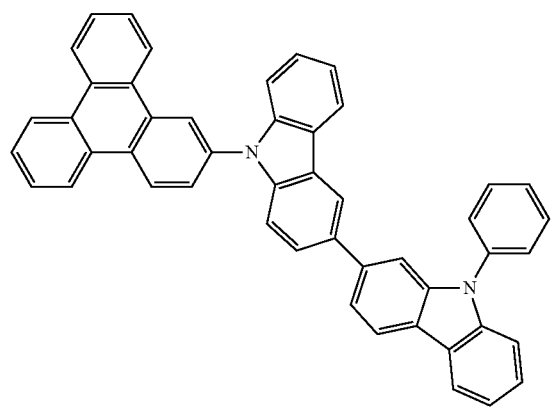
D-13
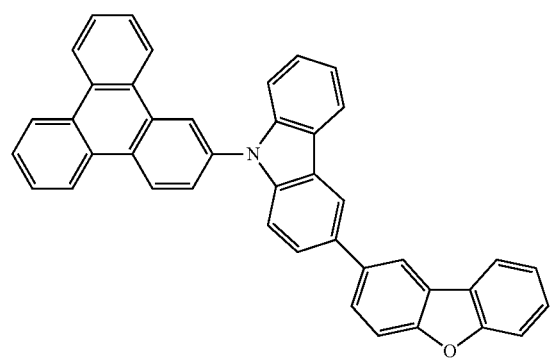
D-14
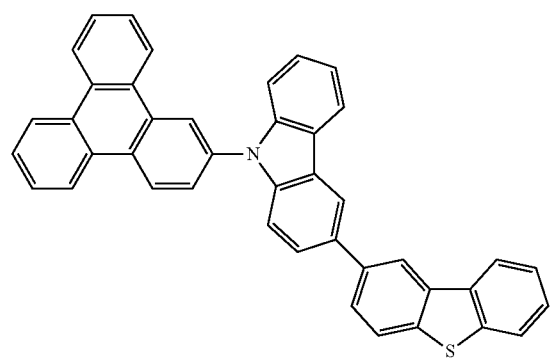
D-15
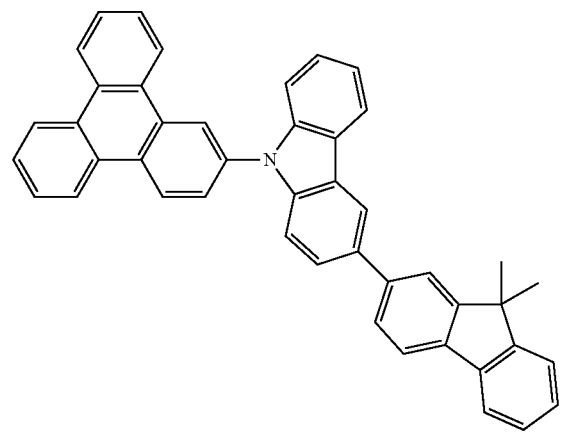
D-16
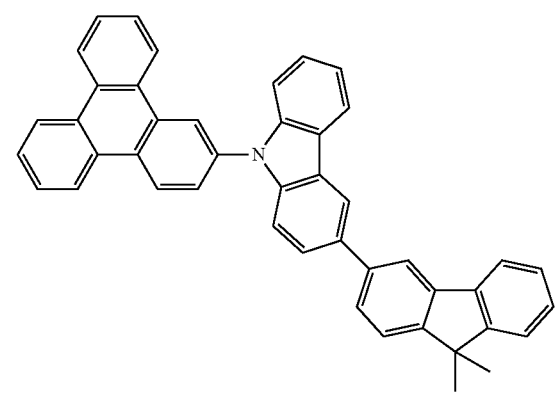
D-17
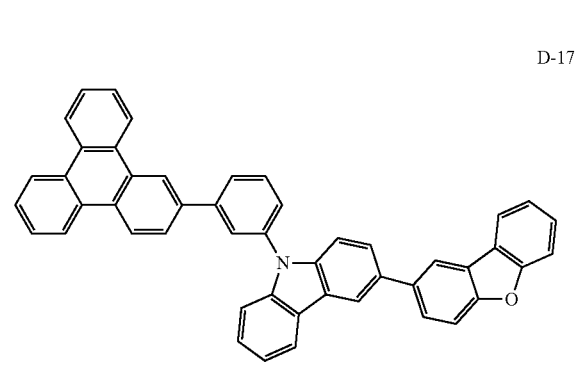
D-18
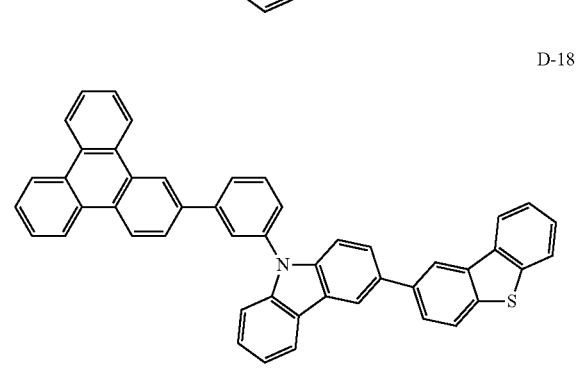

D-19
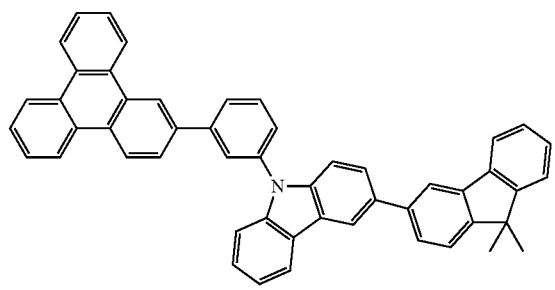
D-23
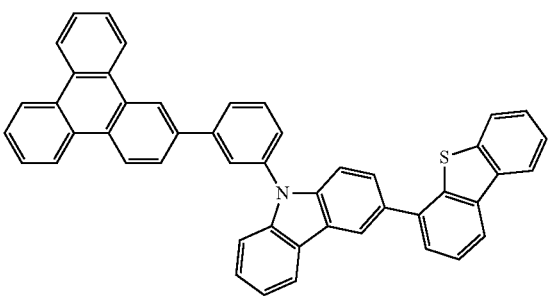
D-20
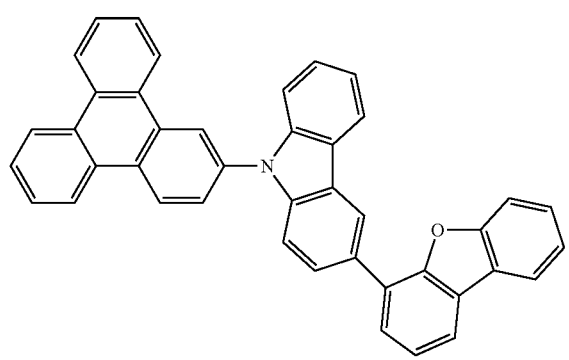
D-24
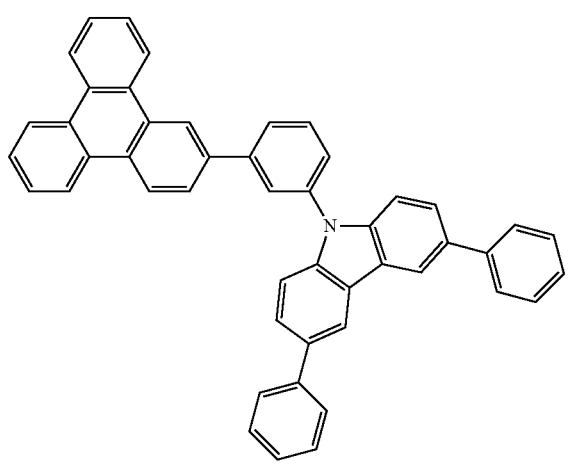
D-21
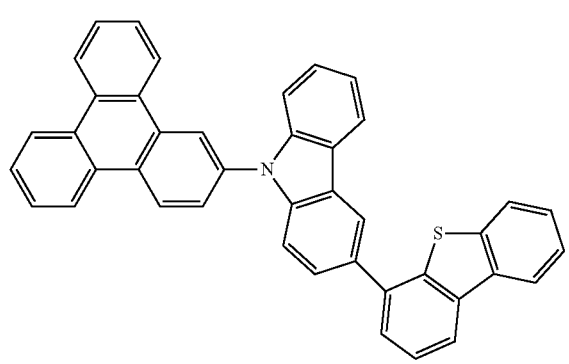
D-25
D-22
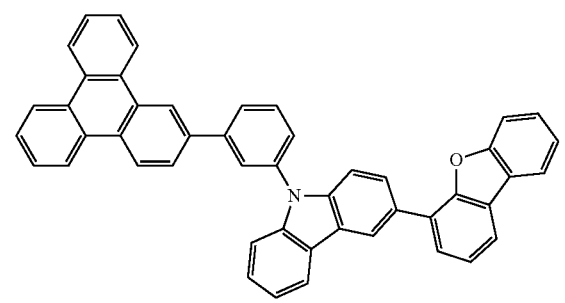
D-26
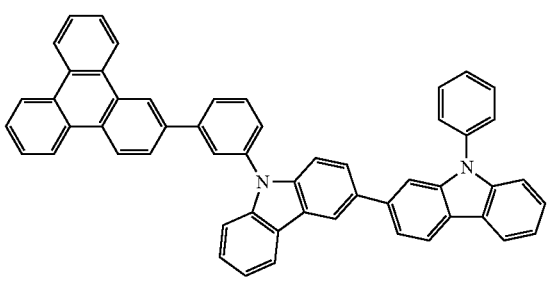

-continued

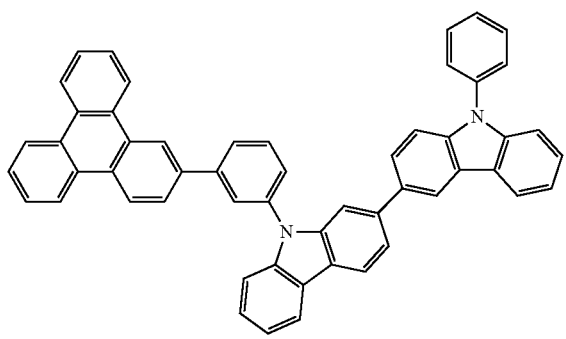
D-27

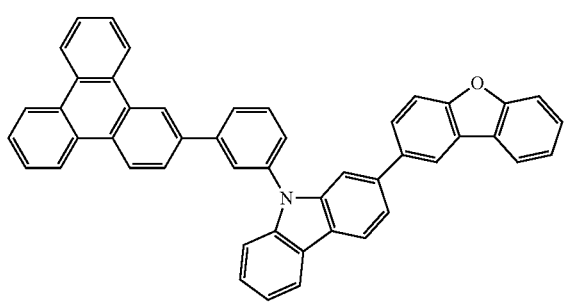
D-28

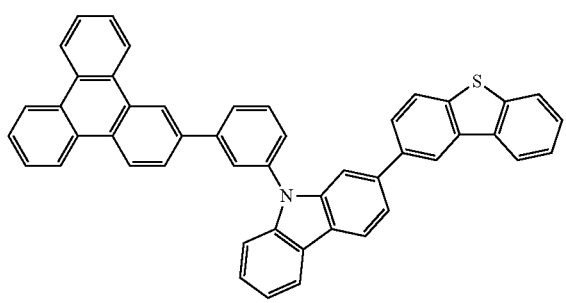
D-29

The second organic compound may be a compound consisting of a moiety represented by Chemical Formula 12 and a moiety represented by Chemical Formula 13.

[Chemical Formula 12]

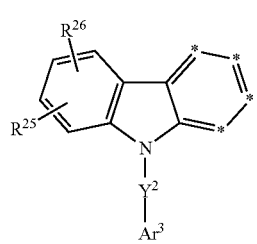

[Chemical Formula 13]

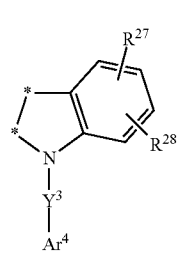

In Chemical Formulae 12 and 13, $Y^2$ and $Y^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heterocyclic group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^{25}$ to $R^{28}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and two adjacent *'s of Chemical Formula 12 are bound to two adjacent *'s of Chemical Formula 13 to provide a fused ring, *'s of not providing a fused ring of Chemical Formula 12 are independently $CR^b$ wherein $R^b$ is hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof.

The second organic compound consisting of the moiety represented by Chemical Formula 12 and the moiety represented by Chemical Formula 13 may be, for example selected from compounds of Group 3, but is not limited thereto.

[Group 3]

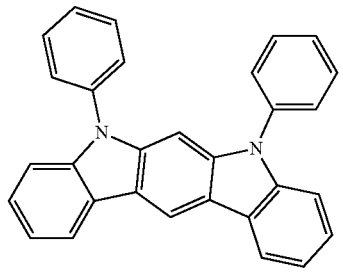
E-1

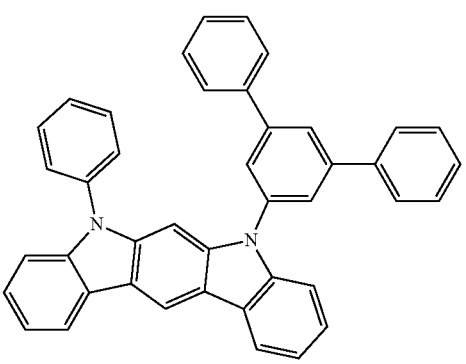
E-2

E-3
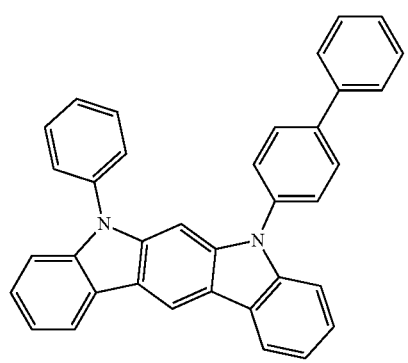
E-4
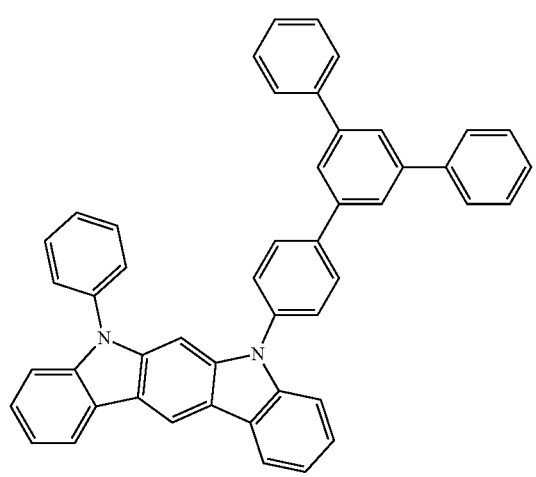
E-5
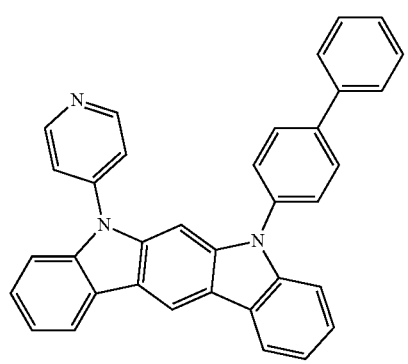
E-6
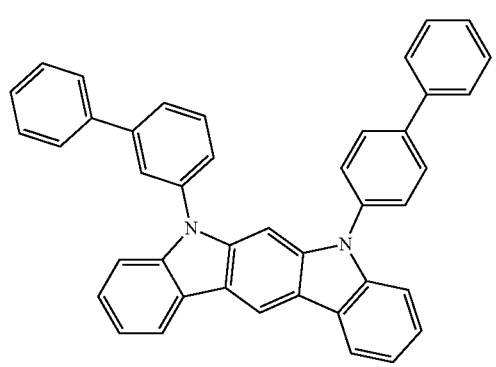
E-7
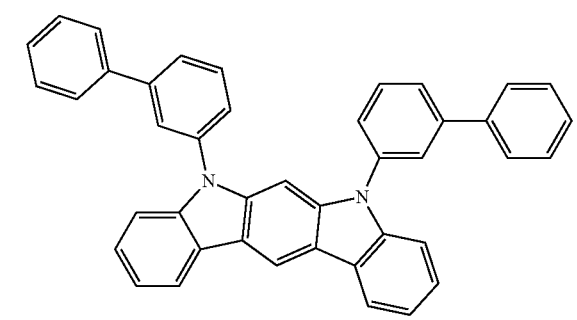
E-8
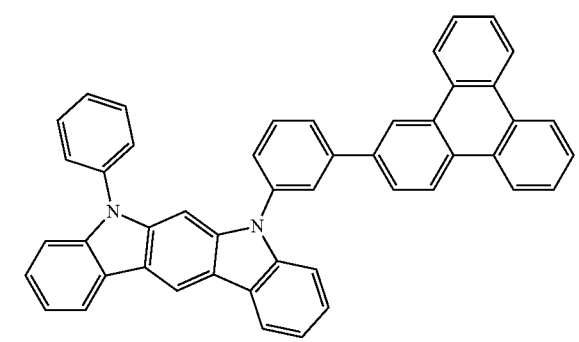
E-9
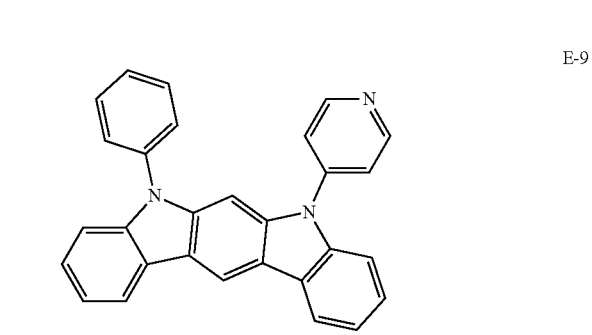
E-10
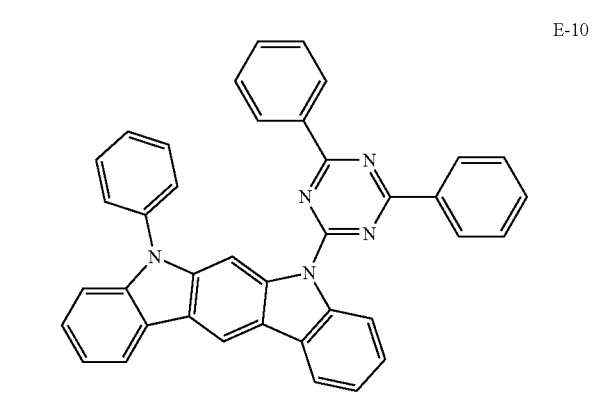

E-11
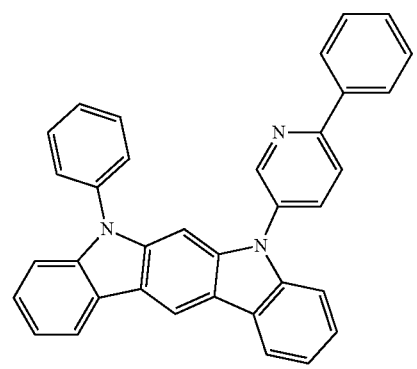
E-14
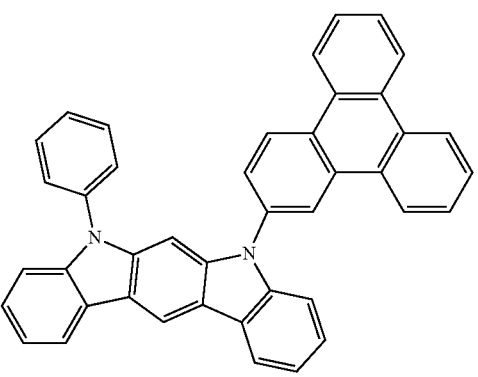
E-12
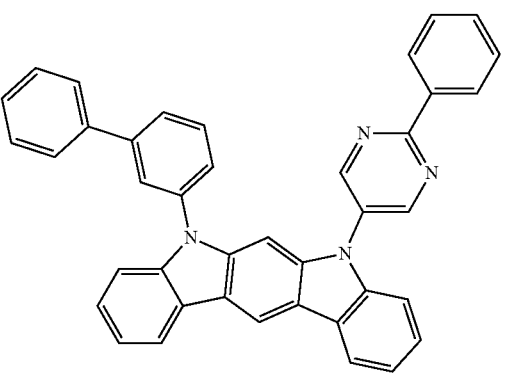
E-15
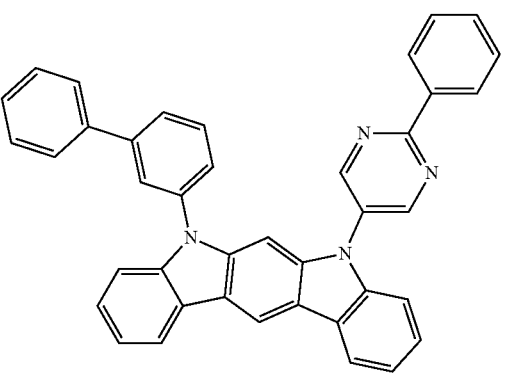
E-16
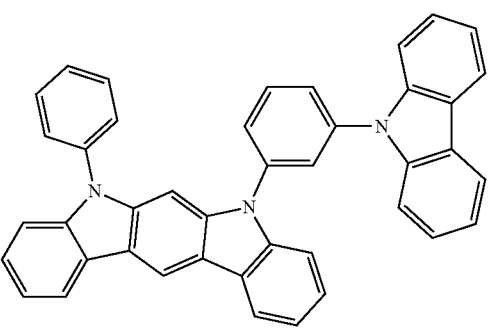
E-13
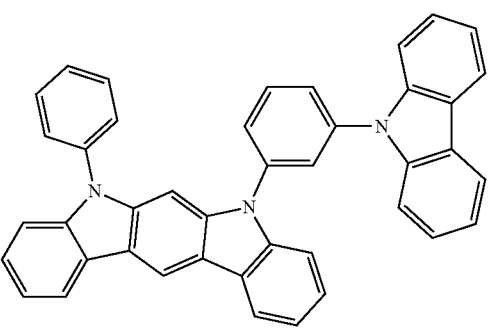
E-17
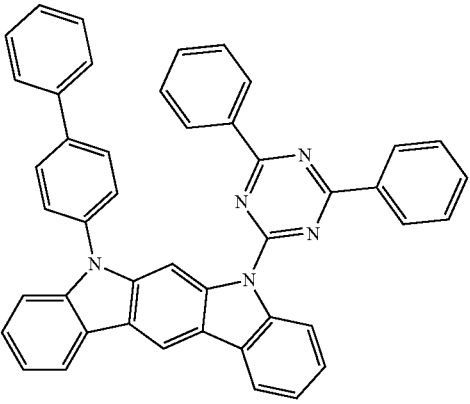

E-18
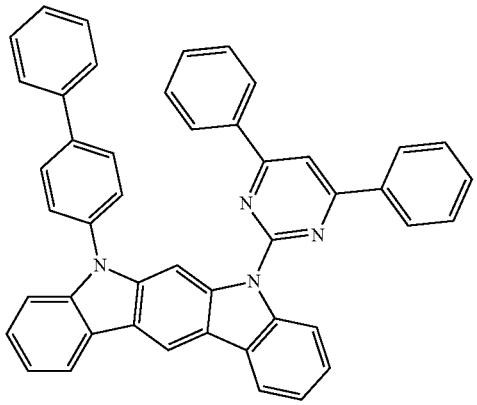
E-19
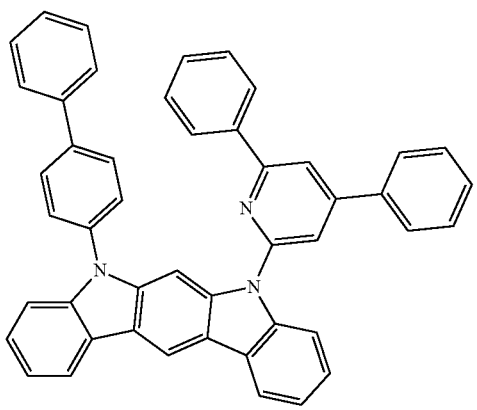
E-20
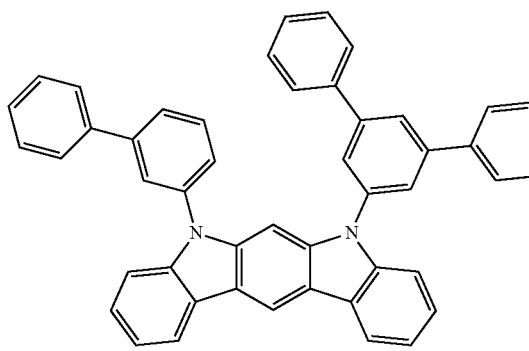
E-21
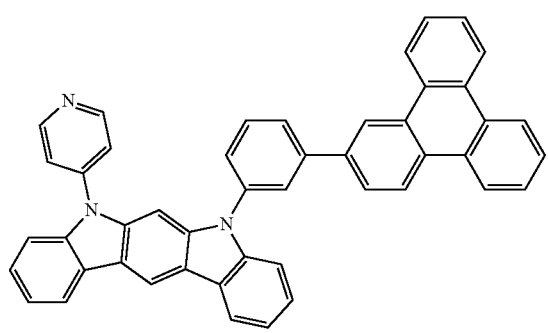
E-22
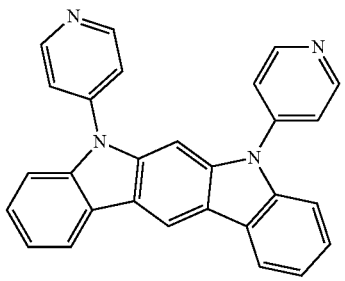
E-23
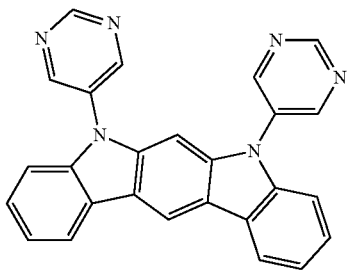
E-24
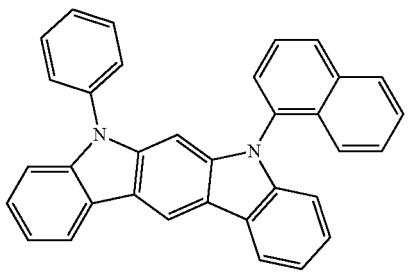
E-25
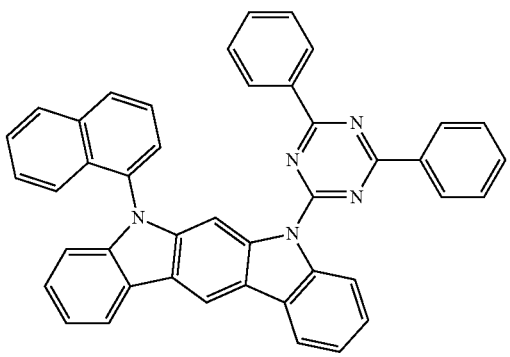
E-26
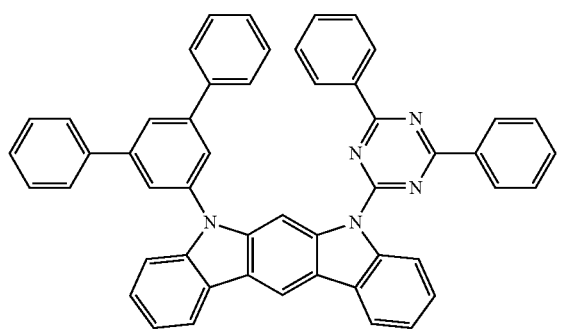

E-27
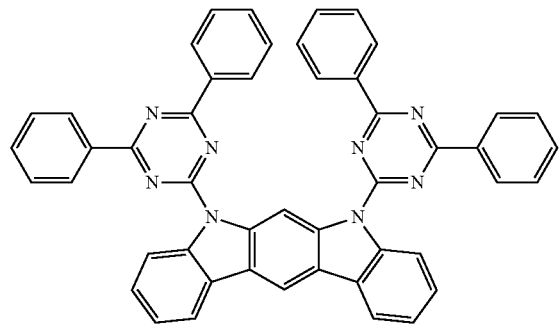
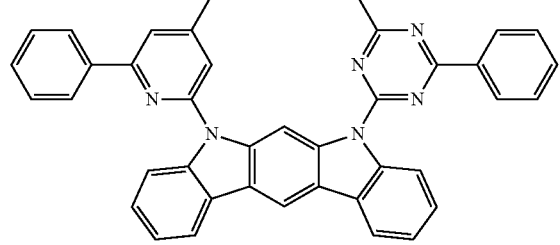
E-29
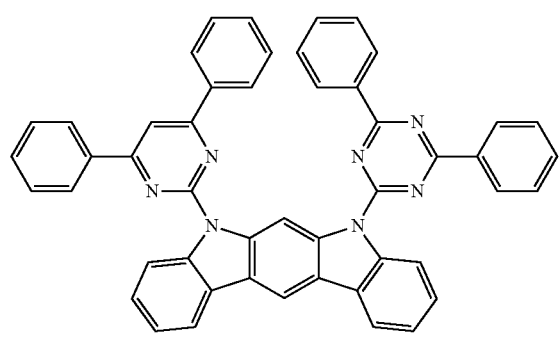
E-30
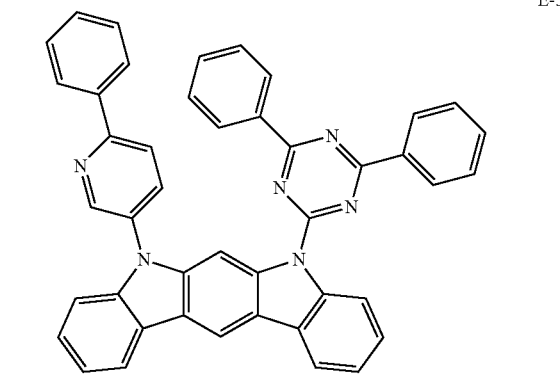
E-31
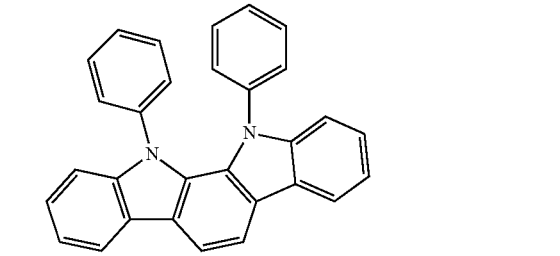
E-32
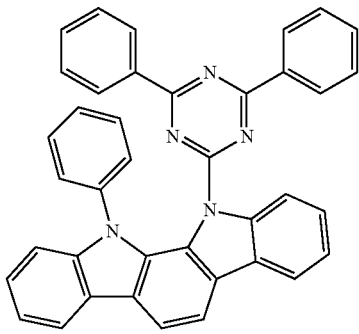
E-33
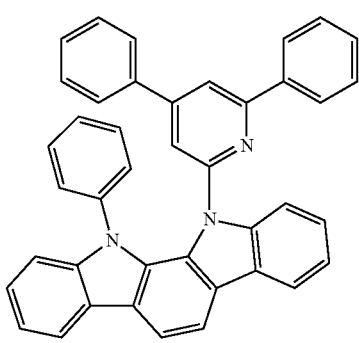
E-34
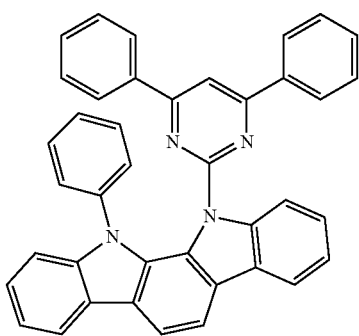
E-35
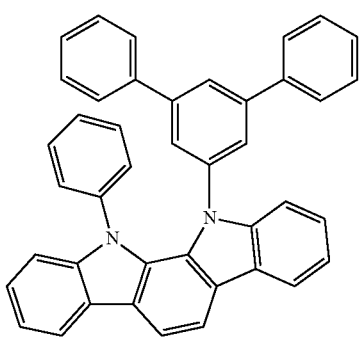

E-36
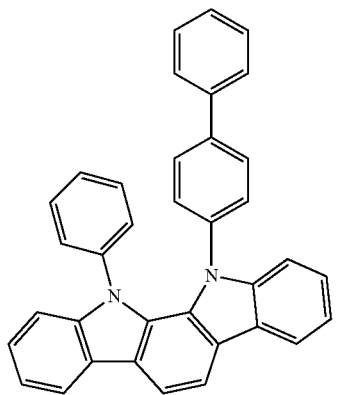
E-37
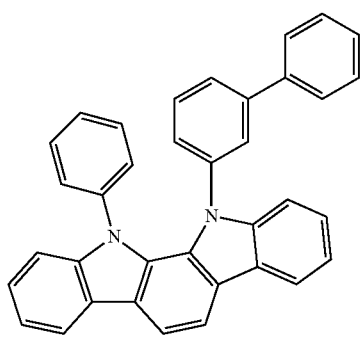
E-38
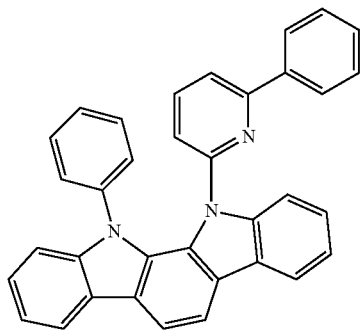
E-39
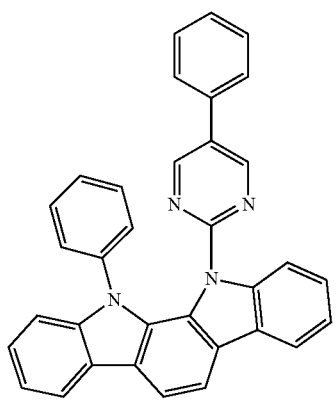
E-40
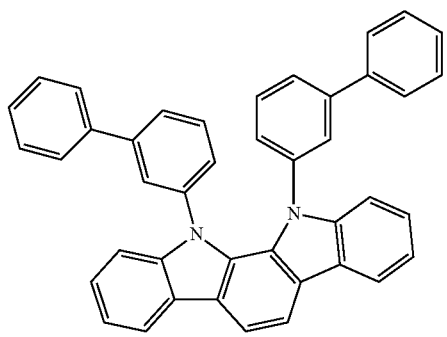
E-41
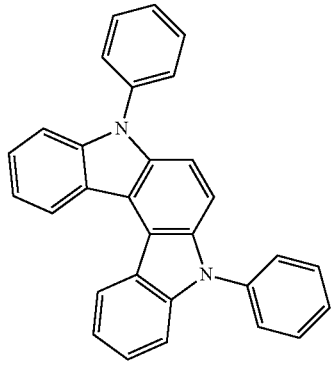
E-42
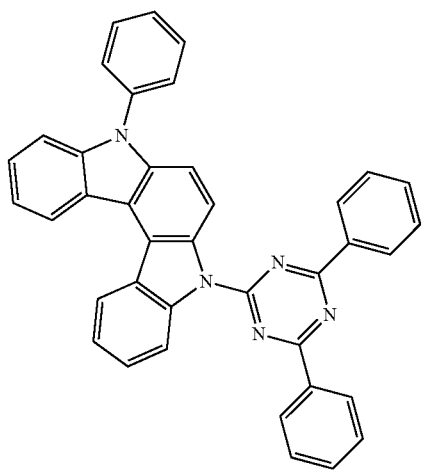
E-43
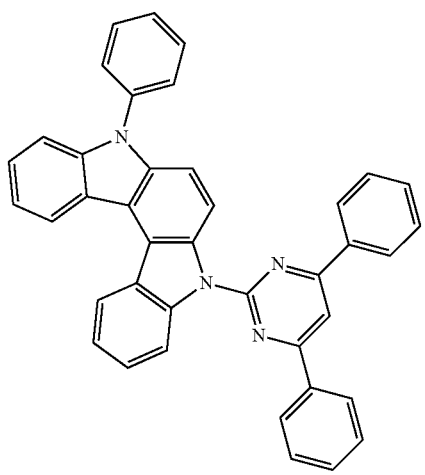

E-44
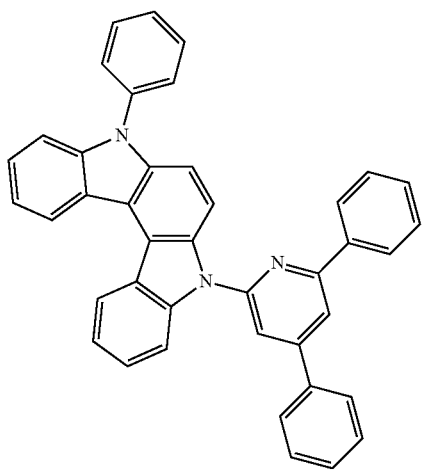
E-45
E-46
E-47
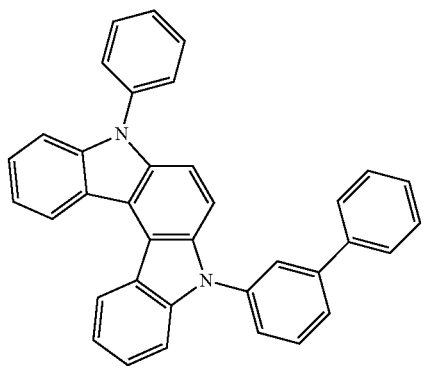
E-48
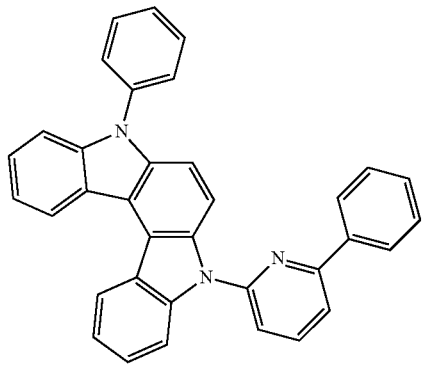
E-49
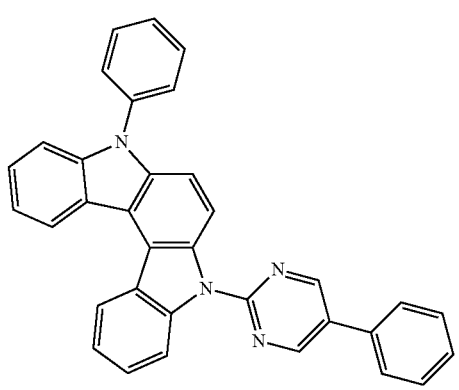

E-50
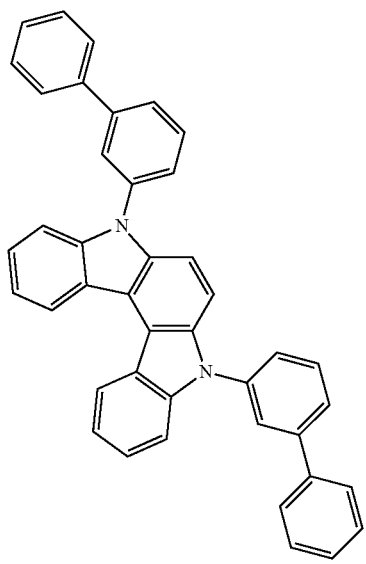
E-51
E-52
E-53
E-54
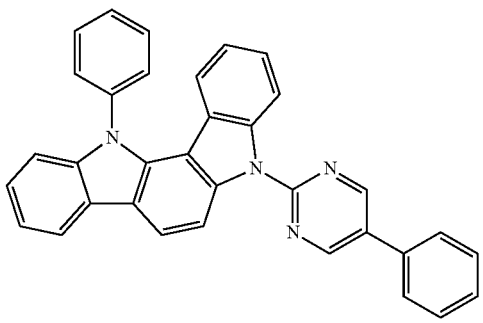
E-55
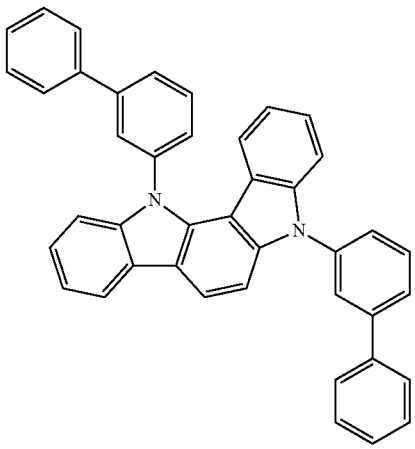
E-56
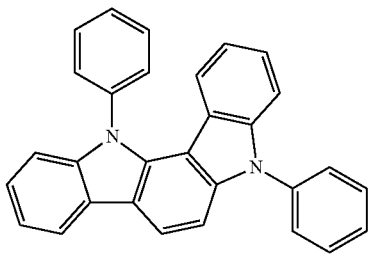
E-57
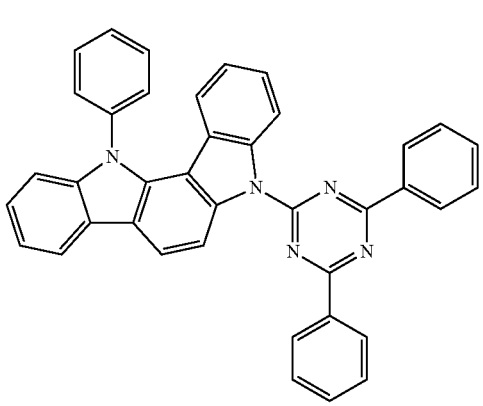

-continued
E-58
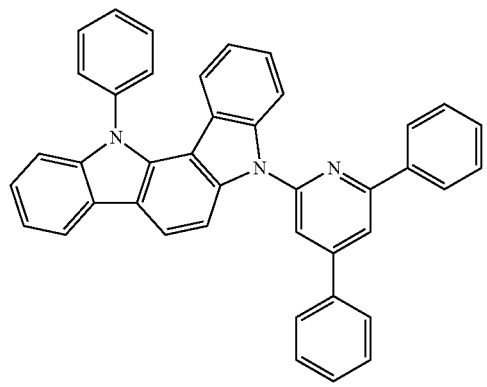
E-59
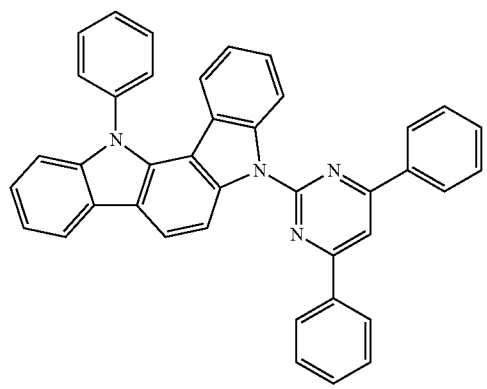
E-60
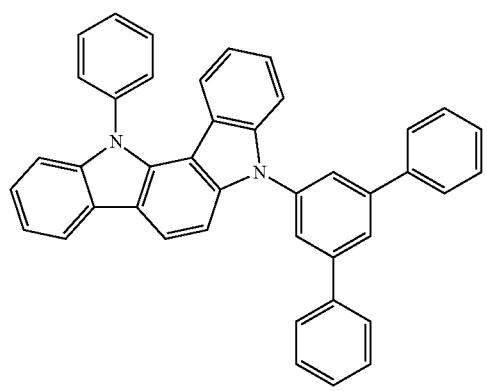
-continued
E-61
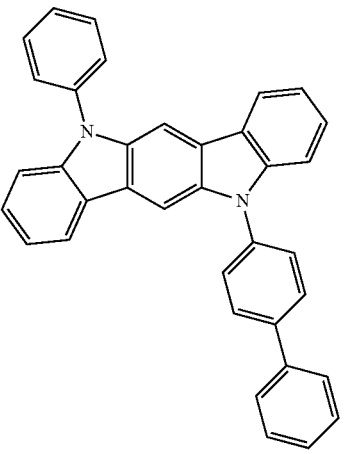
E-62
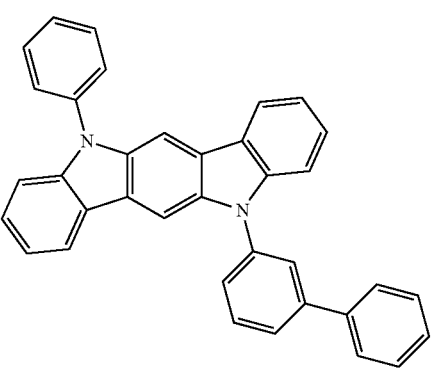
E-63
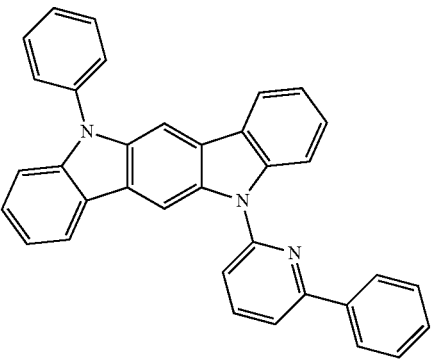
E-64
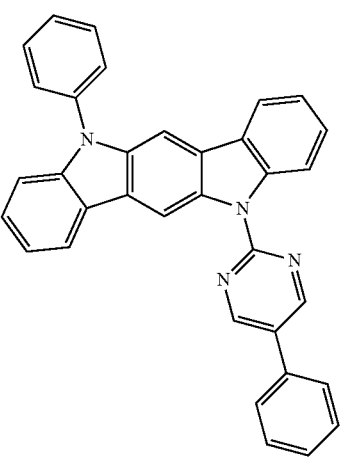

-continued

E-65

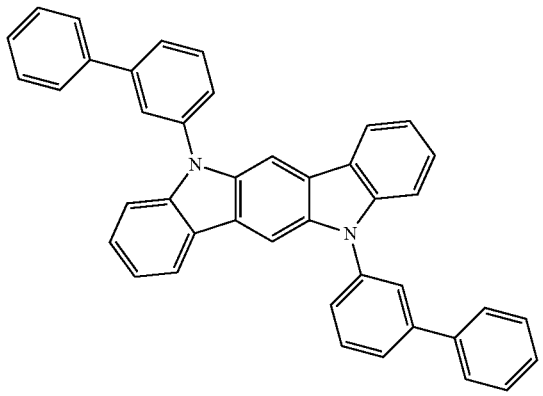

The second organic compound may include at least one of a compound represented by Chemical Formula 11 and a compound consisting of a moiety represented by Chemical Formula 12 and a moiety represented by Chemical Formula 13.

The composition may include the first organic compound and the second organic compound in a weight ratio of about 1:10 to 10:1.

The composition may be applied to an organic layer of an organic optoelectric device, and the first organic compound and the second organic compound may act as a host. Herein, the first organic compound may be a compound having bipolar characteristics wherein electron characteristics are relatively strong and the second organic compound may be a compound having bipolar characteristics wherein hole characteristics are relatively strong and may be employed with the first organic compound to heighten charge mobility and stability and thus to improve luminous efficiency and life-span characteristics.

The composition may further include one or more organic compounds besides the first organic compound and the second organic compound.

The composition may further include a dopant. The dopant may be a red, green, or blue dopant, for example a phosphorescent dopant.

The dopant is mixed with the first organic compound and the second organic compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

Examples of the phosphorescent dopant may be an organic metallic compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be, for example, Ir, Pt, Os, Ti, Zr, Hf, Eu, Tb, Tm, Fe, Co, Ni, Ru, Rh, Pd, or a combination thereof, and the L and X may be, for example a bidendate ligand.

The composition may be formed using a dry film formation method such as chemical vapor deposition (CVD) or a solution process. The dry film formation method may be, for example a chemical vapor deposition (CVD) method, sputtering, plasma plating, and ion plating, and two or more compounds may be simultaneously formed into a film or compound having the same deposition temperature may be mixed and formed into a film. The solution process may be, for example inkjet printing, spin coating, slit coating, bar coating and/or dip coating.

Hereinafter, an organic optoelectric device including the organic compound or the composition is described.

The organic optoelectric device may be any device to convert electrical energy into photoenergy and vice versa without particular limitation, and may be, for example an organic photoelectric device, an organic light emitting diode, an organic solar cell, and an organic photo conductor drum.

The organic optoelectric device may include an anode and a cathode facing each other, at least one organic layer between the anode and the cathode, and the organic layer includes the organic compound or the composition.

Herein, an organic light emitting diode as one example of an organic optoelectric device is described referring to drawings.

FIGS. 1 and 2 are cross-sectional views showing organic light emitting diodes according to an embodiment.

Referring to FIG. 1, an organic light emitting diode 100 according to an embodiment includes an anode 120 and a cathode 110 and an organic layer 105 between the anode 120 and the cathode 110.

The anode 120 may be made of a conductor having a large work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes an emission layer 130 including the organic compound or the composition.

The emission layer 130 may include, for example the organic compound alone and a mixture of two or more of the organic compounds or the composition.

Referring to FIG. 2, an organic light emitting diode 200 further includes a hole auxiliary layer 140 in addition to the emission layer 130. The hole auxiliary layer 140 may improve hole injection and/or hole mobility and block electrons between the anode 120 and the emission layer 130. The hole auxiliary layer 140 may be, for example a hole transport layer (HTL), a hole injection layer (HIL), and/or an electron blocking layer, and may include at least one layer.

For example, the organic layer 105 of FIG. 1 or 2 may further include an electron transport layer (ETL), an electron injection layer (EIL), a hole injection layer (HIL), and the like.

The organic light emitting diode may be applied to an organic light emitting display device.

Hereinafter, the embodiments are illustrated in more detail with reference to examples. These examples, however, are not in any sense to be interpreted as limiting the scope of the invention.

Synthesis of First Organic Compound

Synthesis of Intermediate

Synthesis Example 1: Synthesis of Intermediate I-1

[Reaction Scheme 1]

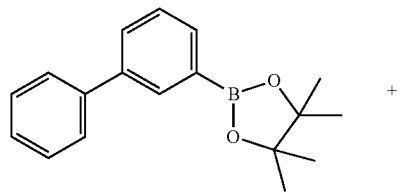

+

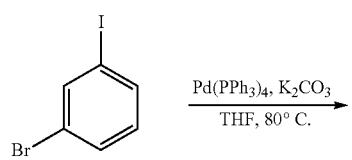

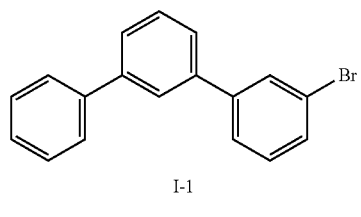

I-1

2-(biphenyl-3-yl)-4,4,5,5-tetramethyl-1,3,2-dioxaborolane (20 g, 71 mmol) was dissolved in 1 L of THF (Tetrahydrofuran) under an nitrogen environment, 1-bromo-3-iodobenzene (22 g, 78 mmol) and tetrakis(triphenylphosphine)palladium (Pd(PPh$_3$)$_4$, 0.8 g, 0.71 mmol) were added thereto, and the mixture was stirred. Potassium carbonate saturated in water (K$_2$CO$_3$, 25 g, 177 mmol) was added thereto, and the resulting mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain an intermediate I-1 (20 g, 91%).

HRMS (70 eV, EI+): m/z calcd for C18H13Br: 308.0201, found: 308 Elemental Analysis: C, 70%; H, 4%.

Synthesis Example 2: Synthesis of Intermediate I-2

[Reaction Scheme 2]

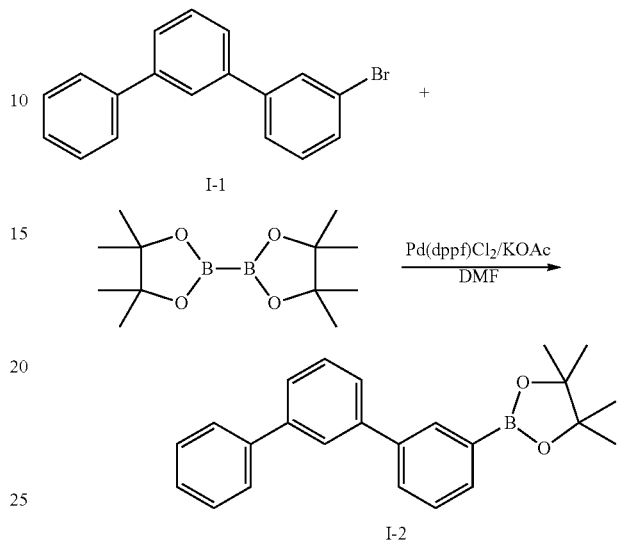

The intermediate I-1 (50 g, 162 mmol) was dissolved in 1 L of dimethylforamide (DMF) under a nitrogen environment, bis(pinacolato)diboron (49 g, 194 mmol), (1,1'-bis(diphenylphosphine)ferrocene)dichloropalladium (II) (Pd(dppf)Cl$_2$, 1.3 g, 1.62 mmol), and potassium acetate (KOAc, 40 g, 405 mmol) were added thereto, and the mixture was heated and refluxed at 150° C. for 12 hours. When the reaction was complete, water was added to the reaction solution, and the mixture was filtered and dried in a vacuum oven. This obtained residue was separated and purified through flash column chromatography to obtain an intermediate I-2 (47 g, 82%).

HRMS (70 eV, EI+): m/z calcd for C24H25BO2: 356.1948, found: 356.

Elemental Analysis: C, 81%; H, 7%

Synthesis Example 3: Synthesis of Intermediate I-3

[Reaction Scheme 3]

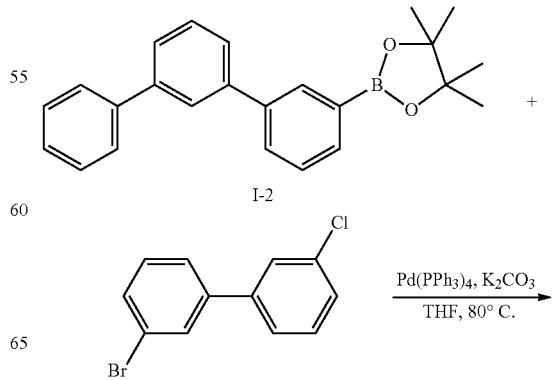

-continued

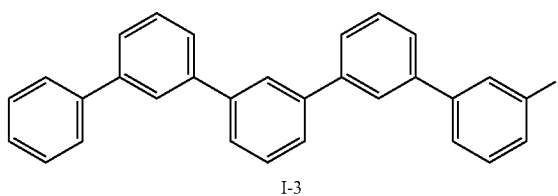

I-3

The intermediate I-2 (50 g, 140 mmol) was dissolved in 1 L of THF under a nitrogen environment, 3-bromo-3'-chlorobiphenyl (56 g, 210 mmol) and tetrakis(triphenylphosphine)palladium (Pd(PPh$_3$)$_4$, 8.1 g, 7.02 mmol) were added thereto, and the mixture was stirred. Potassium carbonate saturated in water (K$_2$CO$_3$, 39 g, 280 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain an intermediate I-3 (57 g, 70%).

HRMS (70 eV, EI+): m/z calcd for C30H21Cl: 416.94, found 416.

Elemental Analysis: C, 86%; H, 5%

Synthesis Example 4: Synthesis of Intermediate I-4

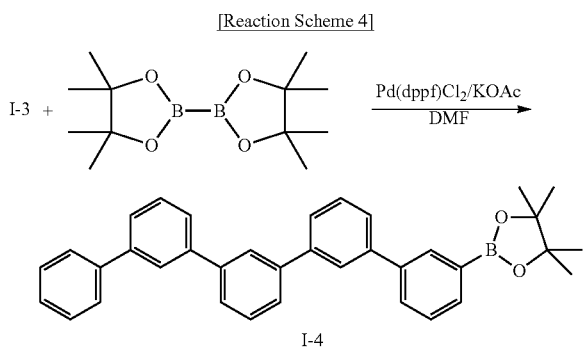

I-4

The intermediate I-3 (55 g, 132 mmol) was dissolved in 1 L of dimethylforamide (DMF) under a nitrogen environment, bis(pinacolato)diboron (40 g, 158 mmol), (1,1'-bis(diphenylphosphine)ferrocene)dichloropalladium (II) (Pd(dppf)Cl$_2$, 4.55 g, 7.9 mmol), and potassium acetate (KOAc, 38.8 g, 396 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain an intermediate I-4 (50 g, 75%).

HRMS (70 eV, EI+): m/z calcd for C361-H33BO2: 508.46, found: 508.

Elemental Analysis: C, 85%; H, 6%

Synthesis Example 5: Synthesis of Intermediate I-5

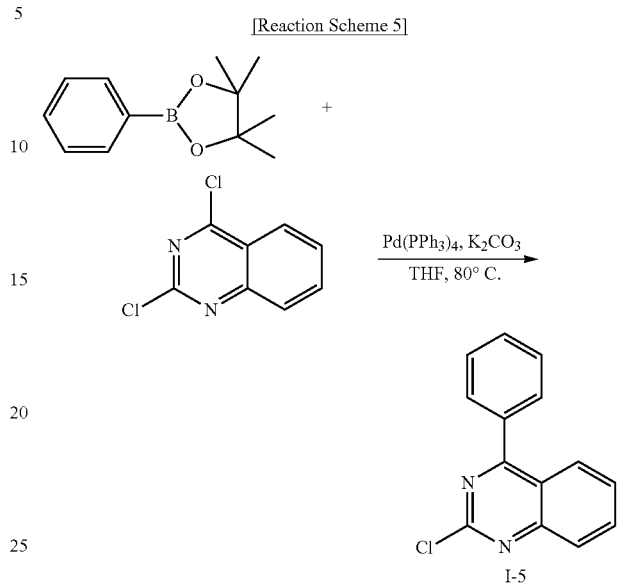

I-5

4,4,5,5-tetramethyl-2-phenyl-1,3,2-dioxaborolane (20 g, 100 mmol) was dissolved in 1 L of THF under a nitrogen environment, 2,4-dichloroquinazoline (20.5 g, 100 mmol) and tetrakis(triphenylphosphine)palladium (Pd(PPh$_3$)$_4$, 2.9 g, 2.51 mmol) were added thereto, and the mixture was stirred. Potassium carbonate saturated in water (K$_2$CO$_3$, 28 g, 200 mmol) was added thereto, and the resulting mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain an intermediate I-5 (17 g, 70%).

HRMS (70 eV, EI+): m/z calcd for C14H9ClN2: 240.69, found 240.

Elemental Analysis: C, 69%; H, 3%

Synthesis Example 6: Synthesis of Intermediate I-6

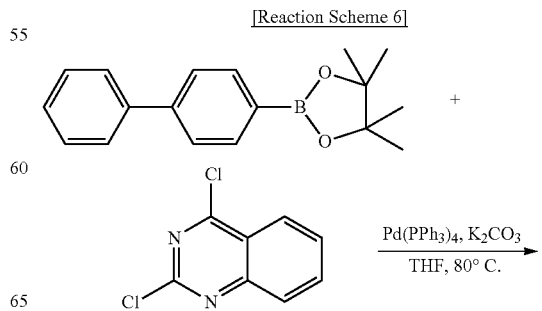

-continued

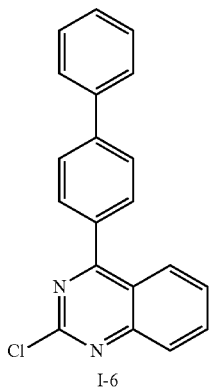

I-6

2-(biphenyl-4-yl)-4,4,5,5-tetramethyl-1,3,2-dioxaborolane (20 g, 100 mmol) was dissolved in 1 L of THF under a nitrogen environment, 2,4-dichloroquinazoline (28.2 g, 100 mmol) and tetrakis(triphenylphosphine)palladium (Pd(PPh$_3$)$_4$, 2.9 g, 2.51 mmol) were added thereto, and the mixture was stirred. Potassium carbonate saturated in water (K$_2$CO$_3$, 28 g, 200 mmol) was added thereto, and the mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain an intermediate I-6 (22.3 g, 70%).

HRMS (70 eV, EI+): m/z calcd for C20I-H13ClN2: 316.78, found 316.

Elemental Analysis: C, 75%; H, 4%

Synthesis Example 7: Synthesis of Intermediate I-7

[Reaction Scheme 7]

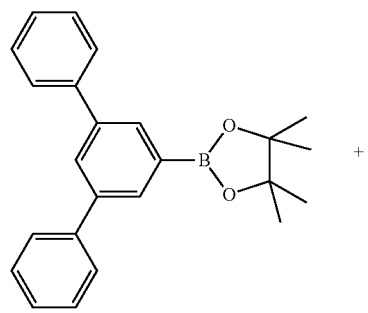

+

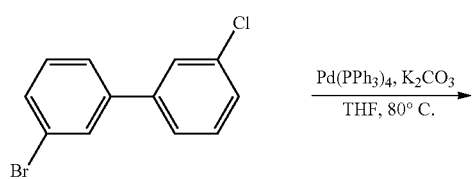

-continued

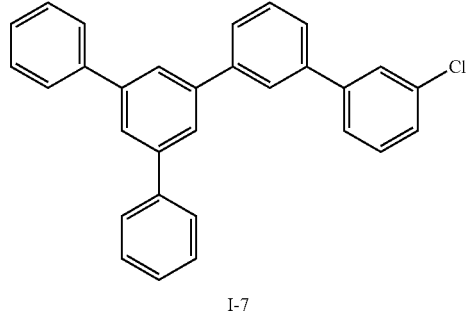

I-7

2-(terphenyl-3-yl)-4,4,5,5-tetramethyl-1,3,2-dioxaborolane (20 g, 56 mmol) was dissolved in 250 ml of THF under a nitrogen environment, 3-bromo-3'-chlorobiphenyl (22.5 g, 84 mmol) and tetrakis(triphenylphosphine)palladium (Pd(PPh$_3$)$_4$) (3.24 g, 2.8 mmol) were added thereto, and the mixture was stirred. Potassium carbonate saturated in water (K$_2$CO$_3$, 15.5 g, 112 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain an intermediate I-7 (21 g, 65%).

HRMS (70 eV, EI+): m/z calcd for C30H21Cl: 416.94, found 416.

Elemental Analysis: C, 86%; H, 5%

Synthesis Example 8: Synthesis of Intermediate I-8

[Reaction Scheme 8]

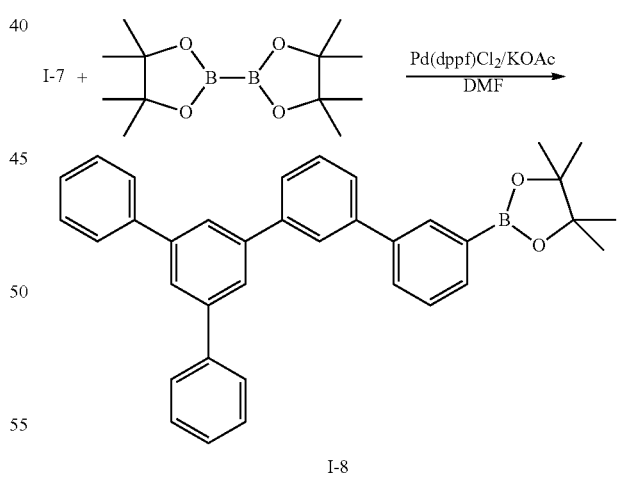

I-8

The intermediate I-7 (55 g, 132 mmol) was dissolved in 1 L of dimethylforamide (DMF) under a nitrogen environment, bis(pinacolato)diboron (40 g, 158 mmol), (1,1'-bis(diphenylphosphine)ferrocene)dichloropalladium (II) (Pd(dppf)Cl$_2$, 4.55 g, 7.9 mmol), and potassium acetate (KOAc, 38.8 g, 396 mmol) were added thereto, and the obtained mixture was heated and refluxed at 150° C. for 5 hours. When the reaction was complete, water was added to the reaction solution, and the mixture was filtered and dried in a vacuum oven. This obtained residue was separated and purified through flash column chromatography to obtain an intermediate I-8 (47 g, 70%).

HRMS (70 eV, EI+): m/z calcd for C36H33BO2: 508.46, found: 508.

Elemental Analysis: C, 85%; H, 6%

Synthesis Example 9: Synthesis of Intermediate I-9

[Reaction Scheme 9]

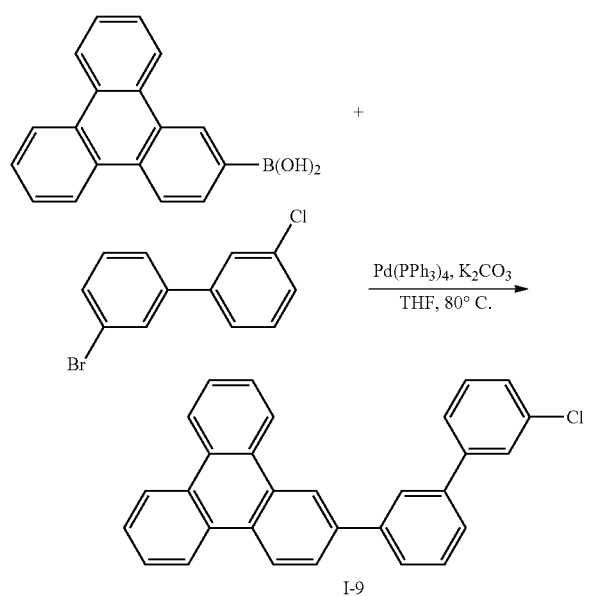

Triphenylen-2-ylboronic acid (20 g, 73.5 mmol) was dissolved in 300 ml of THF under a nitrogen environment, 3-bromo-3'-chlorobiphenyl (30 g, 110 mmol) and tetrakis (triphenylphosphine)palladium (Pd(PPh3)4) (4.25 g, 3.67 mmol) were added thereto, and the mixture was stirred. Potassium carbonate saturated in water (K2CO3, 20.32 g, 138 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO4 and then, concentrated under a reduced pressure. This obtained residue was separated and purified through flash column chromatography to obtain an intermediate I-9 (20 g, 65%).

HRMS (70 eV, EI+): m/z calcd for C30H19Cl: 414.92, found 414.

Elemental Analysis: C, 86%; H, 4%

Synthesis Example 10: Synthesis of Intermediate I-10

[Reaction Scheme 10]

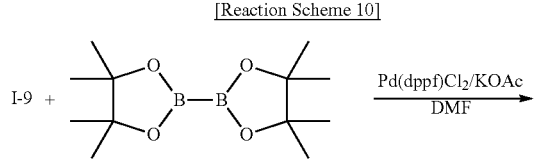

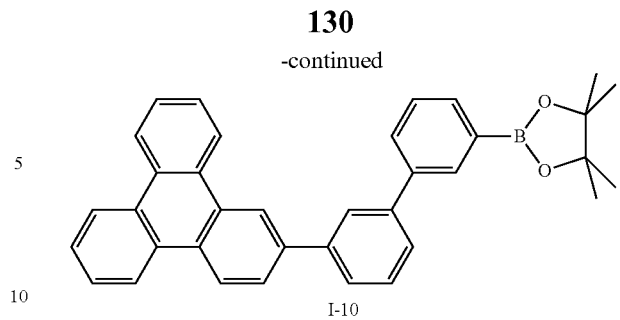

The intermediate I-9 (20 g, 48.2 mmol) was dissolved in 1 L of dimethylforamide (DMF) under a nitrogen environment, bis(pinacolato)diboron (14.7 g, 57.84 mmol), (1,1'-bis(diphenylphosphine)ferrocene)dichloropalladium (II) (Pd (dppf)Cl2, 1.66 g, 3 mmol), and potassium acetate (KOAc, 14.2 g, 144 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain an intermediate I-10 (16 g, 65%).

HRMS (70 eV, EI+): m/z calcd for C36H33BO2: 506.44, found: 506.

Elemental Analysis: C, 85%; H, 6%

Synthesis Example 11: Synthesis of Intermediate I-11

[Reaction Scheme 11]

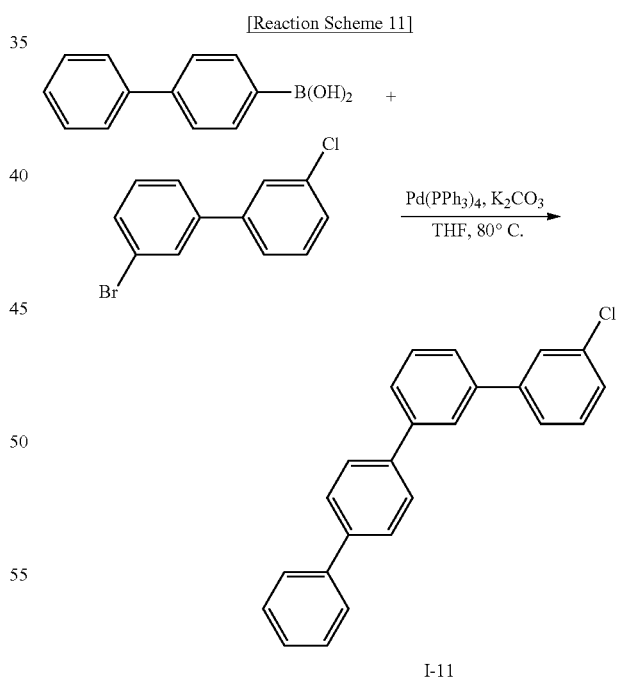

Biphenyl-4-ylboronic acid (15 g, 75.8 mmol) was dissolved in 300 ml of THF under a nitrogen environment, 3-bromo-3'-chlorobiphenyl (30.4 g, 113.6 mmol) and tetrakis(triphenylphosphine)palladium (Pd(PPh3)4) (4.38 g, 3.8 mmol) were added thereto, and the mixture was stirred. Potassium carbonate saturated in water (K2CO3, 21 g, 151 mmol) was added thereto, and the mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO₄ and then, concentrated under a reduced pressure. This obtained residue was separated and purified through flash column chromatography to obtain an intermediate I-11 (14 g, 55%).

HRMS (70 eV, EI+): m/z calcd for C24H17Cl: 340.84, found 340.

Elemental Analysis: C, 84%; H, 5%

Synthesis Example 12: Synthesis of Intermediate I-12

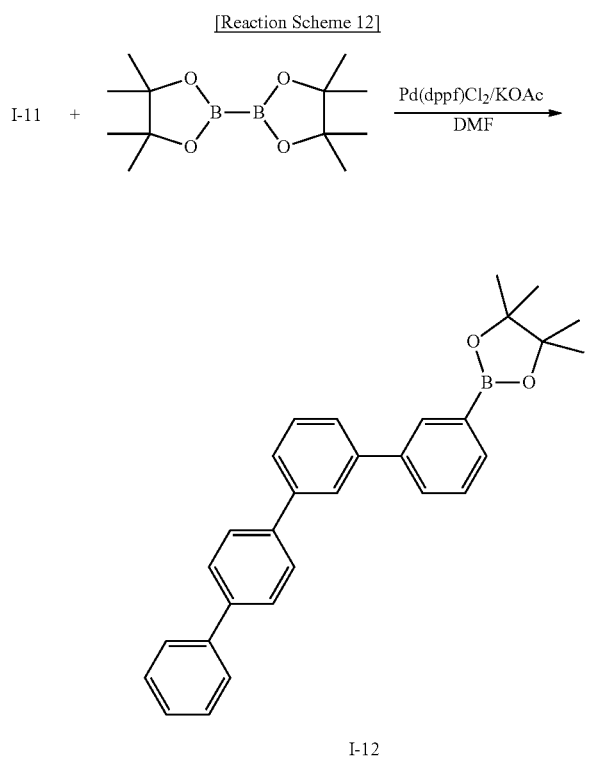

The intermediate I-11 (20 g, 58.7 mmol) was dissolved in 300 ml of dimethylforamide (DMF) under a nitrogen environment, bis(pinacolato)diboron (17.9 g, 70.4 mmol), (1,1'-bis(diphenylphosphine)ferrocene)dichloropalladium (II) (Pd(dppf)Cl₂, 2 g, 3.5 mmol), and potassium acetate (KOAc, 17.3 g, 176 mmol) were added thereto, and the obtained mixture was heated and refluxed at 150° C. for 5 hours. When the reaction was complete, water was added to the reaction solution, and the mixture was filtered and dried in a vacuum oven. This obtained residue was separated and purified through flash column chromatography to obtain an intermediate I-12 (20.3 g, 80%).

HRMS (70 eV, EI+): m/z calcd for C30H29BO2: 432.36, found: 432.

Elemental Analysis: C, 83%; H, 6%

Synthesis of Final Compound

Synthesis Example 13: Synthesis of Compound 19

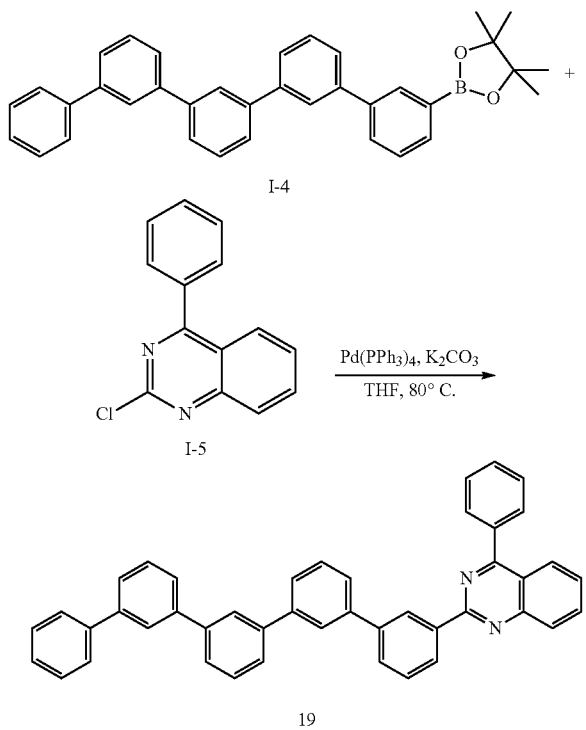

The intermediate I-4 (13 g, 25.6 mmol) was dissolved in 100 ml of THF under a nitrogen environment, the intermediate I-5 (6.78 g, 28.1 mmol) and tetrakis(triphenylphosphine)palladium (Pd(PPh₃)₄, 1.5 g, 1.28 mmol) were added thereto, and the mixture was stirred. Potassium carbonate saturated in water (K₂CO₃, 7 g, 51.1 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO₄ and then, concentrated under a reduced pressure. This obtained residue was separated and purified through flash column chromatography to obtain a compound 19 (12 g, 80%).

HRMS (70 eV, EI+): m/z calcd for C44H30N2: 586.72, found 586.

Elemental Analysis: C, 90%; H, 5%

Synthesis Example 14: Synthesis of Compound 20

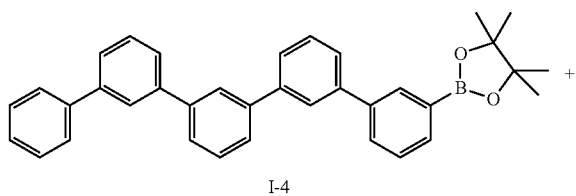

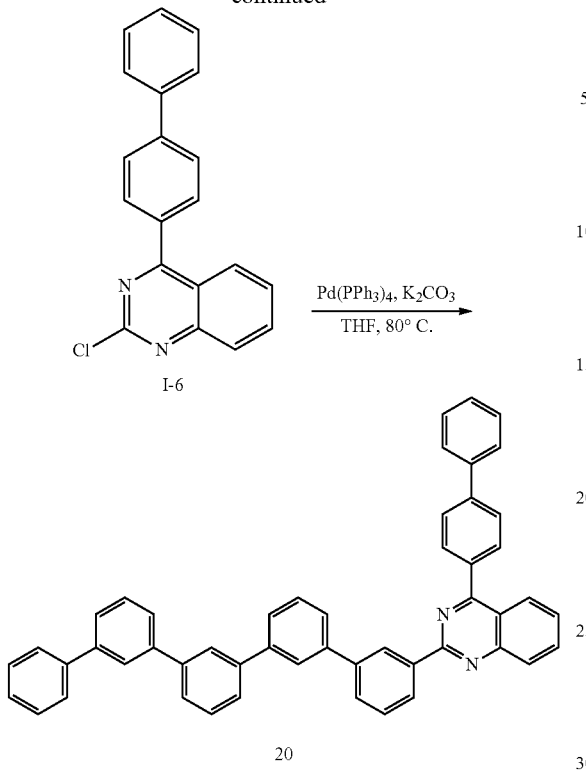

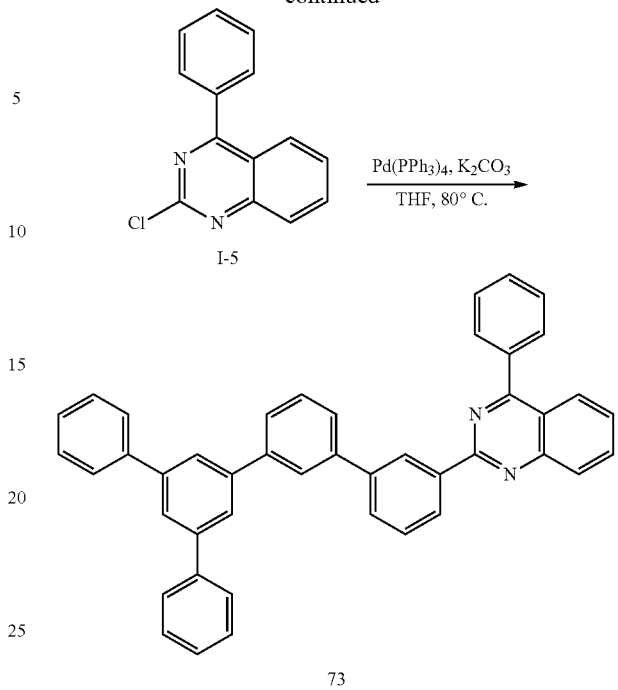

The intermediate I-4 (13 g, 25.6 mmol) was dissolved in 100 ml of THF under a nitrogen environment, the intermediate I-6 (8.9 g, 28.1 mmol) and tetrakis(triphenylphosphine)palladium (Pd(PPh$_3$)$_4$, 1.5 g, 1.28 mmol) were added thereto, and the mixture was stirred. Potassium carbonate saturated in water (K$_2$CO$_3$, 7 g, 51.1 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain a compound 20 (12.7 g, 75%).

HRMS (70 eV, EI+): m/z calcd for C50H34N2: 662.82, found 662.

Elemental Analysis: C, 90%; H, 5%

Synthesis Example 15: Synthesis of Compound 73

The intermediate I-8 (10 g, 19.7 mmol) was dissolved in 100 ml of THF under a nitrogen environment, the intermediate I-5 (5.21 g, 21.6 mmol) and tetrakis(triphenylphosphine)palladium (Pd(PPh$_3$)$_4$, 1.14 g, 0.98 mmol) were added thereto, and the mixture was stirred. Potassium carbonate saturated in water (K$_2$CO$_3$, 5.4 g, 39.3 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain a compound 73 (9.2 g, 80%).

HRMS (70 eV, EI+): m/z calcd for C44H30N2: 586.72, found 586.

Elemental Analysis: C, 90%; H, 5%

Synthesis Example 16: Synthesis of Compound 74

[Reaction Scheme 15]

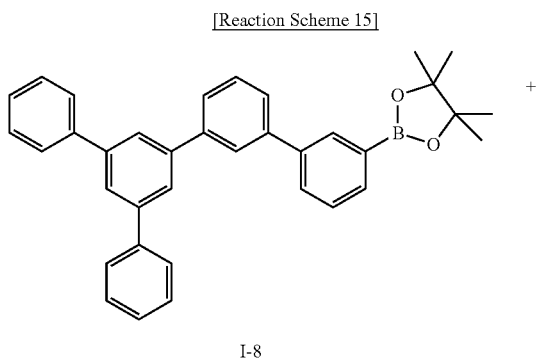

[Reaction Scheme 16]

-continued

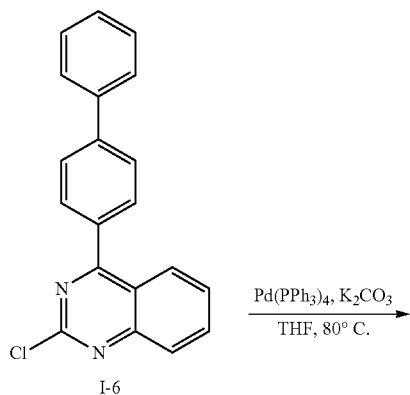

Synthesis Example 17: Synthesis of Compound 128

[Reaction Scheme 17]

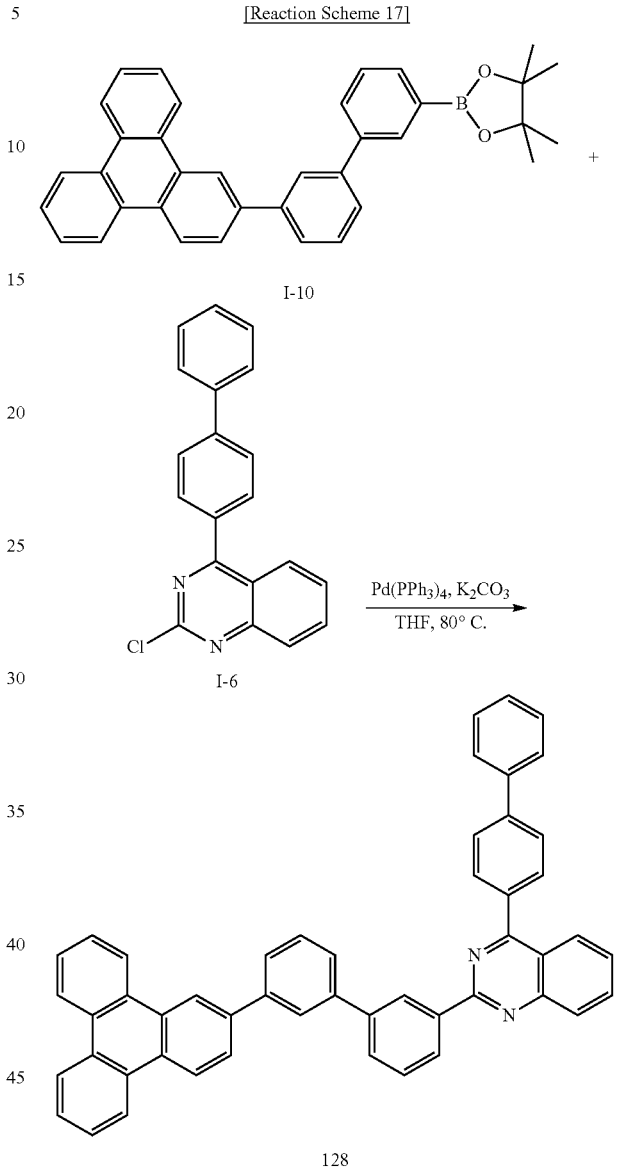

The intermediate I-8 (10 g, 19.6 mmol) was dissolved in 100 ml of THF under a nitrogen environment, the intermediate I-6 (6.85 g, 21.6 mmol) and tetrakis(triphenylphosphine)palladium (Pd(PPh$_3$)$_4$, 1.14 g, 0.98 mmol) were added thereto, and the mixture was stirred. Potassium carbonate saturated in water (K$_2$CO$_3$, 5.4 g, 39.3 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain a compound 74 (11 g, 85%).

HRMS (70 eV, EI+): calcd for C50H34N2: 662.82, found 662.

Elemental Analysis: C, 90%; H, 5%

The intermediate I-10 (10 g, 19.8 mmol) was dissolved in 100 ml of THF under a nitrogen environment, the intermediate I-6 (6.88 g, 21.7 mmol) and tetrakis(triphenylphosphine)palladium (Pd(PPh$_3$)$_4$, 1.14 g, 0.99 mmol) were added thereto, and the obtained mixture was stirred. Potassium carbonate saturated in water (K$_2$CO$_3$, 5.4 g, 39.5 mmol) was added thereto, and the mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain a compound 128 (10 g, 75%).

HRMS (70 eV, EI+): m/z calcd for C50H34N2: 660.80, found 660.

Elemental Analysis: C, 90%; H, 4%

Synthesis Example 18: Synthesis of Compound 186

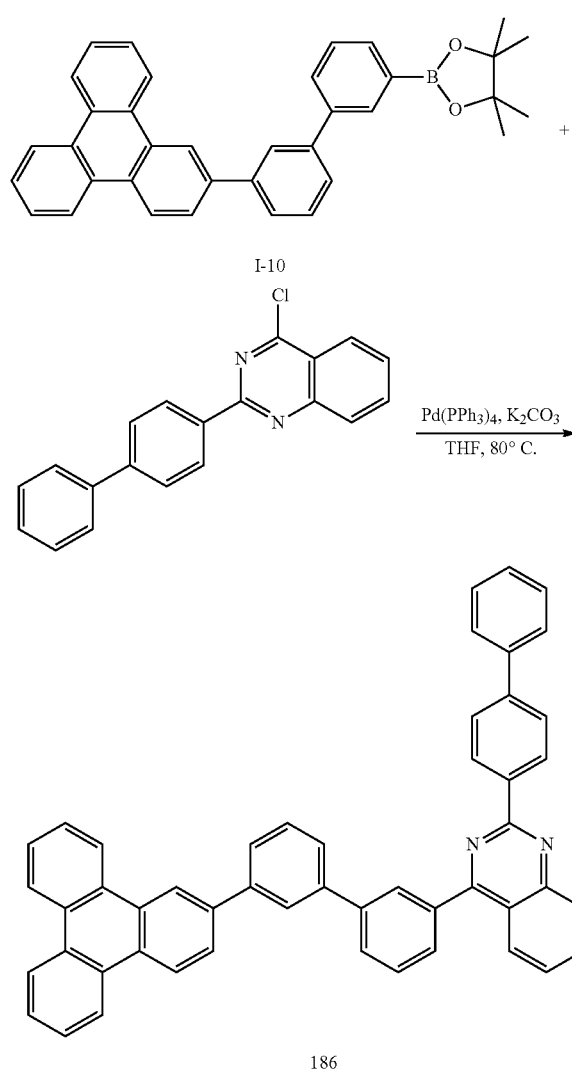

Synthesis Example 19: Synthesis of Compound 187

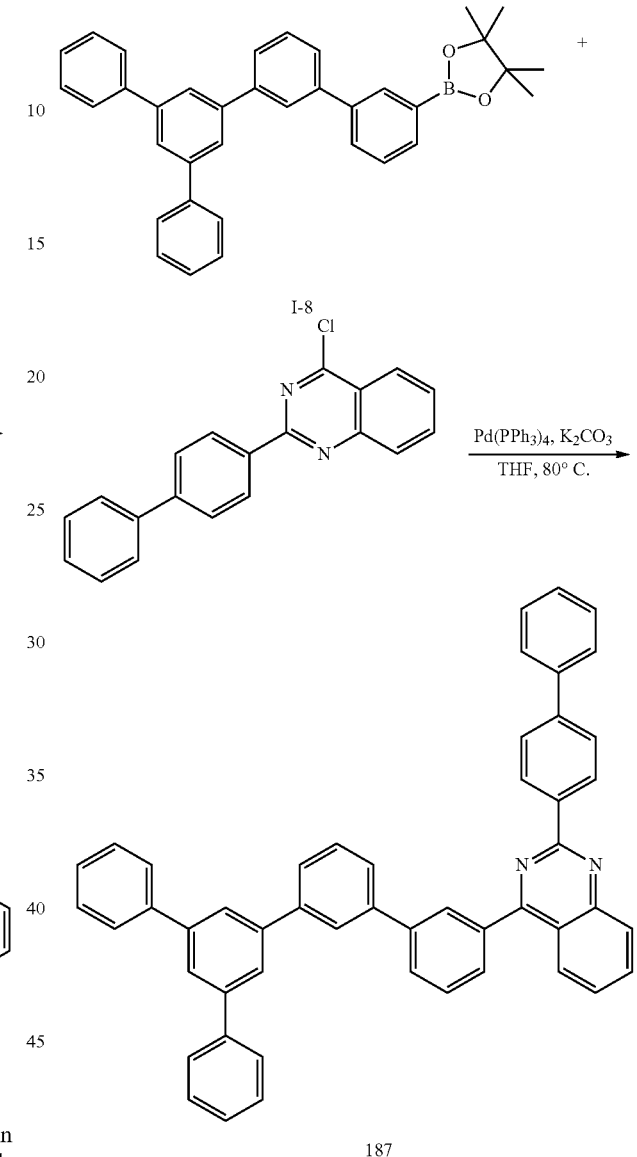

The intermediate I-10 (10 g, 19.8 mmol) was dissolved in 100 ml of THF under a nitrogen environment, 2-(biphenyl-4-yl)-4-chloroquinazoline (6.88 g, 21.7 mmol) and tetrakis(triphenylphosphine)palladium (Pd(PPh$_3$)$_4$, 1.14 g, 0.99 mmol) were added thereto, and the mixture was stirred. Potassium carbonate saturated in water (K$_2$CO$_3$, 5.4 g, 39.5 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain a compound 186 (9.3 g, 70%).

HRMS (70 eV, EI+): m/z calcd for C50H34N2: 660.80, found 660.

Elemental Analysis: C, 90%; H, 4%

The intermediate I-8 (10 g, 19.6 mmol) was dissolved in 100 ml of THE under a nitrogen environment, 2-(biphenyl-4-yl)-4-chloroquinazoline (6.85 g, 21.6 mmol) and tetrakis(triphenylphosphine)palladium (Pd(PPh$_3$)$_4$, 1.14 g, 0.98 mmol) were added thereto, and the mixture was stirred. Potassium carbonate saturated in water (K$_2$CO$_3$, 5.4 g, 39.3 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain a compound 187 (10.4 g, 80%).

HRMS (70 eV, EI+): m/z calcd for C50H34N2: 662.82, found 662.

Elemental Analysis: C, 90%; H, 5%

Synthesis Example 20: Synthesis of Compound 188

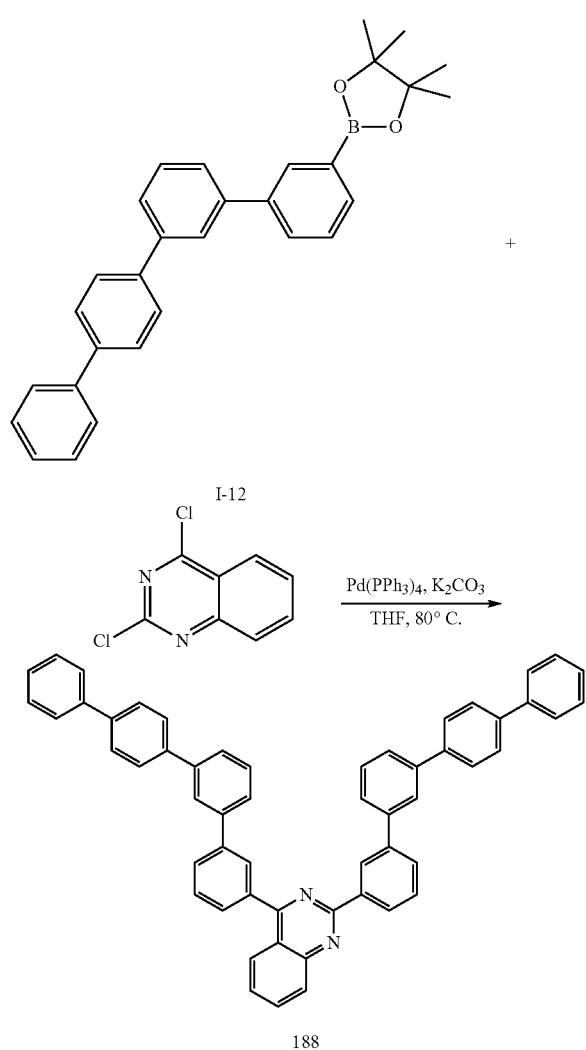

The intermediate I-12 (19 g, 44.2 mmol) was dissolved in 150 ml of THF under a nitrogen environment, 2,4-dichloroquinazoline (4 g, 20.1 mmol) and tetrakis(triphenylphosphine)palladium (Pd(PPh$_3$)$_4$, 1.16 g, 1.00 mmol) were added thereto, and the mixture was stirred. Potassium carbonate saturated in water (K$_2$CO$_3$, 11.11 g, 80.4 mmol) was added thereto, and the obtained mixture was heated and refluxed at 80° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain a compound 188 (10 g, 67%).

HRMS (70 eV, EI+): m/z calcd for C50H34N2: 738.91, found 738.

Elemental Analysis: C, 91%; H, 5%

Evaluation 1: Energy Level of Compounds

Energy level of each compound according to Synthesis Examples 13 to 17 was calculated in a Gaussian 09 method by using a super computer, GATA (IBA power 6).

The results are shown in Table 1.

TABLE 1

|  | Compound | HOMO | LUMO |
| --- | --- | --- | --- |
| Synthesis Example 13 | compound 19 | −5.835 | −1.923 |
| Synthesis Example 14 | compound 20 | −5.833 | −1.967 |
| Synthesis Example 15 | compound 73 | −5.851 | −1.926 |
| Synthesis Example 16 | compound 74 | −5.849 | −1.971 |
| Synthesis Example 17 | compound 128 | −5.626 | −1.973 |
|  | CBP | −5.315 | −1.234 |

Referring to Table 1, the compounds according to Synthesis Examples 13 to 17 turned out to have a relatively low LUMO energy level. Accordingly, when the compounds according to Synthesis Examples 13 to 17 were respectively applied to an emission layer for an organic light emitting diode, electrons were expected to easily move, and thus the organic light emitting diode was expected to have a low driving voltage, high luminous efficiency, and sufficient life-span characteristics.

Manufacture of Organic Light Emitting Diode I

Example 1

An organic light emitting diode was manufactured by using the compound 19 of Synthesis Example 13 as a host and (piq)$_2$Ir(acac) as a dopant.

As for an anode, 1000 Å-thick ITO was used, and as for a cathode, 1000 Å-thick aluminum (Al) was used. Specifically, illustrating a method of manufacturing the organic light emitting diode, the anode is manufactured by cutting an ITO glass substrate having 15 Ω/cm$^2$ of a sheet resistance into a size of 50 mm×50 mm×0.7 mm, ultrasonic wave-cleaning them in acetone, isopropylalcohol, and pure water for 15 minutes respectively, and UV ozone cleaning them for 30 minutes.

On the substrate, an 800 Å-thick hole transport layer (HTL) was formed by depositing N4,N4'-di(naphthalen-1-yl)-N4,N4'-diphenylbiphenyl-4,4'-diamine (NPB) (80 nm) under a vacuum degree of 650×10$^{-7}$ Pa at a deposition rate of 0.1 to 0.3 nm/s. Subsequently, A 300 Å-thick emission layer was formed by using the compound 19 of Synthesis Example 13 under the same vacuum deposition condition, and a phosphorescent dopant of (piq)$_2$Ir(acac) was simultaneously deposited. Herein, the phosphorescent dopant was deposited to be 2 wt % based on 100 wt % of the total weight of the emission layer by adjusting the deposition rate.

On the emission layer, a 50 Å-thick hole blocking layer was formed by depositing bis(2-methyl-8-quinolinolate)-4-(phenylphenolato)aluminum (BAlq) under the same vacuum deposition condition. Subsequently, a 200 Å-thick electron transport layer (ETL) was formed by depositing Alq3 under the same vacuum deposition condition. On the electron transport layer (ETL), a cathode is formed by sequentially depositing LiF and Al to manufacture an organic photoelectric device.

The organic photoelectric device has a structure of ITO/NPB (80 nm)/EML (compound 19 (98 wt %)+(piq)$_2$Ir(acac) (2 wt %), 30 nm)/Balq (5 nm)/Alq3 (20 nm)/LiF (1 nm)/Al (100 nm).

Example 2

An organic light emitting diode was manufactured according to the same method as Example 1 except that the compound 20 of Synthesis Example 14 was used instead of the compound 19 of Synthesis Example 13.

Example 3

An organic light emitting diode was manufactured according to the same method as Example 1 except that the compound 73 of Synthesis Example 15 was used instead of the compound 19 of Synthesis Example 13.

Example 4

An organic light emitting diode was manufactured according to the same method as Example 1 except that the compound 74 of Synthesis Example 16 was used instead of the compound 19 of Synthesis Example 13.

Example 5

An organic light emitting diode was manufactured according to the same method as Example 1 except that the compound 128 of Synthesis Example 17 was used instead of the compound 19 of Synthesis Example 13.

Example 6

An organic light emitting diode was manufactured according to the same method as Example 1 except that the compound 186 of Synthesis Example 18 was used instead of the compound 19 of Synthesis Example 13.

Example 7

An organic light emitting diode was manufactured according to the same method as Example 1 except that the compound 187 of Synthesis Example 19 was used instead of the compound 19 of Synthesis Example 13.

Example 8

An organic light emitting diode was manufactured according to the same method as Example 1 except that the compound 188 of Synthesis Example 20 was used instead of the compound 19 of Synthesis Example 13.

Comparative Example 1

An organic light emitting diode was manufactured according to the same method as Example 1 except that CBP was used instead of the compound 19 of Synthesis Example 13.

The structures of NPB, BAlq, CBP, and (piq)$_2$Ir(acac) used to manufacture the organic light emitting diodes are as follows.

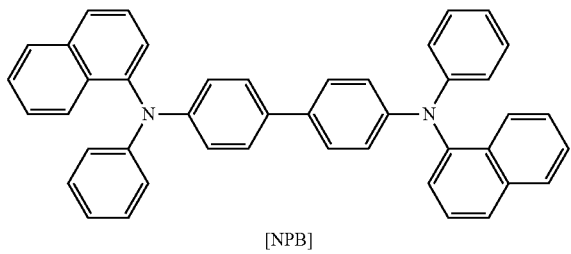

[NPB]

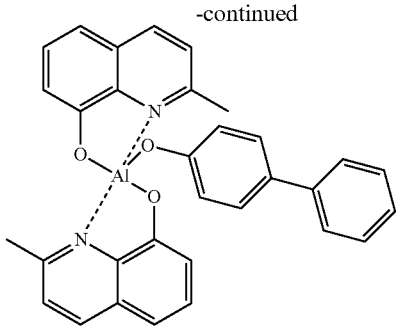

[BAlq]

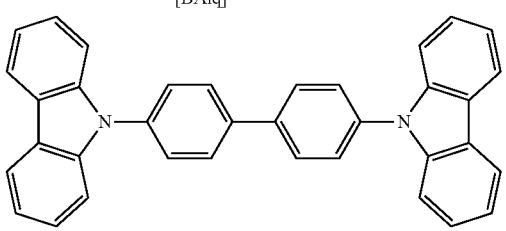

[CBP]

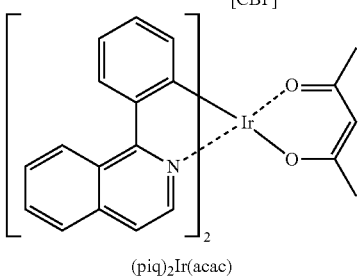

(piq)$_2$Ir(acac)

Evaluation 2

Current density and luminance changes depending on a voltage and luminous efficiency of each organic light emitting diode according to Examples 1 to 8 and Comparative Example 1 were measured.

The measurements were specifically performed in the following methods, and the results are shown in Table 2.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm$^2$) was calculated by using the luminance, current density, and voltages (V) from the items (1) and (2).

(4) Measurement of Life-Span

Life-span was obtained by measuring time taken until current efficiency (cd/A) decreased down to 90% while luminance (cd/m$^2$) was maintained at 2200 cd/m$^2$.

TABLE 2

| No. | Compound | Driving voltage (V) | Color (EL color) | Efficiency (cd/A) | 90% life-span (h) at 2200 cd/m2 |
|---|---|---|---|---|---|
| Example 1 | compound 19 | 4.5 | Red | 15.8 | 100 |
| Example 2 | compound 20 | 4.4 | Red | 12.4 | 95 |
| Example 3 | compound 73 | 4.8 | Red | 10.7 | 80 |
| Example 4 | compound 74 | 4.7 | Red | 10.7 | 75 |
| Example 5 | compound 128 | 5.2 | Red | 6.6 | 90 |
| Example 6 | compound 186 | 5.0 | Red | 8.0 | 85 |
| Example 7 | compound 187 | 5.6 | Red | 20.4 | 70 |
| Example 8 | compound 188 | 4.7 | Red | 18.8 | 70 |
| Comparative Example 1 | CBP | 6.5 | Red | 4.5 | 10 |

Referring to Table 2, the organic light emitting diodes according to Examples 1 to 8 exhibited a low driving voltage, high luminous efficiency, and sufficient life-span characteristics compared with the organic light emitting diode according to Comparative Example 1.

Specifically, the organic light emitting diodes according to the present invention exhibited an energy level capable of easily transferring electrons due to electron strong structural electron characteristics and thus exhibited a low driving voltage and high luminous efficiency characteristics. The organic light emitting diodes of Examples using compounds including consecutive linear meta bonds showed a little longer life-span. The reason is that a phenyl group having hole characteristics at the terminal end and a quinazoline structure having electron characteristics are sufficiently localized and minimized interference effect therebetween.

Synthesis Example of Second Host Compound

Synthesis Example 1 of Second Host Compound: Synthesis of Compound C-10

[Reaction Scheme 54]

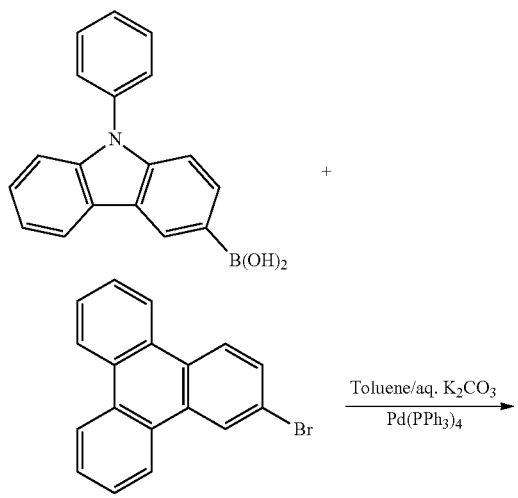

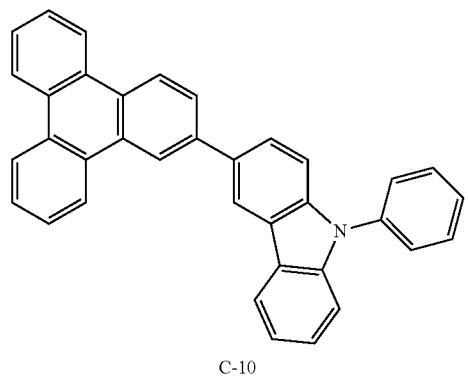

C-10

The compound phenylcarbazolyl boronic acid (10 g, 34.83 mmol) was dissolved in 0.2 L 0.2 L of toluene under a nitrogen environment, 2-bromotriphenylene (11.77 g, 38.31 mmol) and tetrakis(triphenylphosphine)palladium (0.80 g, 0.7 mmmol) were added thereto, and the mixture was stirred. Potassium carbonate saturated in water (14.44 g, 104.49 mmol) was added thereto, and the obtained mixture was heated and refluxed at 120° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. The obtained residue was separated and purified through flash column chromatography to obtain the compound C-10 (14.4 g, 88%).

HRMS (70 eV, EI+): m/z calcd for C36H23N: 469.18, found: 469.

Elemental Analysis: C, 92%; H, 5%

Synthesis Example 2 of Second Host Compound: Synthesis of Compound B-10

[Reaction Scheme 55]

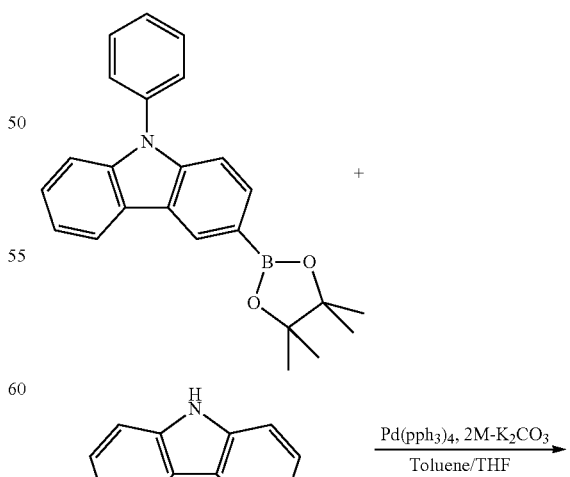

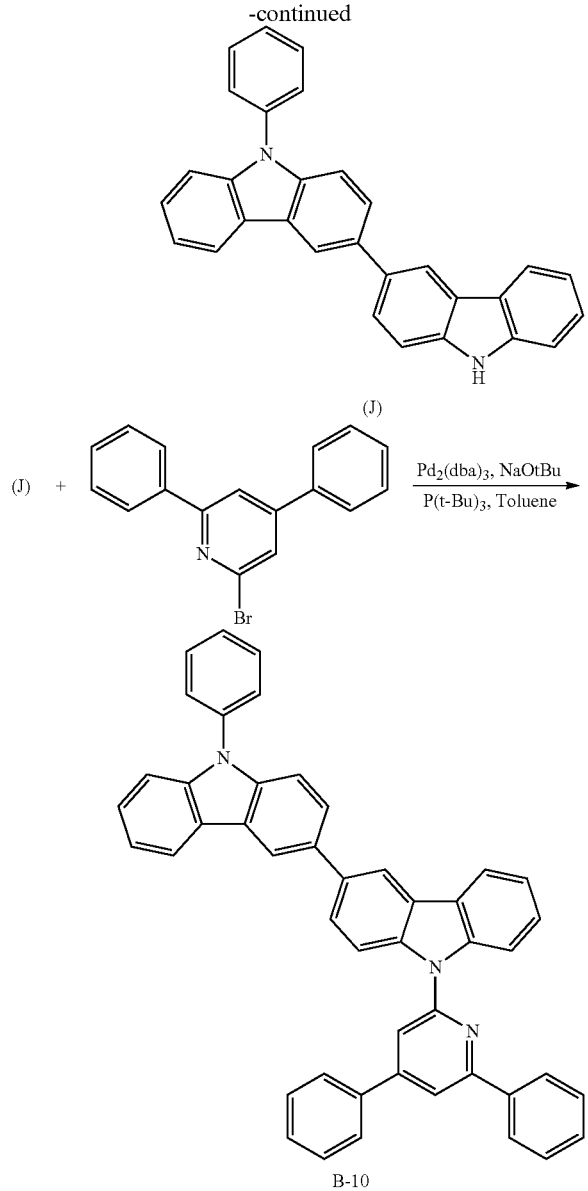

(J)

(J) + [structure] →Pd₂(dba)₃, NaOtBu / P(t-Bu)₃, Toluene→

B-10

First Step: Synthesis of Compound J

The compound 9-phenyl-3-(4,4,5,5-tetramethyl-1,3,2-dioxaborolan-2-yl)-9H-carbazole (26.96 g, 81.4 mmol) was dissolved in 0.2 L of toluene/THF under a nitrogen environment, 3-bromo-9H-carbazole (23.96 g, 97.36 mmol) and tetrakis(triphenylphosphine)palladium (0.90 g, 0.8 mmmol) were added thereto, and the mixture was stirred. Potassium carbonate saturated in water (28 g, 203.49 mmol) was added thereto, and the obtained mixture was heated and refluxed at 120° C. for 12 hours. When the reaction was complete, water was added to the reaction solution, dichloromethane (DCM) was used for an extraction, and an extract therefrom was filtered after removing moisture with anhydrous MgSO₄ and then, concentrated under a reduced pressure. The obtained residue was separated and purified through flash column chromatography to obtain the compound J (22.6 g, 68%).

HRMS (70 eV, EI+): m/z calcd for C30H20N2: 408.16, found: 408.

Elemental Analysis: C, 88%; H, 5%

Second Step: Synthesis of Compound B-10

The compound J (22.42 g, 54.88 mmol) was dissolved in 0.2 L of toluene under a nitrogen environment, 2-bromo-4,6-diphenylpyridine (20.43 g, 65.85 mmol), NaOtBu (7.92 g, 82.32 mmol), tris(dibenzylideneacetone)dipalladium (0, 1.65 g, 1.65 mmol), and tri-tert-butylphosphine (1.78 g, 4.39 mmol) were added thereto, and the mixture was heated and refluxed at 120° C. for 12 hours. When the reaction was complete, water was added to the reaction solution, dichloromethane (DCM) was used for an extraction, and an extract therefrom was filtered after removing moisture with anhydrous MgSO₄ and then, concentrated under a reduced pressure. The obtained residue was separated and purified through flash column chromatography to obtain the compound B-10 (28.10 g, 80%).

HRMS (70 eV, EI+): m/z calcd for C47H31N3: 637.25, found: 637.

Elemental Analysis: C, 89%; H, 5%

Synthesis Example 3 of Second Host Compound: Synthesis of Compound B-31

[Reaction Scheme 56]

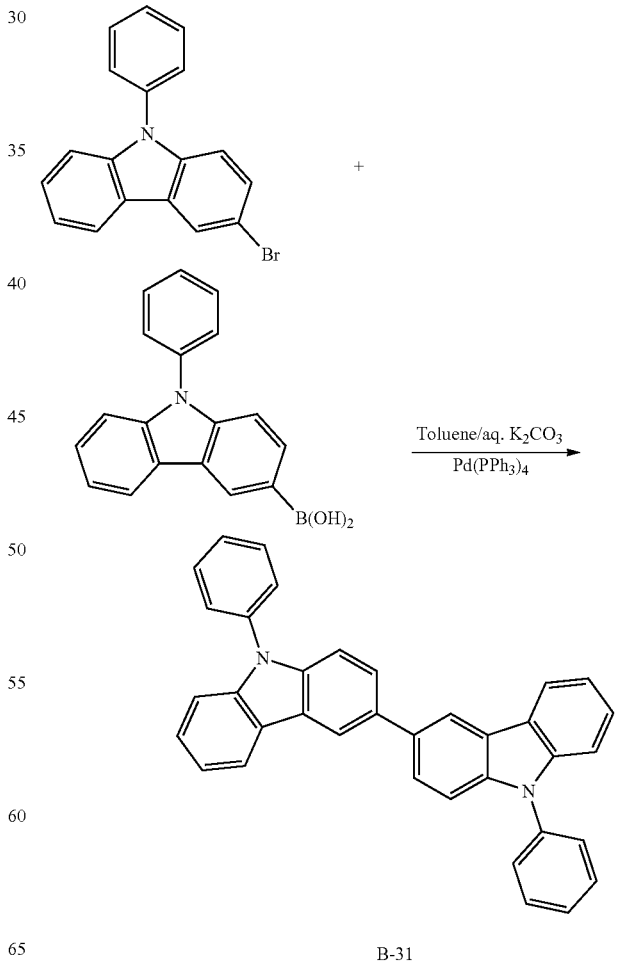

B-31

The compound phenylcarbazolyl bromide (9.97 g, 30.95 mmol) was dissolved in 0.2 L of toluene under a nitrogen environment, phenylcarbazolylboronic acid (9.78 g, 34.05 mmol) and tetrakis(triphenylphosphine)palladium (1.07 g, 0.93 mmmol) were added thereto, and the mixture was stirred. Potassium carbonate saturated in water (12.83 g, 92.86 mmol) was added thereto, and the obtained mixture was heated and refluxed at 120° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. The obtained residue was separated and purified through flash column chromatography to obtain the compound B-31 (13.8 g, 92%).

HRMS (70 eV, EI+): m/z calcd for C36H24N2: 484.19, found: 484.

Elemental Analysis: C, 89%; H, 5%

Synthesis Example 4 of Second Host Compound: Synthesis of Compound B-34

[Reaction Scheme 57]

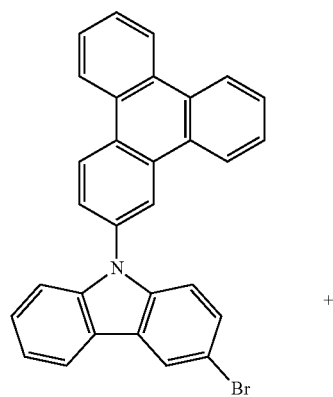

+

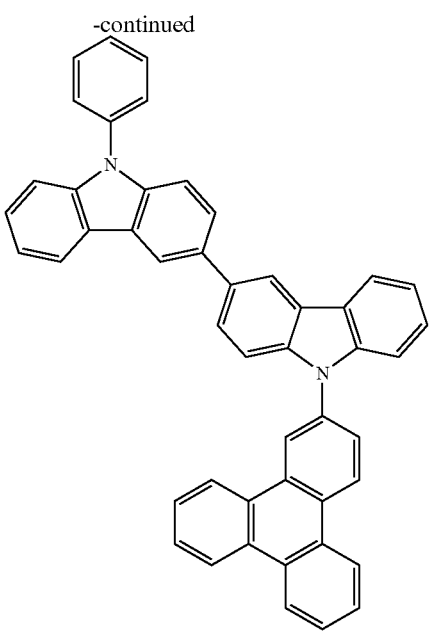

B-34

The compound triphenylcarbazolyl bromide (14.62 g, 30.95 mmol) was dissolved in 0.2 L of toluene under a nitrogen environment, phenylcarbazolylboronic acid (9.78 g, 34.05 mmol) and tetrakis(triphenylphosphine)palladium (1.07 g, 0.93 mmmol) were added thereto, and the mixture was stirred. Potassium carbonate saturated in water (12.83 g, 92.86 mmol) was added thereto, and the obtained mixture was heated and refluxed at 120° C. for 12 hours. When the reaction was complete, water was added to the reaction solution, dichloromethane (DCM) was used for an extraction, and an extract therefrom was filtered after removing moisture with anhydrous MgSO$_4$ and then, concentrated under a reduced pressure. The obtained residue was separated and purified through flash column chromatography to obtain the compound B-34 (16.7 g, 85%).

HRMS (70 eV, EI+): m/z calcd for C47H29N2: 621.23, found: 621.

Elemental Analysis: C, 91%; H, 5%

Synthesis Example 5 of Second Host Compound: Synthesis of Compound B-43

[Reaction Scheme 58]

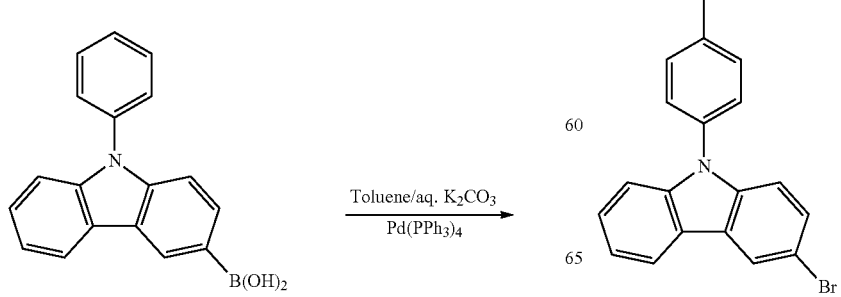

Synthesis Example 6 of Second Host Compound: Synthesis of Compound E-1

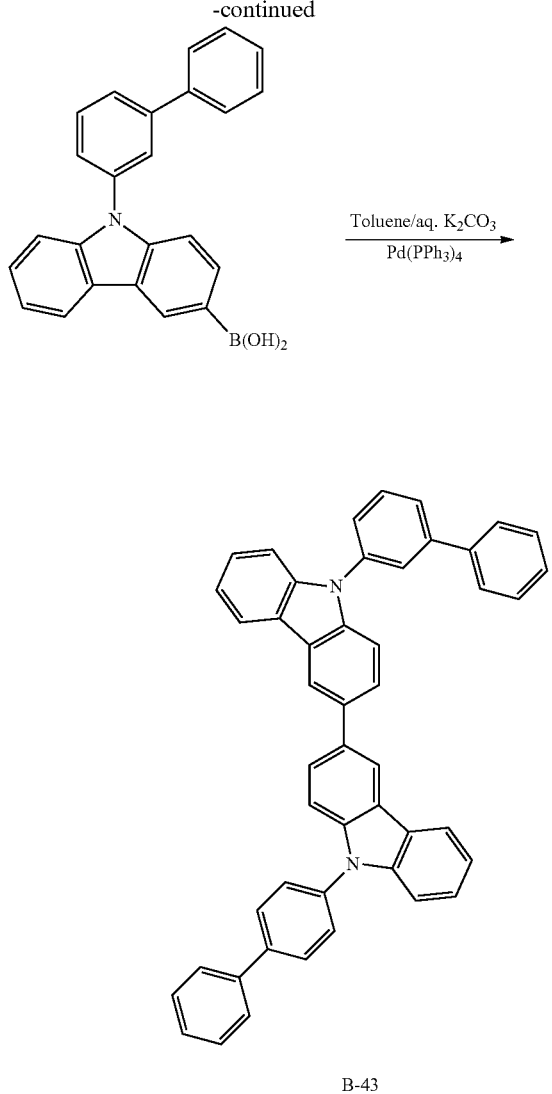

B-43

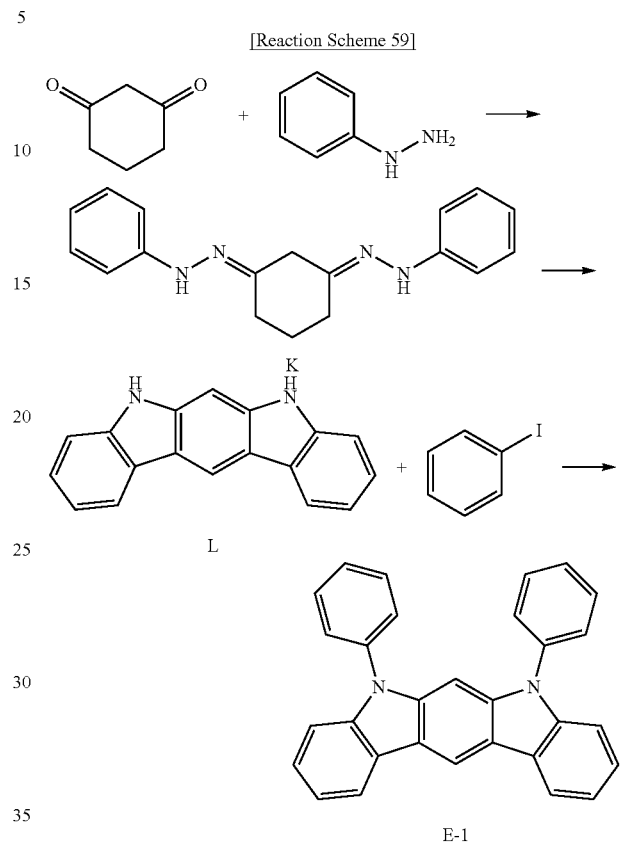

[Reaction Scheme 59]

E-1

The compound, biphenylcarbazolyl bromide (12.33 g, 30.95 mmol) was dissolved in 0.2 L of toluene under a nitrogen environment, biphenylcarbazolylboronic acid (12.37 g, 34.05 mmol) and tetrakis(triphenylphosphine) palladium (1.07 g, 0.93 mmmol) were added thereto, and the mixture was stirred. Potassium carbonate saturated in water (12.83 g, 92.86 mmol) was added thereto, and the obtained mixture was heated and refluxed at 120° C. for 12 hours. When the reaction was complete, water was added to the reaction solution, dichloromethane (DCM) was used for an extraction, and an extract therefrom was filtered after removing moisture with anhydrous $MgSO_4$ and then, concentrated under a reduced pressure. This obtained residue was separated and purified through flash column chromatography to obtain a compound B-43 (18.7 g, 92%).

HRMS (70 eV, EI+): m/z calcd for C48H32N2: 636.26, found: 636.

Elemental Analysis: C, 91%; H, 5%

First Step: Synthesis of Compound K

Phenylhydrazine hydrochloride was dissolved in distilled water, and a 2M NaOH aqueous solution was added thereto. A solid produced therein was filtered to obtain phenylhydrazine. The compound, cyclohexane-1,3-dione (30 g, 267.5 mmol) was dissolved in 1000 ml of ethanol under a nitrogen environment, phenylhydrazine was slowly added thereto, and the mixture was reacted for 20 minutes. When the reaction was complete, ice water was added thereto. A solid produced therein was filtered, while washed with ethanol. The solid was dried under a reduced pressure to obtain a compound K (46.2 g, 38%).

HRMS (70 eV, EI+): m/z calcd for C18H20N4: 292.3782, found: 292.

Elemental Analysis: C, 74%; H, 7%

Second Step: Synthesis of Compound L

The compound K (46.2 g, 102.6 mmol) was slowly put in 140 ml of mixed solution of acetic acid and sulfuric acid in a ratio of 1:4 under a nitrogen environment at 0° C. The obtained mixture was stirred for 5 minutes and heated fast up to 50° C. and slowly up to 110° C. After 20 minutes, the resultant was cooled down to room temperature and stirred for 12 hours. Ethanol was added thereto, and a solid produced one hour later therein was filtered under a reduced pressure and neutralized. The solid was dried under a reduced pressure to obtain the compound L (21.7 g, 51%).

HRMS (70 eV, EI+): m/z calcd for C18H12N2: 256.3013, found: 256.

Elemental Analysis: C, 84%; H, 5%

Third Step: Synthesis of Compound E-1

The compound L (10 g, 39.0 mmol) was added to iodobenzene (10.4 ml, 93.6 mmol), 18-crown-6 (4.2 g, 15.6 mmol), copper (3 g, 46.8 mmol), and potassium carbonate (48.6 g, 351 mmol) under a nitrogen environment, and the mixture was heated and refluxed at 180° C. for 20 hours. When the reaction was complete, water was added to the reaction solution, the mixture was treated with ethyl acetate (e.a) for an extraction, and an extract was filtered after removing moisture with anhydrous MgSO4 and concentrated under a reduced pressure. The obtained residue was separated and purified through flash column chromatography to obtain the compound E-1 (6.7 g, 17.3%).

HRMS (70 eV, EI+): m/z calcd for C30H20N2: 408.4932, found: 408.

Elemental Analysis: C, 88%; H, 5%

Manufacture of Organic Light Emitting Diode II

Example 9

An organic light emitting diode was manufactured by using the compound 20 of Synthesis Example 14 and the compound B-43 as a second host compound of Synthesis Example 5 as a host and (piq)$_2$Ir(acac) as a dopant.

As for an anode, 1000 Å-thick ITO was used, and as for a cathode, 1000 Å-thick aluminum (Al) was used. Specifically, illustrating a method of manufacturing the organic light emitting diode, the anode is manufactured by cutting an ITO glass substrate having 15 Ω/cm$^2$ of a sheet resistance into a size of 50 mm×50 mm×0.7 mm, ultrasonic wave-cleaning them in acetone, isopropylalcohol, and pure water for 15 minutes respectively, and UV ozone cleaning them for 30 minutes.

On the substrate, an 800 Å-thick hole transport layer (HTL) was formed by depositing N4,N4'-di(naphthalen-1-yl)-N4,N4'-diphenylbiphenyl-4,4'-diamine (NPB) (80 nm) under a vacuum degree 650×10$^{-7}$ Pa at a deposition rate of 0.1 to 0.3 nm/s. Subsequently, A 300 Å-thick emission layer was formed by using the compound 20 and the compound B-43 under the same vacuum deposition condition, and a phosphorescent dopant of (piq)$_2$Ir(acac) was simultaneously deposited. Herein, the phosphorescent dopant was deposited to be 2 wt % based on 100 wt % of the total weight of the emission layer by adjusting the deposition rate.

On the emission layer, a 50 Å-thick hole blocking layer was formed by depositing bis(2-methyl-8-quinolinolate)-4-(phenylphenolato)aluminum (BAlq) under the same vacuum deposition condition. Subsequently, a 200 Å-thick electron transport layer (ETL) was formed by depositing Alq3 under the same vacuum deposition condition. On the electron transport layer (ETL), a cathode was formed by sequentially depositing LiF and Al to manufacture an organic photoelectric device.

The organic photoelectric device has a structure of ITO/NPB (80 nm)/EML ((compound 20:compound B-43=7:3 (weight ratio) (total host=98 wt %)+(piq)$_2$Ir(acac) (2 wt %), 30 nm)/Balq (5 nm)/Alq3 (20 nm)/LiF (1 nm)/Al (100 nm).

Example 10

An organic light emitting diode was manufactured according to the same method as Example 1 except that the compound 20 and the compound B-43 were used in a weight ratio of 5:5.

Example 11

An organic light emitting diode was manufactured according to the same method as Example 1 except that the compound 20 and the compound B-43 were used in a weight ratio of 3:7.

Example 12

An organic light emitting diode was manufactured according to the same method as Example 9 except for using the compound C-10 obtained according to Synthesis Example 1 of a second host compound instead of the compound B-43 in a ratio of 1:1.

Example 13

An organic light emitting diode was manufactured according to the same method as Example 9 except for using the compound B-10 obtained according to Synthesis Example 2 of a second host compound instead of the compound B-43 and the compound 20 in a ratio of 1:1.

Example 14

An organic light emitting diode was manufactured according to the same method as Example 9 except for using the compound B-31 obtained according to Synthesis Example 3 of a second host compound instead of the compound B-43 and the compound 20 in a ratio of 1:1.

Example 15

An organic light emitting diode was manufactured according to the same method as Example 9 except for using the compound B-34 obtained according to Synthesis Example 4 of a second host compound instead of the compound B-43 and the compound 20 in a ratio of 1:1.

Example 16

An organic light emitting diode was manufactured according to the same method as Example 9 except for using the compound E-1 obtained according to Synthesis Example 6 of a second host compound instead of the compound B-43 and the compound 20 in a ratio of 1:1.

Example 17

An organic light emitting diode was manufactured according to the same method as Example 9 except for using the compound 128 according to Synthesis Example 17 instead of the compound 20.

Example 18

An organic light emitting diode was manufactured according to the same method as Example 17 except for using the compound 128 and the compound B-43 in a ratio of 5:5.

Example 19

An organic light emitting diode was manufactured according to the same method as Example 17 except for using the compound 128 and the compound B-43 in a ratio of 3:7.

Example 20

An organic light emitting diode was manufactured according to the same method as Example 17 except for using the compound C-10 according to Synthesis Example 1 of a second host compound instead of the compound B-43 and the compound C-10 in a ratio of 1:1.

Example 21

An organic light emitting diode was manufactured according to the same method as Example 17 except for using the compound B-10 according to Synthesis Example 2 of a second host compound instead of the compound B-43 and the compound 128 in a ratio of 1:1.

Example 22

An organic light emitting diode was manufactured according to the same method as Example 17 except for using the compound B-31 according to Synthesis Example 3 of a second host compound instead of the compound B-43 and the compound 128 in a ratio of 1:1.

Example 23

An organic light emitting diode was manufactured according to the same method as Example 17 except for using the compound B-34 according to Synthesis Example 4 of a second host compound instead of the compound B-43 and the compound 128 in a ratio of 1:1.

Example 24

An organic light emitting diode was manufactured according to the same method as Example 17 except for using the compound E-1 according to Synthesis Example 6 of a second host compound instead of the compound B-43 and the compound 128 in a ratio of 1:1.

Example 25

An organic light emitting diode was manufactured according to the same method as Example 17 except for using the compound 187 according to Synthesis Example 19 instead of the compound 20.

Example 26

An organic light emitting diode was manufactured according to the same method as Example 17 except for using the compound 187 and the compound B-43 in a ratio of 5:5.

Example 27

An organic light emitting diode was manufactured according to the same method as Example 17 except for using the compound 187 and the compound B-43 in a ratio of 3:7.

Example 28

An organic light emitting diode was manufactured according to the same method as Example 25 except for using the compound C-10 according to Synthesis Example 1 of a second host compound instead of the compound B-43 and the compound 187 in a ratio of 1:1.

Example 29

An organic light emitting diode was manufactured according to the same method as Example 25 except for using the compound B-10 according to Synthesis Example 2 of a second host compound instead of the compound B-43 and the compound 187 in a ratio of 1:1.

Example 30

An organic light emitting diode was manufactured according to the same method as Example 25 except for using the compound B-31 according to Synthesis Example 3 of a second host compound instead of the compound B-43 and the compound 187 in a ratio of 1:1.

Example 31

An organic light emitting diode was manufactured according to the same method as Example 25 except for using the compound B-34 according to Synthesis Example 4 of a second host compound instead of the compound B-43 and the compound 187 in a ratio of 1:1.

Example 32

An organic light emitting diode was manufactured according to the same method as Example 25 except for using the compound E-1 according to Synthesis Example 6 of a second host compound instead of the compound B-43 and the compound 187 in a ratio of 1:1.

Comparative Example 2

An organic light emitting diode was manufactured according to the same method as Example 9 except for using the compound B-43 as a single host instead of two hosts of the compound 20 and the compound B-43.

Comparative Example 3

An organic light emitting diode was manufactured according to the same method as Example 12 except for using the compound C-10 as a single host instead of two hosts of the compound 20 and the compound C-10.

Comparative Example 4

An organic light emitting diode was manufactured according to the same method as Example 13 except for using the compound B-10 as a single host instead of two hosts of the compound 20 and the compound B-10.

Comparative Example 5

An organic light emitting diode was manufactured according to the same method as Example 14 except for using the compound B-31 as a single host instead of two hosts of the compound 20 and the compound B-31.

Comparative Example 6

An organic light emitting diode was manufactured according to the same method as Example 15 except for using the compound B-34 as a single host instead of two hosts of the compound 20 and the compound B-34.

Comparative Example 7

An organic light emitting diode was manufactured according to the same method as Example 16 except for using the compound E-1 as a single host instead of two hosts of the compound 20 and the compound E-1.

Evaluation 3

Luminous efficiency and life-span characteristics of each organic light emitting diode according to Examples 9 to 32 and Comparative Examples 2 to 7 were measured.

The measurements were specifically performed in the following methods, and the results are shown in Tables 3 and 4.

(1) Measurement of Current Density Change Depending on Voltage Change

Current values flowing in the unit device of the manufactured organic light emitting diodes were measured for, while increasing the voltage from 0 V to 10 V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm$^2$) was calculated by using the luminance, current density, and voltages (V) from the items (1) and (2).

(4) Measurement of Life-Span

Life-span was obtained by measuring time taken until current efficiency (cd/A) decreased down to 90% while luminance (cd/m$^2$) was maintained at 2200 cd/m$^2$.

TABLE 3

|  | First organic compound | Second organic compound | First organic compound:Second organic compound | Luminous efficiency (cd/A) | Life-span T90 (h) |
| --- | --- | --- | --- | --- | --- |
| Example 9 | compound 20 | B-43 | 7:3 | 12.5 | 380 |
| Example 10 | compound 20 | B-43 | 5:5 | 14.5 | 450 |
| Example 11 | compound 20 | B-43 | 3:7 | 13.2 | 400 |
| Example 12 | compound 20 | C-10 | 1:1 | 12.1 | 250 |
| Example 13 | compound 20 | B-10 | 1:1 | 13.5 | 280 |
| Example 14 | compound 20 | B-31 | 1:1 | 12.5 | 180 |
| Example 15 | compound 20 | B-34 | 1:1 | 12.8 | 250 |
| Example 16 | compound 20 | E-1 | 1:1 | 11.5 | 150 |
| Example 17 | compound 128 | B-43 | 7:3 | 8.4 | 450 |
| Example 18 | compound 128 | B-43 | 5:5 | 12.3 | 550 |
| Example 19 | compound 128 | B-43 | 3:7 | 15.6 | 400 |
| Example 20 | compound 128 | C-10 | 1:1 | 10.8 | 300 |
| Example 21 | compound 128 | B-10 | 1:1 | 11.3 | 280 |
| Example 22 | compound 128 | B-31 | 1:1 | 13.0 | 400 |
| Example 23 | compound 128 | B-34 | 1:1 | 10.5 | 350 |
| Example 24 | compound 128 | E-1 | 1:1 | 11.5 | 200 |
| Example 25 | compound 187 | B-43 | 7:3 | 20.0 | 120 |
| Example 26 | compound 187 | B-43 | 5:5 | 16.8 | 150 |
| Example 27 | compound 187 | B-43 | 3:7 | 14.1 | 250 |
| Example 28 | compound 187 | C-10 | 1:1 | 13.5 | 130 |
| Example 29 | compound 187 | B-10 | 1:1 | 14.5 | 150 |
| Example 30 | compound 187 | B-31 | 1:1 | 15.5 | 180 |
| Example 31 | compound 187 | B-34 | 1:1 | 16.0 | 170 |
| Example 32 | compound 187 | E-1 | 1:1 | 12.5 | 190 |
| Comparative Example 2 |  | B-10 | — | 5.0 | — |
| Comparative Example 3 |  | B-31 | — | 4.0 | — |
| Comparative Example 4 |  | C-10 | — | 4.0 | — |
| Comparative Example 5 |  | B-34 | — | 4.2 | — |
| Comparative Example 6 |  | B-43 | — | 5.5 | — |
| Comparative Example 7 |  | E-1 | — | 4.0 | — |

Referring to Table 3, the organic light emitting diodes according to Examples 9 to 32 exhibited remarkably improve luminous efficiency compared with the organic light emitting diodes according to Comparative Examples 2 to 7. In addition, the organic light emitting diodes according to Examples 9 to 32 exhibited much more excellent life-span characteristics compared with the organic light emitting diodes according to Examples 1 to 8.

In Examples 9 to 32, the first organic compound has relatively strong electron characteristics, and the second organic compound has relatively strong hole characteristics, and thus the first and second organic compounds may be used together to more appropriately balance electron and hole flows and further improve efficiency and life-span characteristics of the organic light emitting diodes.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: cathode
120: anode
130: emission layer
140: hole auxiliary layer

What is claimed is:

1. An organic compound represented by one of Chemical Formulae 3 to 6:

[Chemical Formula 3]

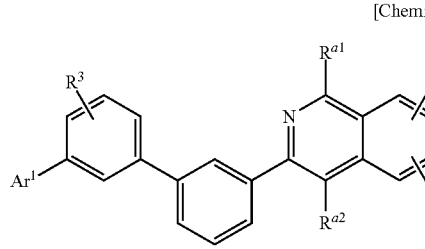

[Chemical Formula 4]

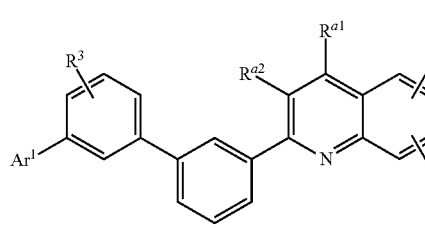

[Chemical Formula 5]

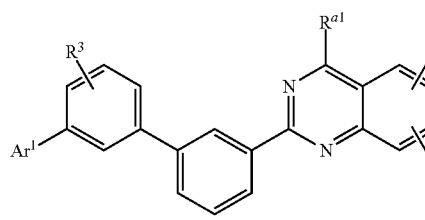

[Chemical Formula 6]

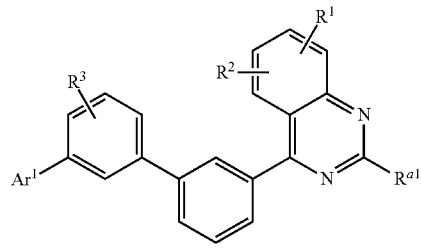

wherein, in Chemical Formulae 3 to 6, $R^1$, $R^2$, $R^{a1}$, and $R^{a2}$ are independently hydrogen, deuterium, a substituted or unsubstituted C1 to C20 alkyl group, a substituted or unsubstituted C6 to C20 aryl group, a substituted or unsubstituted C3 to C30 heterocyclic group, or a combination thereof, $R^3$ is hydrogen, deuterium, a substituted or unsubstituted C1 to C20 alkyl group, a substituted or unsubstituted C6 to C20 aryl group, or a combination thereof, and $Ar^1$ is a substituted or unsubstituted biphenyl group, a substituted or unsubstituted terphenyl group, a substituted or unsubstituted quarterphenyl group, a substituted or unsubstituted triphenylene group, or a combination thereof.

2. The organic compound of claim 1, wherein $R^{a1}$ is a substituted or unsubstituted C6 to C20 aryl group, a substituted or unsubstituted C3 to C30 heterocyclic group, or a combination thereof.

3. An organic compound represented by one of Chemical Formulae 8a to 8c:

[Chemical Formula 8a]

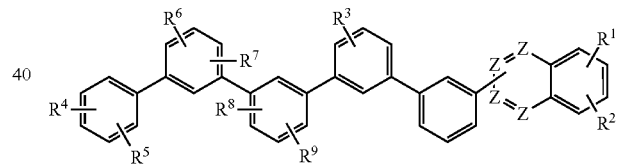

[Chemical Formula 8b]

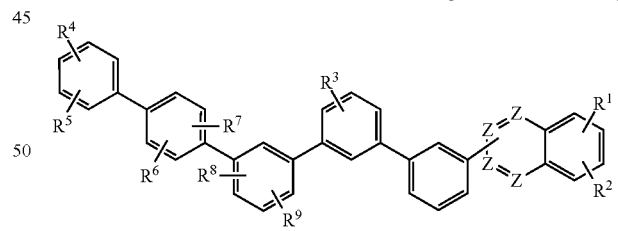

[Chemical Formula 8c]

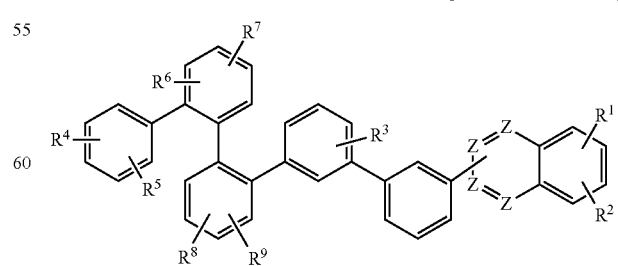

wherein, in Chemical Formulae 8a to 8c,
Z is independently C, N, or $CR^a$, at least one of Z's is N, R$^1$, R$^2$, and R$^a$ are independently hydrogen, deuterium, a substituted or unsubstituted C1 to C20 alkyl group, a substituted or unsubstituted C6 to C20 aryl group, a substituted or unsubstituted C3 to C30 heterocyclic group, or a combination thereof, R$^3$ to R$^9$ are independently hydrogen, deuterium, a substituted or unsubstituted C1 to C20 alkyl group, a substituted or unsubstituted C6 to C20 aryl group, or a combination thereof, and R$^4$ and R$^5$, R$^6$ and R$^7$, and R$^8$ and R$^9$ are independently present or linked with each other to provide a ring.

4. An organic compound represented by Chemical Formula 9a:

[Chemical Formula 9a]

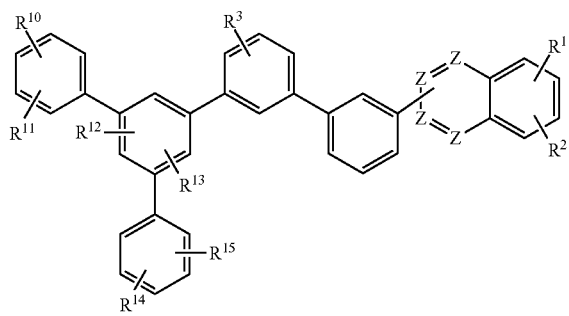

wherein, in Chemical Formula 9a,

Z is independently C, N, or CR$^a$, at least one of Z's is N,

R$^1$, R$^2$, and R$^a$ are independently hydrogen, deuterium, a substituted or unsubstituted C1 to C20 alkyl group, a substituted or unsubstituted C6 to C20 aryl group, a substituted or unsubstituted C3 to C30 heterocyclic group, or a combination thereof, R$^3$ and R$^{10}$ to R$^{15}$ are independently hydrogen, deuterium, a substituted or unsubstituted C1 to C20 alkyl group, a substituted or unsubstituted C6 to C20 aryl group, or a combination thereof, and R$^{10}$ and R$^{11}$, and R$^{14}$ and R$^{15}$ are independently present or linked with each other to provide a ring.

5. A composition for an organic optoelectric device, comprising
the organic compound of claim 1 as a first organic compound, and
at least one second organic compound having a carbazole moiety.

6. The composition for an organic optoelectric device of claim 5, wherein the second organic compound includes at least one of a compound represented by Chemical Formula 11 and a compound consisting of a moiety represented by Chemical Formula 12 and a moiety represented by Chemical Formula 13:

[Chemical Formula 11]

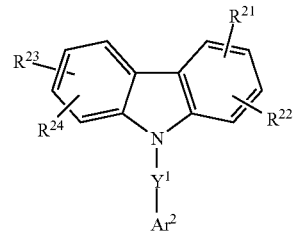

wherein, in Chemical Formula 11,

Y$^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heterocyclic group, or a combination thereof, Ar$^2$ is a substituted or unsubstituted C6 to C30 aryl group, a substituted or unsubstituted C2 to C30 heterocyclic group, or a combination thereof, R$^{21}$ to R$^{24}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and at least one of R$^{21}$ to R$^{24}$ and Ar$^2$ includes a substituted or unsubstituted triphenylene group or a substituted or unsubstituted carbazole group,

[Chemical Formula 12]

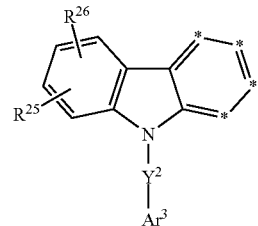

[Chemical Formula 13]

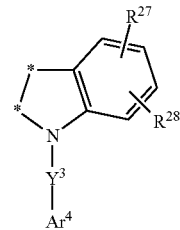

wherein, in Chemical Formulae 12 and 13,

Y$^2$ and Y$^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heterocyclic group, or a combination thereof, Ar$^3$ and Ar$^4$ are independently a substituted or unsubstituted C6 to C30 aryl group, a substituted or unsubstituted C2 to C30 heterocyclic group, or a combination thereof, R$^{25}$ to R$^{28}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and two adjacent *'s of Chemical Formula 12 are bound to two adjacent *'s of Chemical Formula 13 to provide a fused ring, *'s of not providing a fused ring of Chemical Formula 12 are independently $CR^b$, wherein $R^b$ is hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof.

7. The composition for an organic optoelectric device of claim 6, wherein:
the second organic compound includes a compound represented by Chemical Formula 11, and
the second organic compound represented by Chemical Formula 11 is represented by at least one of Chemical Formulae 11-I to 11-III:

[Chemical Formula 11-I]

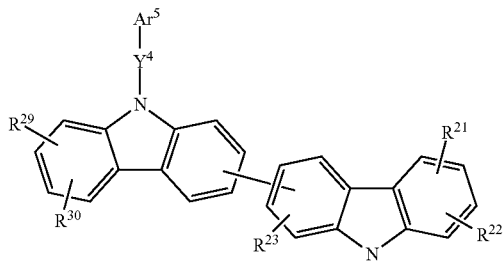

[Chemical Formula 11-II]

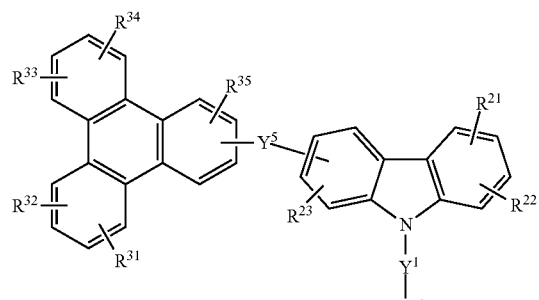

[Chemical Formula 11-III]

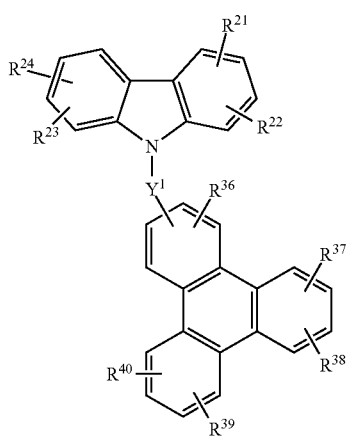

wherein, in Chemical Formulae 11-I to 11-III,
$Y^1$, $Y^4$, and $Y^5$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heterocyclic group, or a combination thereof, $Ar^2$ and $Ar^5$ are independently a substituted or unsubstituted C6 to C30 aryl group, a substituted or unsubstituted C2 to C30 heterocyclic group, or a combination thereof, and $R^{21}$ to $R^{24}$ and $R^{29}$ to $R^{40}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof.

8. The composition for an organic optoelectric device of claim 5, wherein the first organic compound and the second organic compound are included in a weight ratio of 1:10 to 10:1.

9. The composition for an organic optoelectric device of claim 5, further comprising a phosphorescent dopant.

10. An organic optoelectric device, comprising
an anode and a cathode facing each other, and
at least one organic layer between the anode and the cathode, wherein:
the organic layer includes the organic compound of claim 1.

11. The organic optoelectric device of claim 10, wherein:
the organic layer includes an emission layer, and
the emission layer includes the organic compound.

12. The organic optoelectric device of claim 11, wherein the organic compound is included as a host in the emission layer.

13. A display device comprising the organic optoelectric device of claim 10.

14. The organic compound of claim 1, which is one of compounds of Group 1:

[Group 1]

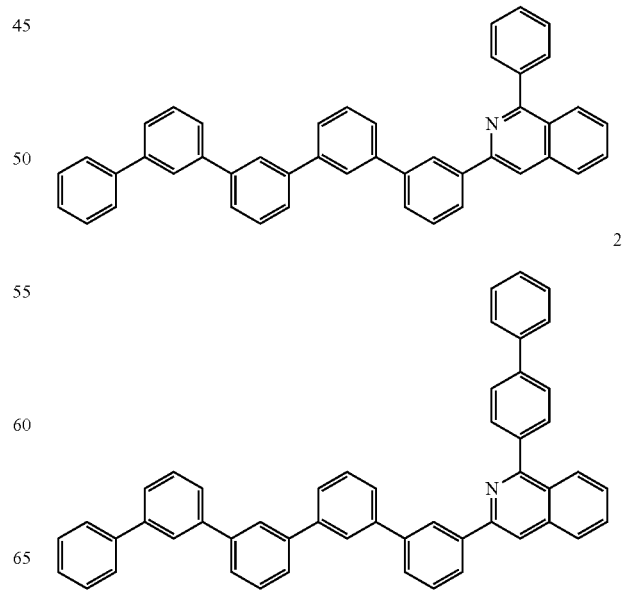

3
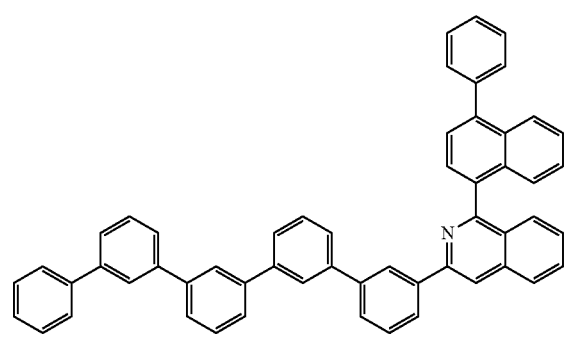
4
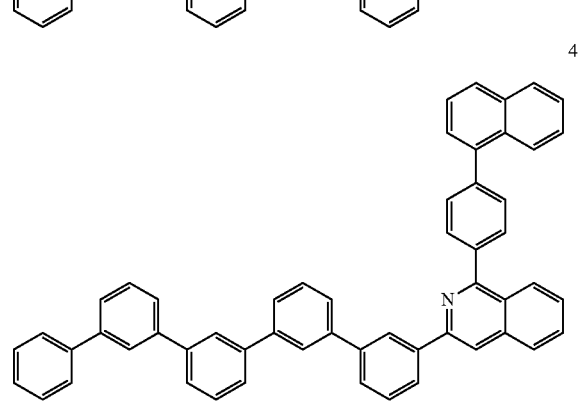
5
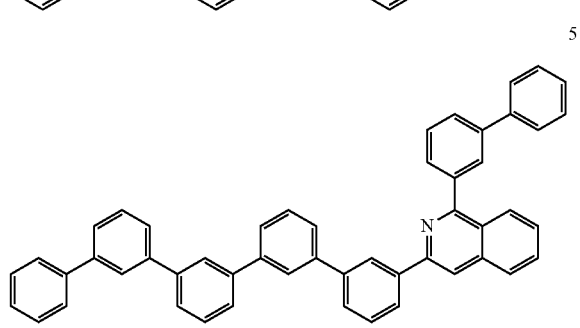
6
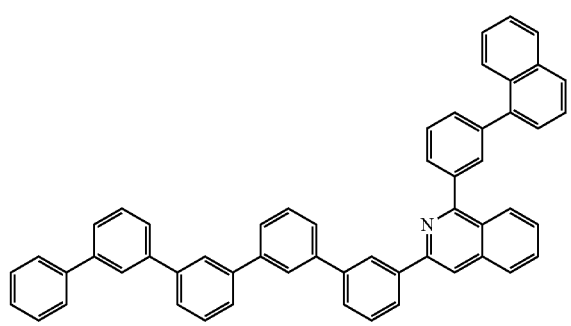
7
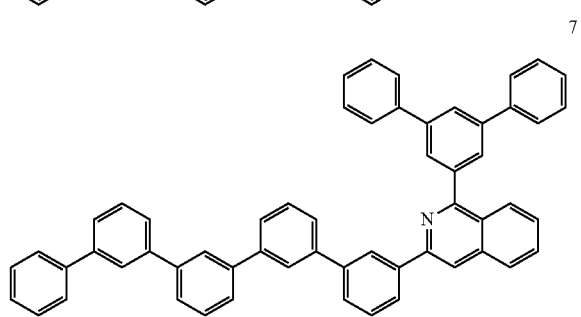
8
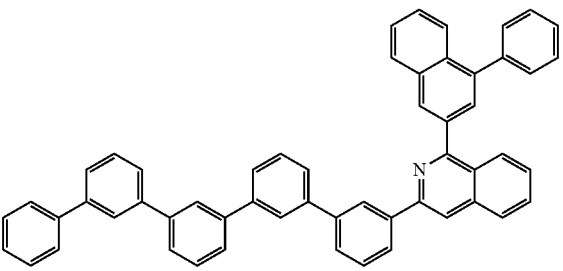
9
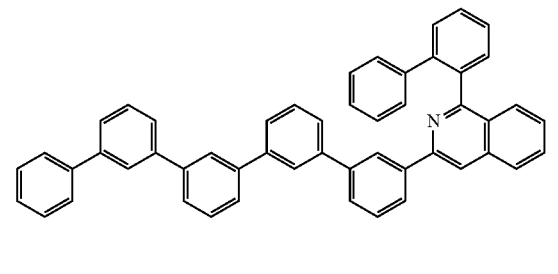
10
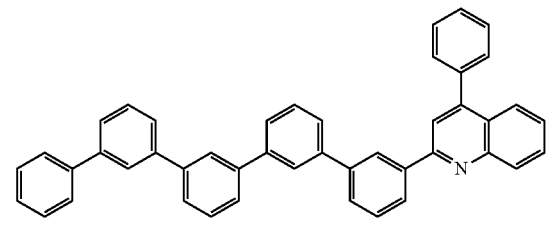
11
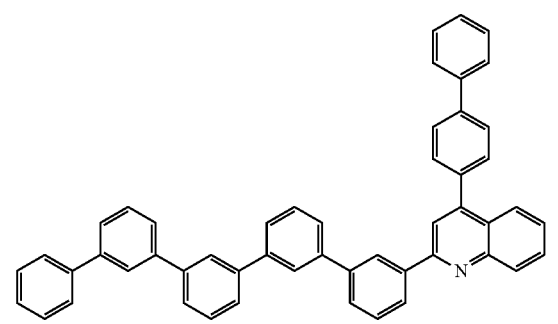
12
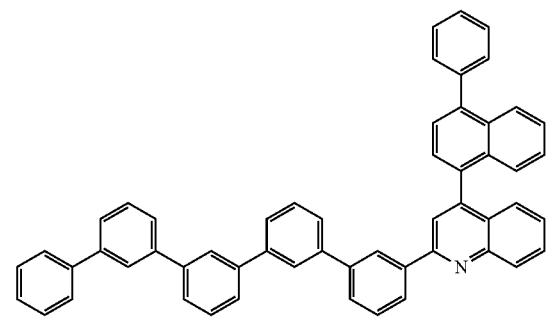

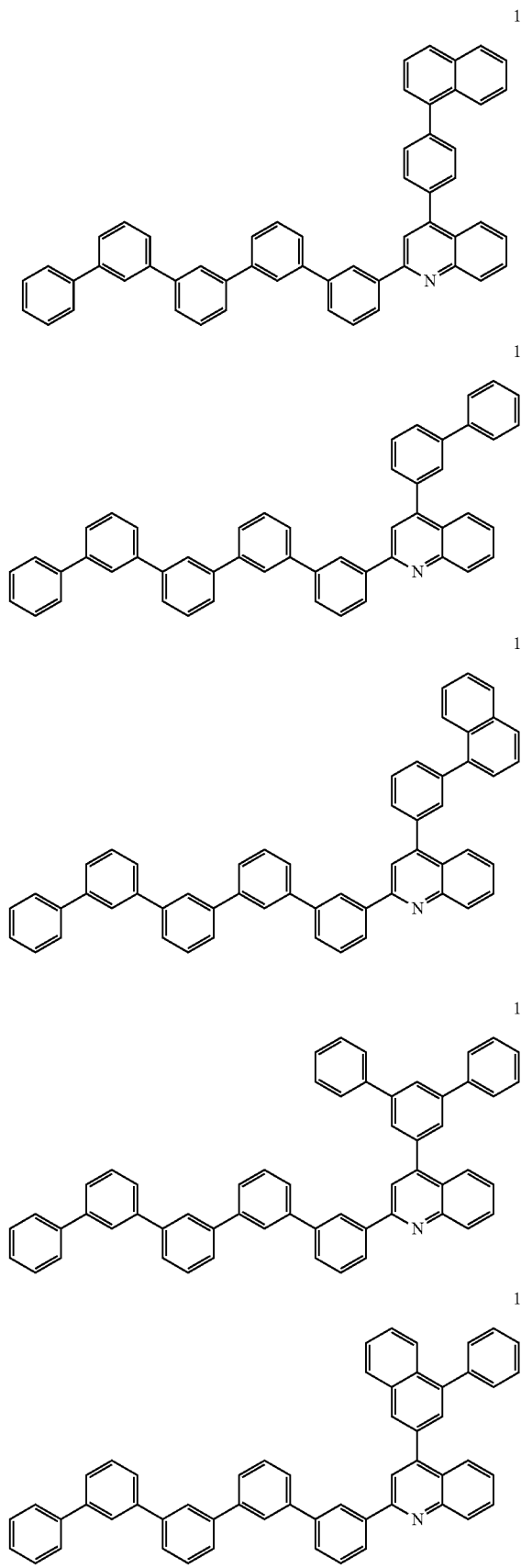
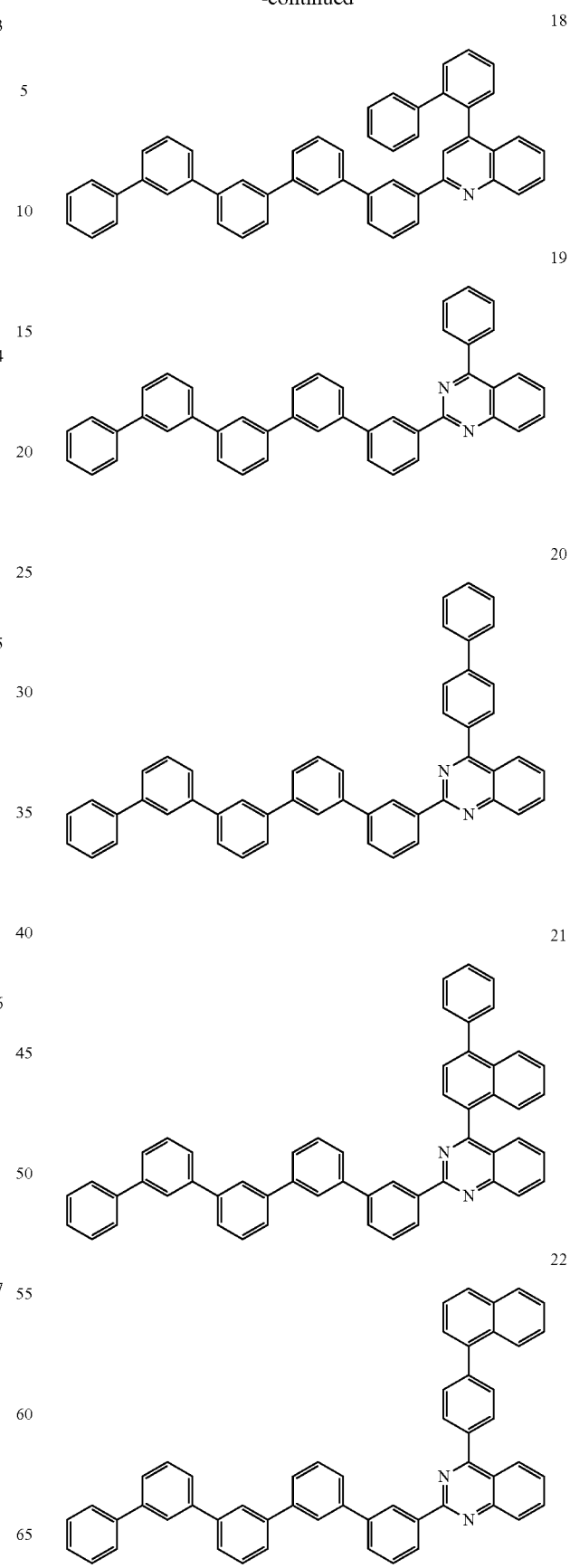

23
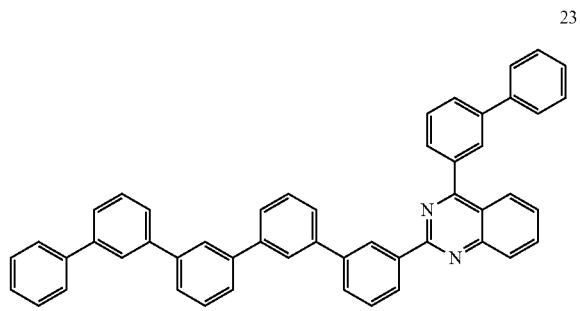
24
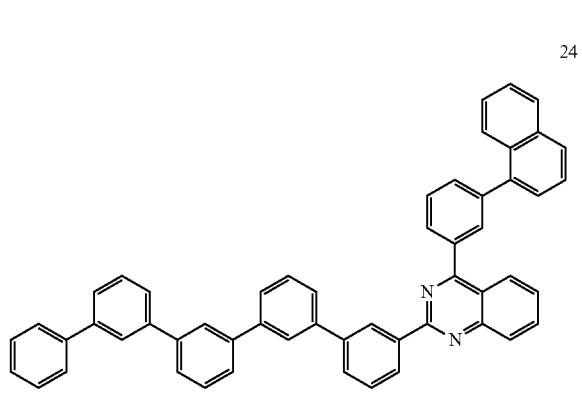
25
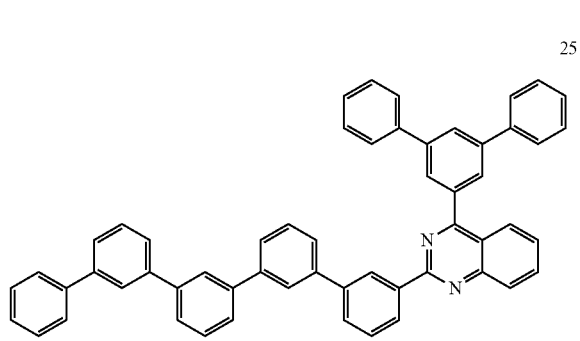
26
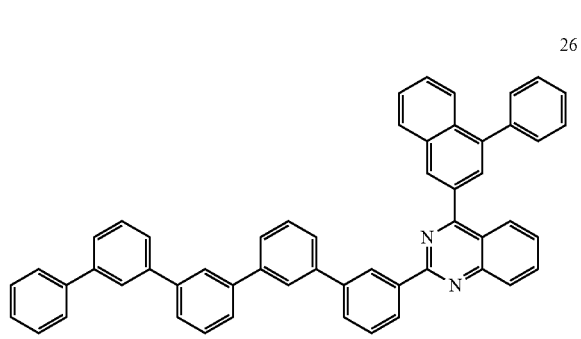
27
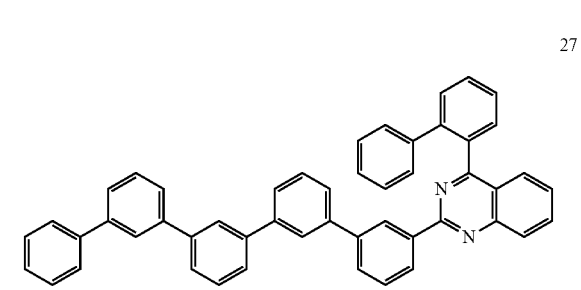
28
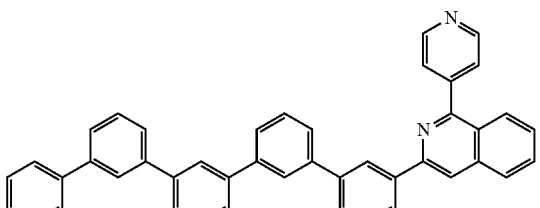
29
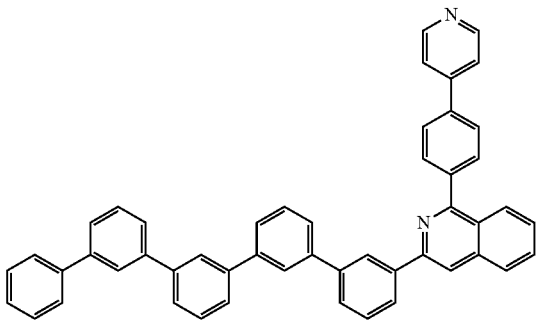
30
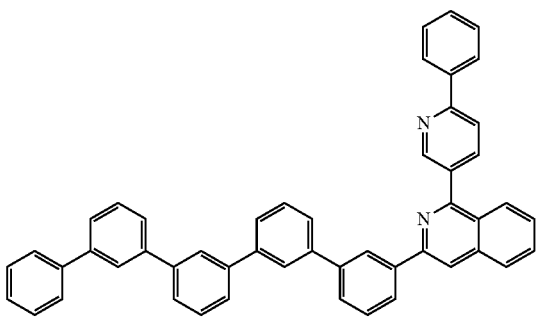
31
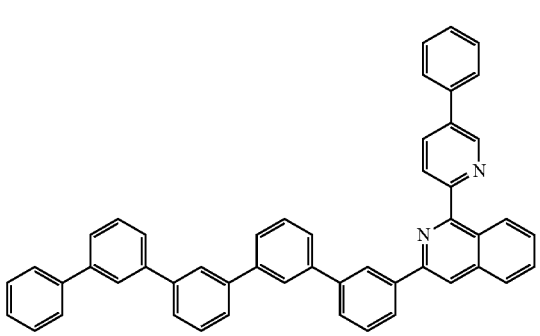
32
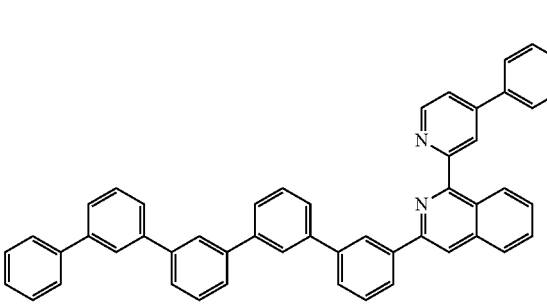

33
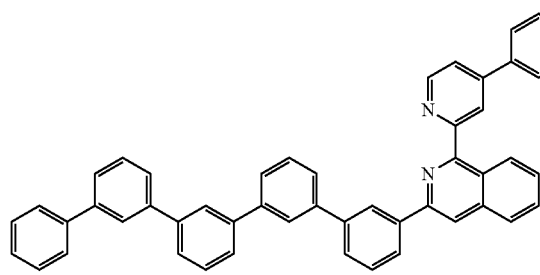
34
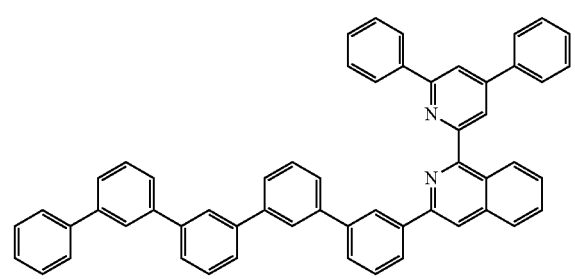
35
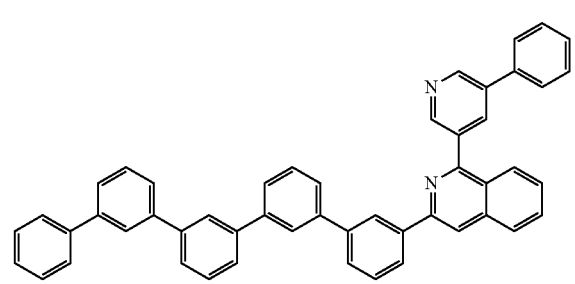
36
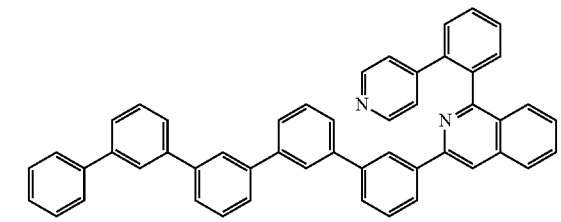
37
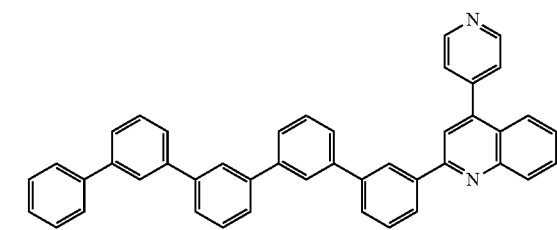
38
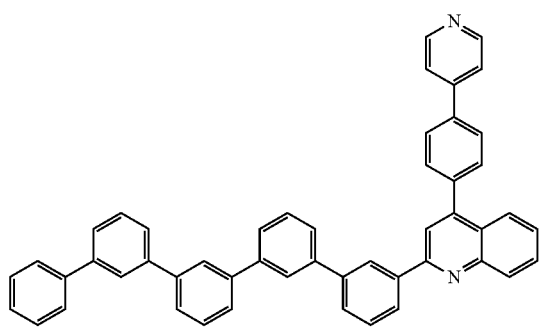
39
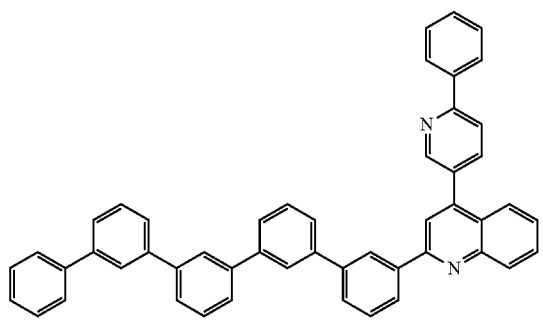
40
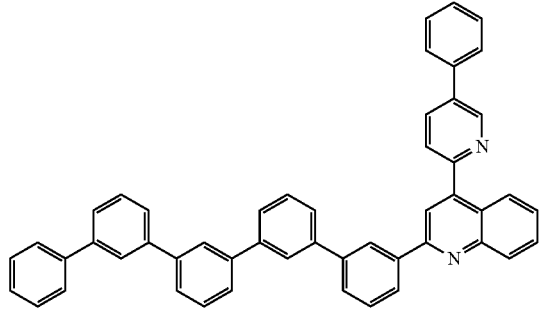
41
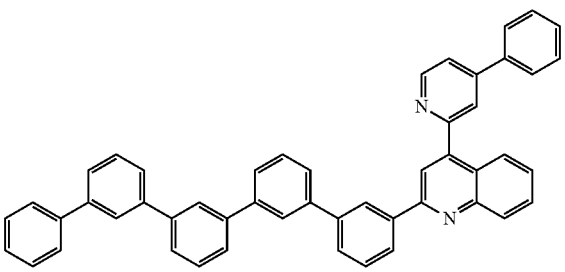
42
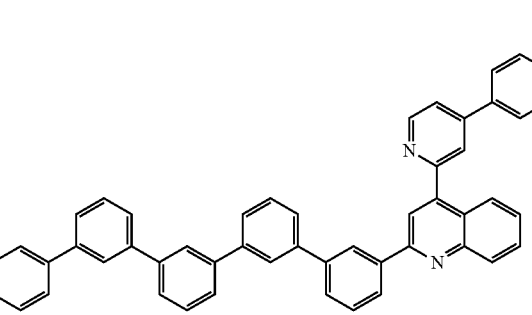

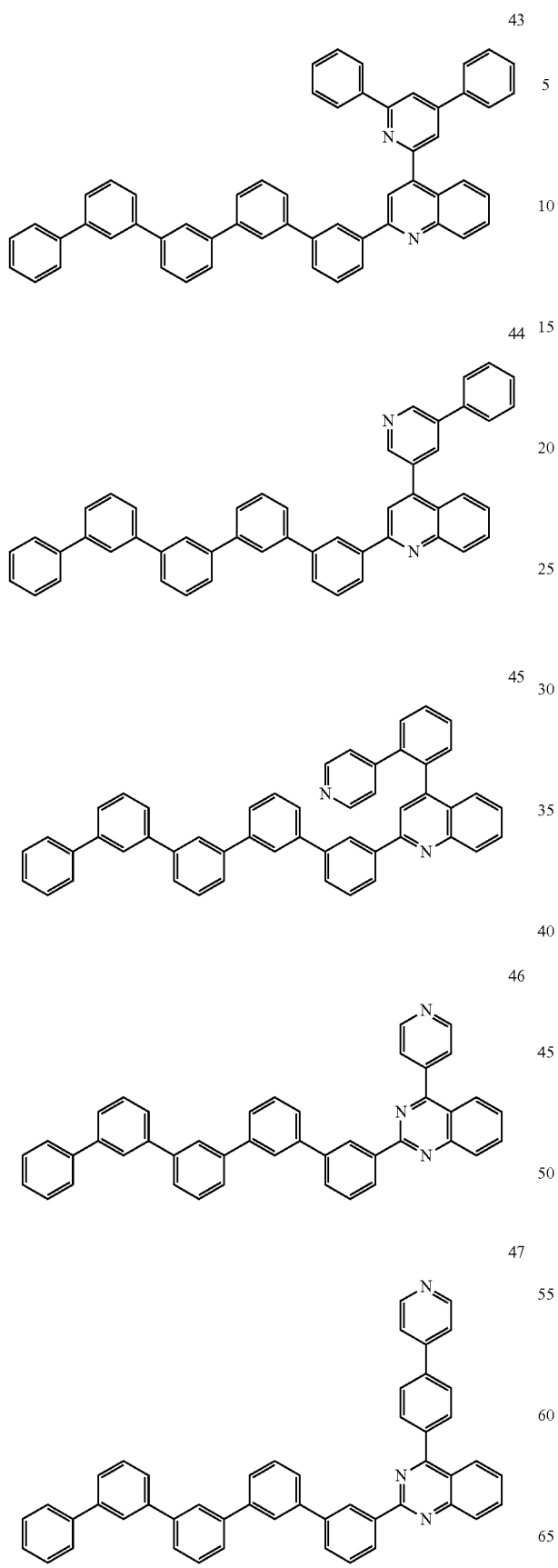
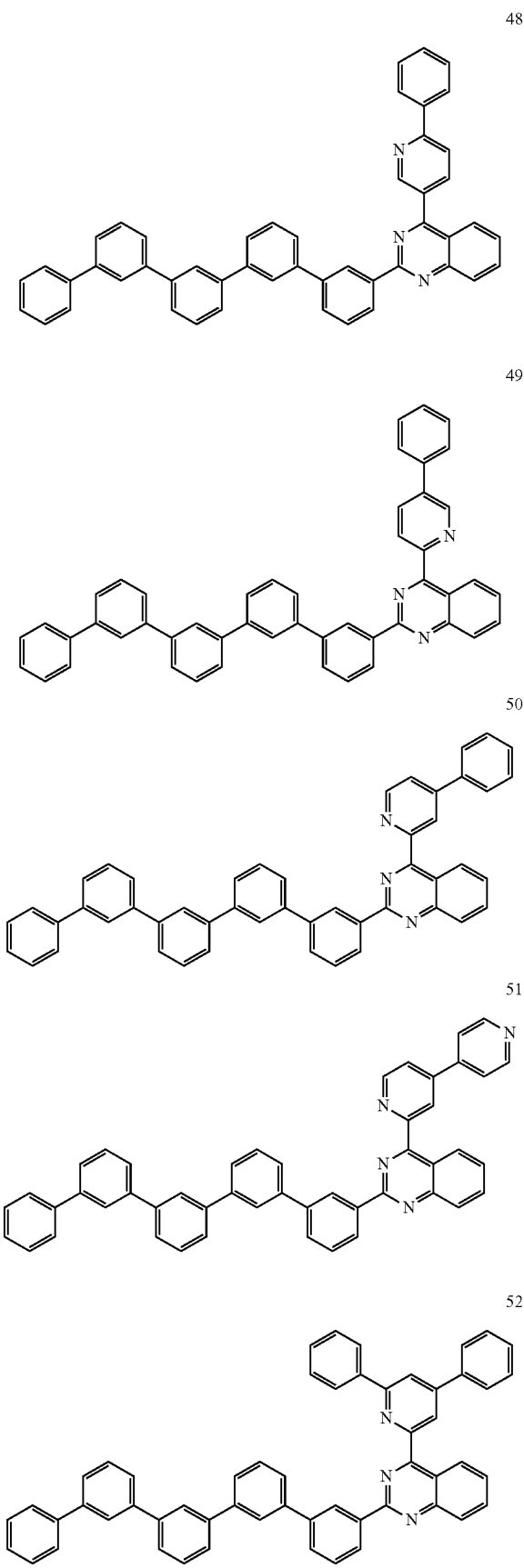

53
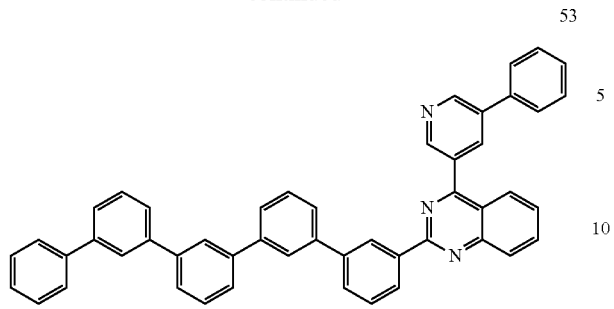
54
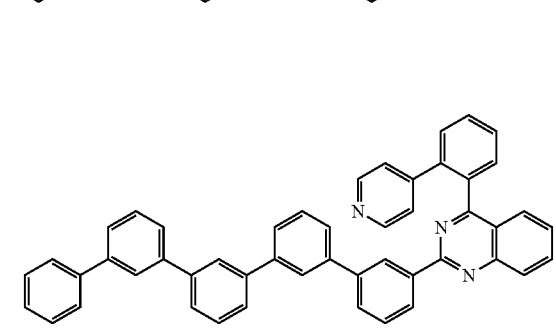
55
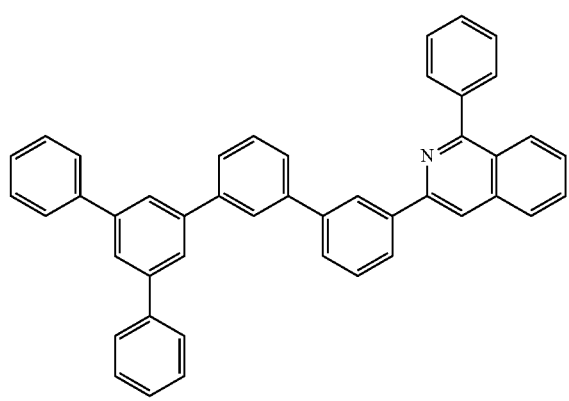
56
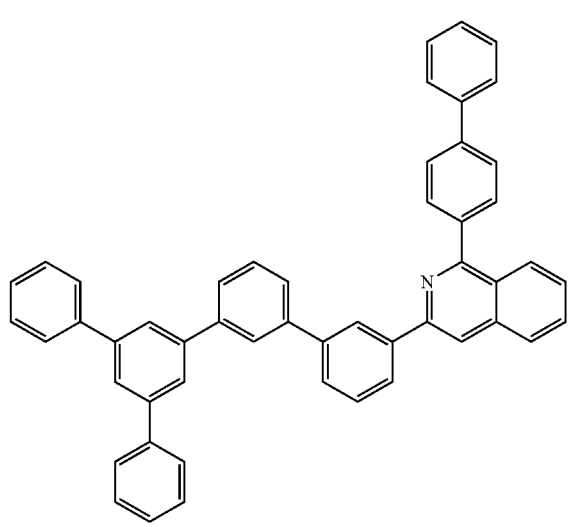
57
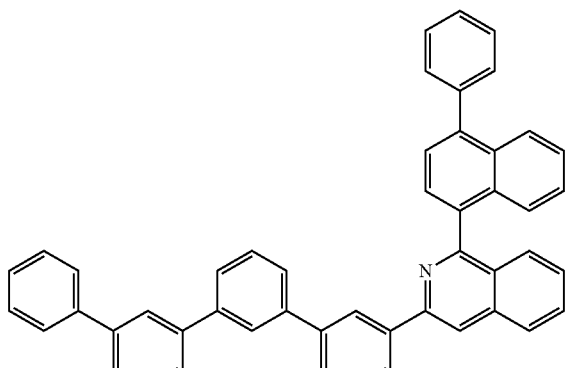
58
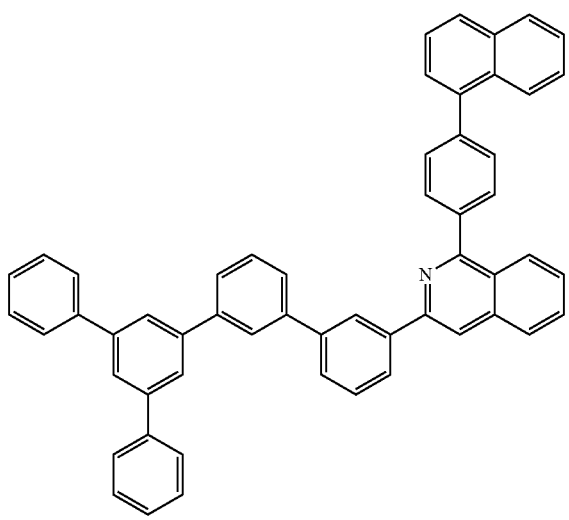
59
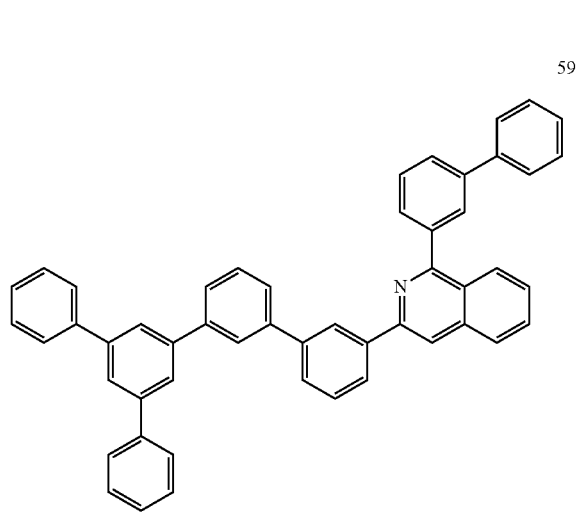

175
-continued
60
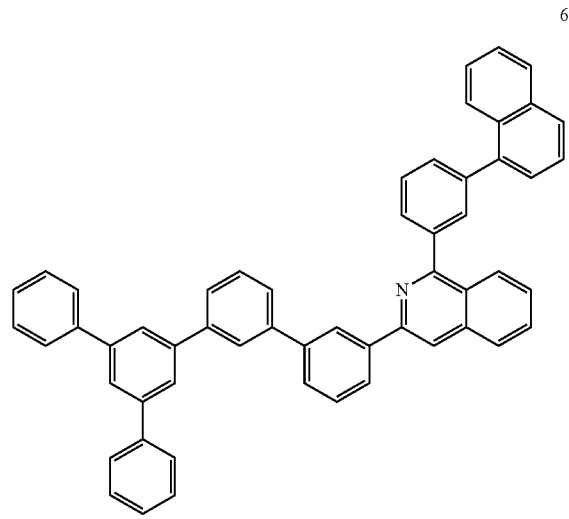
61
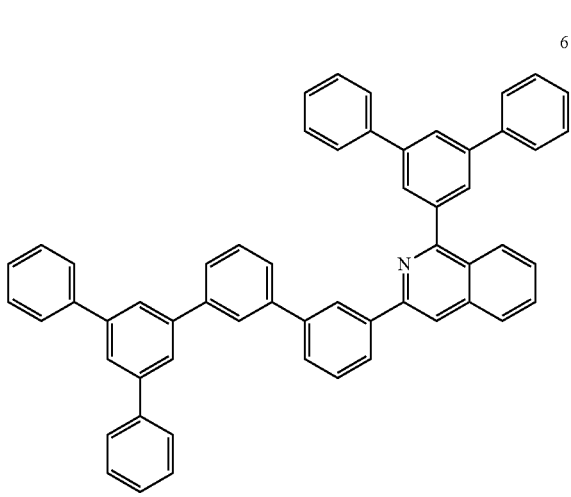
62
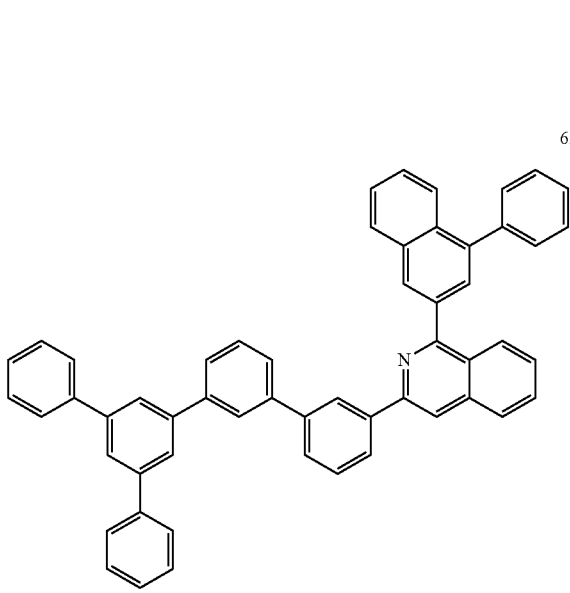
176
-continued
63
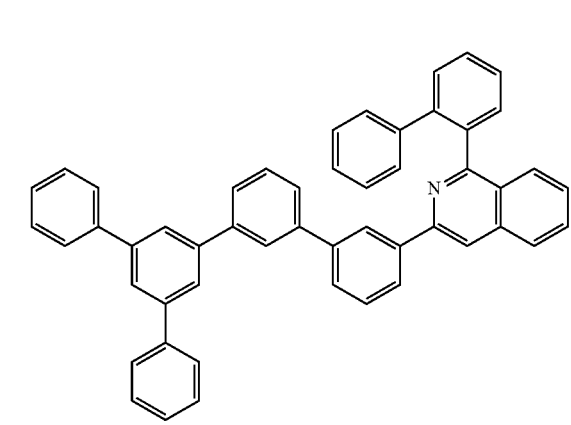
64
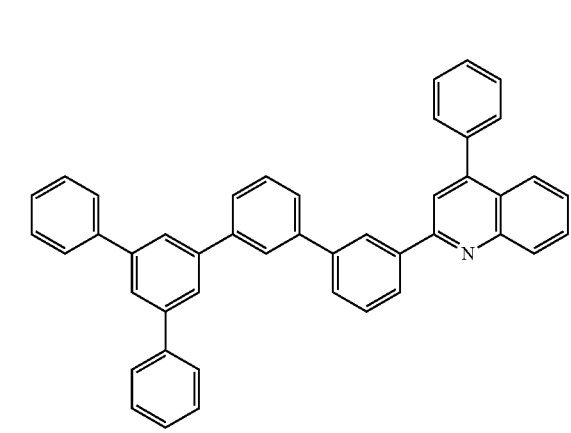
65
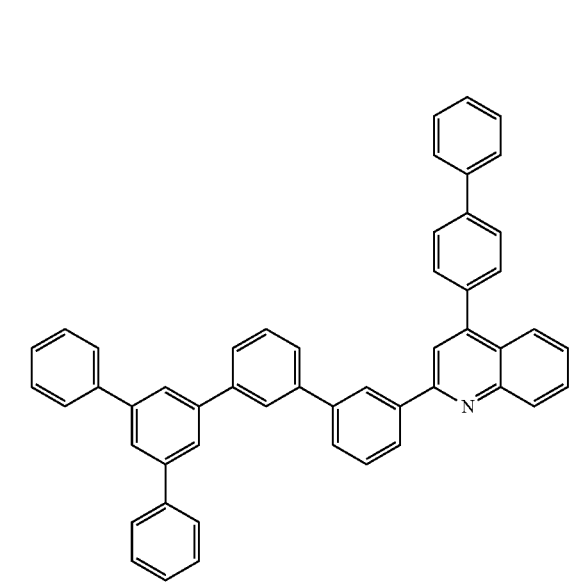

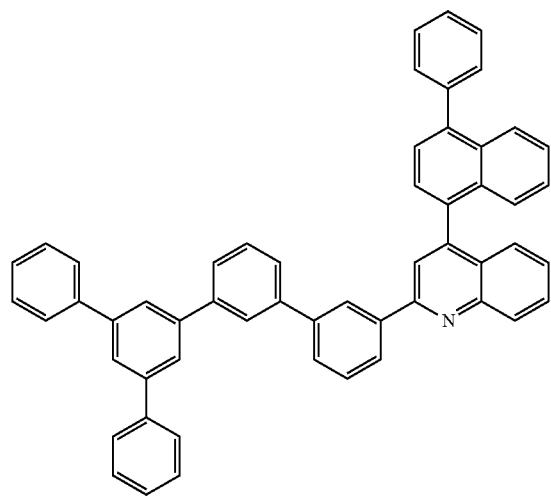
66
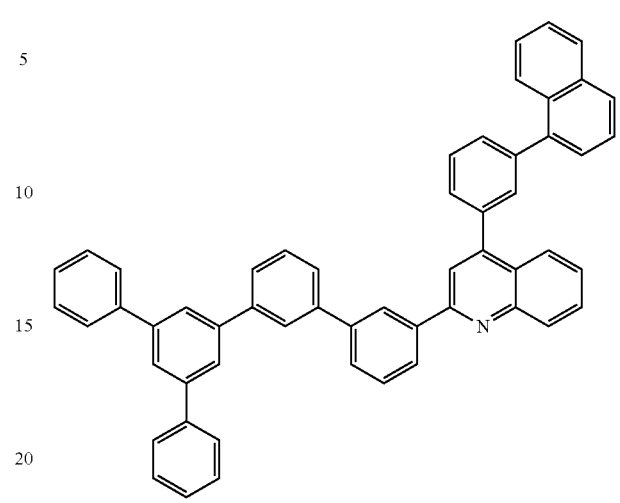
69
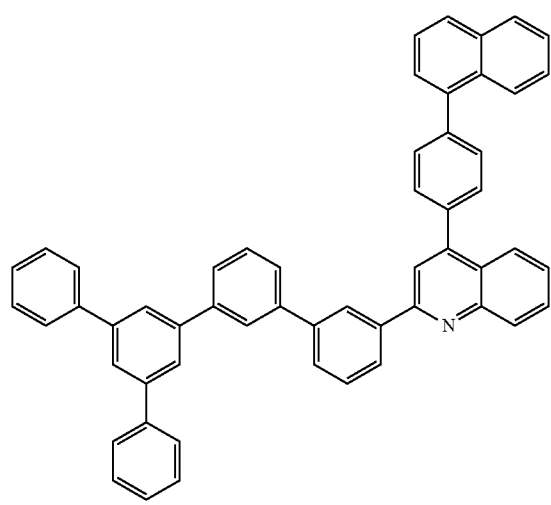
67
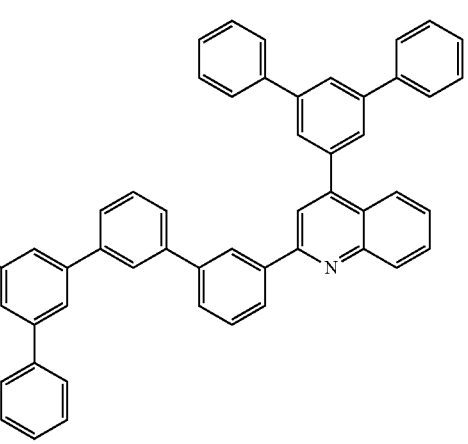
70
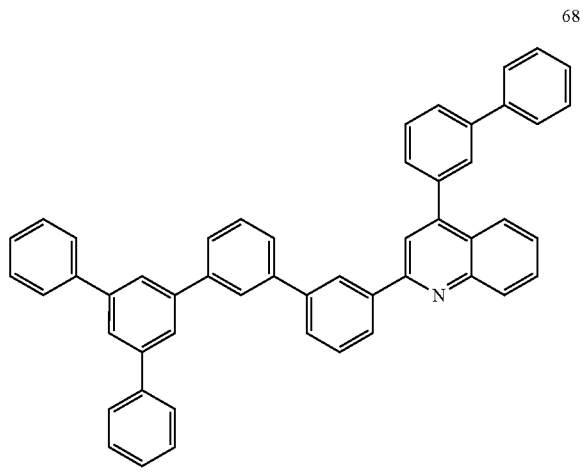
68
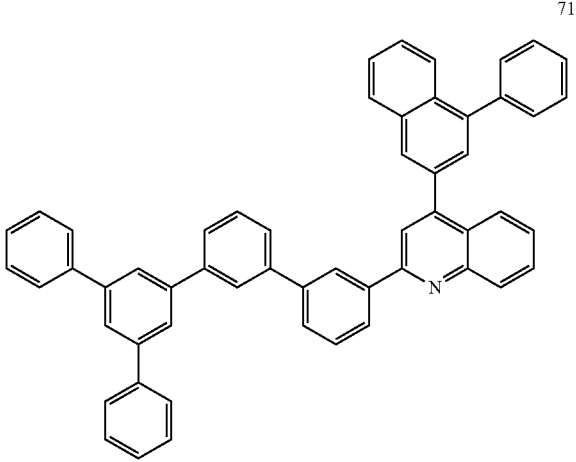
71

72
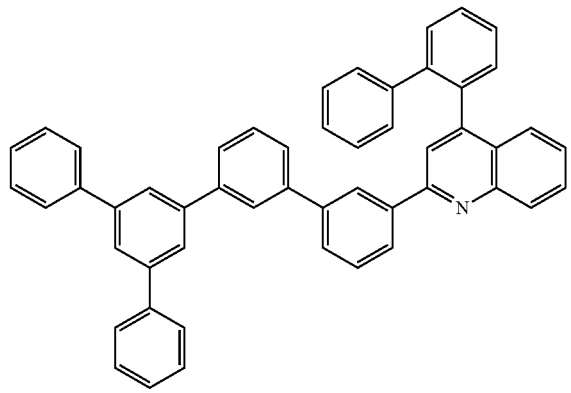
73
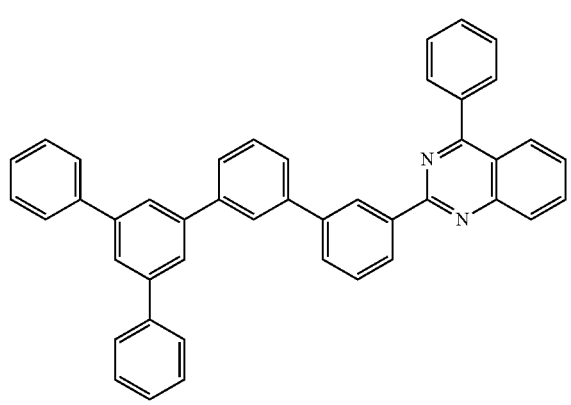
74
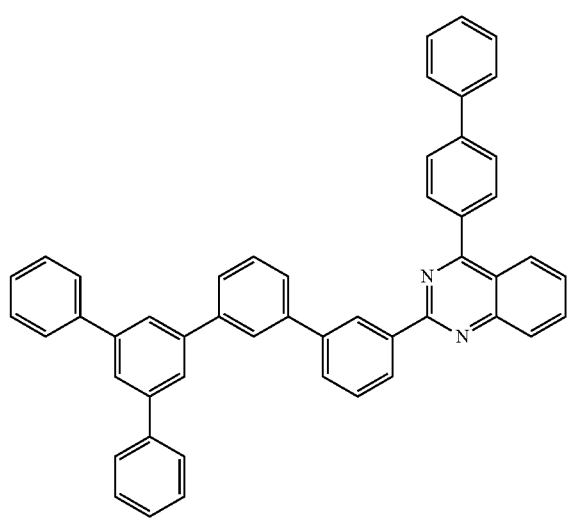
75
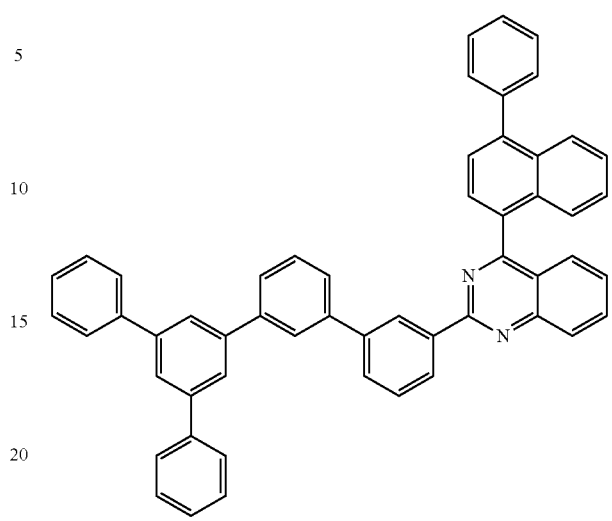
76
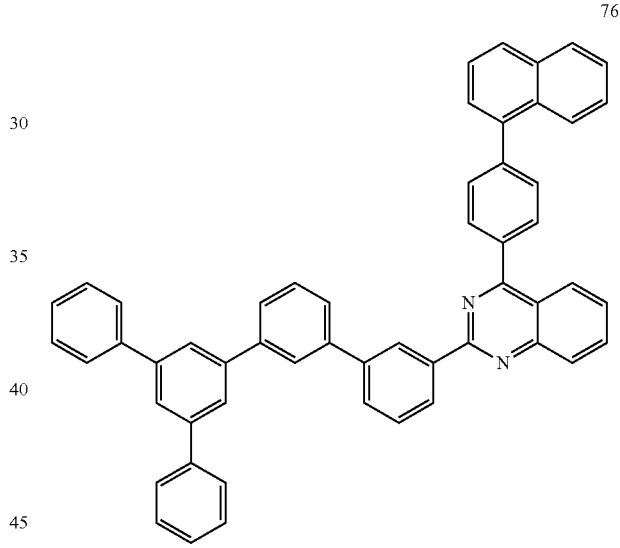
77
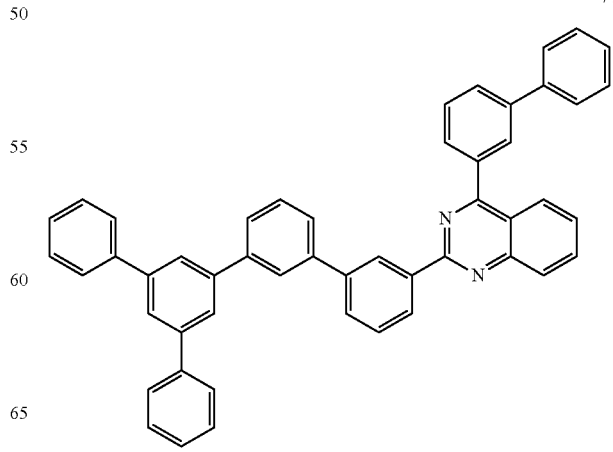

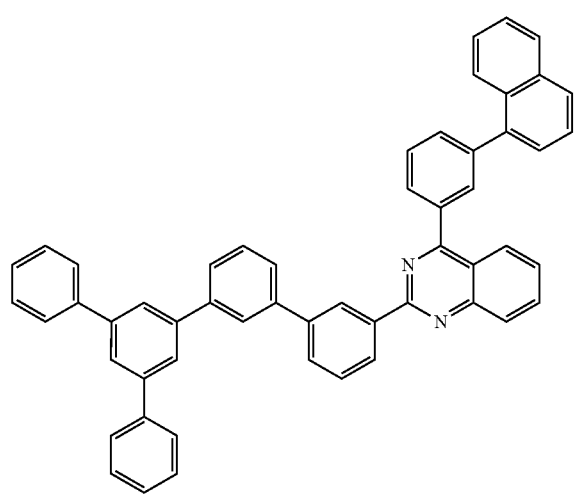
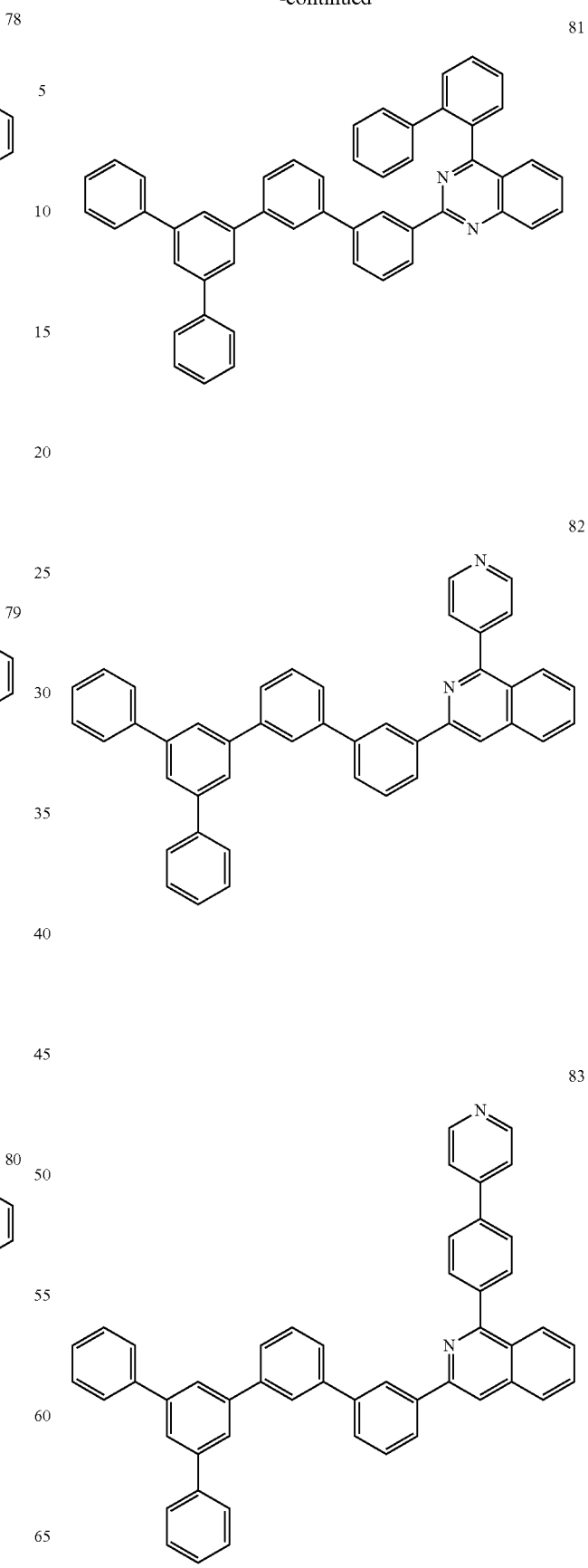

84
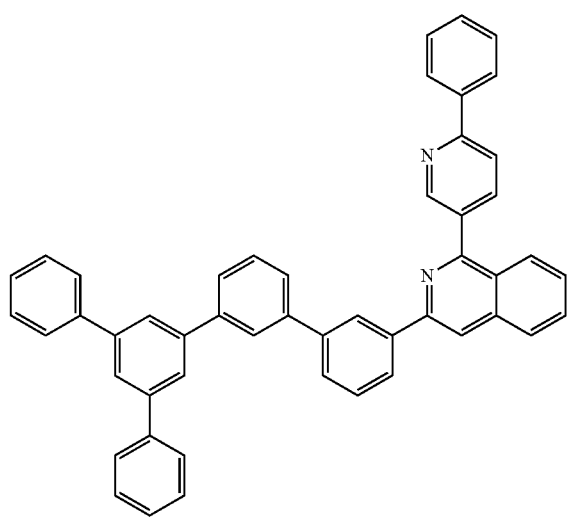
85
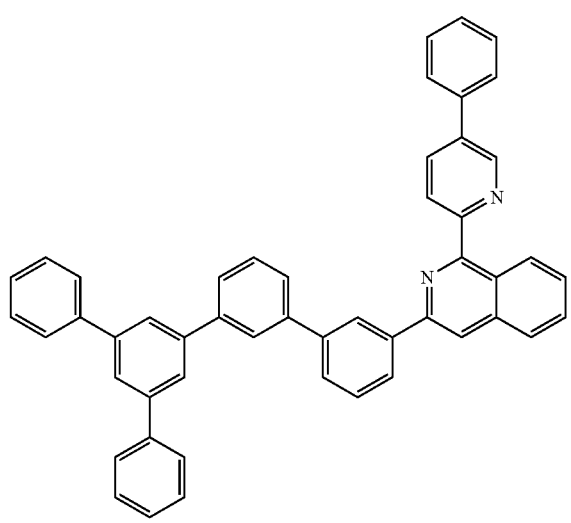
86
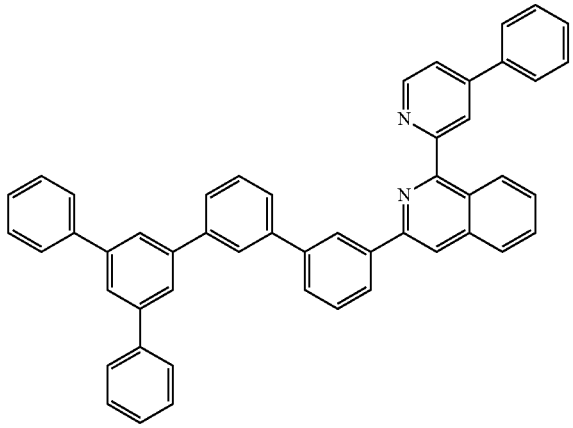
87
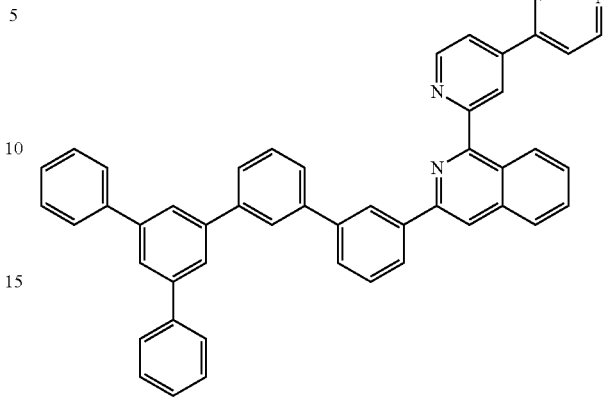
88
89
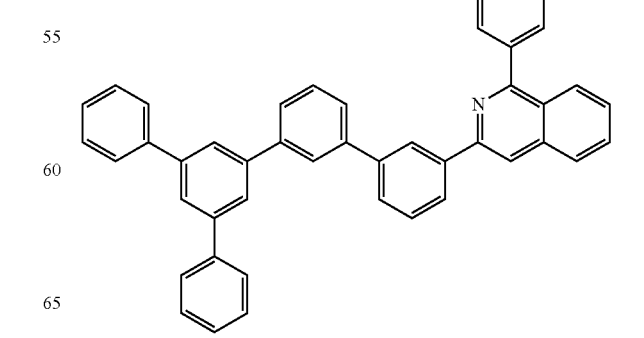

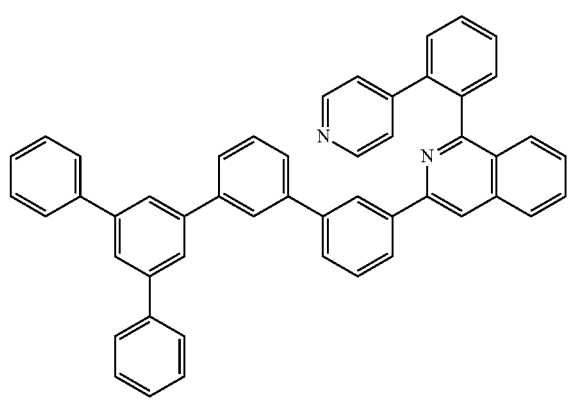
90
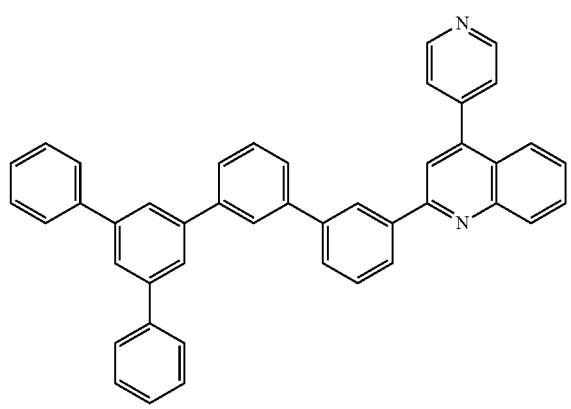
91
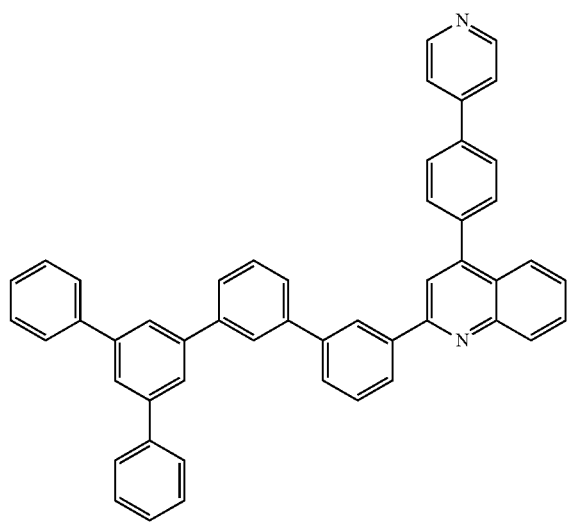
92
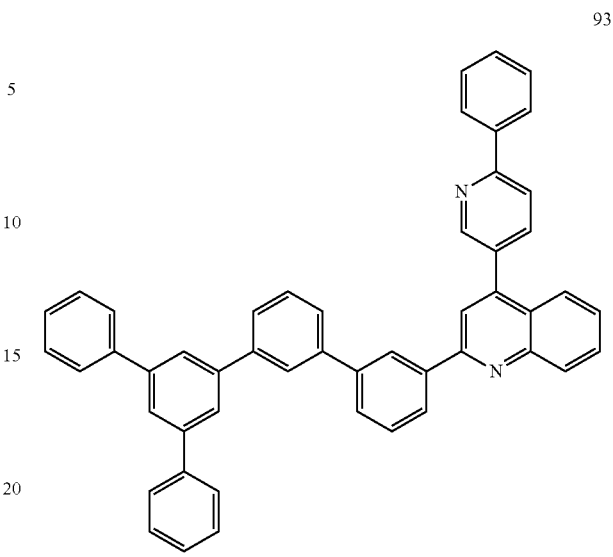
93
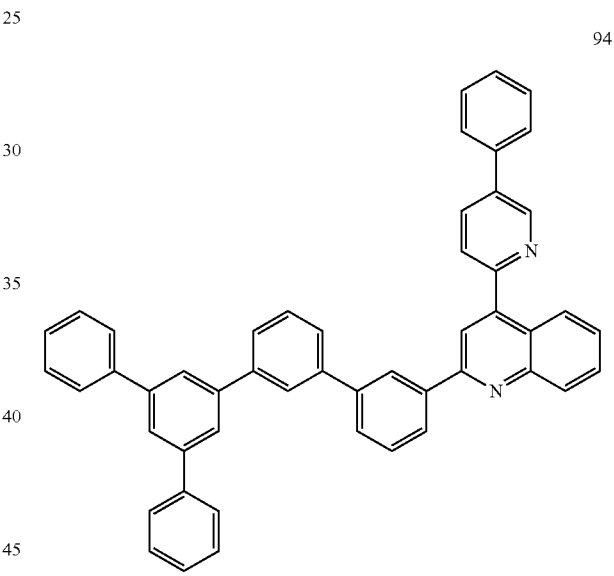
94
95

96
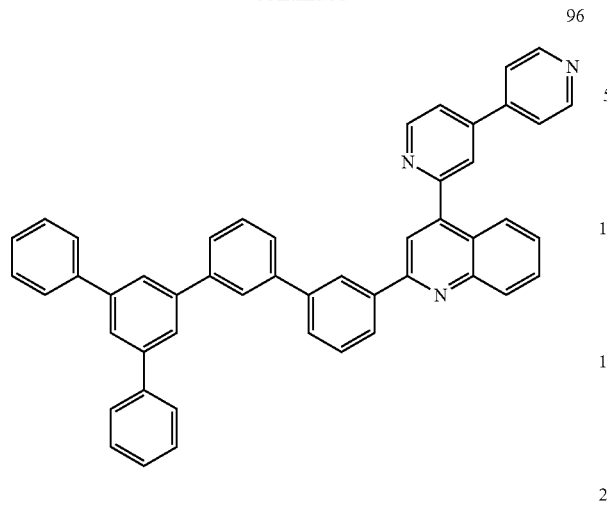
97
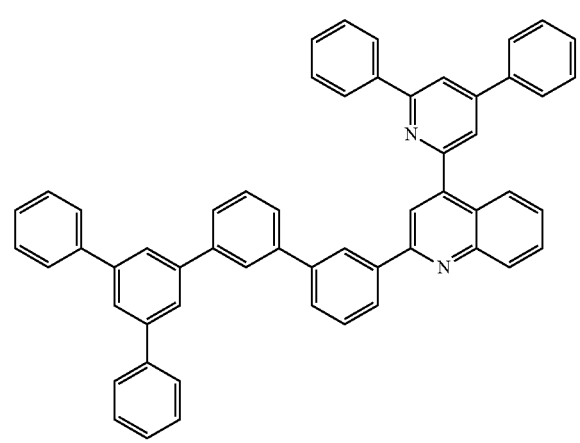
98
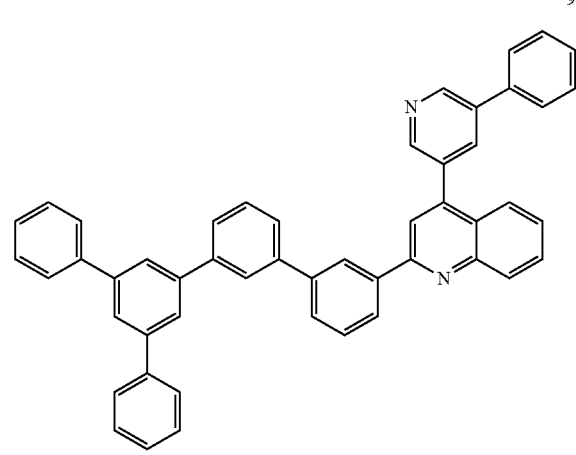
99
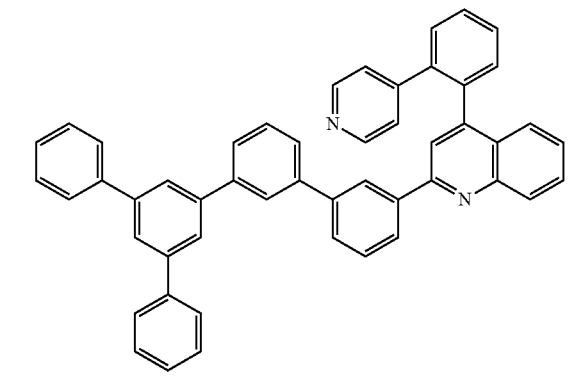
100
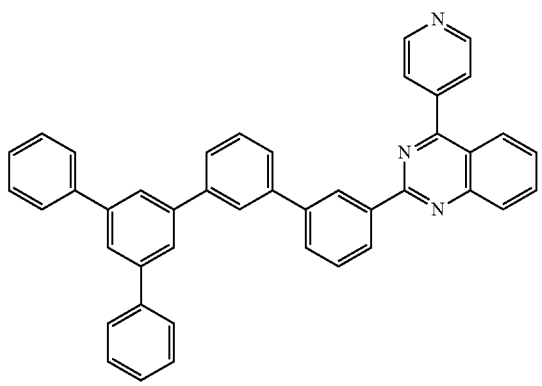
101
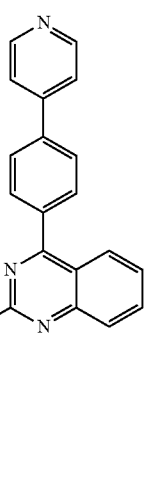

102
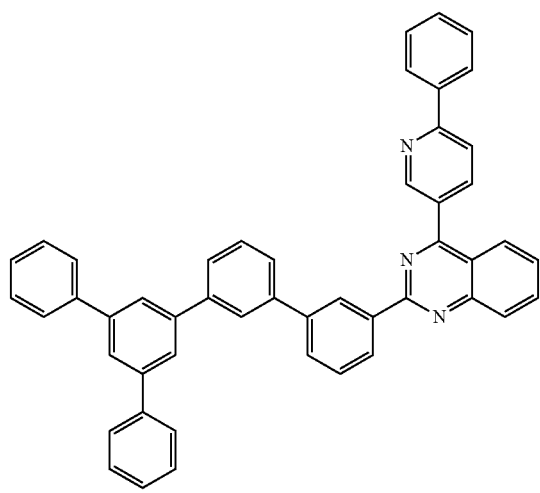
103
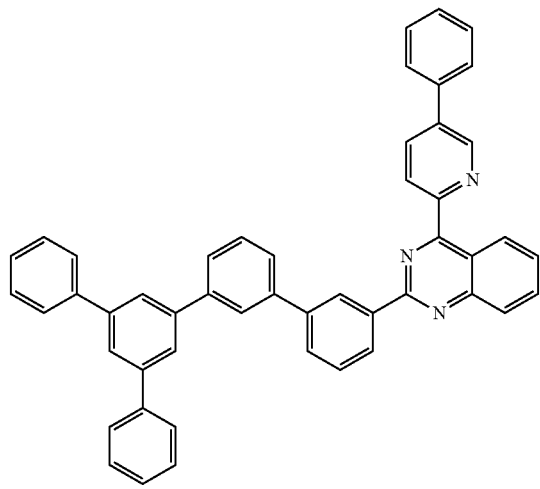
105
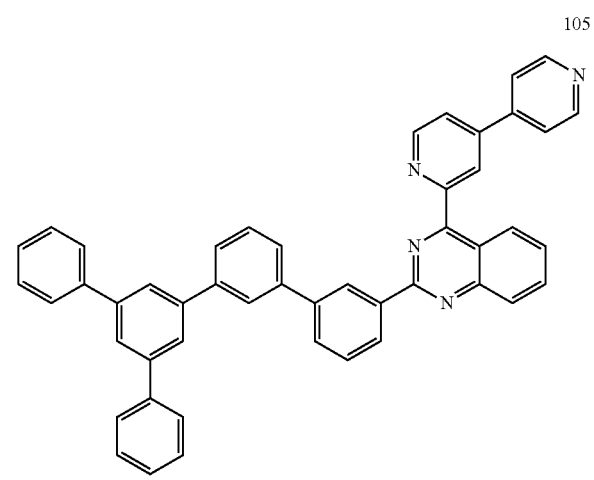
106
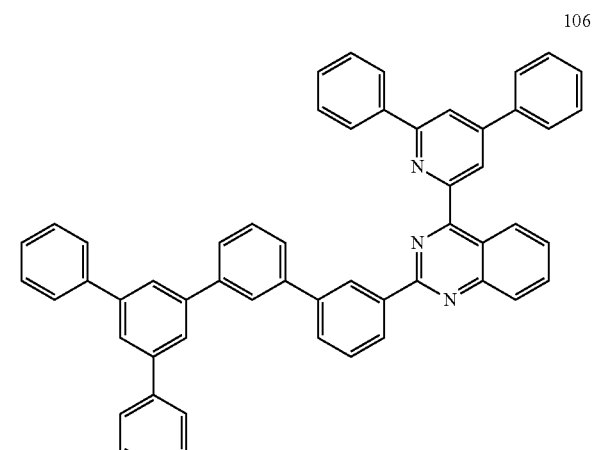
104
107
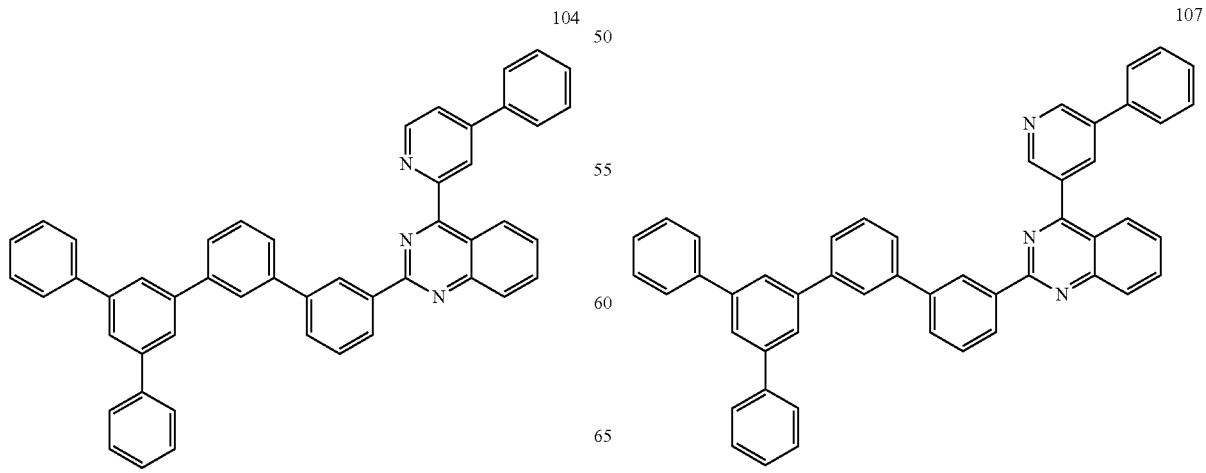

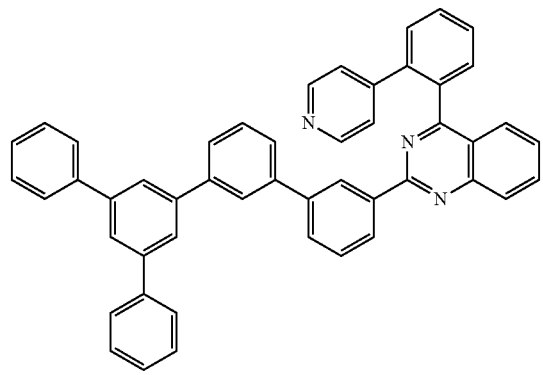
108
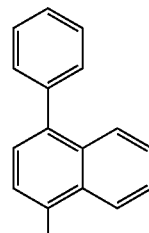
111
109
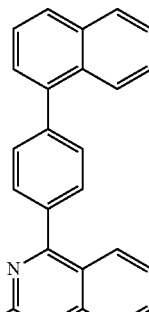
112
110
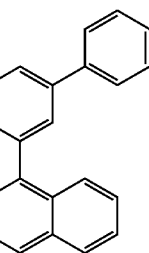
113

114
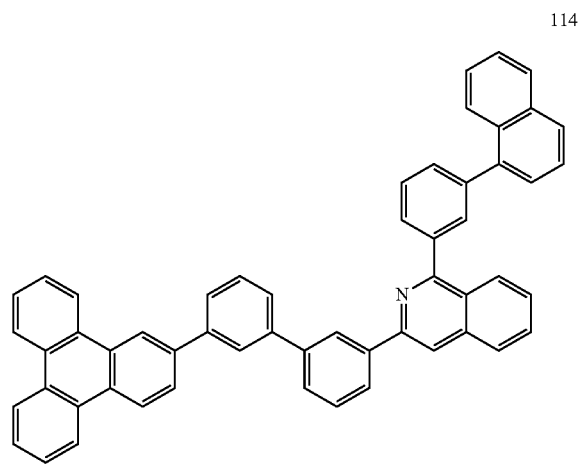
115
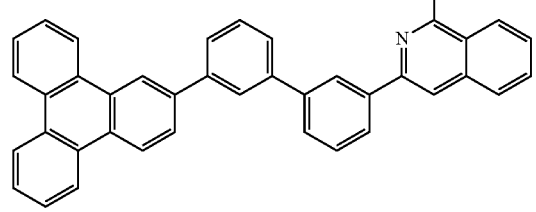
116
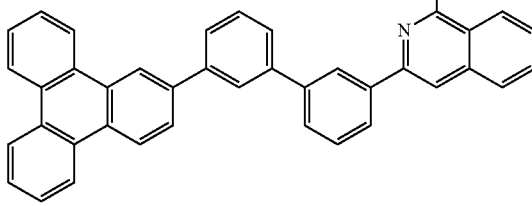
117
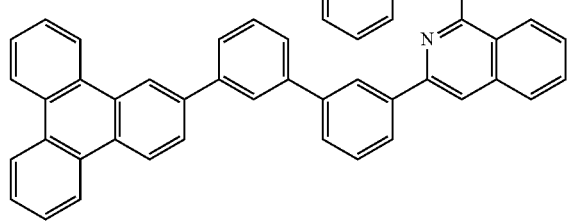
118
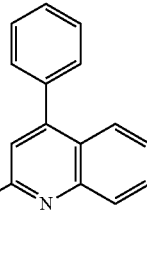
119
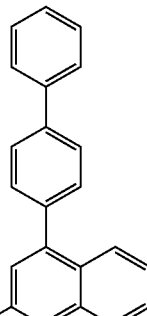
120
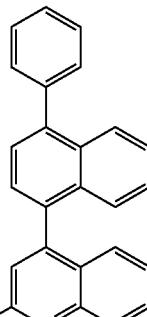

121
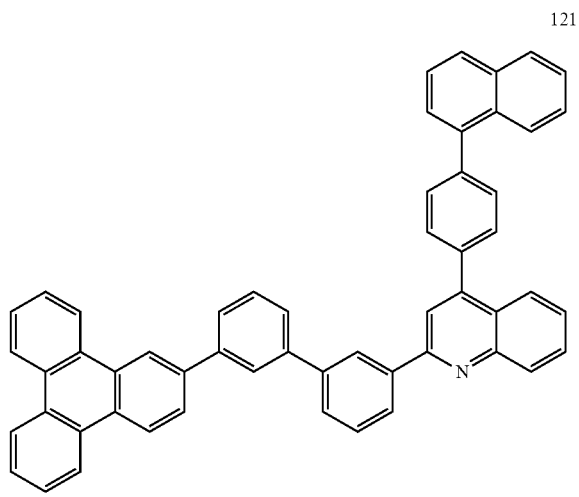
122
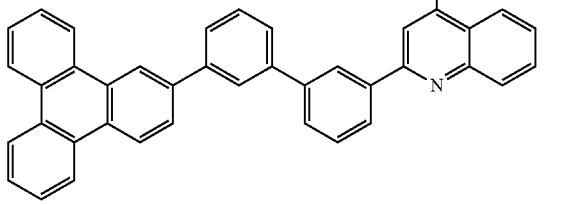
123
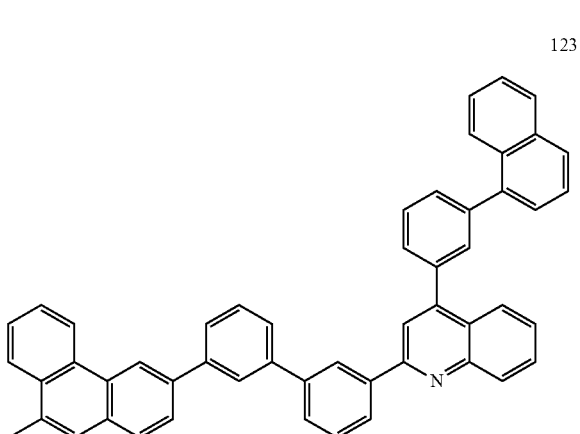
124
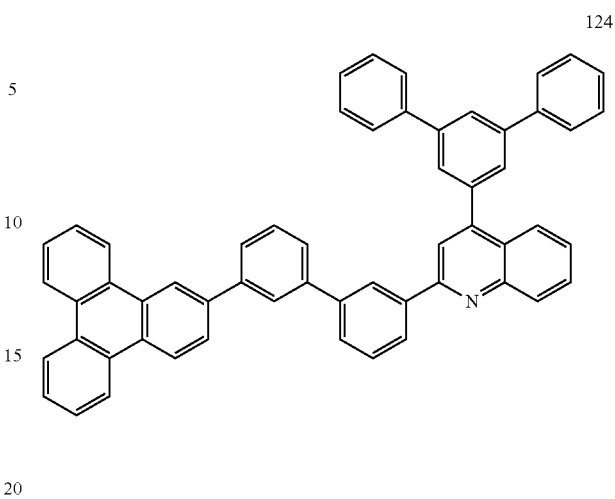
125
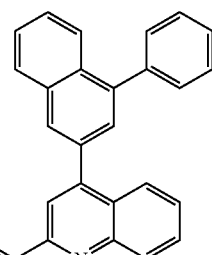
126
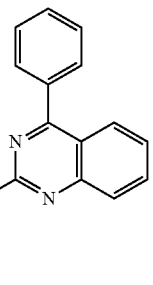
127

128
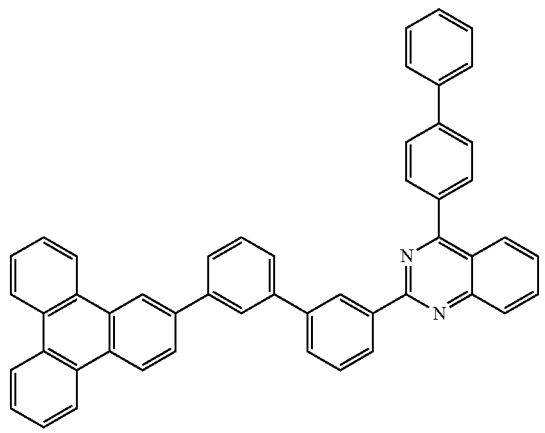
129
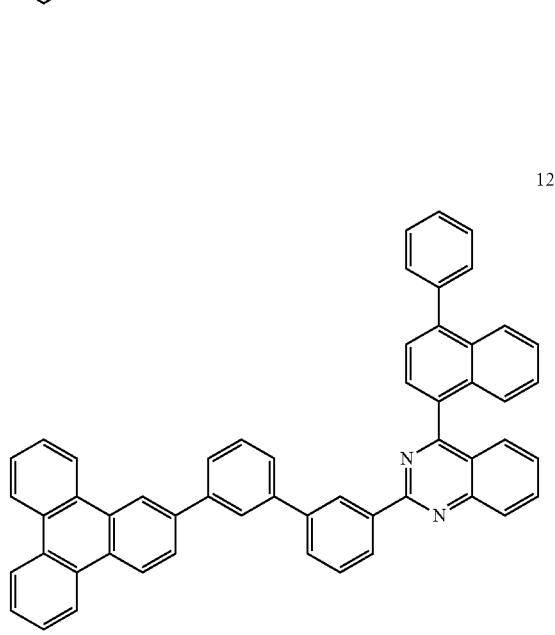
130
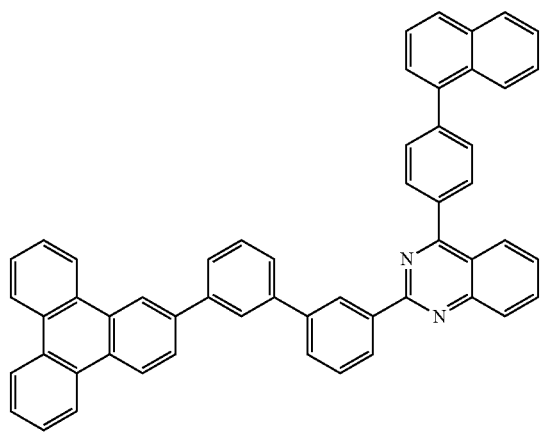
131
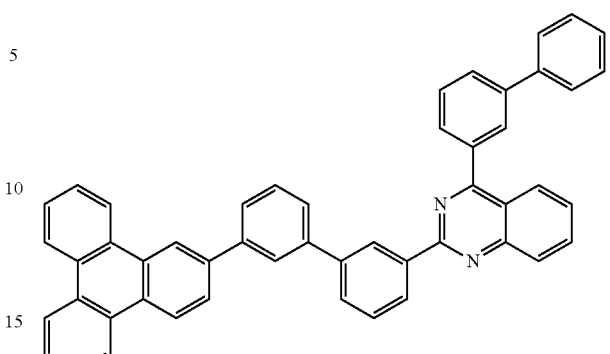
132
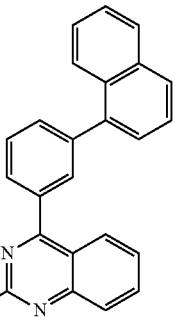
133
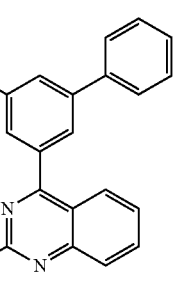
134
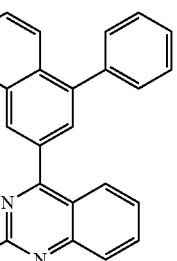

135
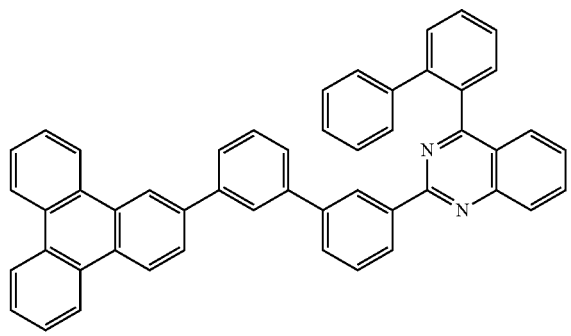
136
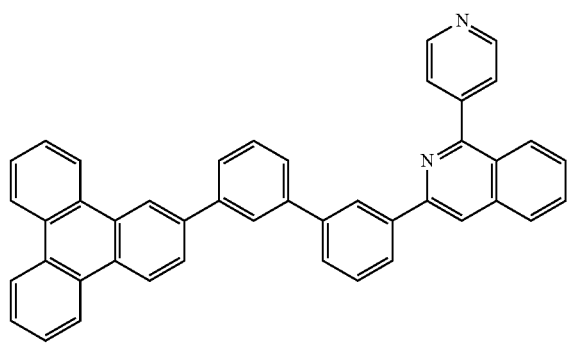
137
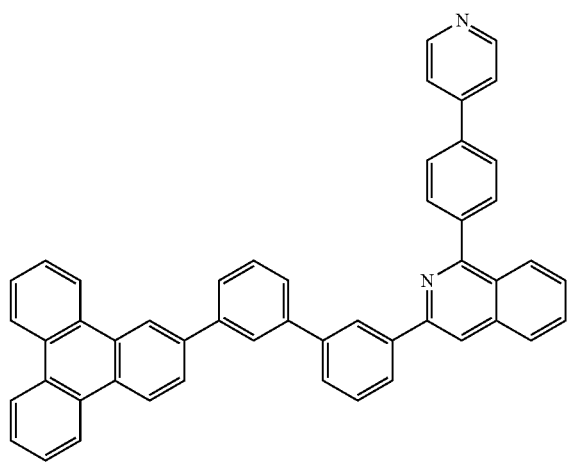
138
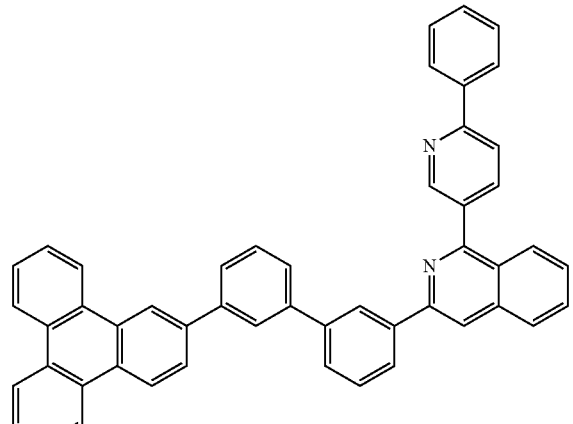
139
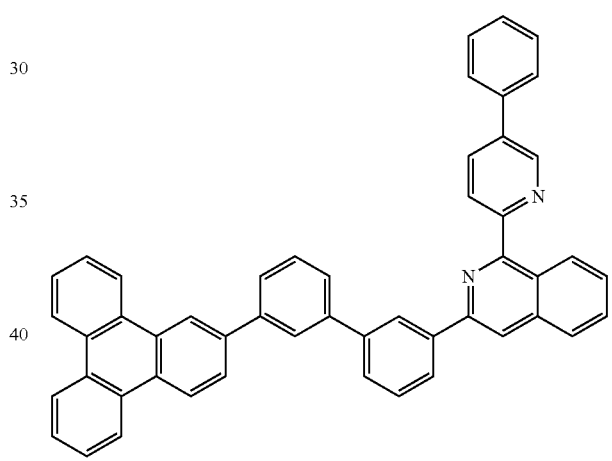
140
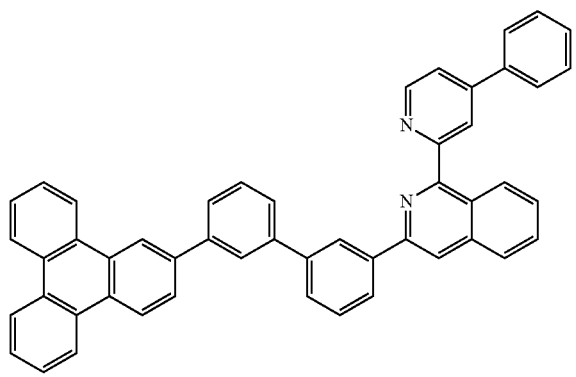

141
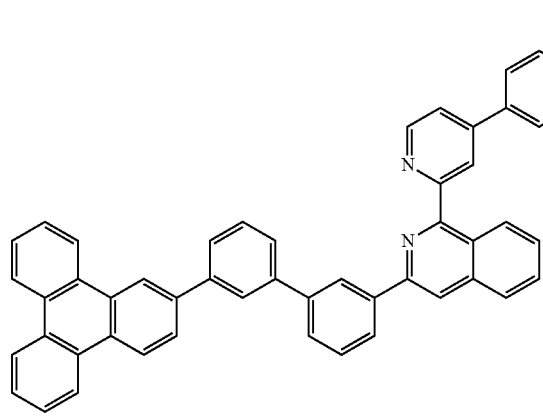
142
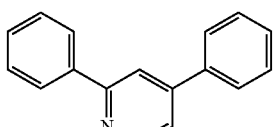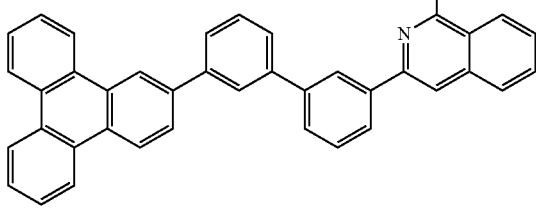
143
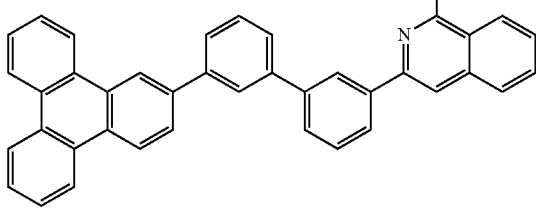
144
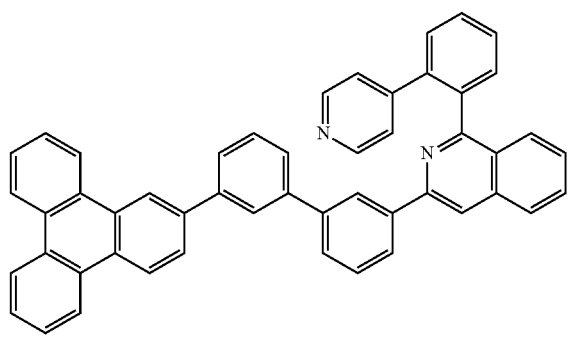
145
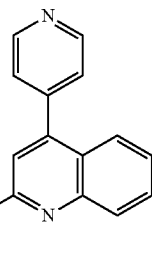
146
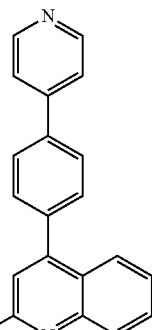
147
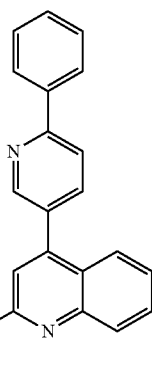

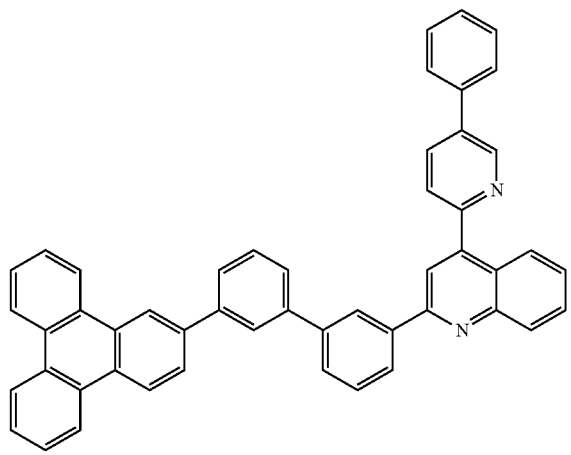
148
149
150
151
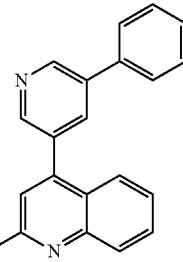
152
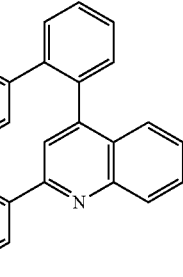
153
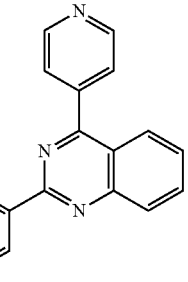
154
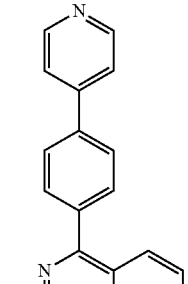
155

156
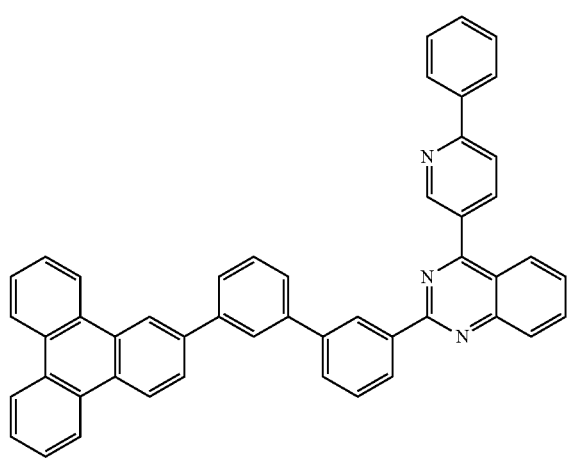
157
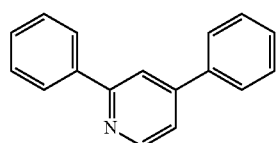
158
159
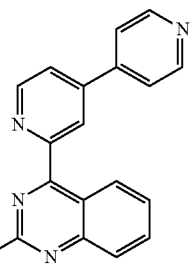
160
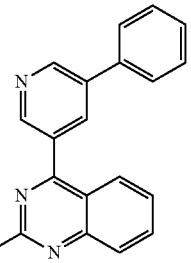
161
162
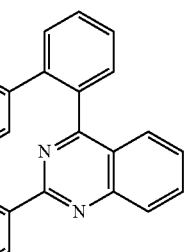

163
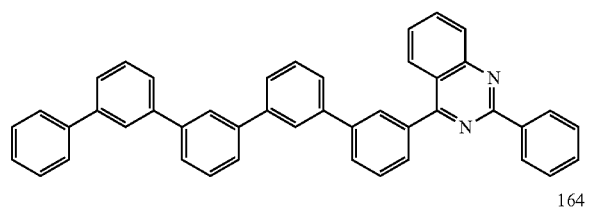
164
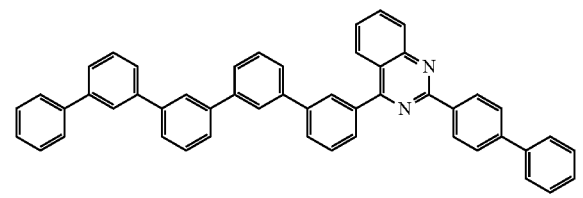
165
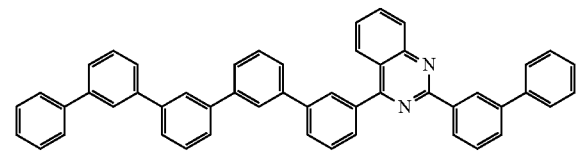
166
167
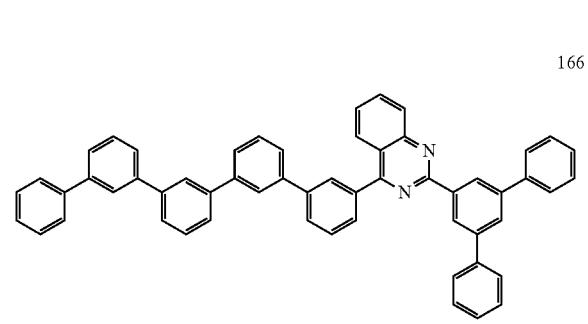
168
169
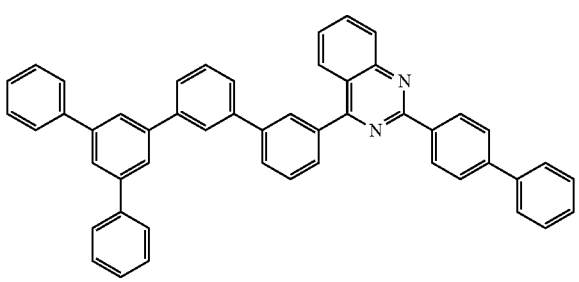
170
171
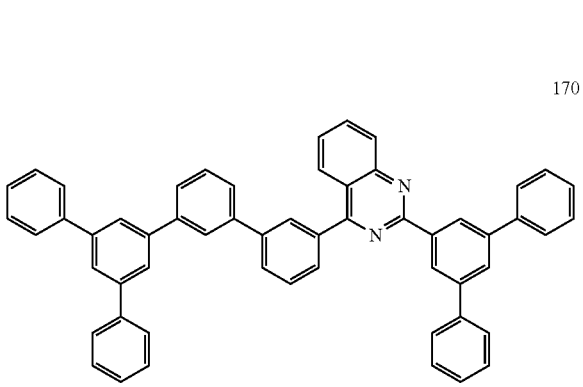
172
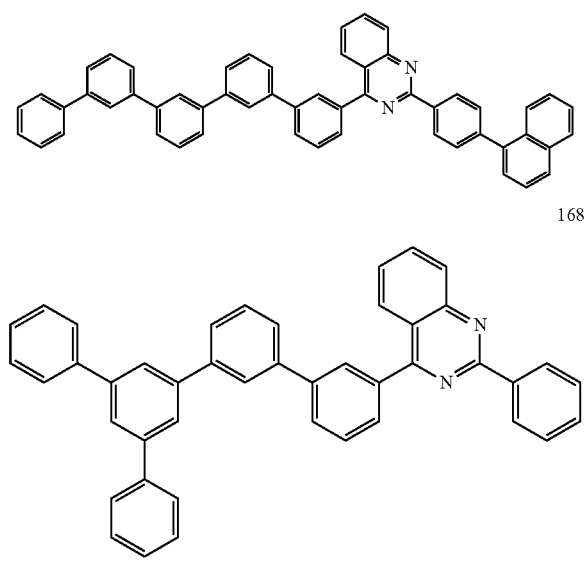
173
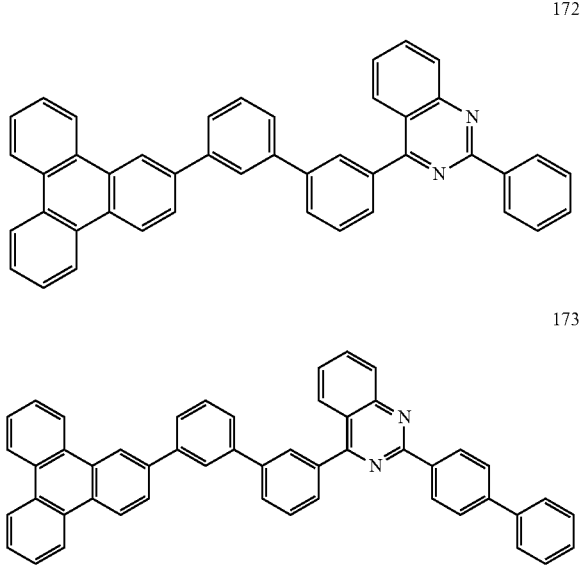

174
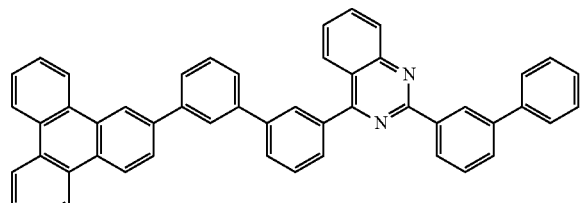
175
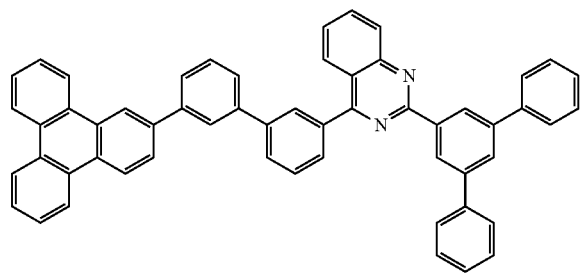
176
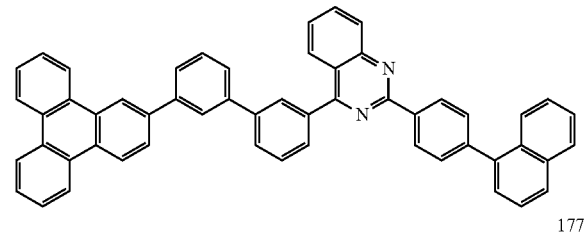
177
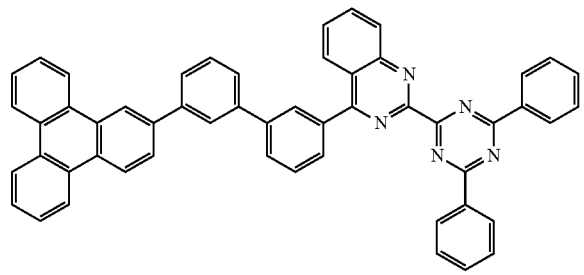
178
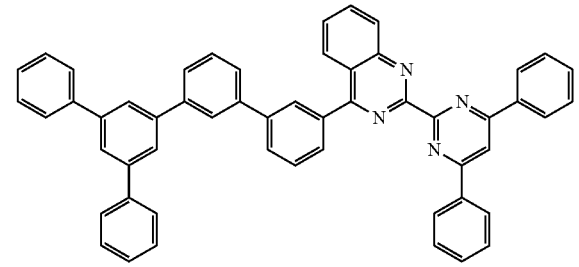
179
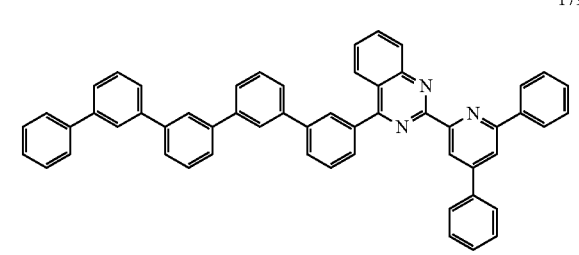
180
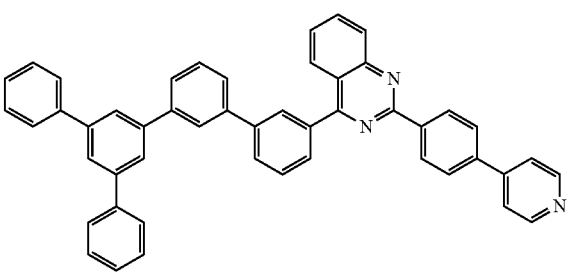
181
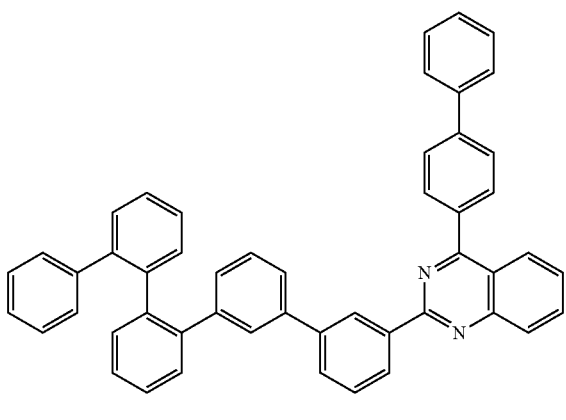
182
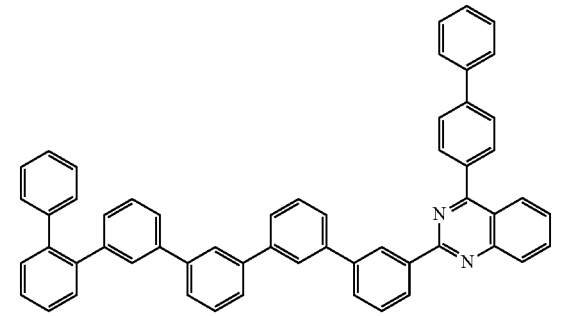
186
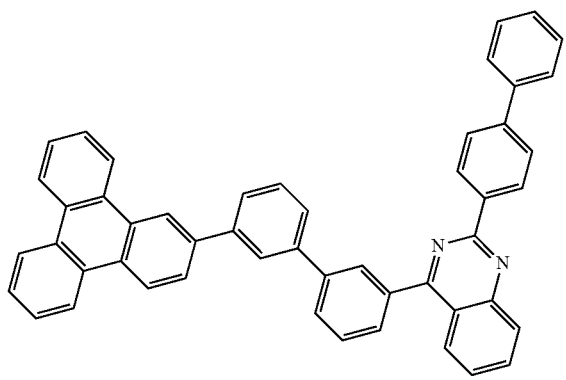

187
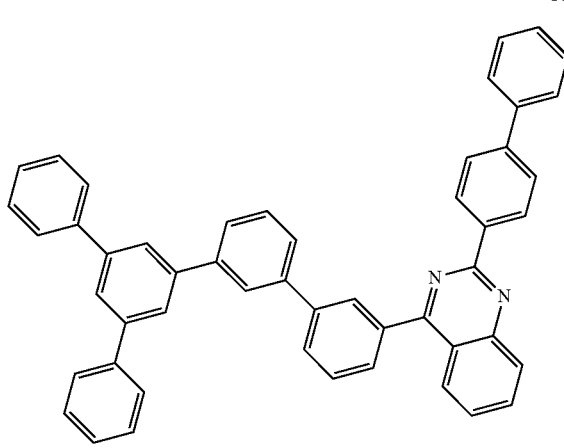
[Group 2]
B-10
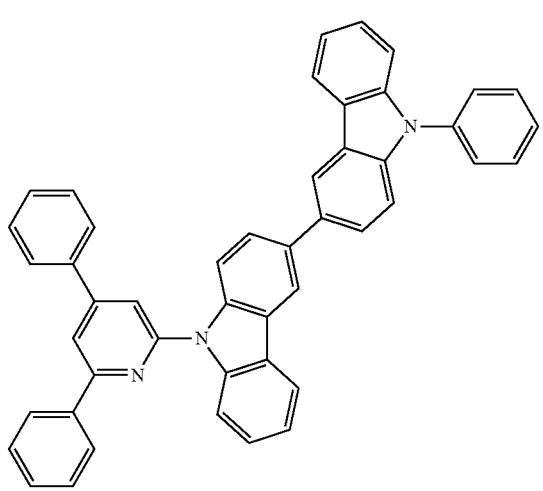
188
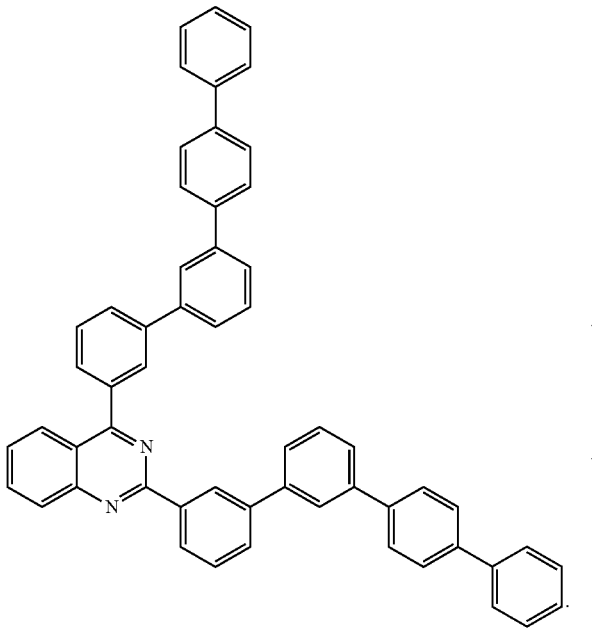
B-11
B-12
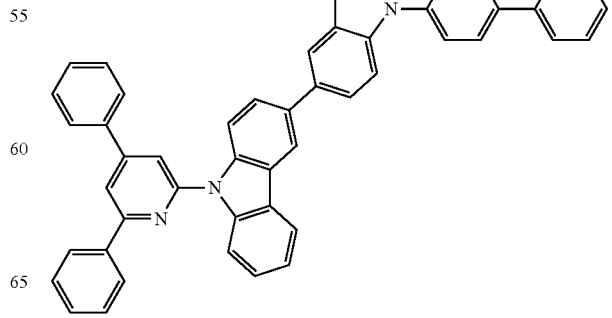
15. The composition for an organic optoelectric device of claim 6, wherein:
the second organic compound includes a compound represented by Chemical Formula 11, and
the second organic compound represented by Chemical Formula 11 is selected from compounds of Group 2:

B-13
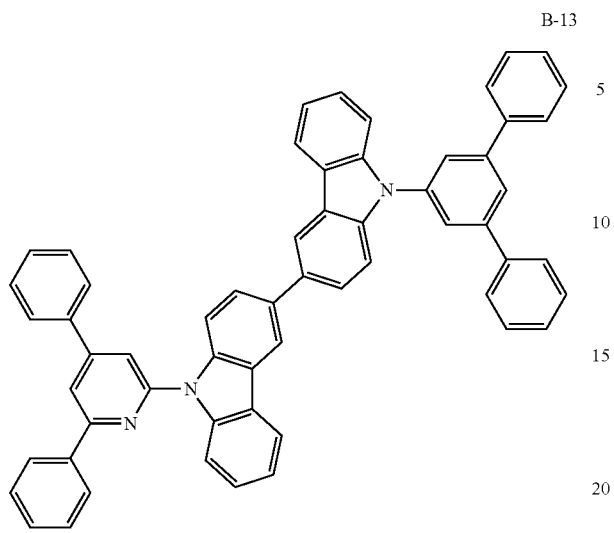
B-16
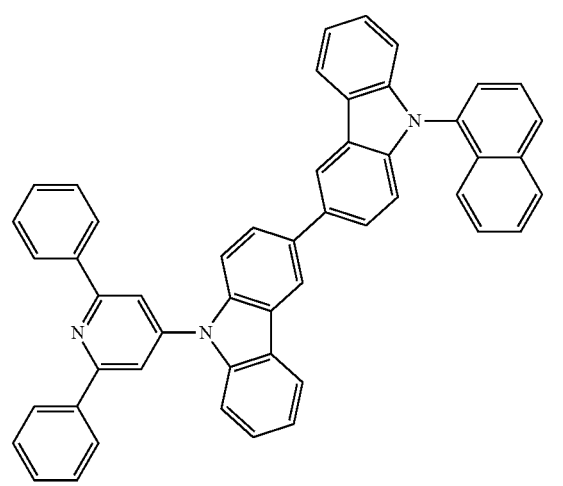
B-14
B-17
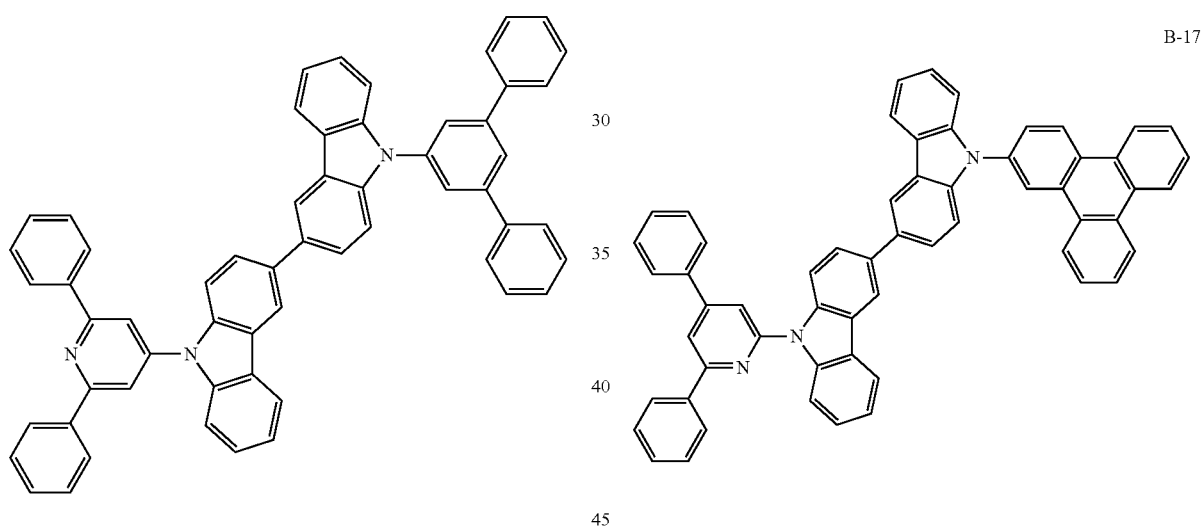
B-15
B-18
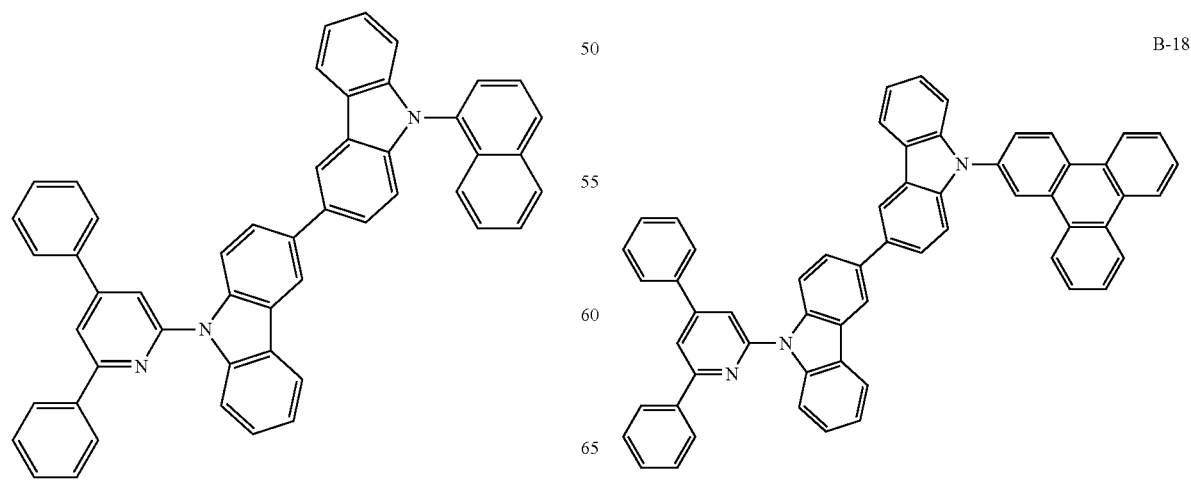

B-19
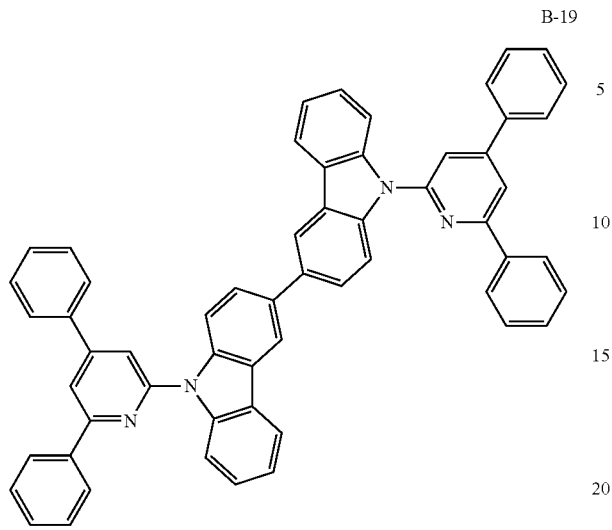
B-22
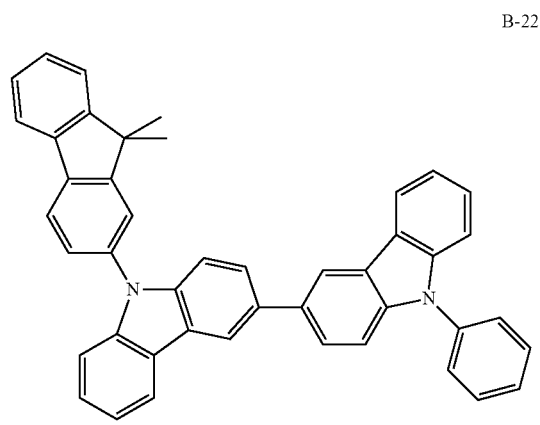
B-20
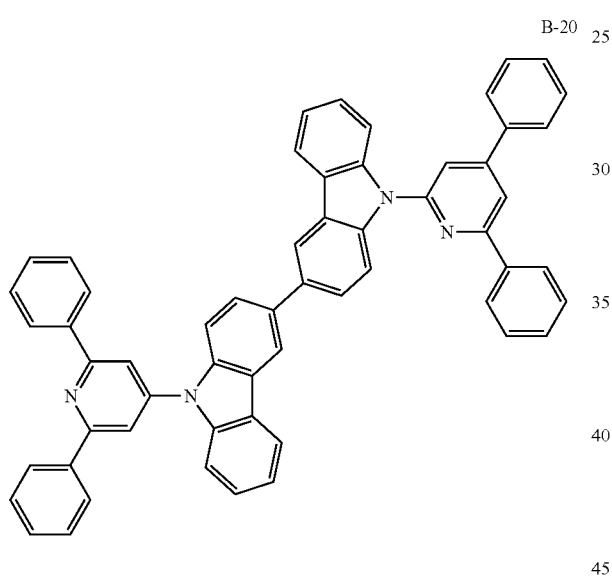
B-23
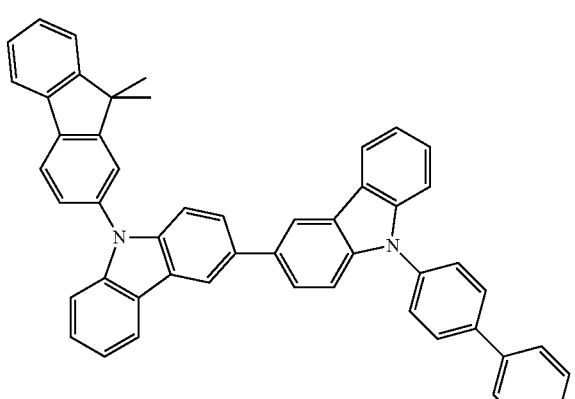
B-21
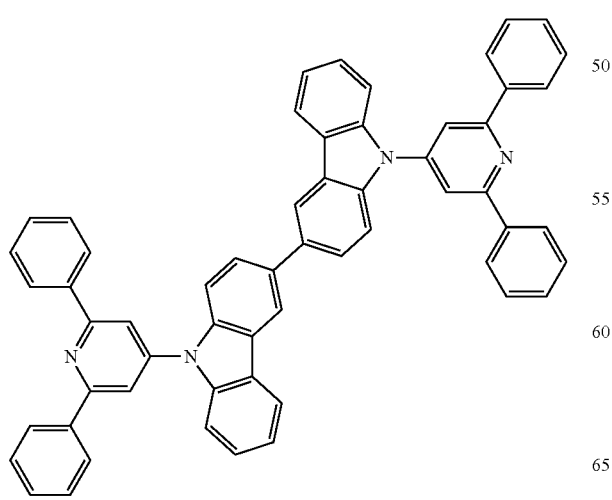
B-24
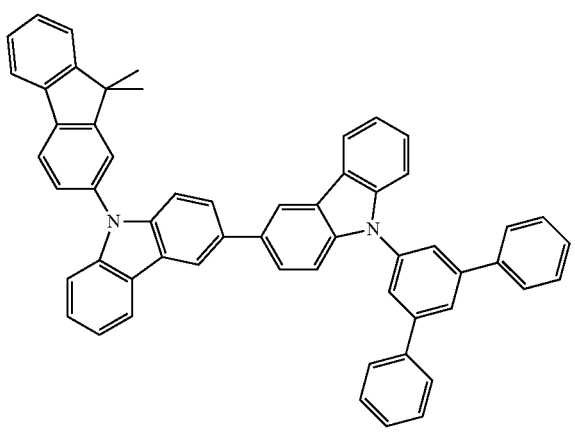

B-25
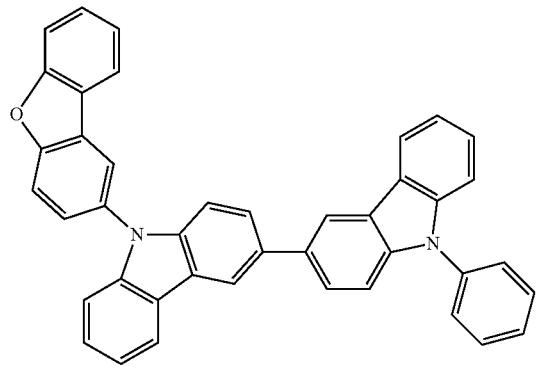
B-28
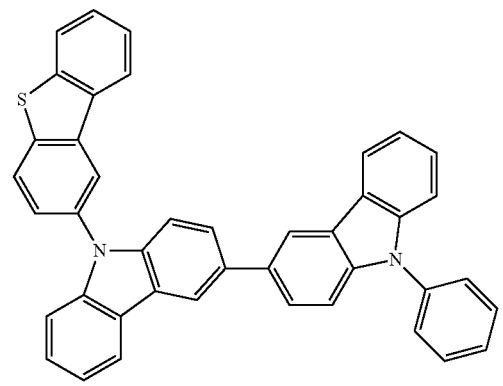
B-26
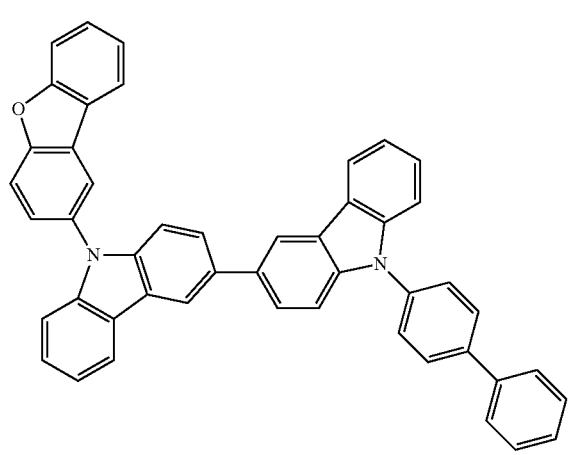
B-29
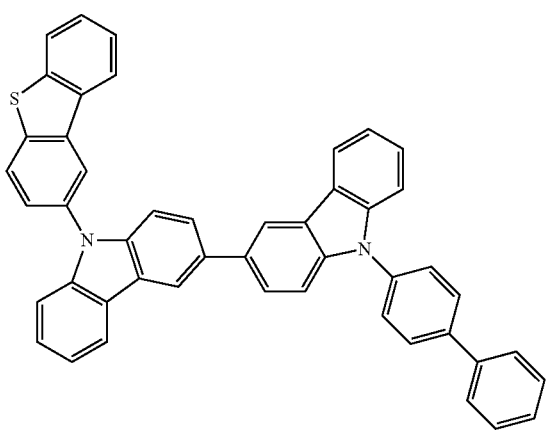
B-27
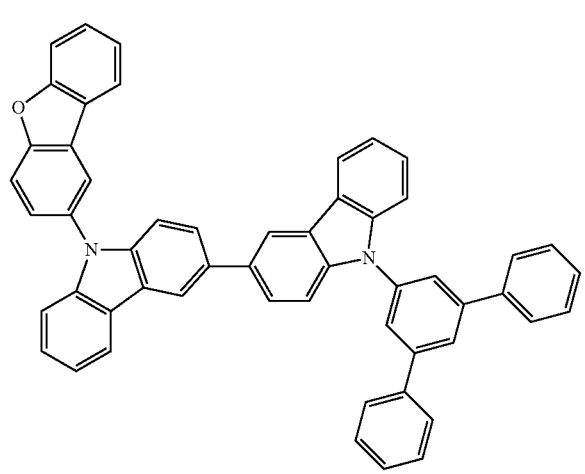
B-30
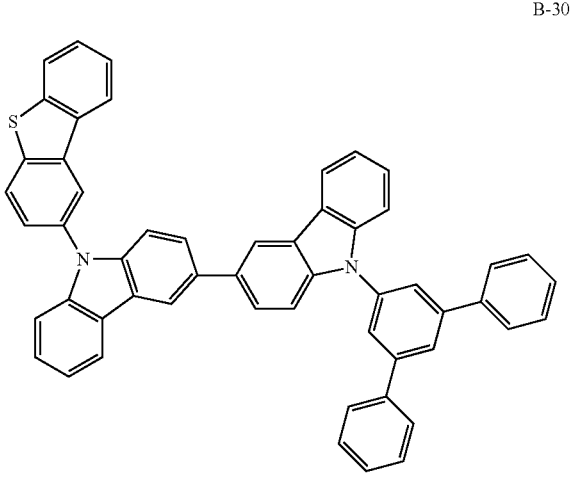

B-31
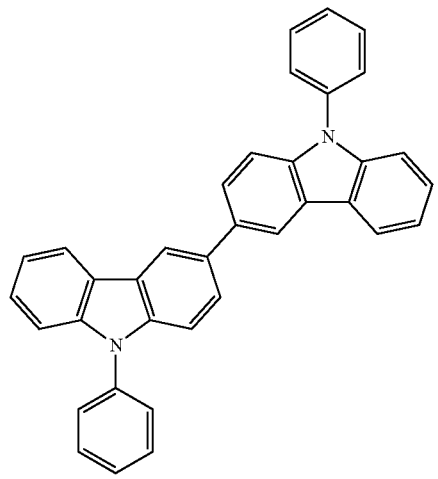
B-32
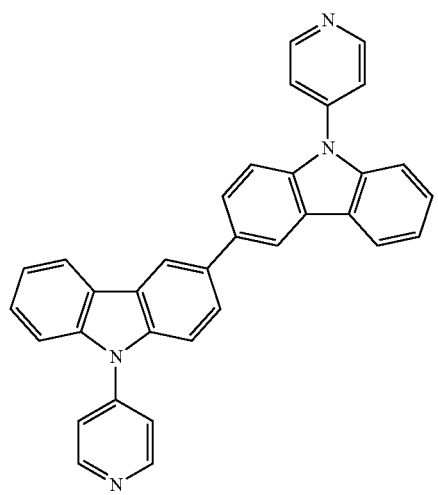
B-33
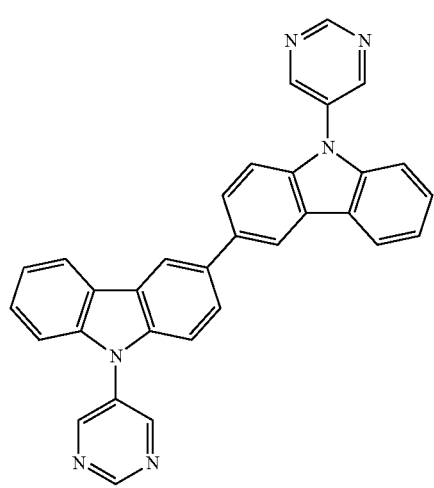
B-34
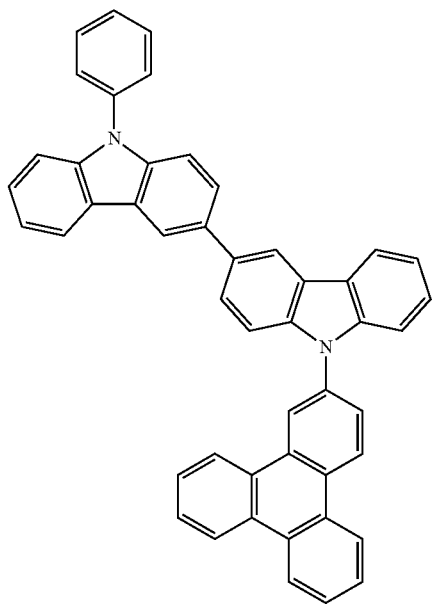
B-35
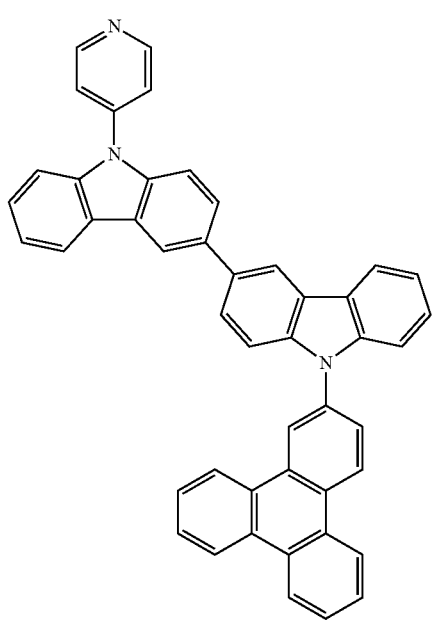

B-37
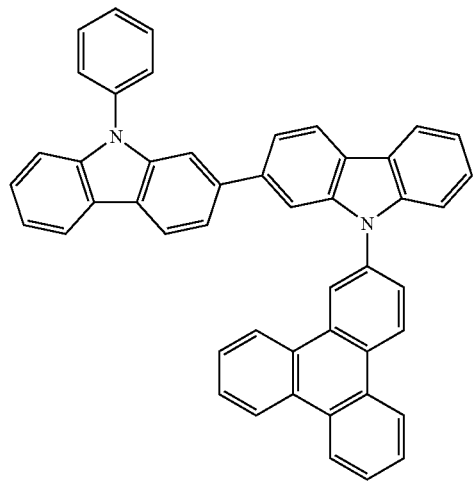
B-38
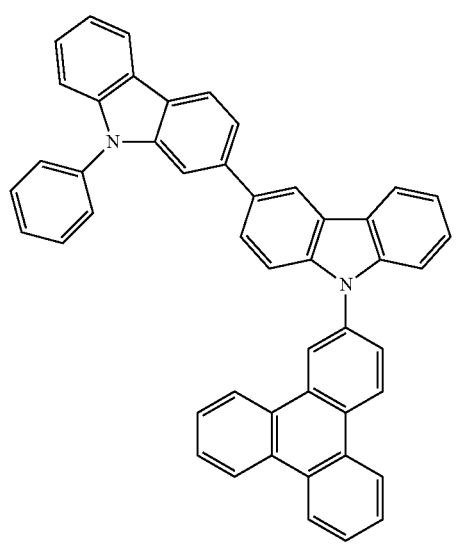
B-40
B-41
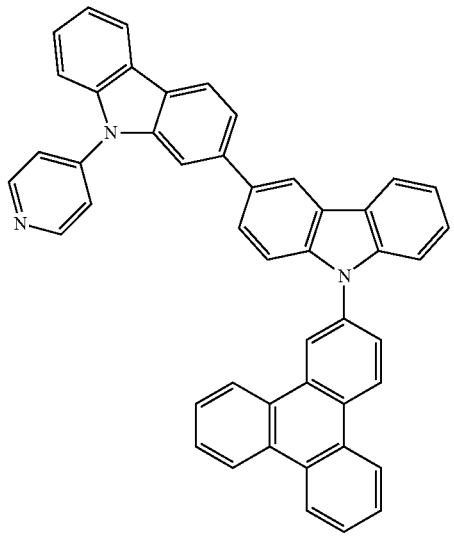
B-43
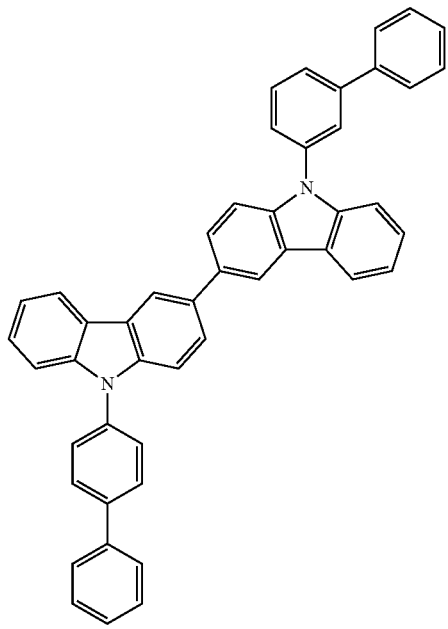

B-44
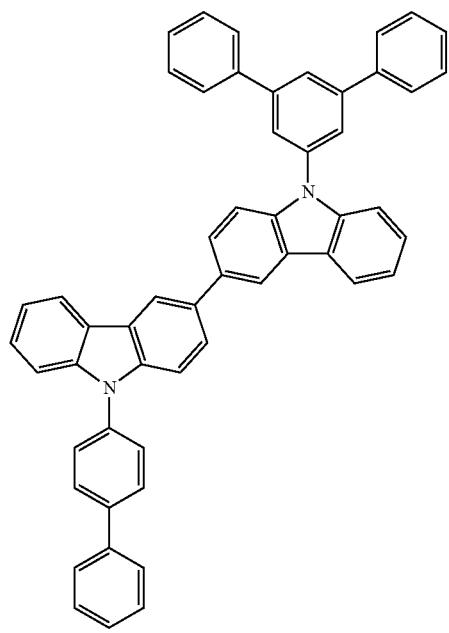
B-45
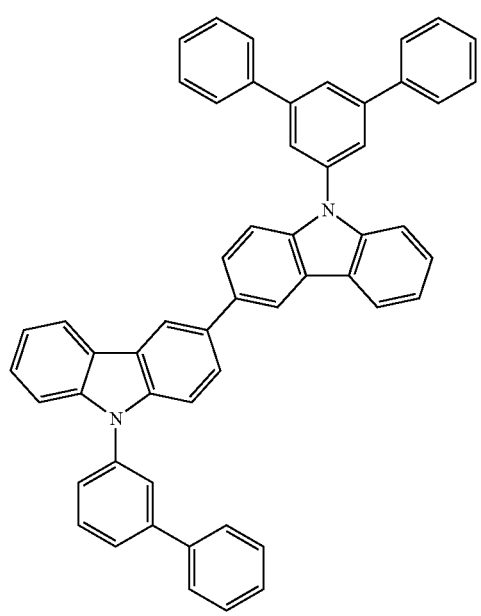
B-46
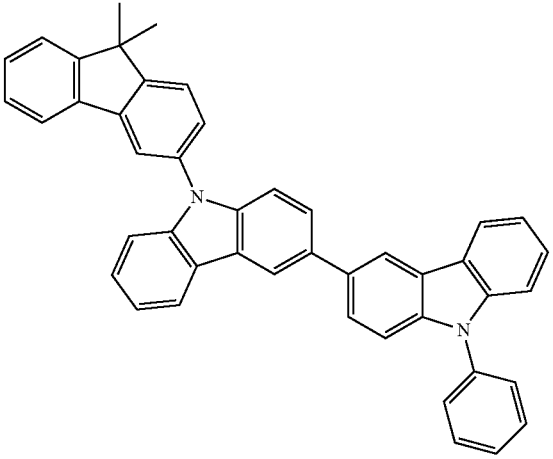
B-47
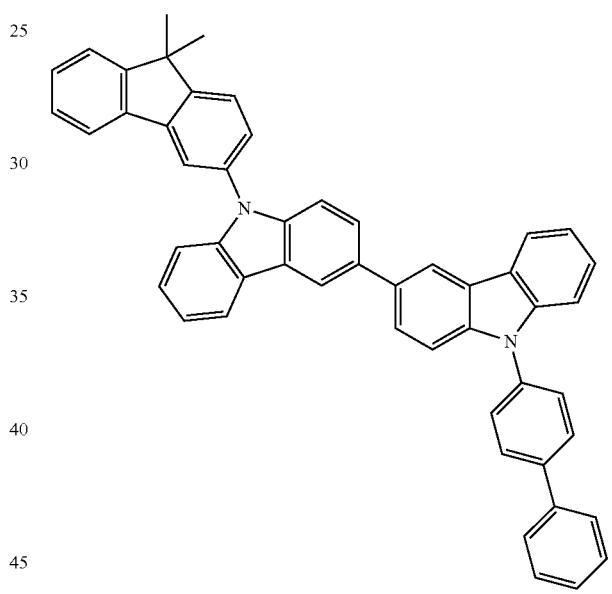
B-48
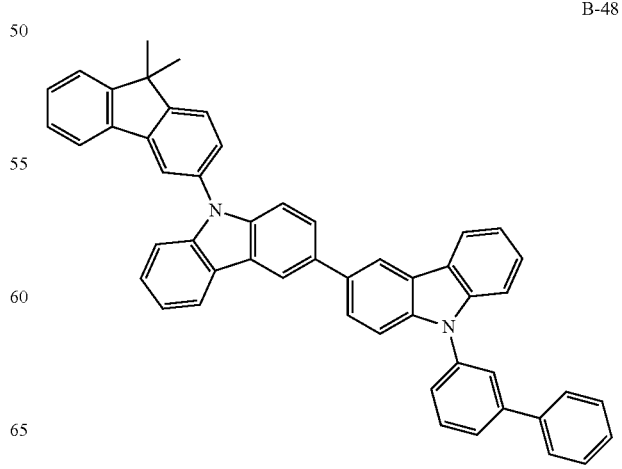

B-49
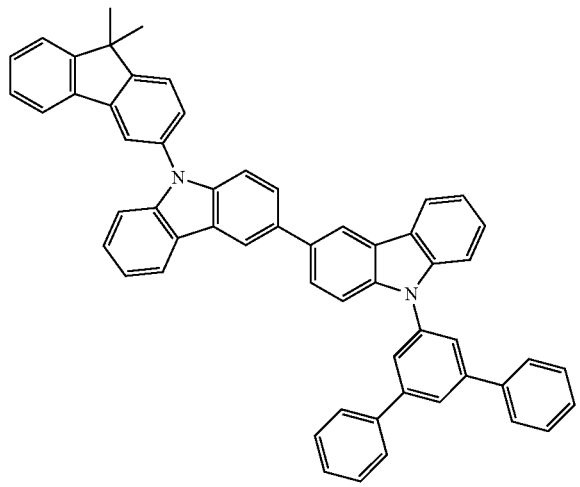
B-50
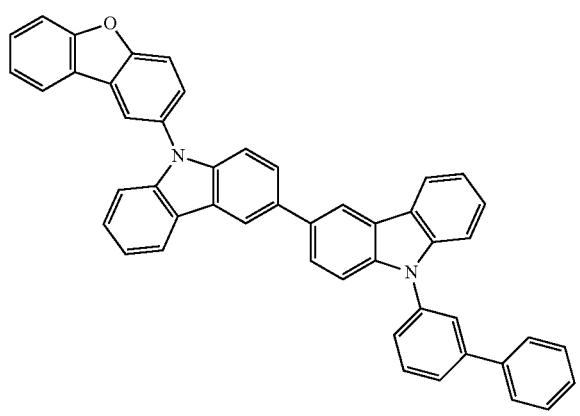
B-51
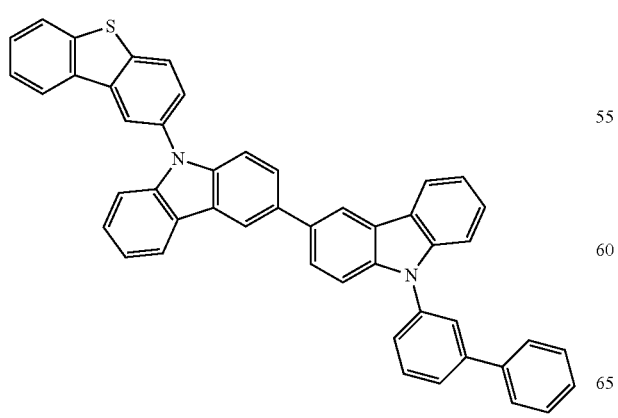
B-52
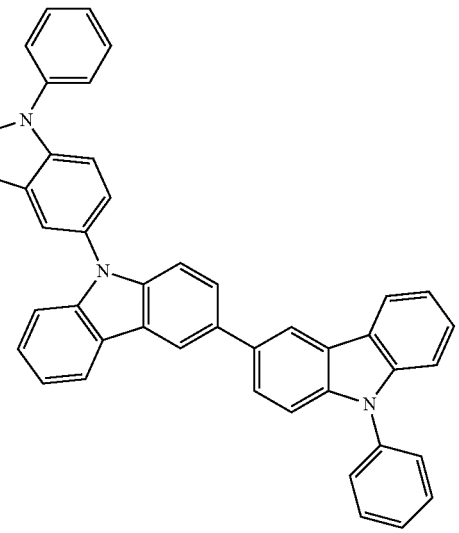
B-53
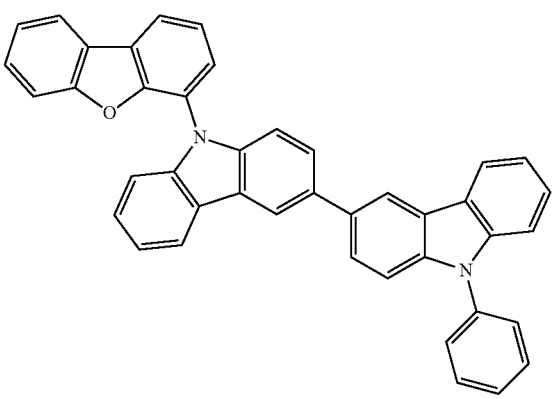
B-54
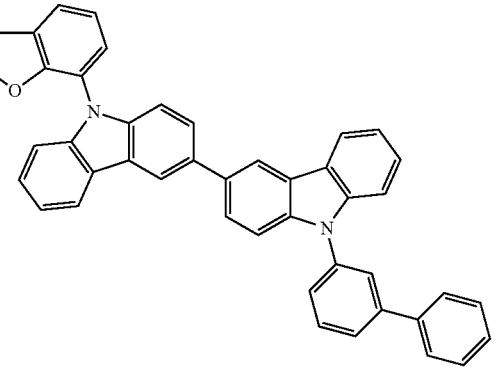

B-55
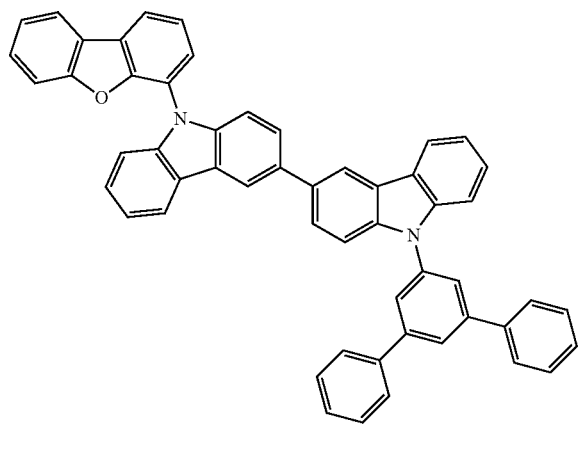
B-58
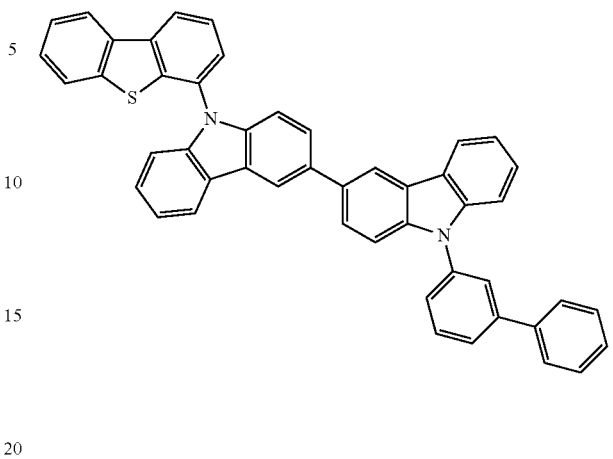
B-56
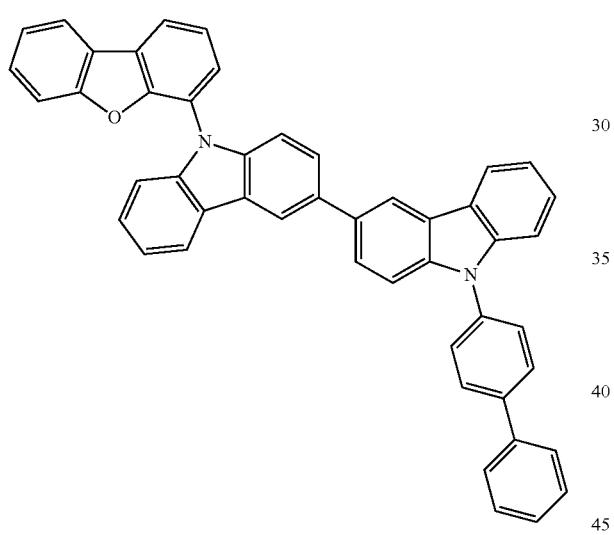
B-59
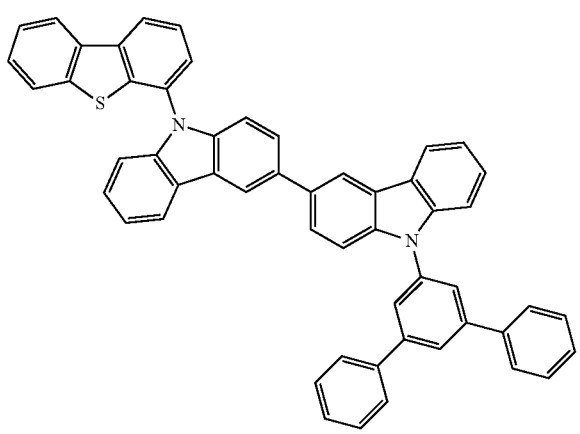
B-57
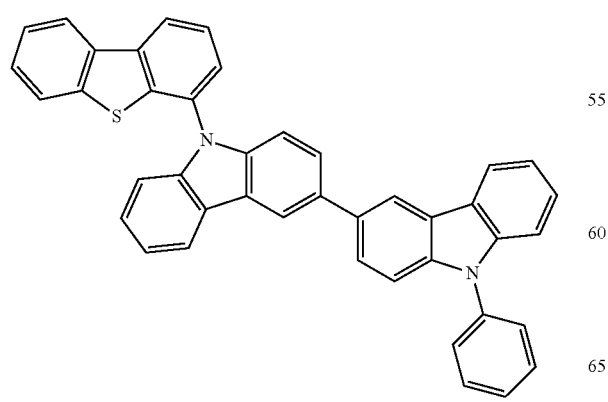
B-60
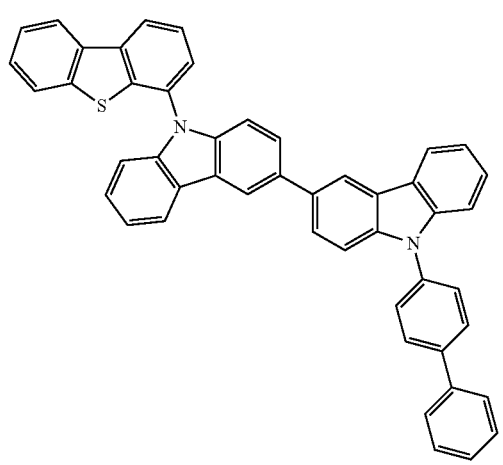

B-61
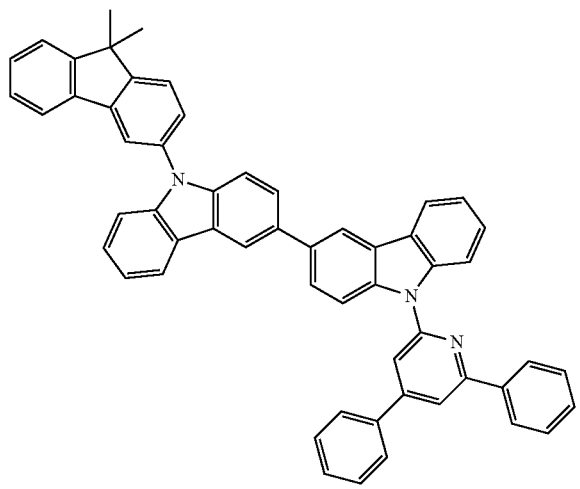
B-64
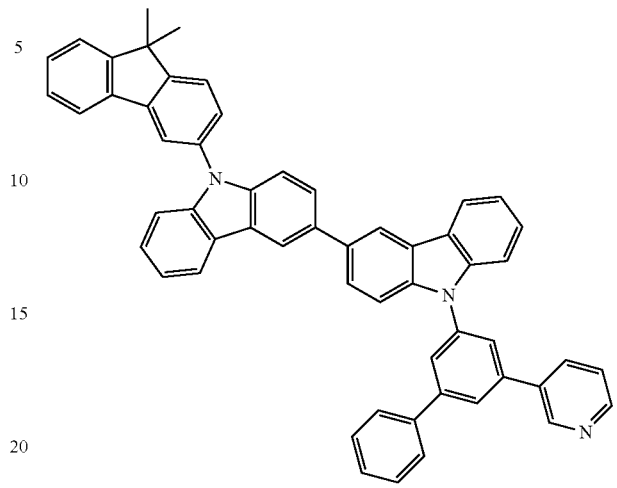
B-62
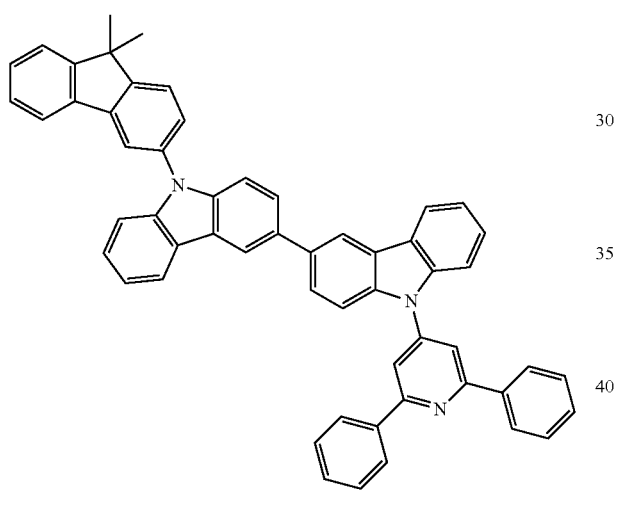
B-65
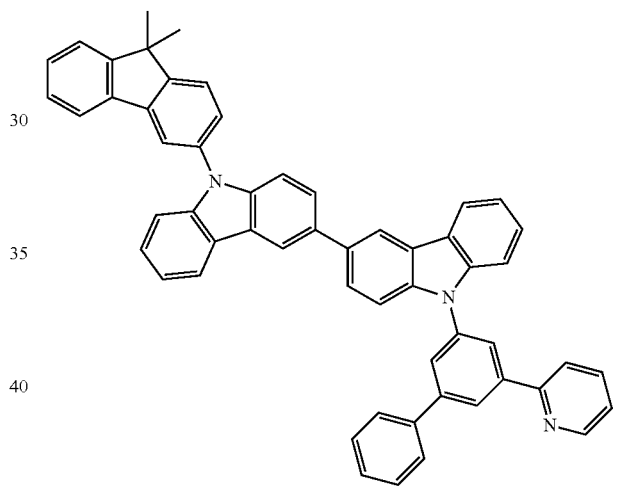
B-63
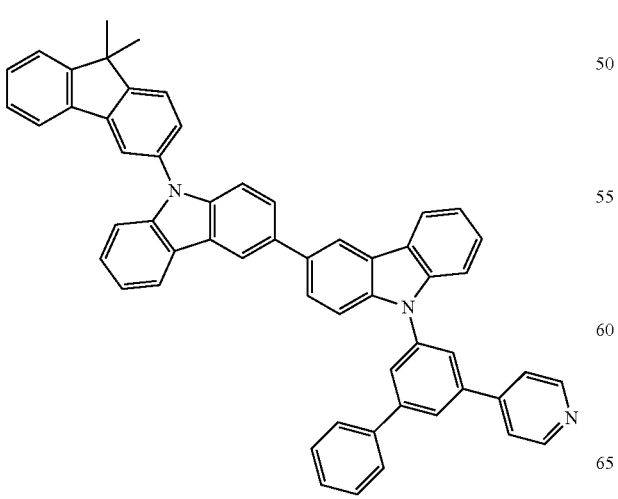
B-66
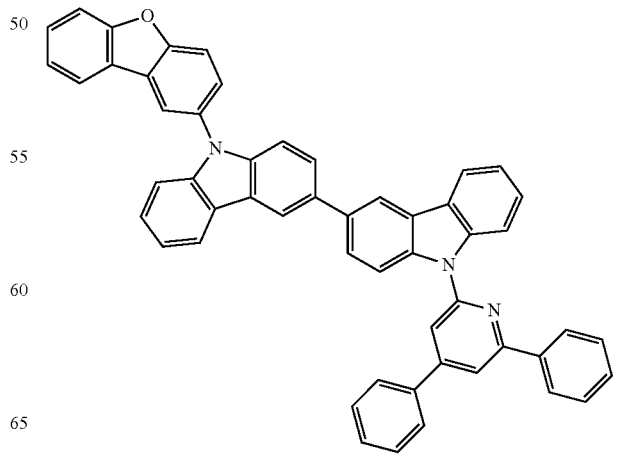

B-67
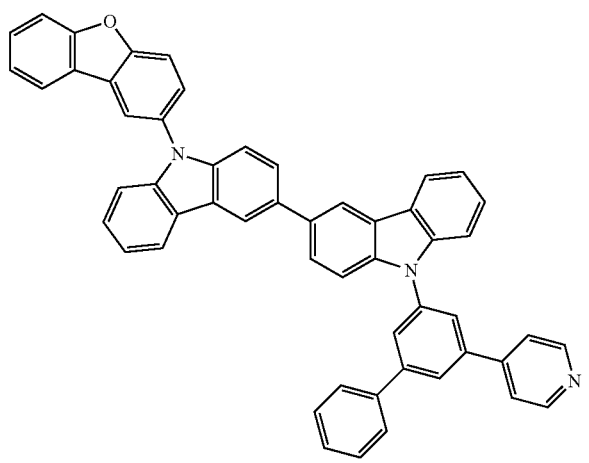
B-70
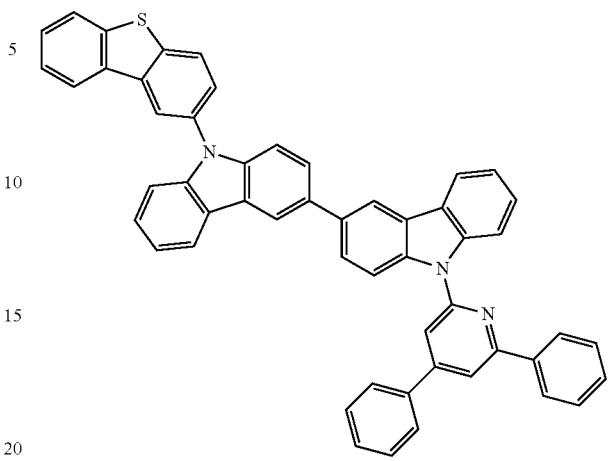
B-68
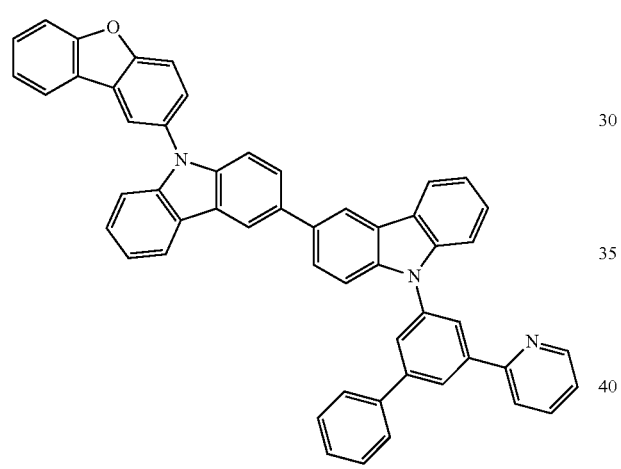
B-71
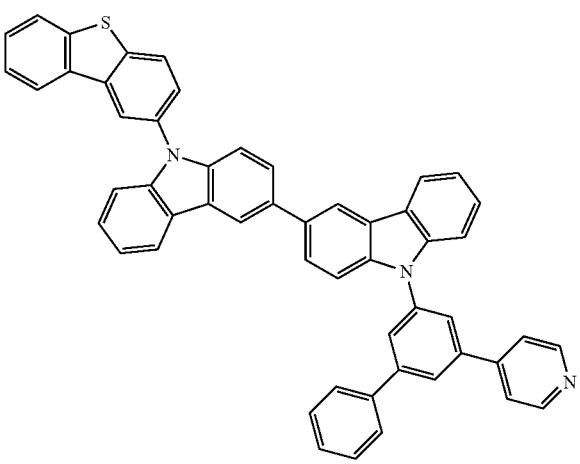
B-69
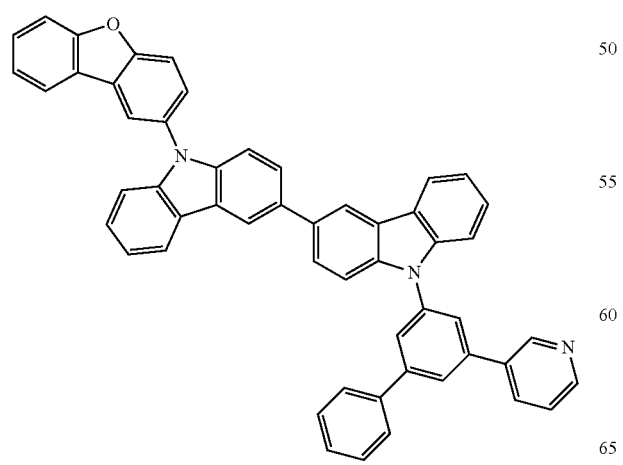
B-72

-continued
B-73
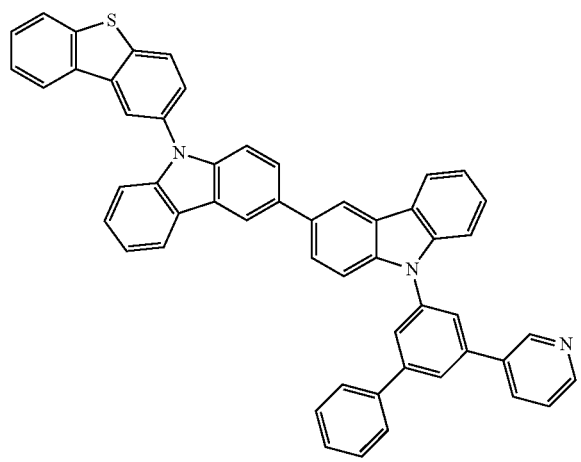
B-77
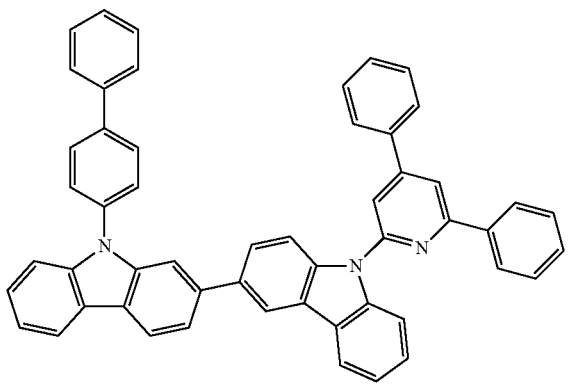
B-74
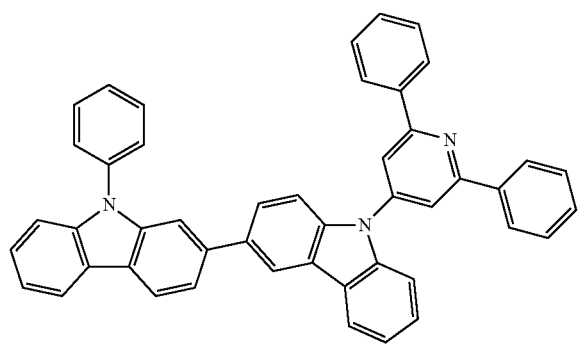
B-78
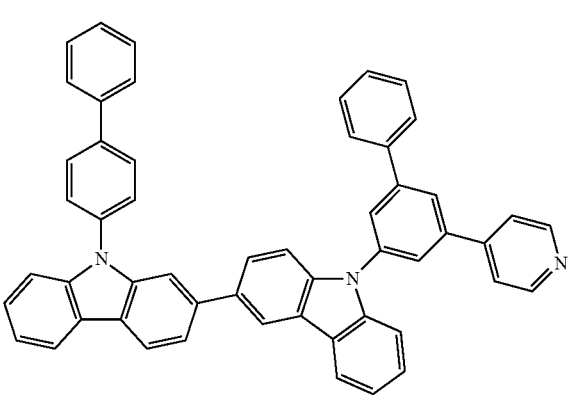
B-75
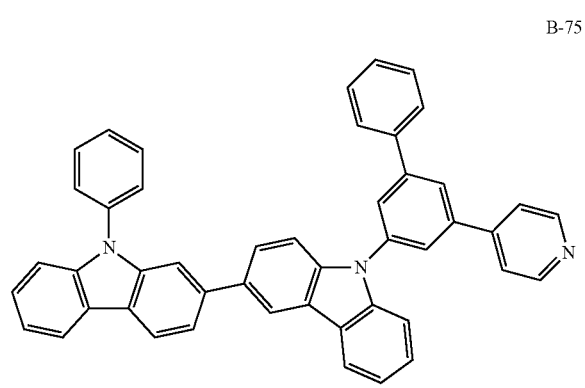
B-79
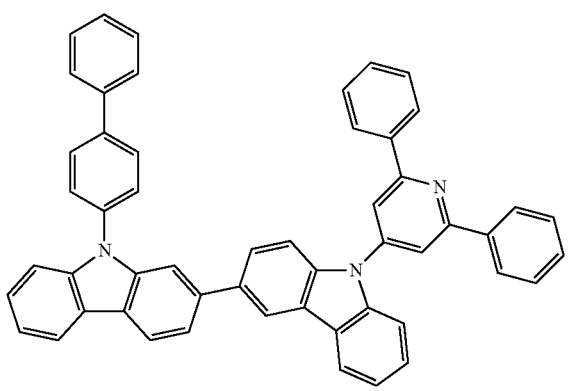
B-76
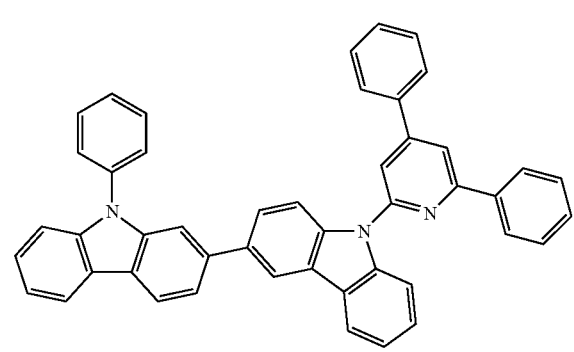
B-80
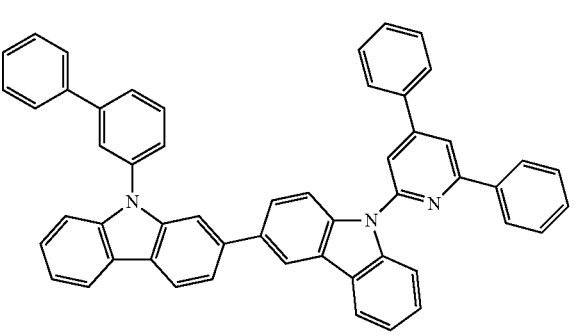

B-81
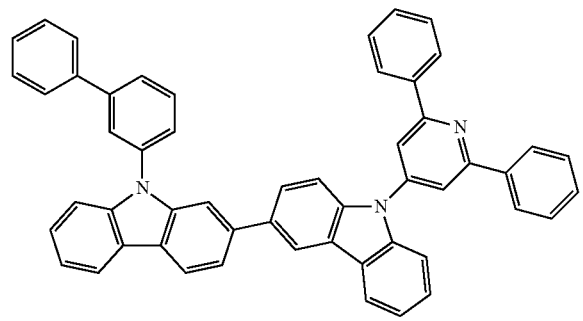
B-85
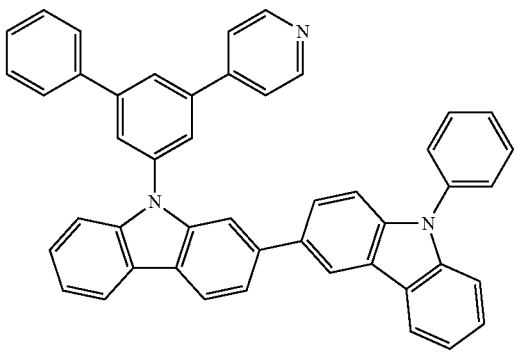
B-82
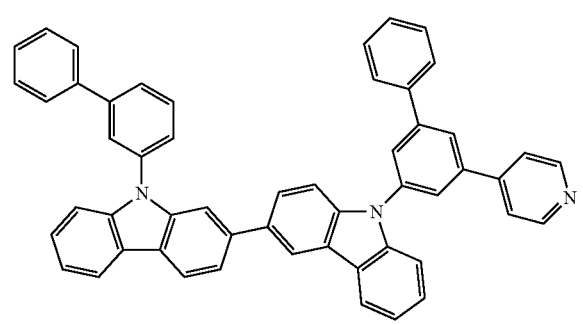
B-86
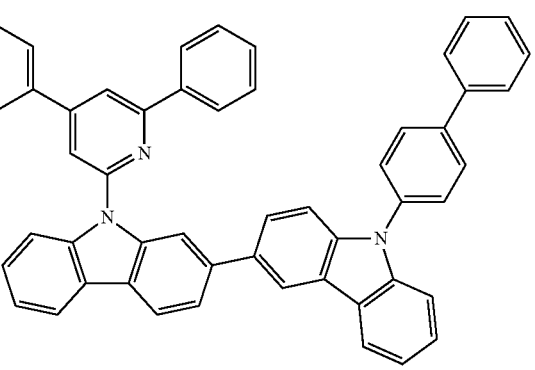
B-83
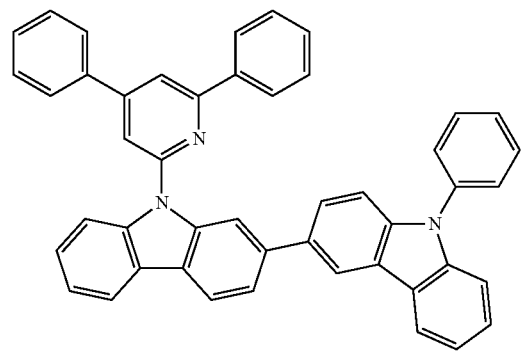
B-87
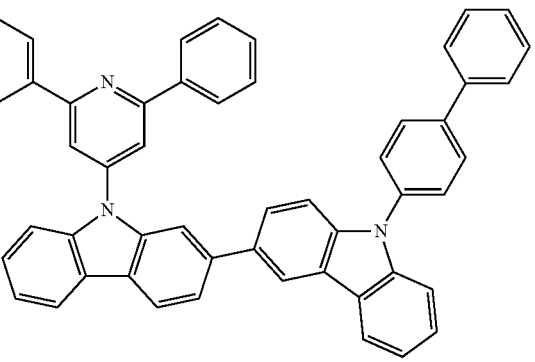
B-84
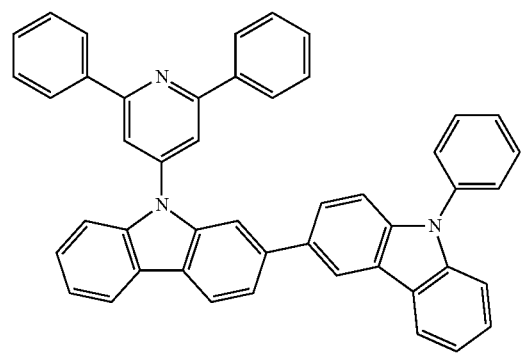
B-88
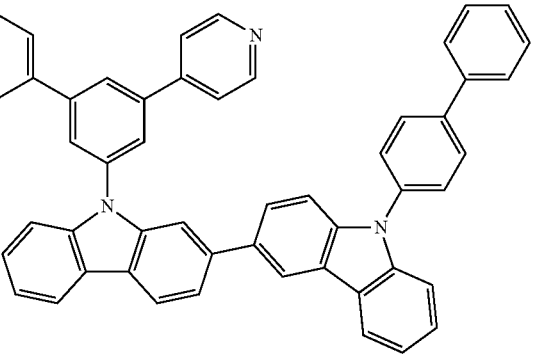

B-89
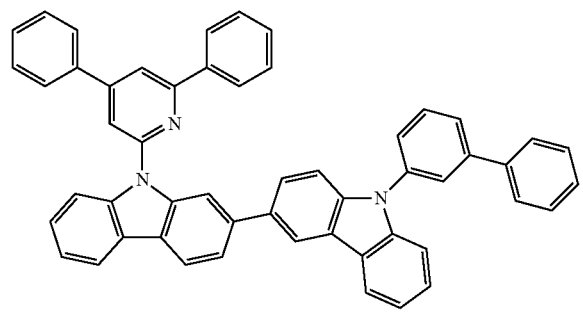
B-93
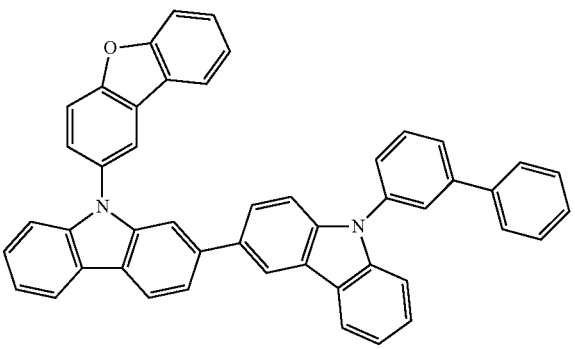
B-90
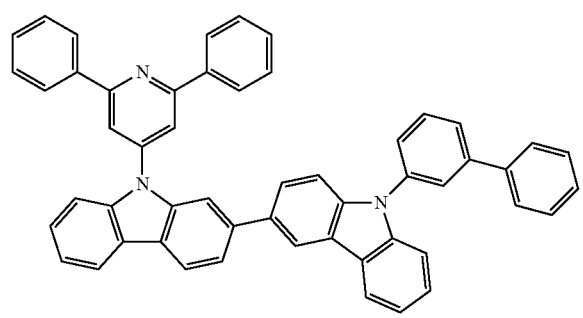
B-94
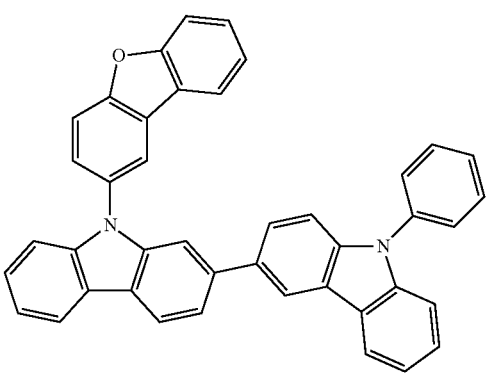
B-91
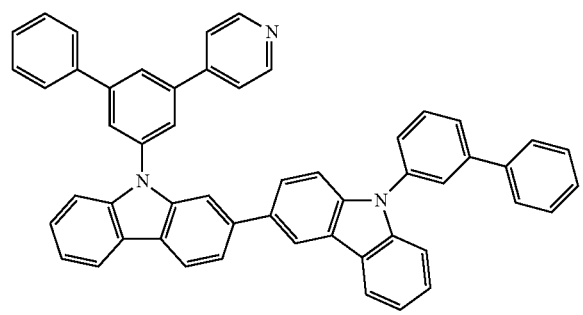
B-95
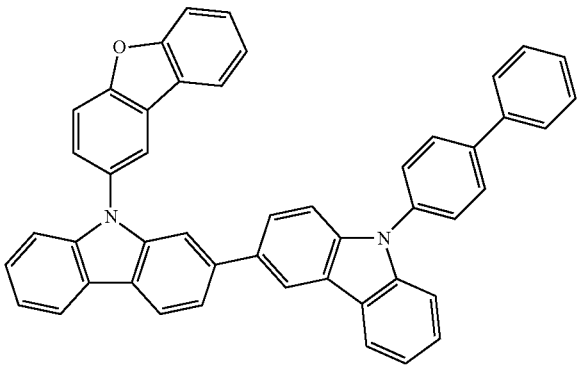
B-92
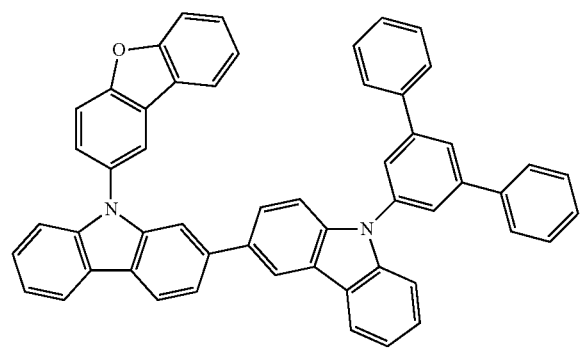
B-96
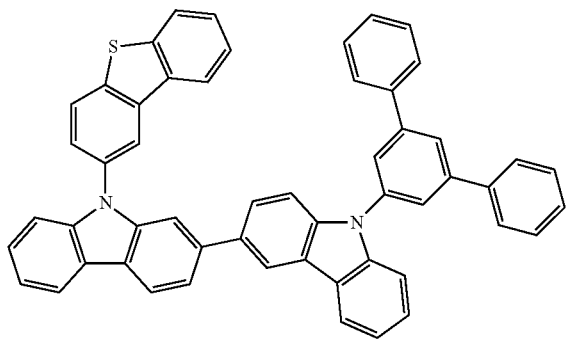

B-97
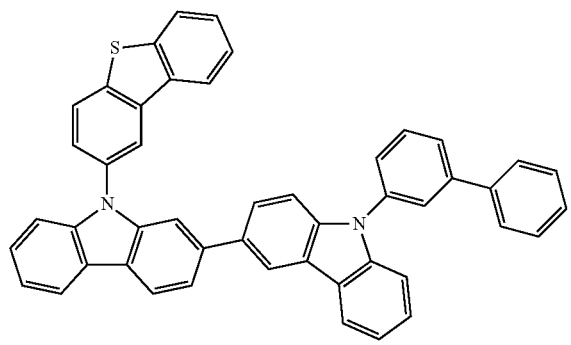
B-98
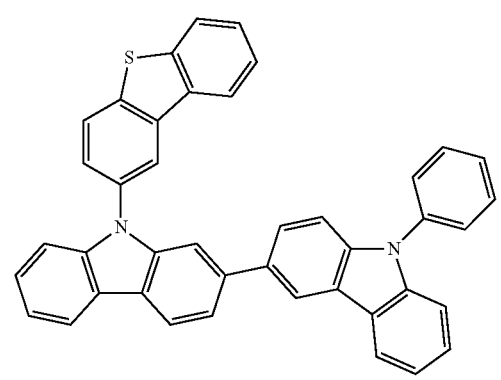
B-99
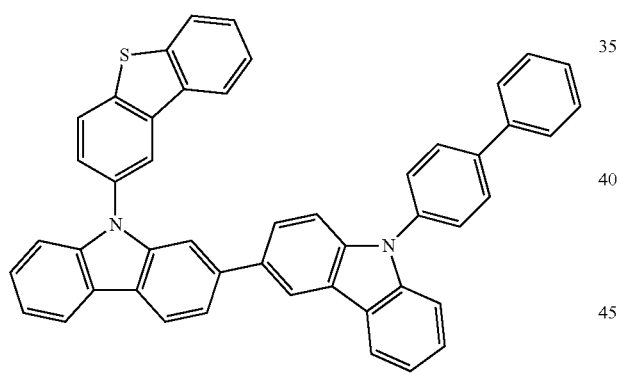
B-100
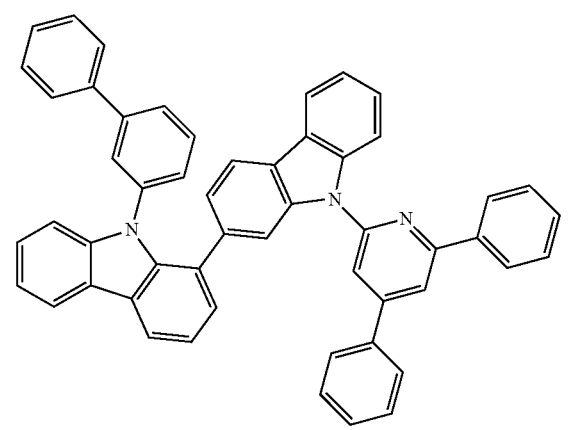
B-101
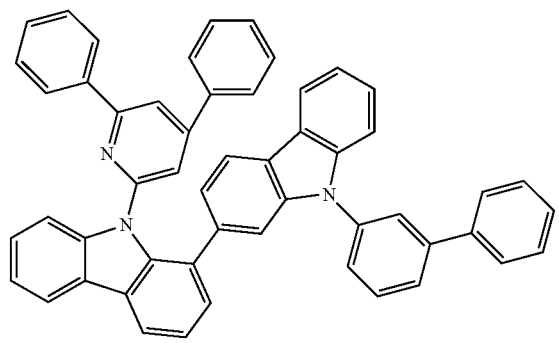
B-102
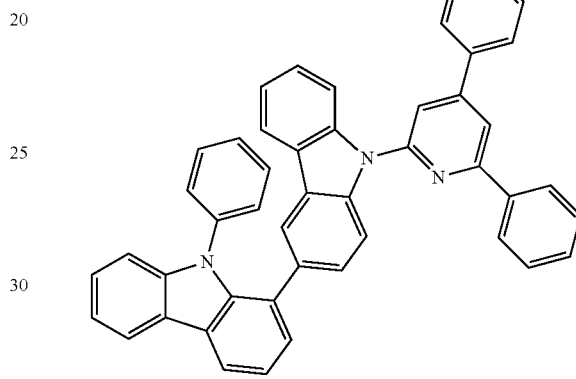
B-103
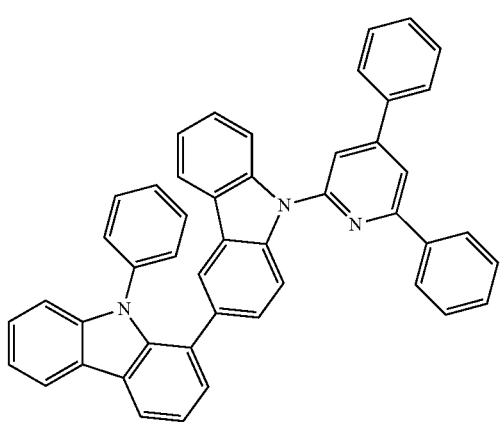
B-104
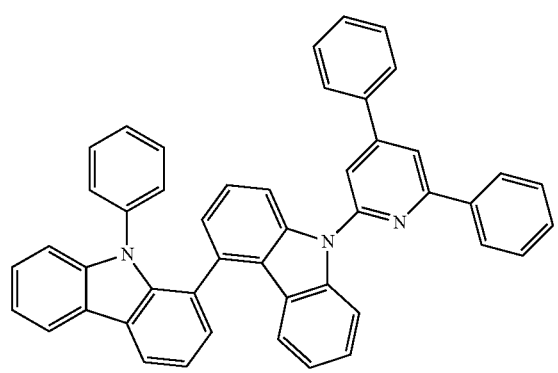

B-105
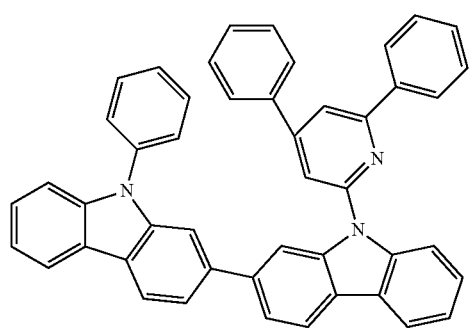
B-109
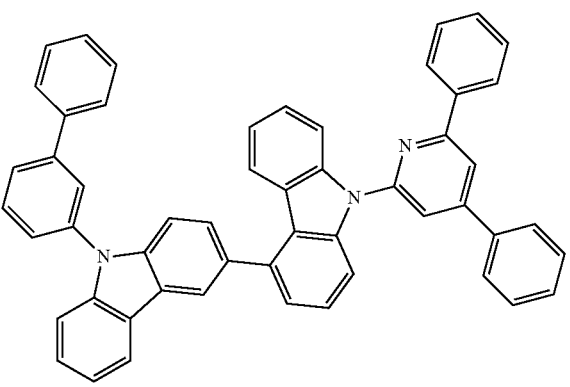
B-106
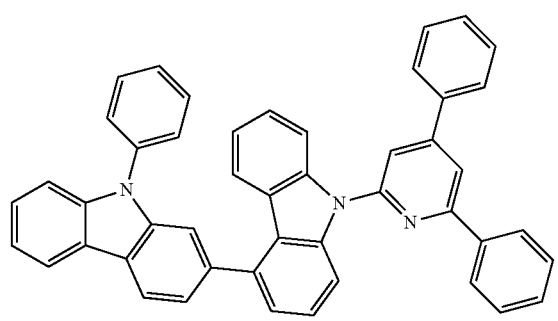
B-110
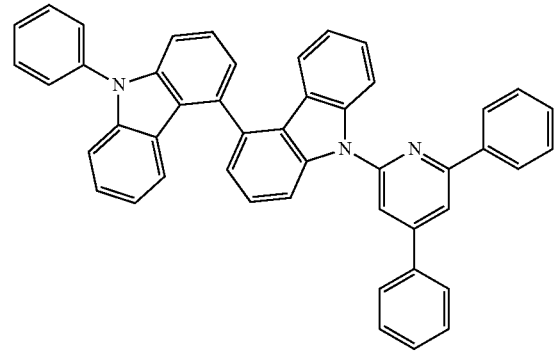
B-107
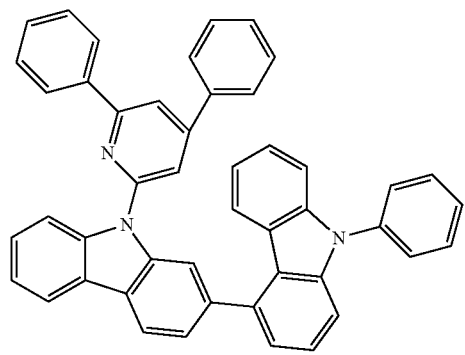
B-111
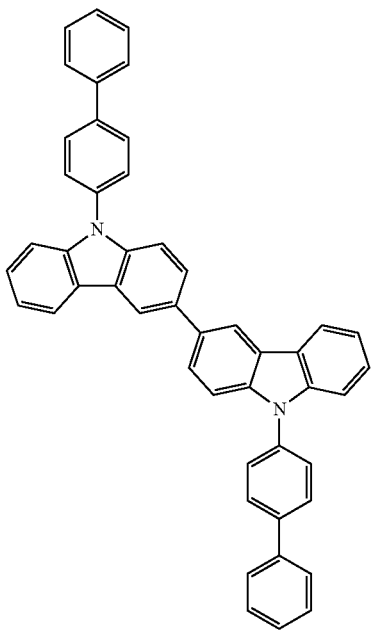
B-108
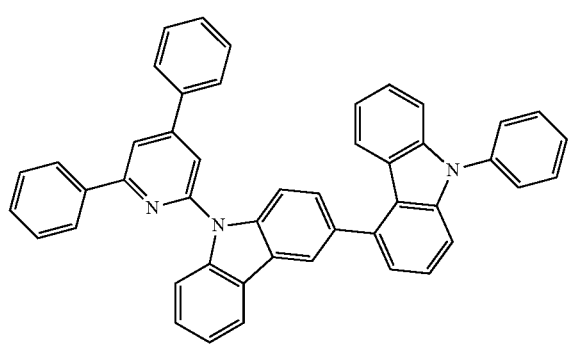

B-112
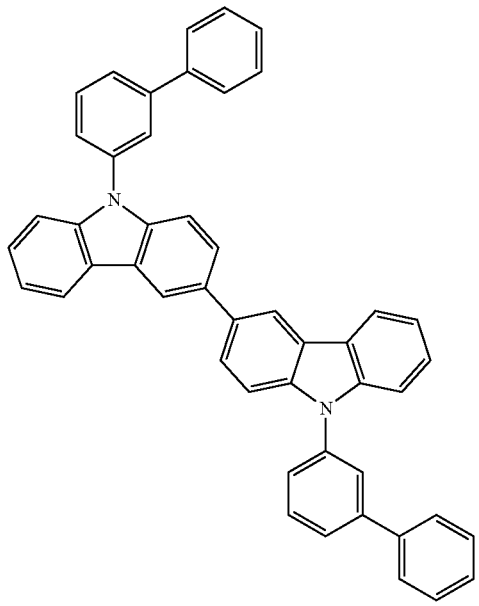
B-113
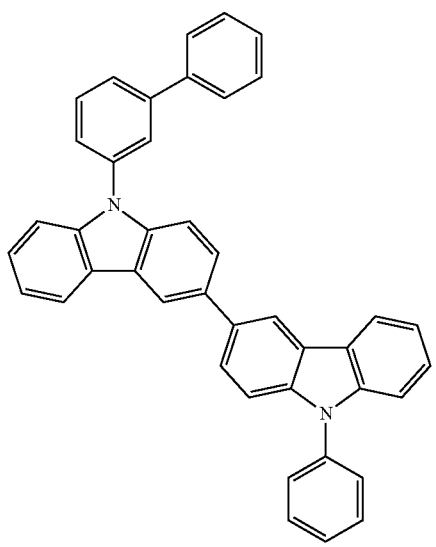
C-10
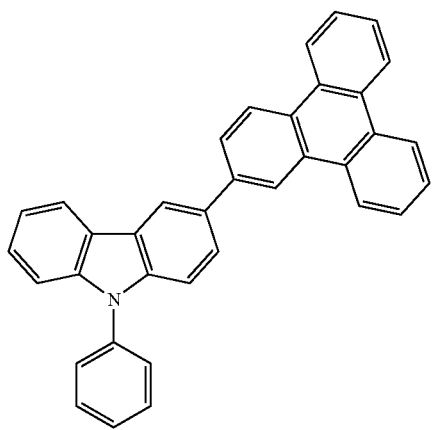
C-11
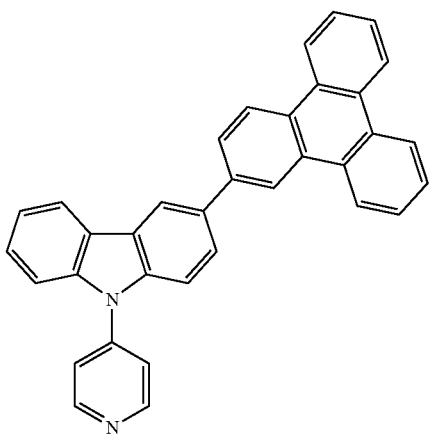
C-12
C-13
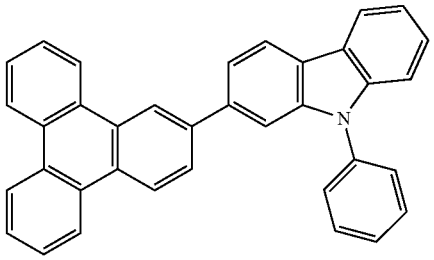
C-14
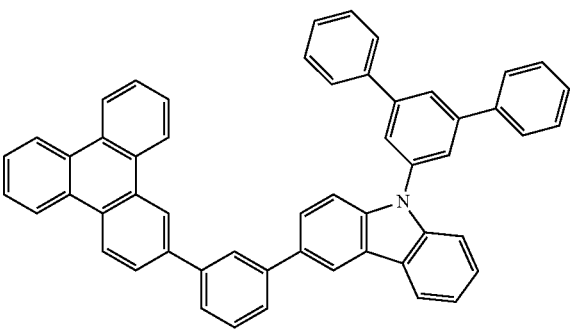

-continued
C-15
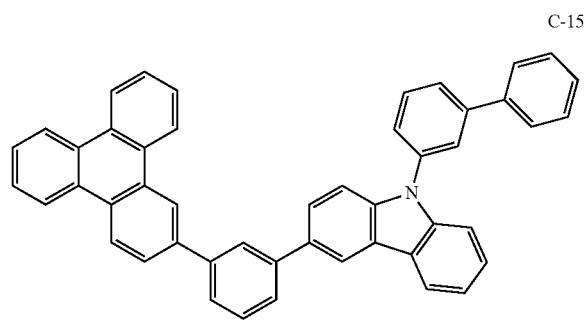
C-16
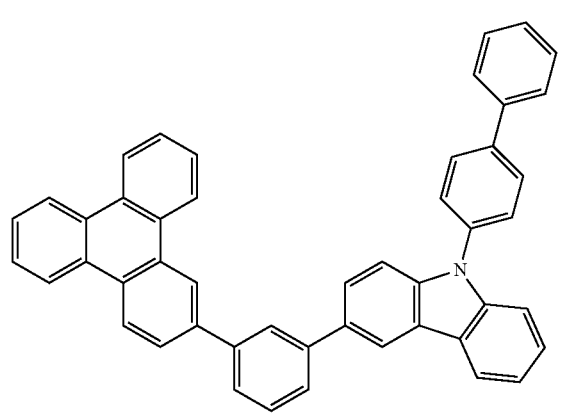
C-17
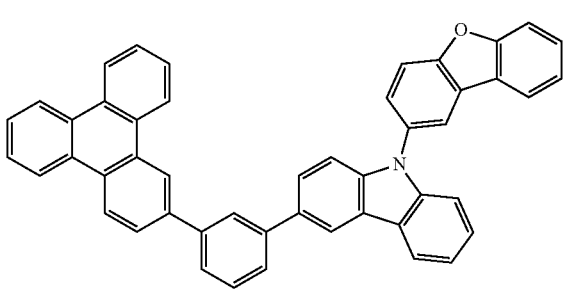
C-18
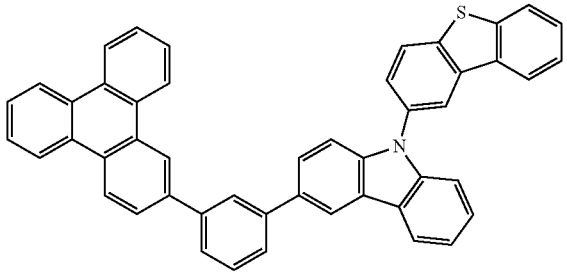
C-19
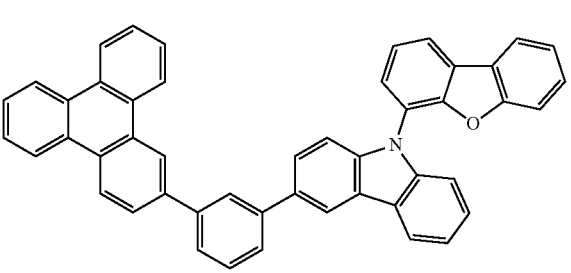
-continued
C-20
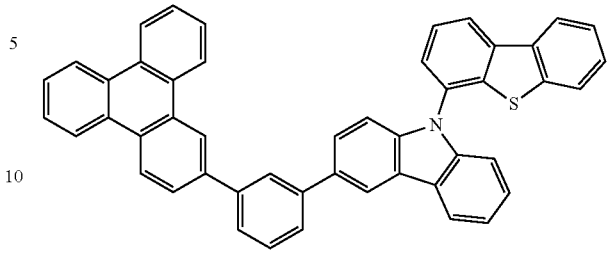
C-21
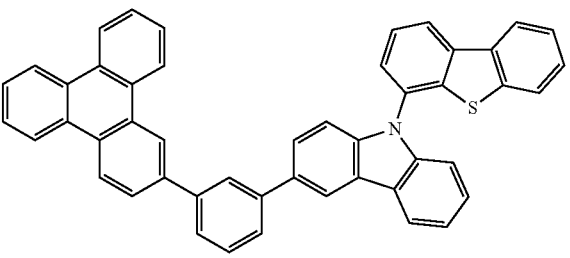
C-22
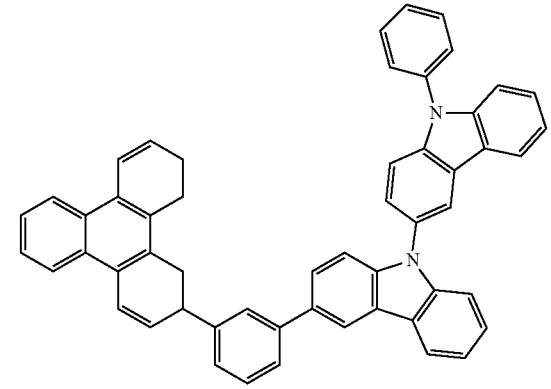
C-23
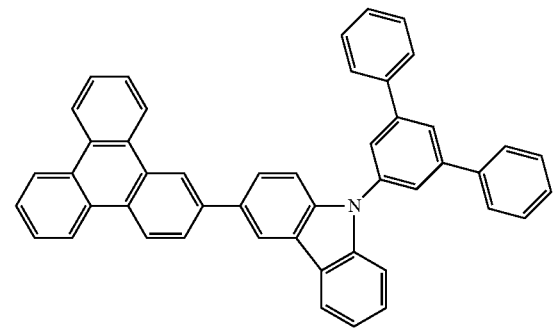

C-24
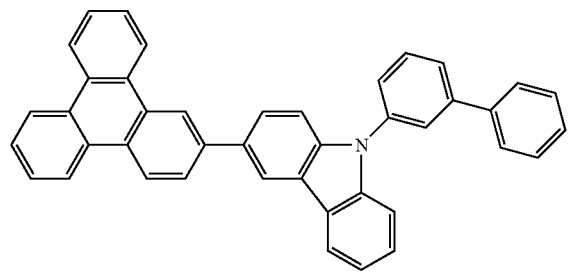
C-25
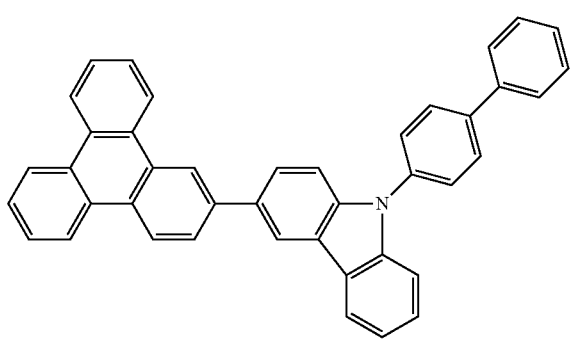
C-26
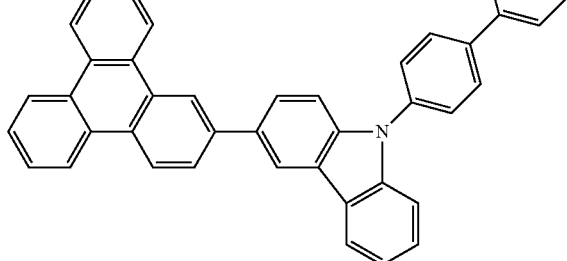
C-27
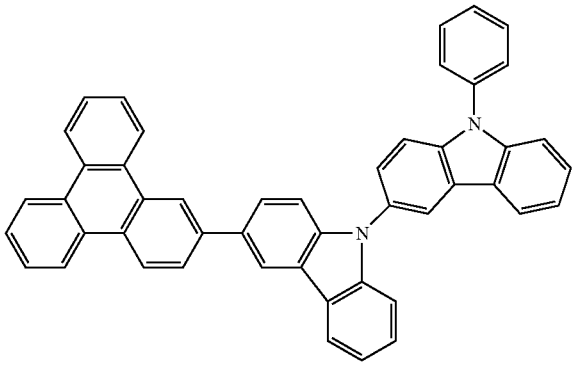
C-28
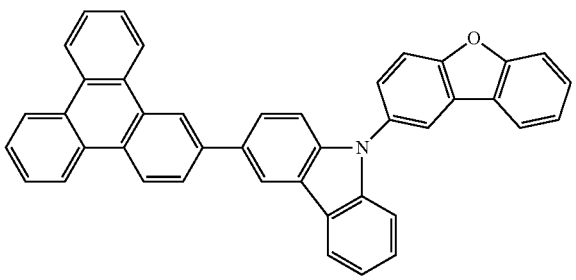
C-29
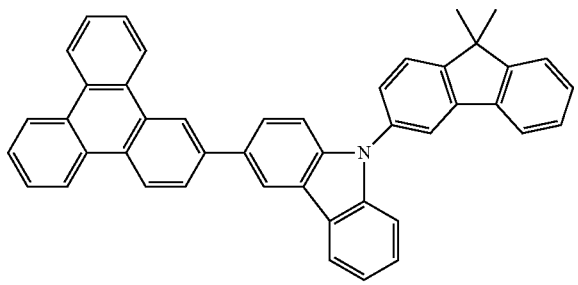
C-30
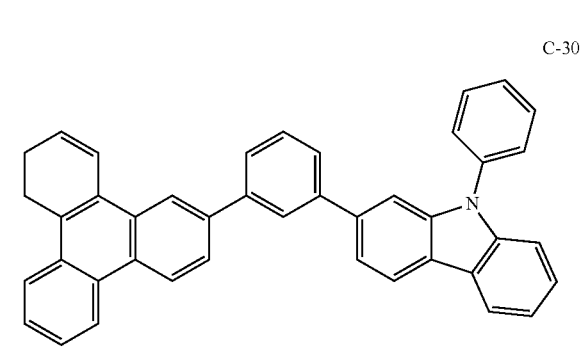
C-31
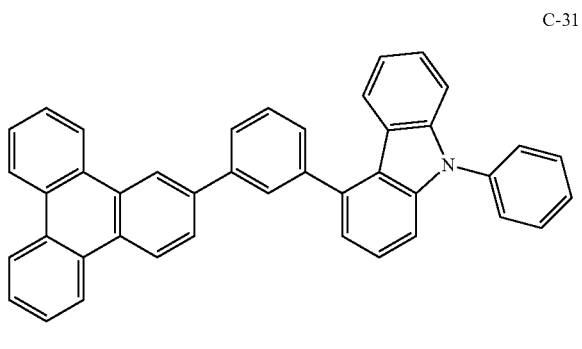
C-32
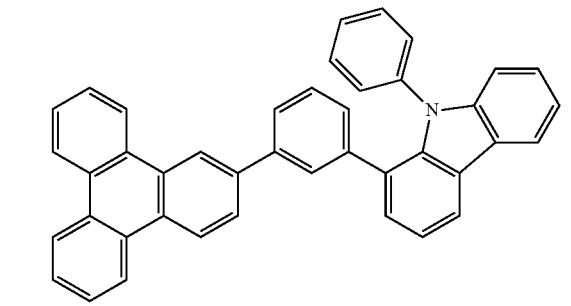
C-33
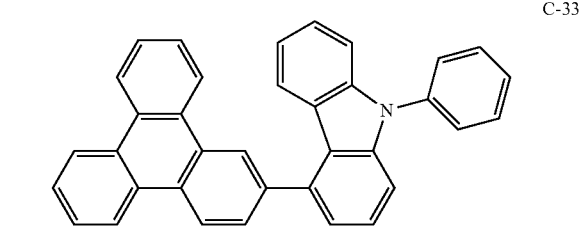

D-10
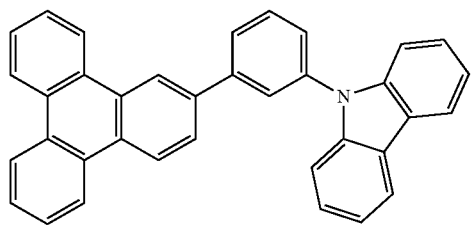
D-11
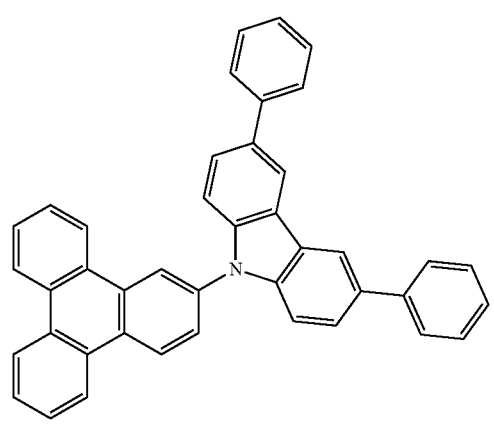
D-12
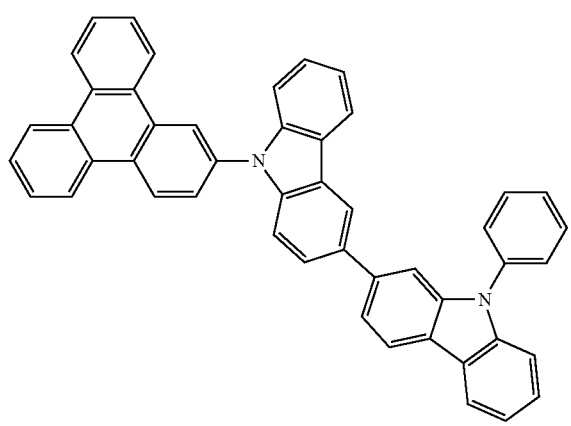
D-13
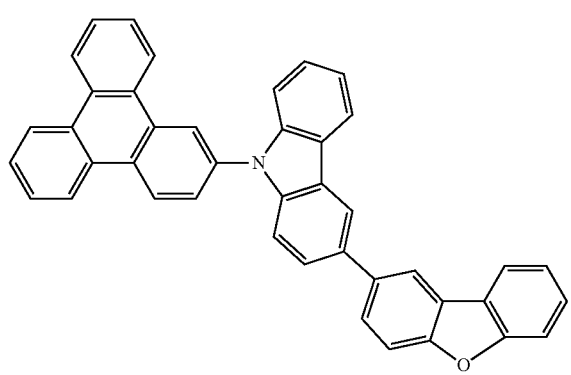
D-14
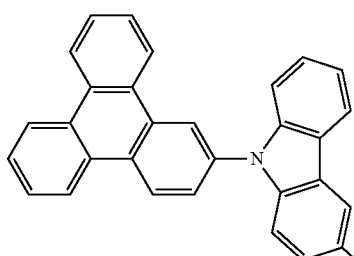
D-15
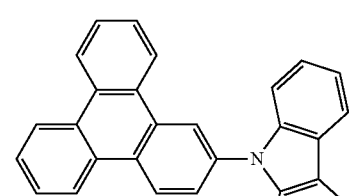
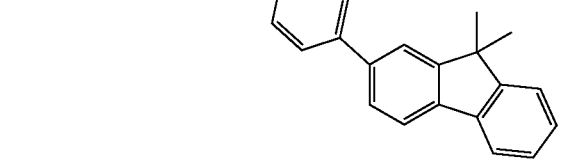
D-16
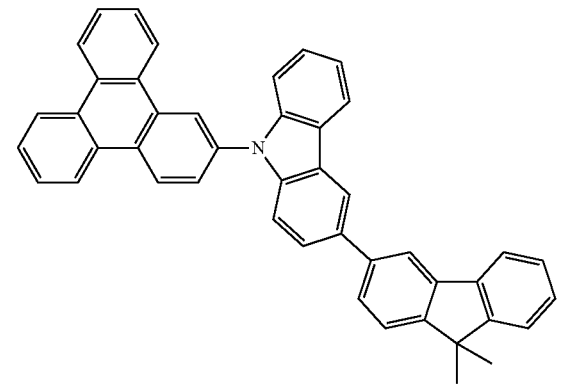
D-17
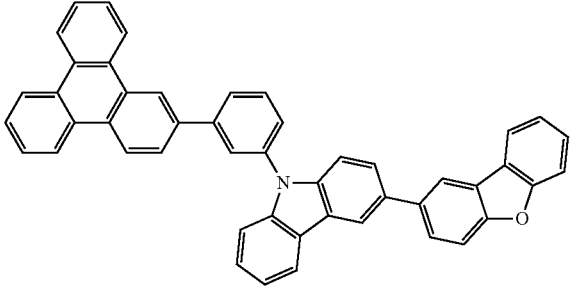

D-18
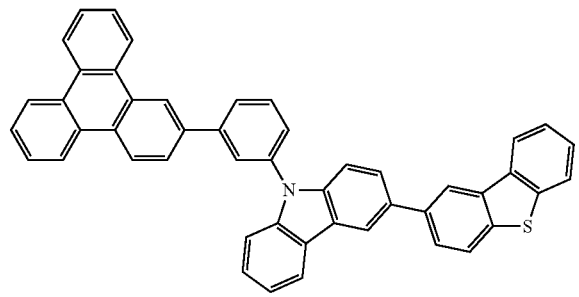
D-19
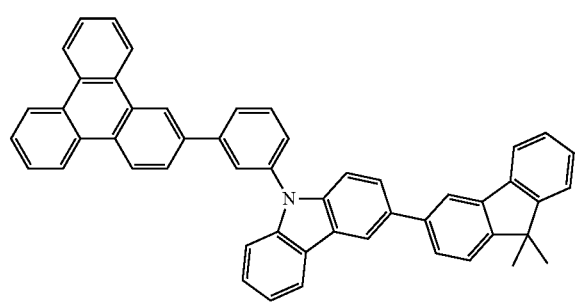
D-20
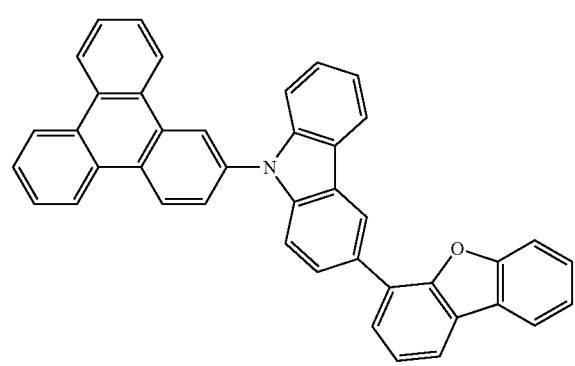
D-21
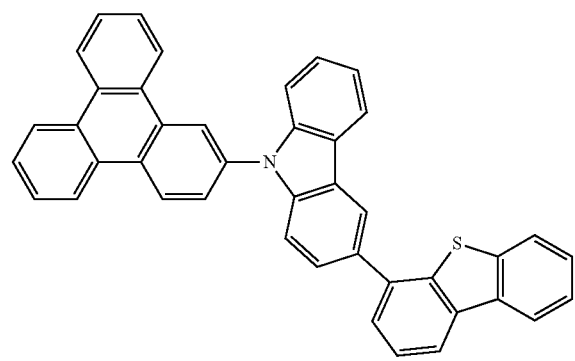
D-22
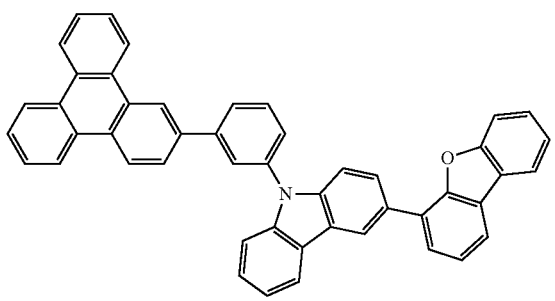
D-23
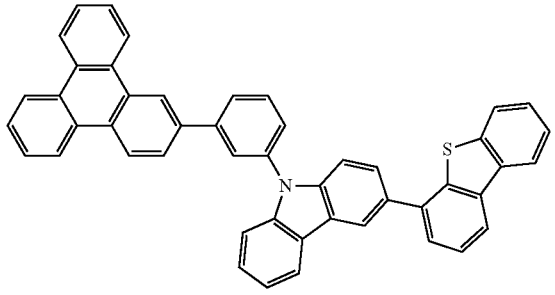
D-24
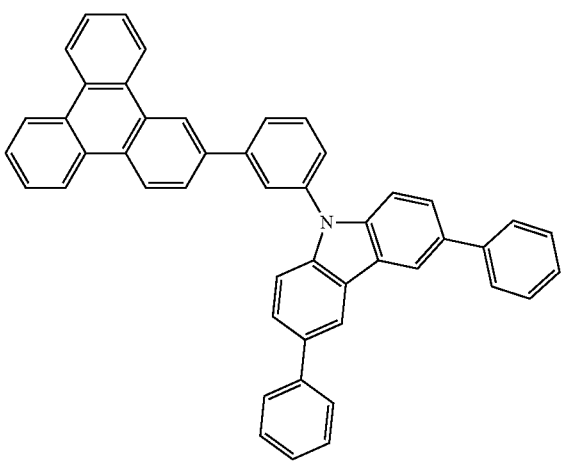
D-25
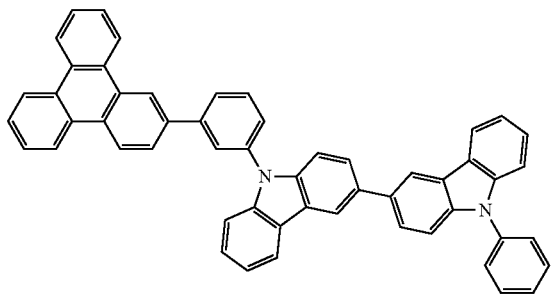

D-26

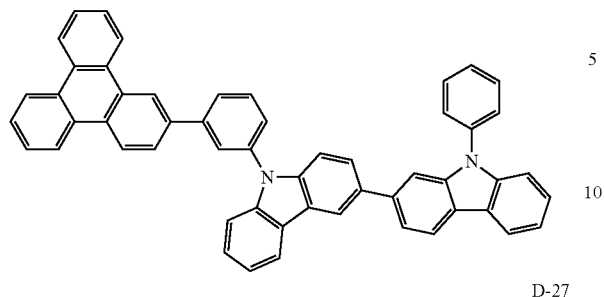

[Group 3]

E-1

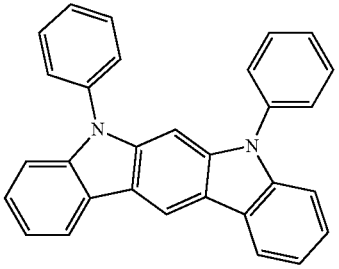

D-27

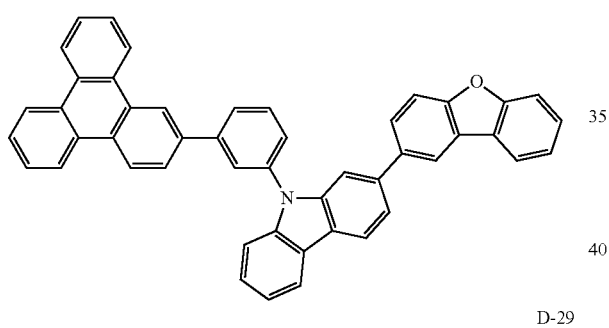

E-2

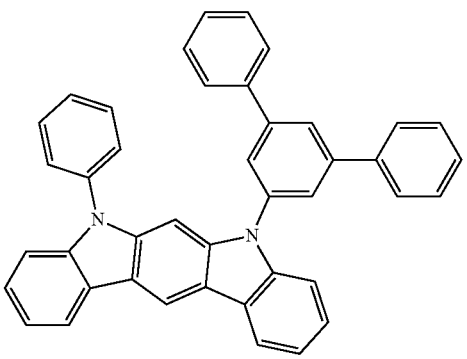

D-28

E-3

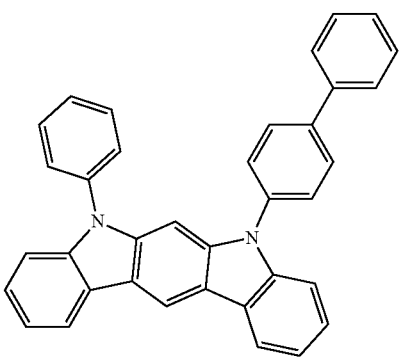

D-29

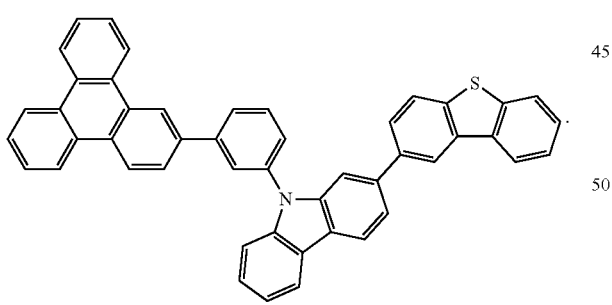

E-4

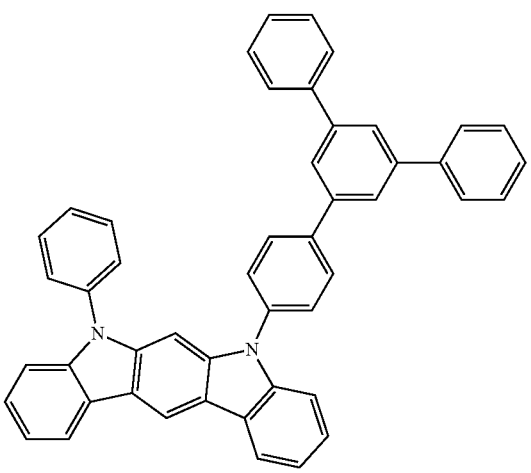

16. The composition for an organic optoelectric device of claim 6, wherein:
the second organic compound includes a compound consisting of a moiety represented by Chemical Formula 12 and a moiety represented by Chemical Formula 13, and
the second organic compound consisting of the moiety represented by Chemical Formula 12 and the moiety represented by Chemical Formula 13 is selected from compounds of Group 3:

E-5
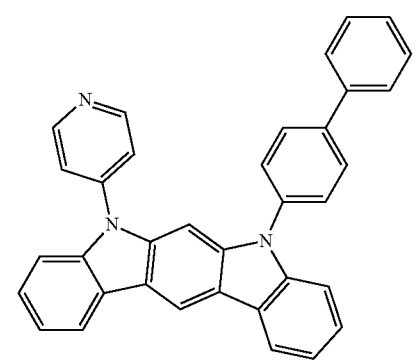
E-6
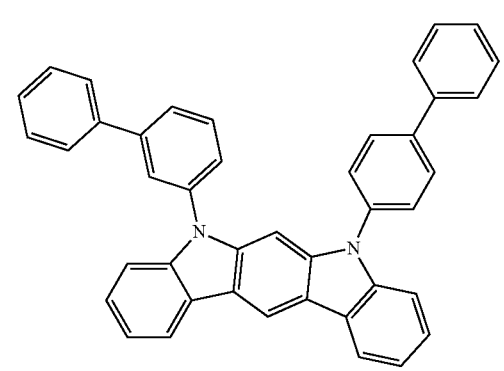
E-7
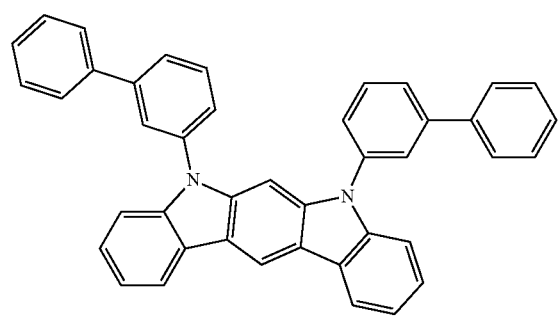
E-8
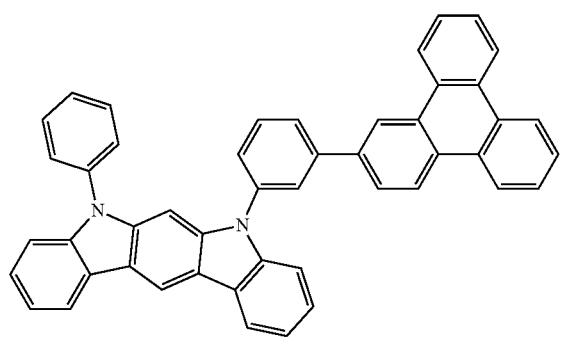
E-9
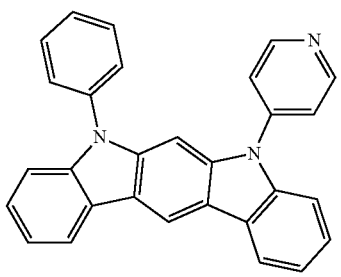
E-10
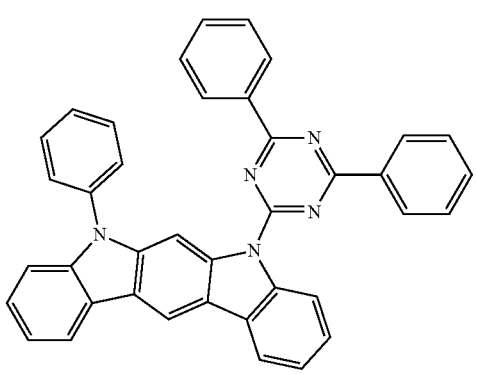
E-11
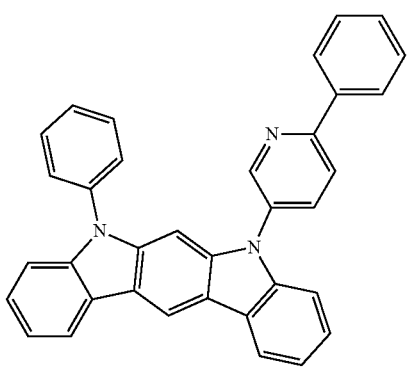
E-12
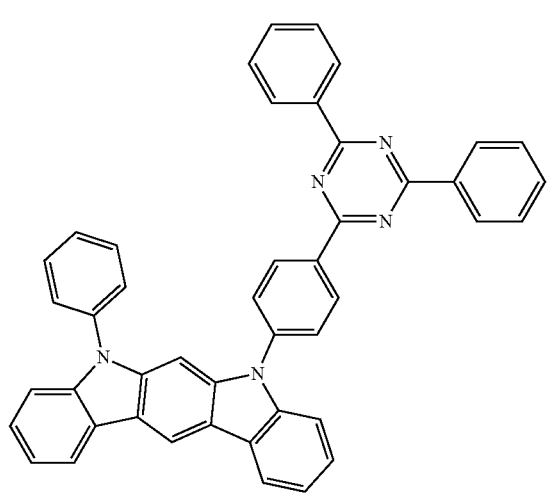

-continued
E-13
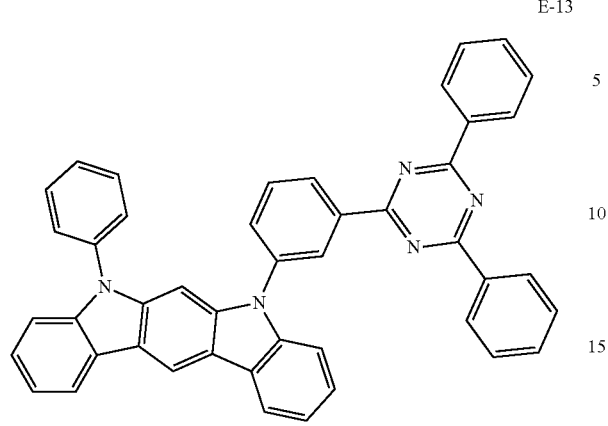
E-14
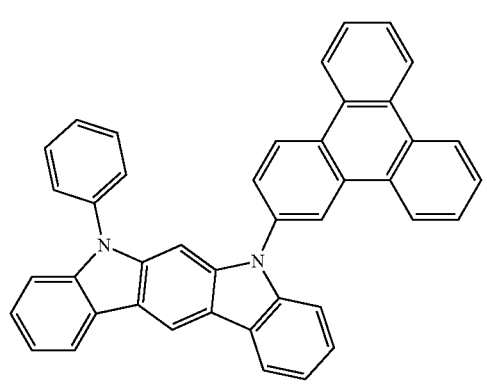
E-15
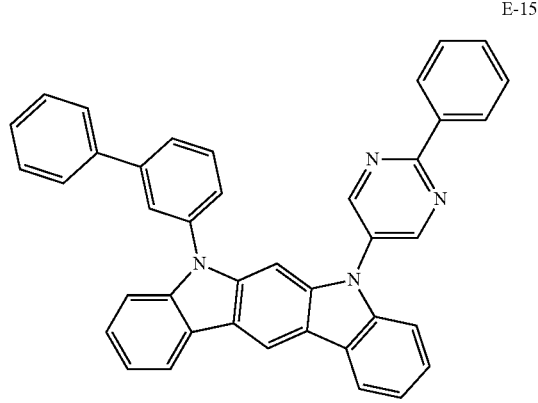
E-16
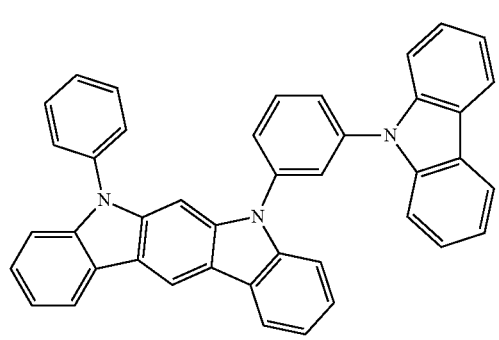
-continued
E-17
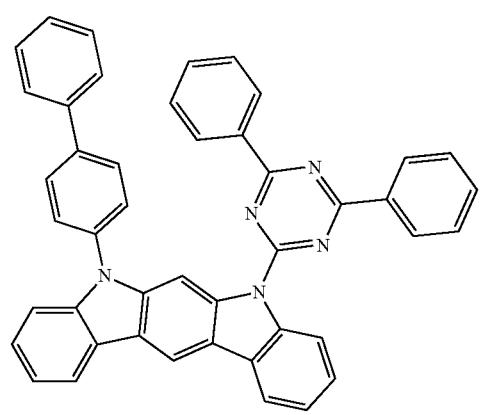
E-18
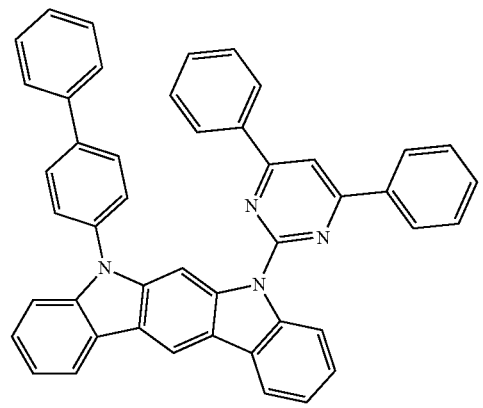
E-19
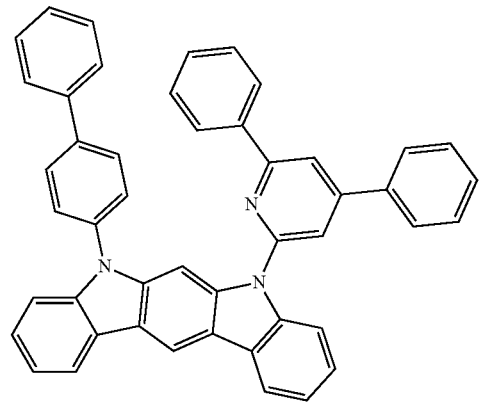
E-20
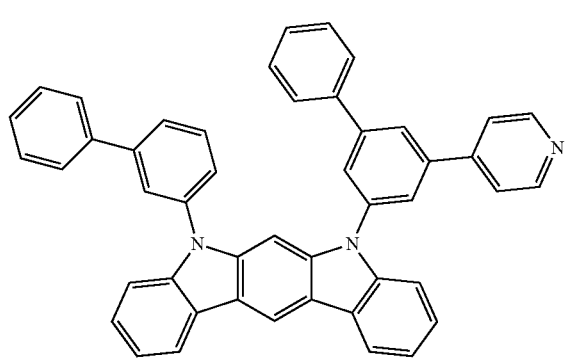

E-21
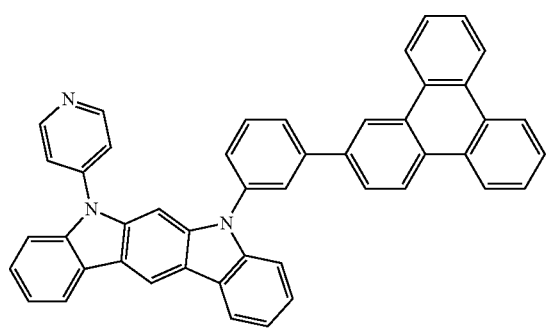
E-22
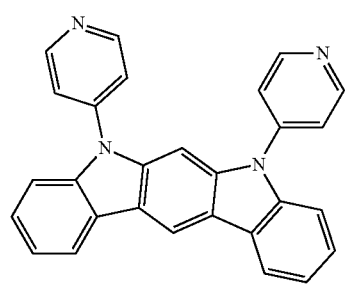
E-23
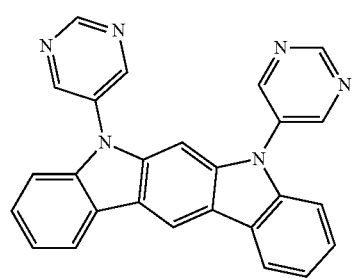
E-24
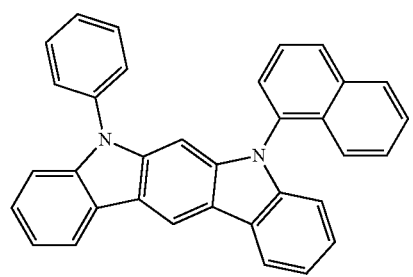
E-25
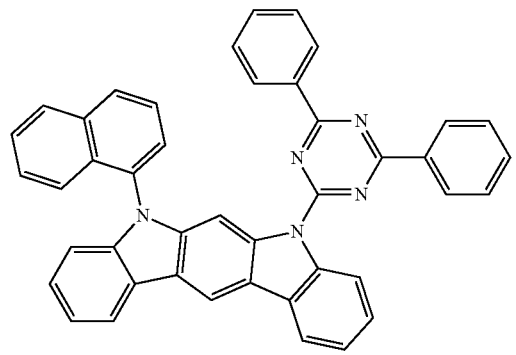
E-26
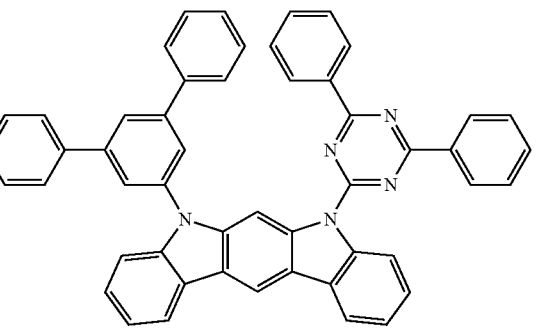
E-27
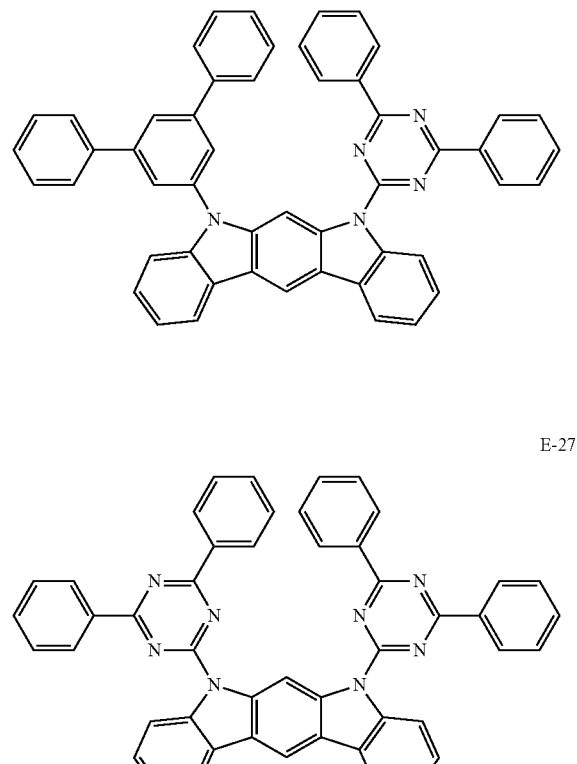
E-28
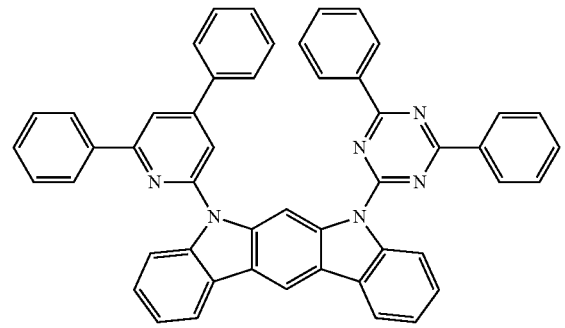
E-29
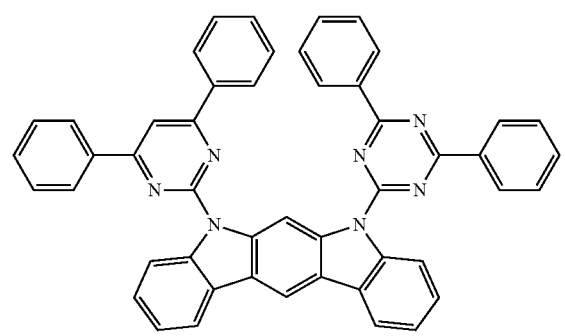

E-30
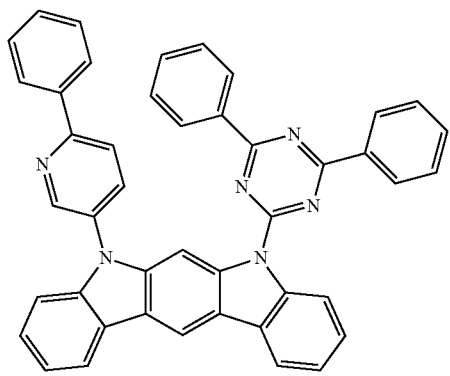
E-31
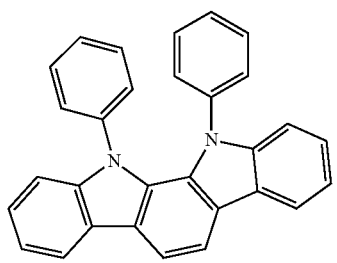
E-32
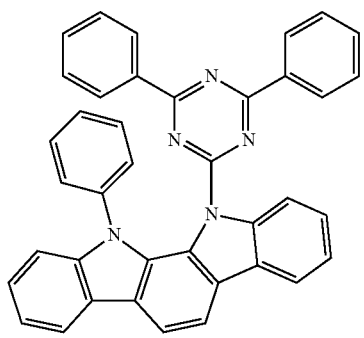
E-33
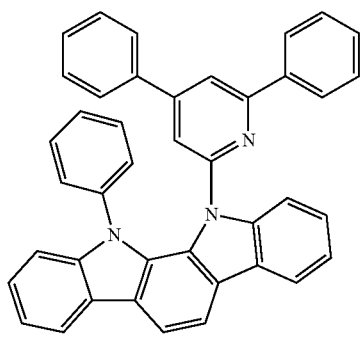
E-34
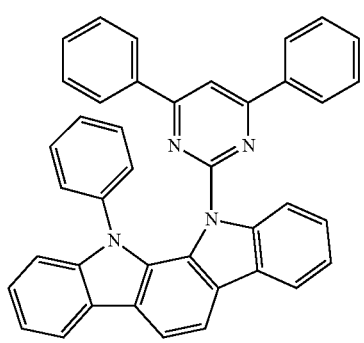
E-35
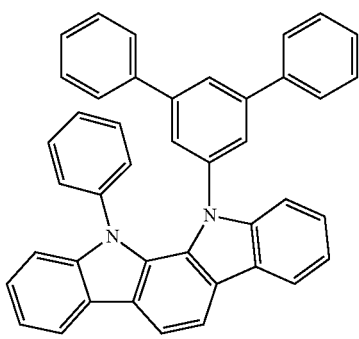
E-36
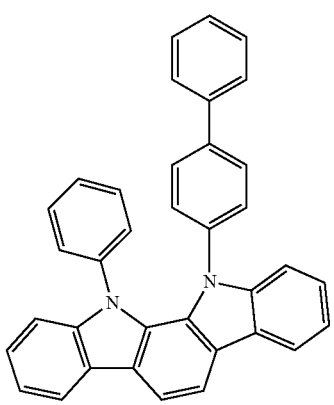
E-37
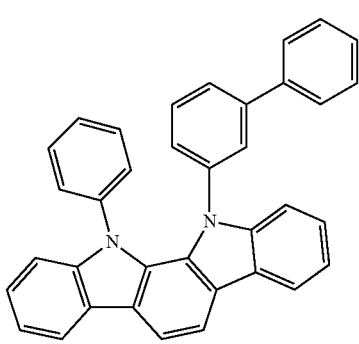
E-38
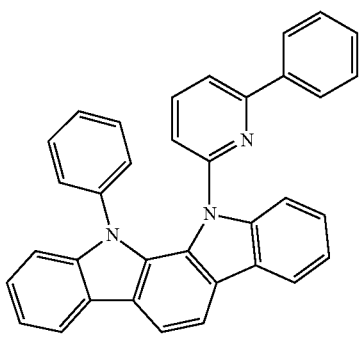

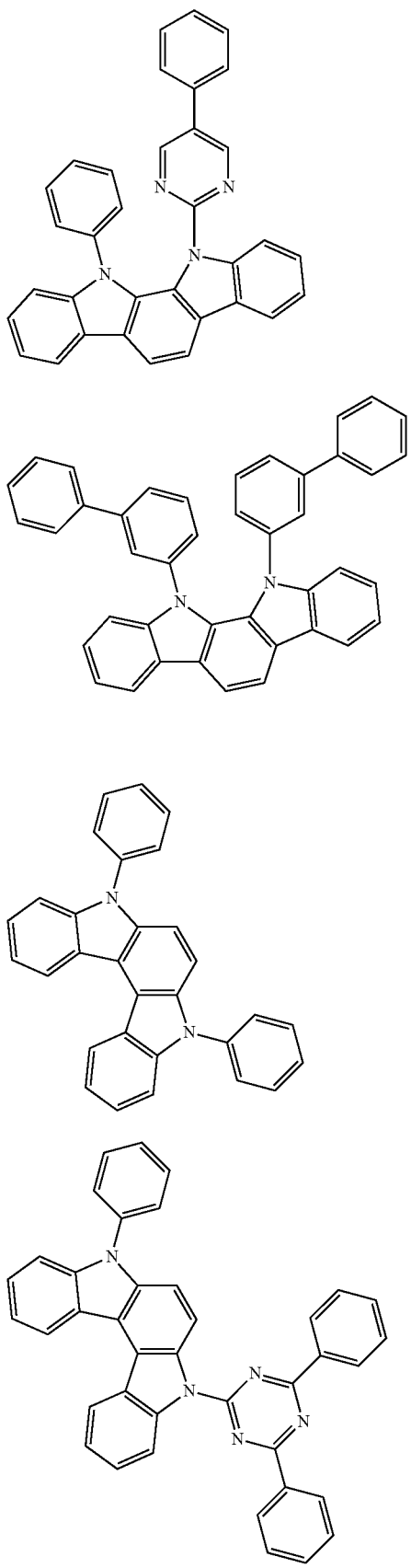
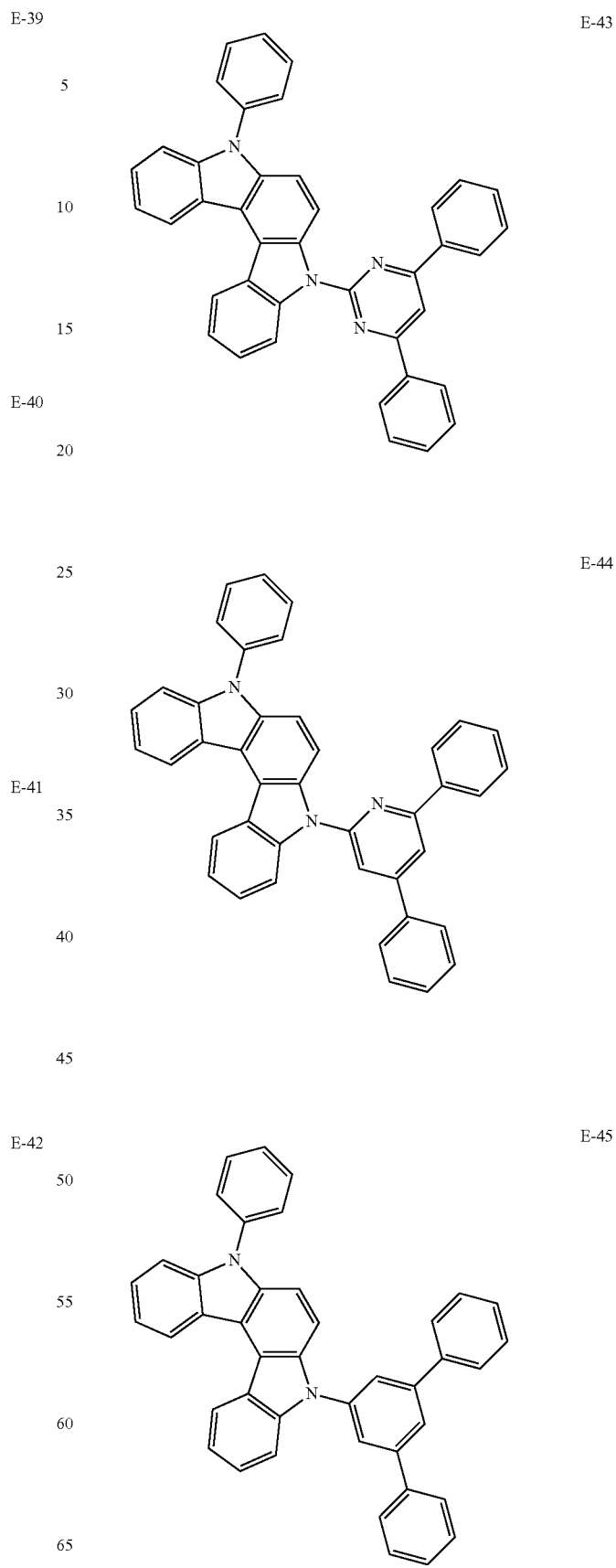

E-46
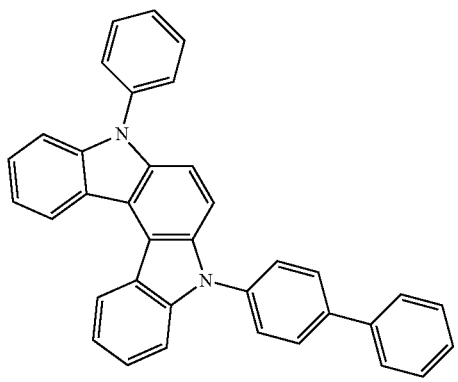
E-47
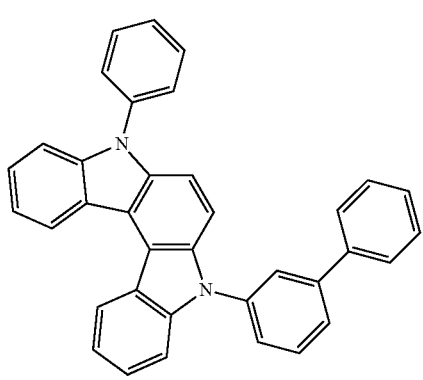
E-48
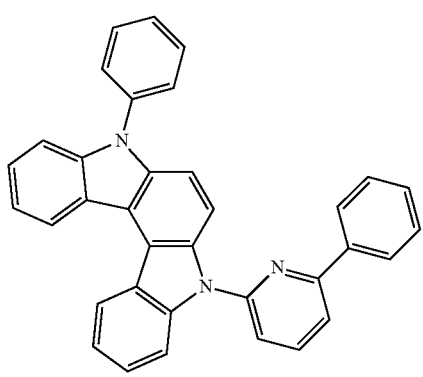
E-49
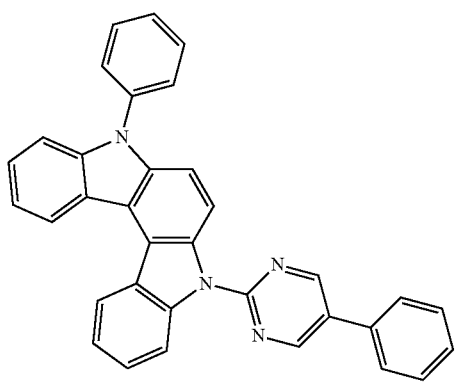
E-50
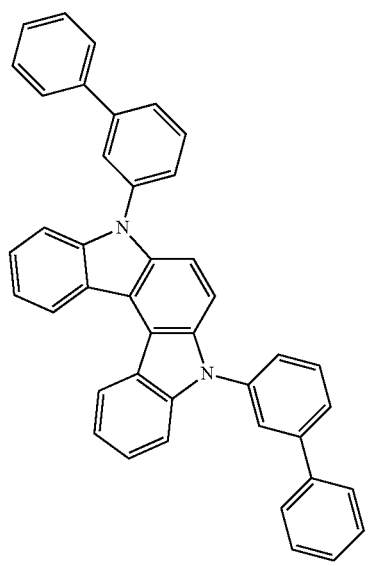
E-51
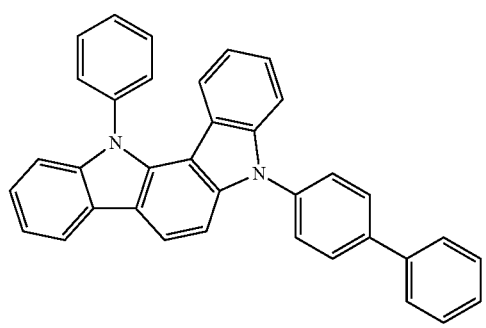
E-52
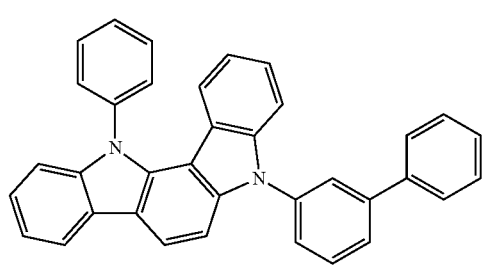
E-53
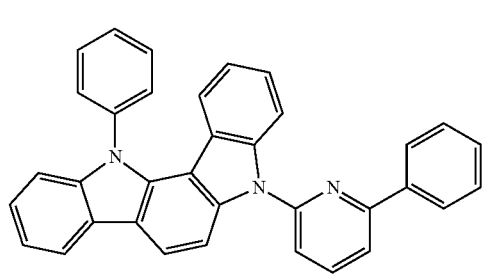

E-54
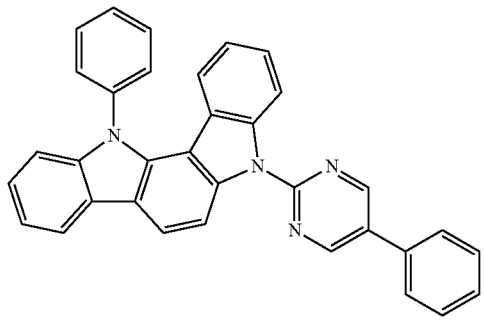
E-55
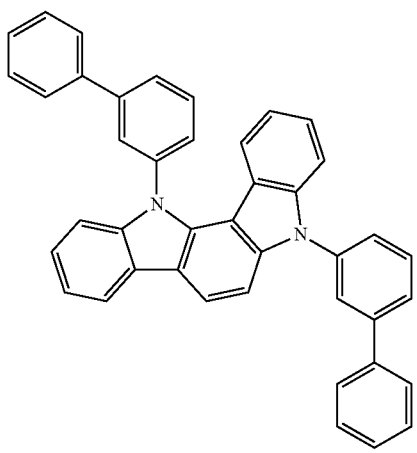
E-56
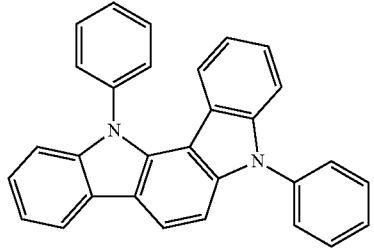
E-57
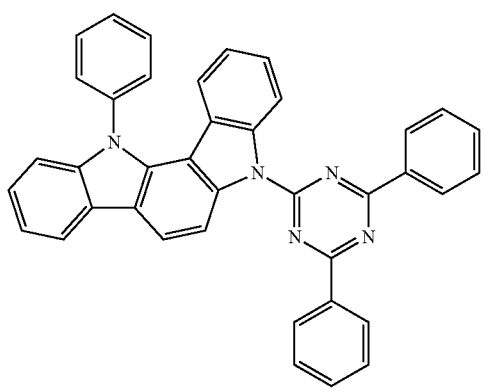
E-58
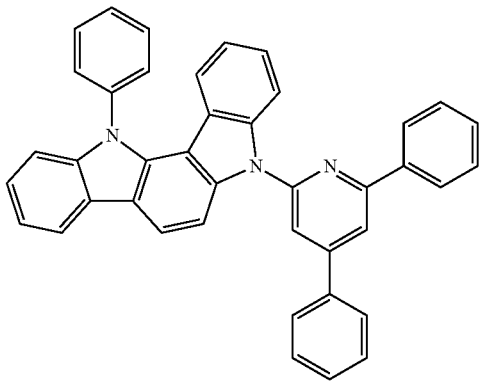
E-59
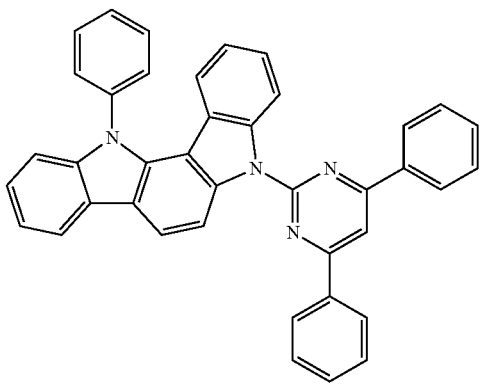
E-60
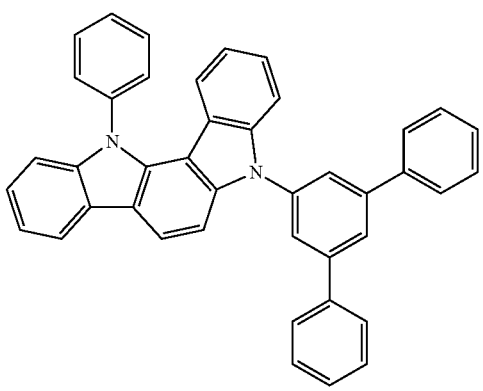

-continued
E-61
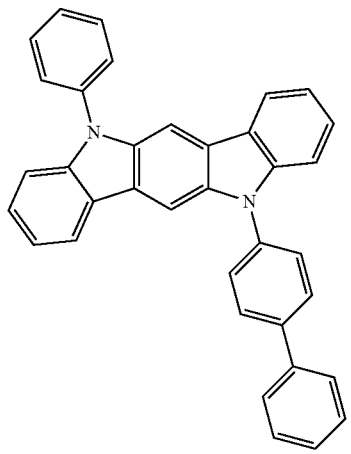
E-62
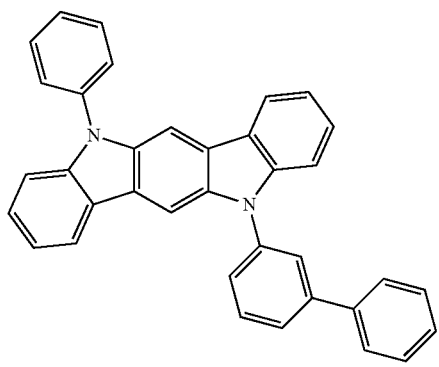
E-63
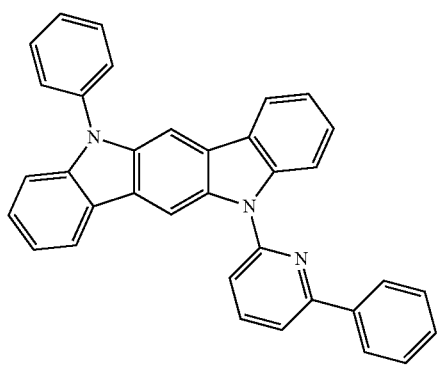
-continued
E-64
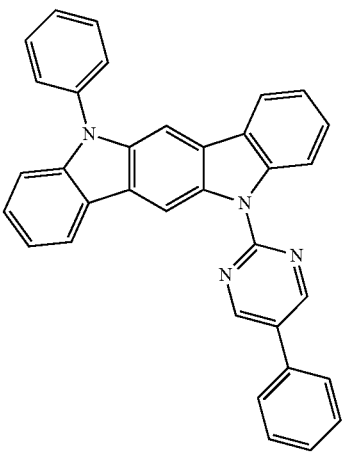
E-65
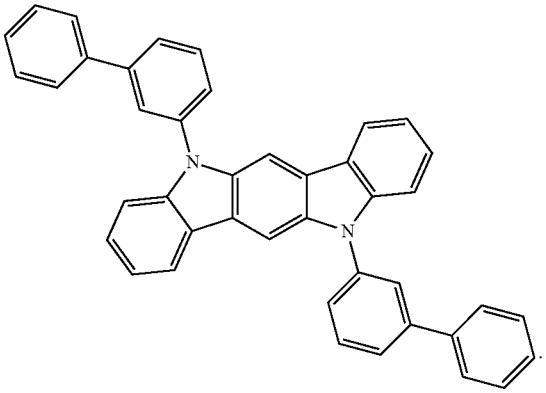
* * * * *